(12) United States Patent
Nagamiya et al.

(10) Patent No.: US 9,085,578 B2
(45) Date of Patent: Jul. 21, 2015

(54) HETEROCYCLIC COMPOUND

(71) Applicant: Takeda Pharmaceutical Company Limited, Osaka (JP)

(72) Inventors: Hiroyuki Nagamiya, Kanagawa (JP); Masato Yoshida, Kanagawa (JP); Masaki Seto, Kanagawa (JP); Shogo Marui, Kanagawa (JP); Tsuneo Oda, Kanagawa (JP); Yuji Ishichi, Kanagawa (JP); Hideo Suzuki, Kanagawa (JP); Tomokazu Kusumoto, Kanagawa (JP); Takatoshi Yogo, Kanagawa (JP); Chul Yun Rhim, Gyeonggi-Do (KR); Cheolhwan Yoon, Gyeonggi-Do (KR); Gil Nam Lee, Gyeonggi-Do (KR); Hyun Bin Kang, Gyeonggi-Do (KR); Kwang Ok Kim, Gyeonggi-Do (KR); Hye Sun Jeon, Gyeonggi-Do (KR)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/379,343

(22) PCT Filed: Feb. 19, 2013

(86) PCT No.: PCT/JP2013/054054
§ 371 (c)(1),
(2) Date: Aug. 18, 2014

(87) PCT Pub. No.: WO2013/125543
PCT Pub. Date: Aug. 29, 2013

(65) Prior Publication Data
US 2015/0045349 A1    Feb. 12, 2015

(30) Foreign Application Priority Data

Feb. 20, 2012    (JP) ................. 2012-034440

(51) Int. Cl.
| | | |
|---|---|---|
| *C07D 401/14* | (2006.01) | |
| *A61K 31/437* | (2006.01) | |
| *C07D 471/04* | (2006.01) | |
| *C07D 519/00* | (2006.01) | |

(52) U.S. Cl.
CPC ............ *C07D 471/04* (2013.01); *C07D 519/00* (2013.01)

(58) Field of Classification Search
CPC ............................. C07D 401/14; A61K 31/437
USPC .......................................... 514/303; 546/119
See application file for complete search history.

(56) References Cited

U.S. PATENT DOCUMENTS

| | | |
|---|---|---|
| 2008/0039491 A1 | 2/2008 | Ronan et al. |
| 2010/0099683 A1 | 4/2010 | Tomkinson et al. |
| 2011/0190337 A1 | 8/2011 | Ronan et al. |
| 2011/0269739 A1 | 11/2011 | Kim et al. |
| 2013/0096104 A1 | 4/2013 | Lai et al. |
| 2013/0143915 A1 | 6/2013 | Ellard et al. |
| 2014/0113891 A1 | 4/2014 | Tomkinson et al. |

FOREIGN PATENT DOCUMENTS

| | | |
|---|---|---|
| JP | 2008-527025 | 7/2008 |
| WO | 2008/0124838 | 10/2008 |
| WO | 2011/053861 | 5/2011 |
| WO | 2011/113802 | 9/2011 |
| WO | 2012/000970 | 1/2012 |

OTHER PUBLICATIONS

Kumar et al., Journal of the Chemical Society, Perkin Transactions 1: Organic and Bio-Organic Chemistry (1972-1999) (1978), (8), 857-62.*

International Search Report issued Apr. 23, 2014, in International (PCT) Application No. PCT/JP2013/054054.

Smyth et al., "Synthesis and reactivity of 3-amino-1H-pyrazolo[4,3-c]pyridin-4(5H)-ones: development of a novel kinase-focused library", Tetrahedron, Feb. 2010, vol. 66, No. 15, pp. 2843-2854.

Smyth et al. "Design and evaluation of 3-aminopyrazolopyridinone kinase inhibitors inspired by the natural product indirubin", Bioorganic & Medicinal Chemistry, Apr. 2011, vol. 19, No. 11, pp. 3569-3578.

Elgemeie et al., "Synthesis of some novel α-cyanoketene S,S-acetals and their use in heterocyclic synthesis", J. Chem. Soc., Perkin Trans., 1997, 21, pp. 3285-3290.

Tominaga et al., "Synthesis and Reactions of 6-Aryl- and 6-Styryl-3-cyano-4methylthio-2*H*-pyran-2-ones", Chem. Pharm. Bull., vol. 32(9), 1984, pp. 3384-3395.

Kumar et al., "Keten Dithioacetals. Part 11.[1] Reaction of 3-Cyano-4methylthylthio-2(1H)-pyridones with Hydrazine and Guanidine: Synthesis of Novel Substituted and Fused Pyrazolo[4,3-*c*]pyridone and Pyrido[4,3-*d*]pyrimidine derivatives", J. Chem. Soc., Perkin Trans. 1: Organic and Bio-organic Chemistry (1972-1999) (1978), (8), pp. 857-862.

(Continued)

*Primary Examiner* — Niloofar Rahmani
(74) *Attorney, Agent, or Firm* — Wenderoth, Lind & Ponack, L.L.P.

(57) ABSTRACT

The present invention provides an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like, which has a superior Tyk2 inhibitory action.

The present invention relates to a compound represented by the formula (I)

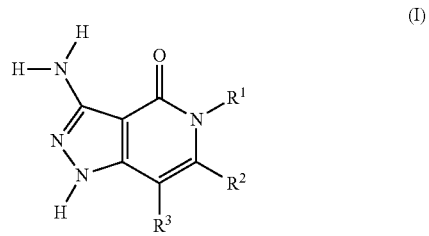

wherein each symbol is as defined in the specification, or a salt thereof.

8 Claims, No Drawings

(56) References Cited

OTHER PUBLICATIONS

Elgemeie et al., "A new general method for substituted 4-Alkylthio-N-Arylsulphonyl-Amino-2-Pyridones: Reaction of Ketene-SS-Acetals with Arylsulphonylhydrazides", Phosphorus, Sulfur and Silicon and the Related Elements, 2001, vol. 170, pp. 171-179.
STN Search Results, 2012, for compounds which entered STN Mar. 22, 1985, May 12, 1994, Dec. 8, 1997, Oct. 21, 2001, Sep. 20-21, 2006, and Apr. 29-30, 2008, including CAS Registry Nos. (RN): 1018564-99-2, 1018564-95-8, 1018564-87-8, 1018497-28-3, 1018497-20-5, 1018497-18-1, 1018497-16-9, 1018497-14-7, 1018497-12-5, 1018497-10-3, 1018274-50-4, 1018249-54-1, 1018249-46-1, 908069-44-3, 908068-91-7, 907970-80-3, 908069-29-4.
Extended European Search Report issued Mar. 13, 2015 in European Application No. 13751296.8.

* cited by examiner

HETEROCYCLIC COMPOUND

TECHNICAL FIELD

The present invention relates to a heterocyclic compound having a tyrosine kinase 2 (In the present specification, sometimes to be abbreviated as "Tyk2") inhibitory action, which is useful as an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like, a pharmaceutical composition containing thereof, and the like.

BACKGROUND OF THE INVENTION

Cytokines are proteins secreted by a cell of the immune system and transduce a signal to a specific cell. They have various kinds, and many of them are especially associated with immunity and inflammation and also associated with cell growth, differentiation, cell death, wound healing and the like (Curr Opin Cell Biol. 1991 April; 3(2):171-5.).

The janus kinase (JAK) family plays a role in cytokine-dependent regulation of the function of cells associated with growth and immune response. Tyk2 is one of the four kinds of janus kinases (JAK1 (also known as janus kinase 1), JAK2 (also known as janus kinase 2), JAK3 (also known as janus kinase 3) and Tyk2 (also known as tyrosine kinase 2)), and it is known to be involved in signal transduction of cytokines such as IFN(interferon)-α, IFN-β, IL(interleukin)-6, IL-10 family (IL-10, IL-19, IL-20, IL-22, IL-28, IL-29), IL-12, IL-23 and the like (Nature Immunology 10, 356-360 (2009), New York Academy of Science 1246, 34-40 (2011)). These cytokines play an important role in immune response when exist in an appropriate amount. However, excessive production of them is thought to be involved in many autoimmune diseases such as psoriasis, rheumatoid arthritis, inflammatory bowel disease, Sjogren's syndrome, Behcet's disease, multiple sclerosis, systemic lupus erythematosus and the like (Journal of Allergy and Clinical Immunology 127, 3,701-721.e70 (2011), Cytokine & Growth Factor Reviews 19, 41-52 (2008), Invest Ophthalmol Vis Sci. 2008 July; 49(7): 3058-3064, Ann Rheum Dis. 2010 July; 69(7):1325-1328). For example, Ustekinumab, which is an anti-IL-12/23 monoclonal antibody, has been approved as a therapeutic drug for moderate to severe psoriasis patient in Europe, and furthermore, clinical trials for various diseases in which the IL-12/23 signaling pathway is suggested to be involved are performed. From the foregoing, a Tyk2 inhibitor is a potential therapeutic drug for various autoimmune diseases (Front Biosci. 2011 Jun. 1; 17:3214-32).

Examples of the compound having a structure similar to the compound described in the present specification include the following compounds.

(1) a compound represented by the following formula:

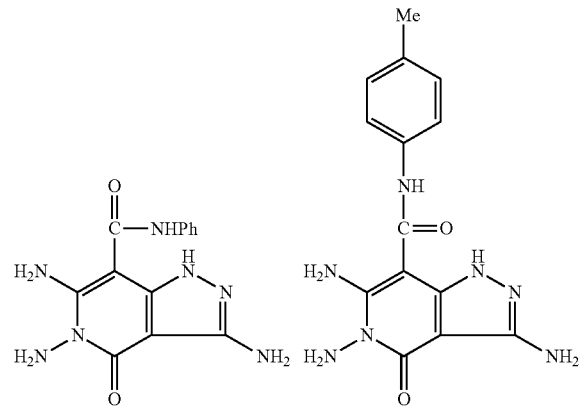

(Non-Patent Document 1)

(2) a compound represented by the following formula:

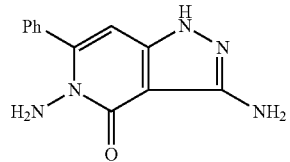 [SMILES: Nc1n[nH]c2cc(-c3ccccc3)n(N)c(=O)c12]

(Non-Patent Document 2).

(3) a compound represented by the following formula:

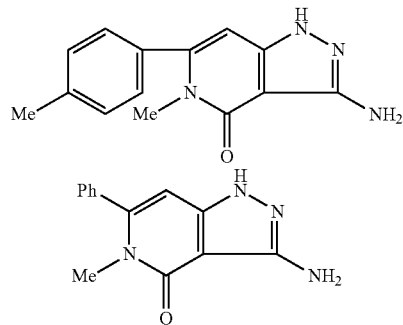

(Non-Patent Document 3).

(4) a compound represented by the following formula:

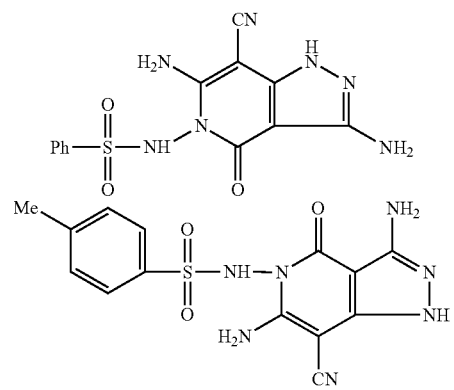

(Non-Patent Document 4).

(5) In chemical abstract, the following compounds are registrated.

registration number: 1018564-99-2

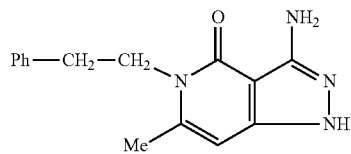

1)

registration number: 1018564-95-8

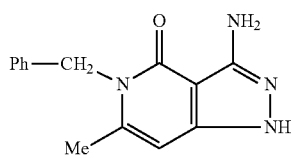

2)

registration number: 1018564-87-8

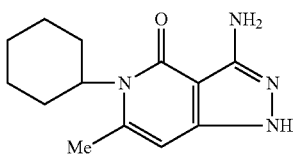

3)

registration number: 1018497-28-3

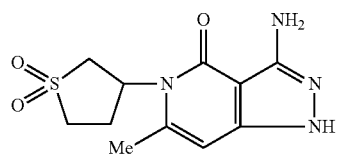

4)

registration number: 1018497-20-5

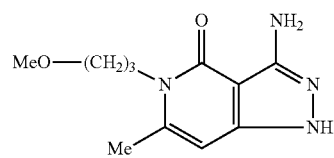

5)

registration number: 1018497-18-1

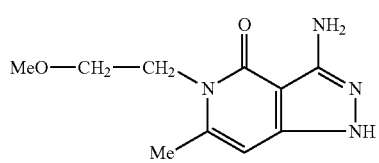

6)

registration number: 1018497-16-9

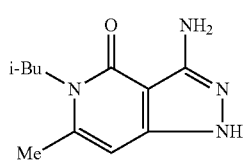

7)

registration number: 1018497-14-7

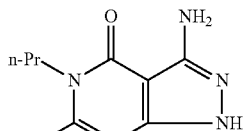

8)

registration number: 1018497-12-5

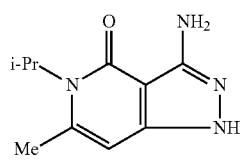

9)

registration number: 1018497-10-3

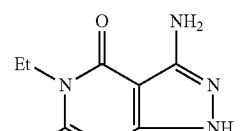

10)

registration number: 1018274-50-4

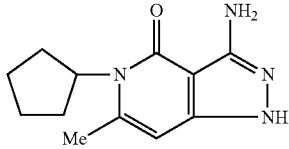

11)

registration number: 1018249-54-1

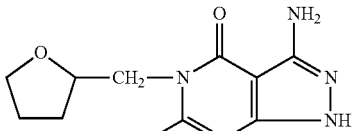

12)

registration number: 1018249-46-1

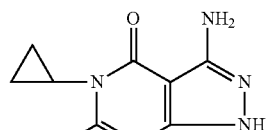

13)

registration number: 908069-44-3

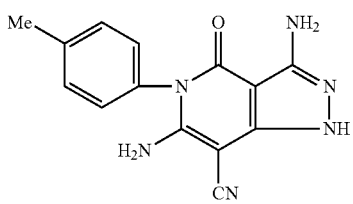

14)

registration number: 908068-91-7

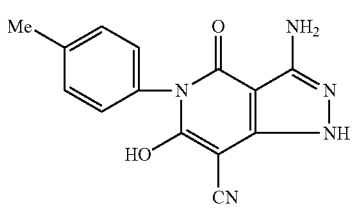

15)

-continued registration number: 907970-80-3

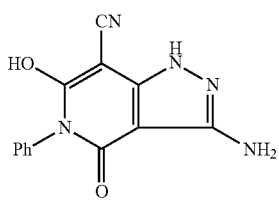

16)

registration number: 908069-29-4

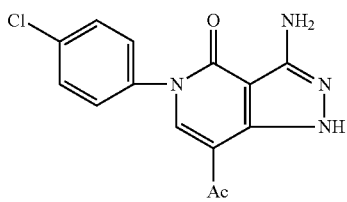

17)

DOCUMENT LIST

Non-Patent Document

[Non-Patent Document 1] Journal of the Chemical Society, Perkin Transactions 1: Organic and Bio-Organic Chemistry (1997), (21), 3285-3290.

[Non-Patent Document 2] Chemical & Pharmaceutical Bulletin (1984), 32(9), 3384-95 CODEN: CPBTAL; ISSN: 0009-2363.

[Non-Patent Document 3] Journal of the Chemical Society, Perkin Transactions 1: Organic and Bio-Organic Chemistry (1972-1999) (1978), (8), 857-62.

[Non-Patent Document 4] Phosphorus, Sulfur and Silicon and the Related Elements (2001), 170, 171-179.

SUMMARY OF THE INVENTION

Problems to be Solved by the Invention

An object of the present invention is to provide an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like, which has a superior Tyk2 inhibitory action.

Means of Solving the Problems

The present inventors have conducted intensive studies in an attempt to solve the above-mentioned problem and found that compound (I) represented by the following formula has a superior Tyk2 inhibitory action, which resulted in the completion of the present invention.

Accordingly, the present invention provides the following.

Accordingly, the present invention provides the following.

[1] A compound represented by the formula (I):

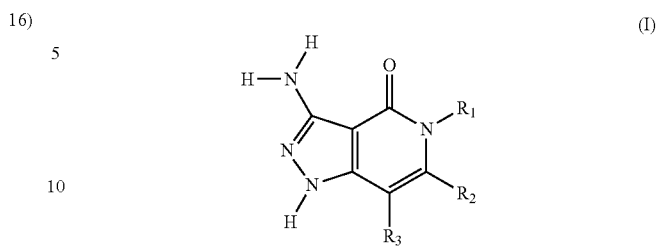

(I)

wherein
$R^1$ is an optionally substituted $C_{1-6}$ alkyl group or an optionally substituted cyclic group;
$R^2$ is a hydrogen atom or a cyano group; and
$R^3$ is a hydrogen atom, a halogen atom, a 5-membered aromatic ring group optionally having one substituent, or an optionally substituted 6- to 12-membered aromatic ring group, or a salt thereof.

[2] The compound or salt of the above-mentioned [1], wherein $R^2$ is a hydrogen atom.

[3] The compound or salt of the above-mentioned [1], wherein $R^1$ is
(1) a $C_{1-6}$ alkyl group optionally substituted by 1 to 3 substituents selected from (a) a halogen atom, and (b) a $C_{3-8}$ cycloalkyl,
(2) a $C_{3-10}$ cycloalkyl group optionally substituted by 1 to 3 substituents selected from (a) a halogen atom, and (b) a $C_{1-6}$ alkyl group,
(3) a $C_{6-14}$ aryl group optionally substituted by 1 to 3 substituents selected from (a) a halogen atom, (b) a $C_{1-6}$ alkyl group optionally substituted by 1 to 3 halogen atoms, (c) a cyano group, (d) an amino group optionally mono- or di-substituted by $C_{1-6}$ alkyl-carbonyl group(s), and (e) a $C_{1-6}$ alkoxy group,
(4) a 3- to 8-membered monocyclic non-aromatic heterocyclic group, or
(5) a 5- or 6-membered monocyclic aromatic heterocyclic group optionally substituted by 1 to 3 substituents selected from (a) a halogen atom, and (b) a cyano group;
$R^2$ is a hydrogen atom or a cyano group; and
$R^3$ is
(1) a hydrogen atom,
(2) a halogen atom,
(3) a $C_{6-12}$ aryl group optionally substituted by 1 to 3 halogen atoms,
(4) a 5-membered monocyclic aromatic heterocyclic group optionally substituted by one substituent selected from the following Substituent Group C,
(5) a 6-membered monocyclic aromatic heterocyclic group optionally substituted by 1 to 3 substituents selected from following Substituent Group C, or
(6) a 8- to 12-membered fused aromatic heterocyclic group optionally substituted by 1 to 3 substituents selected from following Substituent Group C

[Substituent Group C:
(a) a $C_{1-6}$ alkyl group optionally substituted by 1 to 3 substituents selected from (i) a hydroxy group, (ii) a $C_{1-6}$ alkoxy group, (iii) a $C_{1-5}$ alkylsulfonyl group, (iv) an amino group optionally mono- or di-substituted by substituent(s) selected from a $C_{1-6}$ alkyl-carbonyl group, a formyl group and a $C_{1-6}$ alkyl group, (v) a cyano group, (vi) a 3- to 8-membered monocyclic non-aromatic heterocyclic group optionally substituted by 1 to 3 $C_{1-6}$ alkyl groups, (vii) a 3- to 8-membered monocyclic non-aromatic heterocyclylcarbonyl group optionally substituted by 1 to 3 hydroxy groups, and (viii) a carbamoyl group optionally mono- or di-substituted by substituent(s) selected from a 3- to 8-membered monocyclic non-aromatic heterocyclic group and a $C_{1-6}$ alkyl group,
(b) a cyano group,
(c) an amino group optionally mono- or di-substituted by substituent(s) selected from (i) a formyl group, (ii) a $C_{1-6}$ alkyl group optionally substituted by 1 to 3 amino groups optionally mono- or di-substituted by $C_{1-6}$ alkyl group(s), and (iii) a $C_{1-6}$ alkyl-carbonyl group,
(d) a carbamoyl group optionally mono- or di-substituted by substituent(s) selected from (i) a $C_{1-6}$ alkyl group optionally substituted by 1 to 3 substituents selected from a hydroxy group and a $C_{1-6}$ alkoxy group, and (ii) a 3- to 8-membered monocyclic non-aromatic heterocyclic group,
(e) a $C_{1-6}$ alkoxy-carbonyl group,
(f) a $C_{1-6}$ alkoxy group optionally substituted by 1 to 3 substituents selected from (i) a $C_{1-6}$ alkoxy group, (ii) an amino group optionally mono- or di-substituted by substituent(s) selected from a $C_{1-6}$ alkyl group and a $C_{1-6}$ alkyl-carbonyl group, (iii) a carbamoyl group optionally mono- or di-substituted by $C_{1-6}$ alkyl group(s), (iv) a 3- to 8-membered monocyclic non-aromatic heterocyclic group optionally substituted by oxo group(s), (v) a hydroxy group, and (vi) a $C_{6-14}$ aryl group optionally substituted by 1 to 3 $C_{1-6}$ alkoxy groups,
(g) a 3- to 8-membered monocyclic non-aromatic heterocyclic group optionally substituted by 1 to 3 substituents selected from (i) a $C_{1-6}$ alkyl group optionally substituted by 1 to 3 hydroxy groups, (ii) a $C_{1-6}$ alkoxy group, (iii) a $C_{1-6}$ alkyl-carbonyl group, (iv) an oxo group, (v) a hydroxy group, and
(vi) a halogen atom,
(h) a 3- to 8-membered monocyclic non-aromatic heterocyclylcarbonyl group,
(i) a 3- to 8-membered monocyclic non-aromatic heterocyclyloxy group,
(j) a $C_{3-8}$ cycloalkyloxy group, and
(k) a hydroxy group].
[4] 3-Amino-5-(2,6-difluorophenyl)-7-(1-methyl-1H-pyrazol-3-yl)-1,5-dihydro-4H-pyrazolo[4,3-c]pyridin-4-one or a salt thereof.
[5] 2-(3-Amino-7-(1-methyl-1H-pyrazol-3-yl)-4-oxo-1,4-dihydro-5H-pyrazolo[4,3-c]pyridin-5-yl)-3-fluorobenzonitrile or a salt thereof.
[6] 3-Amino-5-(1-cyclopropylethyl)-7-(1-methyl-1H-pyrazol-3-yl)-1,5-dihydro-4H-pyrazolo[4,3-c]pyridin-4-one or a salt thereof.
[7] A medicament comprising the compound or salt of the above-mentioned [1].
[8] The medicament of the above-mentioned [7], which is a tyrosine kinase 2 inhibitor.
[9] The medicament of the above-mentioned [7], which is an agent for the prophylaxis or treatment of autoimmune diseases.
[10] The medicament of the above-mentioned [9], wherein the autoimmune diseases is psoriasis, rheumatoid arthritis, inflammatory bowel disease, Sjogren's syndrome, Behcet's disease, multiple sclerosis or systemic lupus erythematosus.
[11] The compound or salt of the above-mentioned [1] for use in the prophylaxis or treatment of autoimmune diseases.
[12] The compound or salt of the above-mentioned [11], wherein the autoimmune diseases is psoriasis, rheumatoid arthritis, inflammatory bowel disease, Sjogren's syndrome, Behcet's disease, multiple sclerosis or systemic lupus erythematosus.
[13] A method of inhibiting tyrosine kinase 2 in a mammal, which comprises administering an effective amount of the compound or salt of the above-mentioned [1] to the mammal.
[14] A method for the prophylaxis or treatment of autoimmune diseases, which comprises administering an effective amount of the compound or salt of the above-mentioned [1] to the mammal.
[15] The method of the above-mentioned [14], wherein the autoimmune diseases is psoriasis, rheumatoid arthritis, inflammatory bowel disease, Sjogren's syndrome, Behcet's disease, multiple sclerosis or systemic lupus erythematosus.
[16] Use of the compound or salt of the above-mentioned [1] for the production of an agent for the prophylaxis or treatment of autoimmune diseases.
[17] The use of the above-mentioned [16], wherein the autoimmune diseases is psoriasis, rheumatoid arthritis, inflammatory bowel disease, Sjogren's syndrome, Behcet's disease, multiple sclerosis or systemic lupus erythematosus.

Effect of the Invention

Compound (I) has a superior Tyk2 inhibitory action, which is useful as an agent for the prophylaxis or treatment of autoimmune diseases (e.g., psoriasis, rheumatoid arthritis, inflammatory bowel disease (e.g., Crohn's disease, ulcerative colitis etc.), Sjogren's syndrome, Behcet's disease, multiple sclerosis, systemic lupus erythematosus etc.) and the like.

DETAILED DESCRIPTION OF THE INVENTION

In the present specification, the "halogen atom" means a fluorine atom, a chlorine atom, a bromine atom or iodine atom.

In the present specification, the "$C_{1-6}$ alkyl (group)" means, for example, methyl, ethyl, propyl, isopropyl, butyl, isobutyl, sec-butyl, tert-butyl, pentyl, isopentyl, neo-pentyl, 1-ethylpropyl, 1-methylbutyl, hexyl, isohexyl, 1,1-dimethylbutyl, 2,2-dimethylbutyl, 3,3-dimethylbutyl, 2-ethylbutyl, 1-ethyl-2-methylpropyl, 1,2-dimethylpropyl or the like.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, neo-pentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "$C_{1-6}$ alkylsulfonyl (group)" means, for example, methylsulfonyl, ethylsulfonyl, propylsulfonyl, isopropylsulfonyl, butylsulfonyl, isobutylsulfonyl, tert-butylsulfonyl or the like.

In the present specification, the "$C_{3-8}$ cycloalkyl (group)" means, for example, cyclopropyl, cyclobutyl, cyclopentyl, cyclohexyl, cycloheptyl, cyclooctyl or the like.

In the present specification, the "$C_{3-10}$ cycloalkyl (group)" means, for example, cyclopropyl, cyclobutyl, cyclopentyl, cyclohexyl, cycloheptyl, cyclooctyl, cyclononyl, cyclodecyl or the like. Among them, a $C_{3-6}$ cycloalkyl, group is preferable.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "$C_{3-10}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl), cycloheptenyl (e.g., 2-cyclohepten-1-yl, 3-cyclohepten-1-yl), cyclooctenyl (e.g., 2-cycloocten-1-yl, 3-cycloocten-1-yl) or the like. Among them, a $C_{3-6}$ cycloalkenyl group is preferable.

In the present specification, the "$C_{4-10}$ cycloalkadienyl (group)" means, for example, 2,4-cyclopentadien-1-yl, 2,4-cyclohexadien-1-yl, 2,5-cyclohexadien-1-yl or the like. Among them, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

The above-mentioned $C_{3-10}$ cycloalkyl group, $C_{3-10}$ cycloalkenyl group and $C_{4-10}$ cycloalkadienyl group each optionally form a spiro ring group with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{6-14}$ aryl (group)" means, for example, phenyl, 1-naphthyl, 2-naphthyl or the like. Among them, a $C_{6-10}$ aryl (group) is preferable.

In the present specification, the "$C_{6-12}$ aryl (group)" means, for example, phenyl, 1-naphthyl, 2-naphthyl or the like. Among them, a $C_{6-10}$ aryl (group) is preferable.

In the present specification, the "$C_{6-14}$ aryloxy (group)" means, for example, phenoxy, 1-naphthyloxy, 2-naphthyloxy or the like.

In the present specification, the "$C_{7-14}$ aralkyl (group)" means, for example, benzyl, phenethyl or the like.

In the present specification, the "$C_{7-14}$ aralkyloxy (group)" means, for example, benzyloxy, phenethyloxy or the like.

In the present specification, the "heterocyclic group" means an aromatic heterocyclic group or a non-aromatic heterocyclic group.

In the present specification, the "aromatic heterocyclic group" means a monocyclic aromatic heterocyclic group and a fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized), for example, furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "fused aromatic heterocyclic group" include an 8- to 21-membered (preferably 8- to 12-membered) fused aromatic heterocyclic group, specifically, a group derived from a fused ring wherein a ring corresponding to the above-mentioned 5- to 7-membered monocyclic aromatic heterocyclic group is fused with a $C_{6-14}$ aromatic hydrocarbon; and a group derived from a fused ring wherein rings corresponding to the above-mentioned 5- to 7-membered monocyclic aromatic heterocyclic groups are fused, for example, quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl, 2H-imidazo[1,2-a]pyridin-2-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group and a fused non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized), for example, azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), 1,1-dioxidothiomorpholinyl (e.g., 1,1-dioxidothiomorpholin-4-yl), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidetetrahydrothiopyranyl (e.g., 1-oxidetetrahydrothiopyran-4-yl), 1,1-dioxidotetrahydrothiopyranyl (e.g., 1,1-dioxidotetrahydrothiopyran-4-yl, 1,1-dioxidotetrahydrothiopyran-3-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl) and the like.

In the present specification, examples of the "fused non-aromatic heterocyclic group" include an 8- to 22-membered fused non-aromatic heterocyclic group, specifically, a group derived from a fused ring wherein a ring corresponding to the above-mentioned 3- to 8-membered monocyclic non-aromatic heterocyclic group is fused with a $C_{6-14}$ aromatic hydrocarbon; a group derived from a fused ring wherein rings corresponding to the above-mentioned 3- to 8-membered monocyclic non-aromatic heterocyclic groups are fused; a group derived from a fused ring wherein a ring corresponding to the above-mentioned 3- to 8-membered monocyclic non-aromatic heterocyclic group is fused with a ring corresponding to the above-mentioned 5- to 7-membered monocyclic aromatic heterocyclic group; and a group wherein the above-mentioned group is partially saturated, for example, dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

In the present specification, examples of the "$C_{6-14}$ aromatic hydrocarbon" include benzene and naphthalene.

Each symbol of the formula (I) is explained below.

In the formula (I), $R^1$ is an optionally substituted $C_{1-6}$ alkyl group or an optionally substituted cyclic group.

The "$C_{1-6}$ alkyl group" of the "optionally substituted $C_{1-6}$ alkyl group" for $R^1$ optionally has 1 to 5 (preferably 1 to 3) substituents at substitutable position(s). Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
   (a) a halogen atom,
   (b) a cyano group,
   (c) a $C_{1-6}$ alkyl group optionally substituted by 1 to 3 halogen atoms, and
   (d) a $C_{1-6}$ alkoxy group optionally substituted by 1 to 3 halogen atoms;
(6) a $C_{6-14}$ aryl group optionally substituted by 1 to 3 substituents selected from
   (a) a halogen atom,
   (b) a cyano group,
   (c) a $C_{1-6}$ alkyl group optionally substituted by 1 to 3 halogen atoms, and
   (d) a $C_{1-6}$ alkoxy group optionally substituted by 1 to 3 halogen atoms;
(7) a $C_{1-5}$ alkoxy group optionally substituted by 1 to 3 substituents selected from
   (a) a halogen atom,
   (b) a cyano group,
   (c) a $C_{3-8}$ cycloalkyl group optionally having 1 to 3 halogen atoms,
   (d) a $C_{3-8}$ cycloalkenyl group optionally having 1 to 3 halogen atoms, (e) a $C_{6-14}$ aryl group optionally substituted by 1 to 3 substituents selected from
(i) a halogen atom, and
(ii) a $C_{1-6}$ alkoxy group,
(f) a 5- or 6-membered monocyclic aromatic heterocyclic group;
(g) a $C_{1-6}$ alkoxy group;
(h) an amino group optionally mono- or di-substituted by substituent(s) selected from
(i) a $C_{1-6}$ alkyl group, and
(ii) a $C_{1-6}$ alkyl-carbonyl group,
(i) a carbamoyl group optionally mono- or di-substituted by $C_{1-6}$ alkyl group(s),
(j) a 3- to 8-membered monocyclic non-aromatic heterocyclic group optionally substituted by oxo group(s), and
(k) a hydroxy group;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
(a) a $C_{1-6}$ alkyl group optionally substituted by 1 to 3 substituents selected from
(i) a hydroxy group, and
(ii) a $C_{1-6}$ alkoxy group,
(b) a $C_{3-8}$ cycloalkyl group,
(c) a $C_{6-14}$ aryl group,
(d) a $C_{1-6}$ alkoxy group,
(e) a 5- or 6-membered monocyclic aromatic heterocyclic group,
(f) an 8- to 12-membered fused aromatic heterocyclic group,
(g) a 3- to 8-membered monocyclic non-aromatic heterocyclic group, and
(h) an 8- to 12-membered fused non-aromatic heterocyclic group;
(15) a sulfamoyl group optionally mono- or di-substituted by substituent(s) selected from
(a) a $C_{1-6}$ alkyl group,
(b) a $C_{3-8}$ cycloalkyl group,
(c) a $C_{6-14}$ aryl group,
(d) a $C_{1-6}$ alkoxy group,
(e) a 5- or 6-membered monocyclic aromatic heterocyclic group,
(f) an 8- to 12-membered fused aromatic heterocyclic group,
(g) a 3- to 8-membered monocyclic non-aromatic heterocyclic group, and
(h) an 8- to 12-membered fused non-aromatic heterocyclic group;
(16) formyl;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) an 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl, morpholinylcarbonyl);
(29) an 8- to 12-membered fused non-aromatic heterocyclylcarbonyl group (e.g., dihydrobenzofuranyl);
(30) an amino group optionally mono- or di-substituted by substituent(s) selected from
(a) a $C_{1-6}$ alkyl group optionally substituted by 1 to 3 substituents selected from
(i) a halogen atom, and
(ii) an amino group optionally mono- or di-substituted by $C_{1-6}$ alkyl group(s),
(b) a $C_{1-6}$ alkyl-carbonyl group optionally having 1 to 3 halogen atoms,
(c) a $C_{3-8}$ cycloalkyl-carbonyl group,
(d) a $C_{6-14}$ aryl-carbonyl group optionally having 1 to 3 halogen atoms,
(e) a 5- or 6-membered monocyclic aromatic heterocyclylcarbonyl group,
(f) an 8- to 12-membered fused aromatic heterocyclylcarbonyl group,
(g) a 3- to 8-membered monocyclic non-aromatic heterocyclylcarbonyl group, and
(h) an 8- to 12-membered fused non-aromatic heterocyclylcarbonyl group, and
(i) a formyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);

(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) an 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) an 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl, morpholinyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(62) an 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl, morpholinyl, 1,1-dioxidothiomorpholinyl, tetrahydropyranyl) optionally substituted by 1 to 3 substituents selected from
  (a) a halogen atom,
  (b) a $C_{1-6}$ alkyl group optionally substituted by 1 to 3 halogen atoms or hydroxy groups,
  (c) a $C_{1-6}$ alkoxy group optionally substituted by 1 to 3 halogen atoms,
  (d) an oxo group,
  (e) a $C_{1-6}$ alkoxy group,
  (f) a $C_{1-6}$ alkyl-carbonyl group, and
  (g) a hydroxy group;
(64) an 8- to 12-membered fused non-aromatic heterocyclic group (e.g., dihydrobenzofuranyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) an 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy, tetrahydropyranyloxy);
(68) an 8- to 12-membered fused non-aromatic heterocyclyloxy group (e.g., dihydrobenzofuranyloxy);
(69) a carboxy group;
(70) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, tert-butoxycarbonyl);
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-6}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethylokycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);

(78) a $C_{7-14}$ aralkyloxy-carbonyl group (e.g., benzyloxycarbonyl, phenethyloxycarbonyl);
(79) a mono-$C_{1-6}$ alkylthio-carbamoyl group (e.g., methylthiocarbamoyl, ethylthiocarbamoyl, propylthiocarbamoyl);
(80) a di-$C_{1-6}$ alkylthio-carbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

Examples of the "cyclic group" of the "optionally substituted cyclic group" for $R^1$ include a $C_{3-10}$ cycloalkyl group, a $C_{3-10}$ cycloalkenyl group, a $C_{4-10}$ cycloalkadienyl group, a $C_{6-14}$ aryl group and a heterocyclic group.

The "cyclic group" of the "optionally substituted cyclic group" for $R^1$ optionally has 1 to 5 (preferably 1 to 3) substituents at substitutable position(s). Examples of the substituent include substituents selected from the following Substituent Group B. When the number of the substituents is plural, the respective substituents may be the same or different.

Substituent Group B:
(1) the above-mentioned Substituent Group A;
(2) a $C_{1-6}$ alkyl group optionally substituted by 1 to 3 substituents selected from
  (a) a halogen atom,
  (b) a cyano group,
  (c) a hydroxy group,
  (d) a $C_{3-10}$ cycloalkyl group optionally substituted by 1 to 3 substituents selected from
    (i) a halogen atom,
    (ii) a cyano group, and
    (iii) a $C_{1-6}$ alkyl group optionally substituted by 1 to 3 halogen atoms;
  (e) a $C_{6-14}$ aryl group optionally substituted by 1 to 3 substituents selected from
    (i) a halogen atom,
    (ii) a cyano group, and
    (iii) a $C_{1-6}$ alkyl group optionally substituted by 1 to 3 halogen atoms,
  (f) a $C_{1-6}$ alkoxy group optionally substituted by 1 to 3 halogen atoms,
  (g) an amino group optionally mono- or di-substituted by substituent(s) selected from
    (i) a $C_{1-6}$ alkyl-carbonyl group,
    (ii) a formyl group, and
    (iii) a $C_{1-6}$ alkyl group,
  (h) a 5- or 6-membered monocyclic aromatic heterocyclic group,
  (i) a 8- to 12-membered fused aromatic heterocyclic group,
  (j) a 3- to 8-membered monocyclic non-aromatic heterocyclic group,
  (k) a 8- to 12-membered fused non-aromatic heterocyclic group,
  (l) a carboxy group,
  (m) a $C_{1-6}$ alkoxy-carbonyl group optionally substituted by 1 to 3 halogen atoms,
  (n) a $C_{1-6}$ alkylsulfonyl group (e.g., methylsulfonyl, ethylsulfonyl, propylsulfonyl, isopropylsulfonyl, butylsulfonyl, isobutylsulfonyl, tert-butylsulfonyl),
  (o) a 3- to 8-membered monocyclic non-aromatic heterocyclylcarbonyl group optionally substituted by 1 to 3 hydroxy groups, and
  (p) a carbamoyl group optionally mono- or di-substituted by substituent(s) selected from
    (i) a 3- to 8-membered monocyclic non-aromatic heterocyclic group, and
    (ii) a $C_{1-6}$ alkyl group;
(3) a $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono- or di-substituted by $C_{1-6}$ alkyl group(s),
  (e) a carboxy group, and
  (f) a $C_{1-6}$ alkoxy-carbonyl group;
(4) a $C_{7-14}$ aralkyl group optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group optionally substituted by 1 to 3 halogen atoms; and
(5) an oxo group.

$R^1$ is preferably an optionally substituted $C_{1-6}$ alkyl group, an optionally substituted $C_{3-10}$ cycloalkyl group or an optionally substituted $C_{6-14}$ aryl group.

$R^1$ is more preferably
(1) a $C_{1-6}$ alkyl group (e.g., propyl, isopropyl, 1,2-dimethylpropyl) optionally substituted by 1 to 3 halogen atoms (e.g., a fluorine atom),
(2) a $C_{3-10}$ cycloalkyl group (e.g., cyclohexyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom), and
  (c) a cyano group.

In another embodiment, $R^1$ is preferably an optionally substituted $C_{1-6}$ alkyl group, an optionally substituted $C_{3-10}$ cycloalkyl group, an optionally substituted $C_{6-14}$ aryl group, an optionally substituted 3- to 8-membered monocyclic non-aromatic heterocyclic group or an optionally substituted 5- or 6-membered monocyclic aromatic heterocyclic group.

$R^1$ is more preferably
(1) a $C_{1-5}$ alkyl group (e.g., ethyl, propyl, 1,2-dimethylpropyl, isobutyl, sec-butyl, 1-methylbutyl, 1-ethyl-2-methylpropyl) optionally substituted by 1 to 3 substituents selected from
  (a) a halogen atom (e.g., a fluorine atom), and
  (b) a $C_{3-8}$ cycloalkyl group (e.g., cyclopropyl, cyclobutyl),
(2) a $C_{3-10}$ cycloalkyl group (e.g., cyclopentyl, cyclohexyl) optionally substituted by 1 to 3 substituents selected from
  (a) a halogen atom (e.g., a fluorine atom), and
  (b) a $C_{1-6}$ alkyl group (e.g., methyl),
(3) a $C_{6-14}$ aryl group (e.g., phenyl) optionally substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a cyano group,
  (d) an amino group optionally mono- or di-substituted by $C_{1-6}$ alkyl-carbonyl group(s) (e.g., acetyl), and
  (e) a $C_{1-6}$ alkoxy group (e.g., methoxy),
(4) a 3- to 8-membered monocyclic non-aromatic heterocyclic group (e.g., 1,1-dioxidotetrahydrothiopyranyl), or (5) a 5- or 6-membered monocyclic aromatic heterocyclic group (e.g., pyridyl) optionally substituted by 1 to 3 substituents selected from
  (a) a halogen atom (e.g., a chlorine atom), and
  (b) a cyano group.

In the formula (I), $R^2$ is a hydrogen atom or a cyano group. $R^2$ is preferably a hydrogen atom.

In the formula (I), $R^3$ is a hydrogen atom, a halogen atom or an optionally substituted aromatic ring group.

Examples of the "aromatic ring group" of the "optionally substituted aromatic ring group" for $R^3$ include a $C_{6-14}$ aryl group and an aromatic heterocyclic group.

The "aromatic ring group" of the "optionally substituted aromatic ring group" for $R^3$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

$R^3$ is preferably a hydrogen atom, a halogen atom, an optionally substituted $C_{6-14}$ aryl group (e.g., phenyl) or an optionally substituted 5- to 7-membered (preferably 5- or 6-membered) monocyclic aromatic heterocyclic group (e.g., pyrazolyl, oxazolyl, thiazolyl, isothiazolyl, thienyl, furyl, pyridyl, pyrimidinyl, pyrazinyl).

$R^3$ is more preferably
(1) a hydrogen atom,
(2) a halogen atom (e.g., a bromine atom),
(3) a $C_{6-14}$ aryl group (e.g., phenyl) optionally substituted by 1 to 3 halogen atoms (e.g., a fluorine atom), or
(4) a 5- to 7-membered (preferably 5- or 6-membered) monocyclic aromatic heterocyclic group (e.g., pyrazolyl, oxazolyl, thiazolyl, isothiazolyl, thienyl, furyl, pyridyl, pyrimidinyl, pyrazinyl) optionally substituted by 1 to 3 substituents selected from
  (a) a $C_{1-6}$ alkyl group (e.g., methyl, ethyl) optionally substituted by 1 to 3 substituents selected from
    (i) a hydroxy group,
    (ii) a $C_{1-6}$ alkoxy group (e.g., methoxy),
    (iii) a $C_{1-6}$ alkylsulfonyl group (e.g., methylsulfonyl),
    (iv) an amino group optionally mono- or di-substituted by substituent(s) selected from
      (A) a $C_{1-6}$ alkyl-carbonyl group (e.g., acetyl), and
      (B) a $C_{1-6}$ alkyl group (e.g., methyl),
    (v) a cyano group, and
    (vi) a 3- to 8-membered monocyclic non-aromatic heterocyclic group (e.g., pyrrolidinyl),
  (b) a cyano group,
  (c) an amino group,
  (d) an carbamoyl group,
  (e) a $C_{1-6}$ alkoxy-carbonyl group (e.g., ethoxycarbonyl), and
  (f) a 3- to 8-membered monocyclic non-aromatic heterocyclic group (e.g., piperazinyl, piperidyl) optionally substituted by 1 to 3 $C_{1-6}$ alkyl groups (e.g., ethyl) optionally substituted by 1 to 3 hydroxy groups.

In another embodiment, In the formula (I), $R^3$ is a hydrogen atom, a halogen atom, a 5-membered aromatic ring group optionally having one substituent, or an optionally substituted 6- to 12-membered aromatic ring group.

Examples of the "5-membered aromatic ring group" of the "5-membered aromatic ring group optionally having one substituent" for $R^3$ include a 5-membered monocyclic aromatic heterocyclic group (a 5-membered group from among the above-mentioned monocyclic aromatic heterocyclic group). Examples of the substituent of the "5-membered aromatic ring group optionally having one substituent" for $R^3$ include substituents selected from the above-mentioned Substituent Group B.

Examples of the "6- to 12-membered aromatic ring group" of the "optionally substituted 6- to 12-membered aromatic ring group" for $R^3$ include a $C_{6-12}$ aryl group and a 6- to 12-membered aromatic heterocyclic group. Examples of the 6- to 12-membered aromatic heterocyclic group include a 6- or 7-membered (preferably 6-membered) monocyclic aromatic heterocyclic group (a 6- or 7-membered (preferably 6-membered) group from among the above-mentioned monocyclic aromatic heterocyclic group) and a 8- to 12-membered fused aromatic heterocyclic group.

The "6- to 12-membered aromatic ring group" of the "optionally substituted 6- to 12-membered aromatic ring group" for $R^3$ has 1 to 5 (preferably 1 to 3) substituents at substitutable position(s). Examples of the substituent include substituents selected from the above-mentioned Substituent Group B. When the number of the substituents is plural, the respective substituents may be the same or different.

The tautomeric form of the "5-membered aromatic ring group optionally having one substituent" or the "optionally substituted 6- to 12-membered aromatic ring group" for $R^3$ is also encompassed therein.

For example, as shown in the following formula, the "optionally substituted non-aromatic ring group containing NHCO-" (B) is encompassed in the "optionally substituted aromatic ring group containing —N=C(OH)—" (A). In the present specification, (B) is described as (A) for convenience sake. The compound is described by mainly spectroscopically-identified structure.

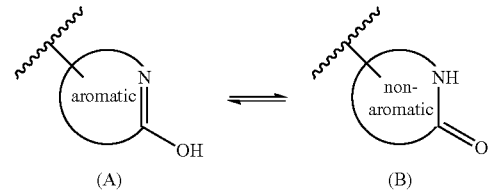

(A)       (B)

Specifically, when substituent is referred to in the present specification, "1-isopropyl-6-oxo-1,6-dihydropyrimidin-4-yl" (e.g., $R^3$ in Example 55) is encompassed in "6-hydroxy-1-isopropylpyrimidin-4-yl", "6-oxo-1,6-dihydropyrimidin-4-yl" (e.g., $R^3$ in Example 152) is encompassed in "6-hydroxypyrimidin-4-yl", "3-oxo-3,4-dihydropyrazin-2-yl" (e.g., $R^3$ in Example 153) is encompassed in "3-hydroxy-pyrazin-2-yl", "5-oxo-4,5-dihydropyrazin-2-yl" (e.g., $R^3$ in Example 154) is encompassed in "5-hydroxypyrazin-2-yl", and "6-oxo-1-(tetrahydro-2H-pyran-4-yl)-1,6-dihydropyrimidin-4-yl" (e.g., $R^3$ in Example 155) is encompassed in "6-hydroxy-1-(tetrahydro-2H-pyran-4-yl)-pyrimidin-4-yl".

$R^3$ is preferably a hydrogen atom, a halogen atom (e.g., a bromine atom), an optionally substituted $C_{6-12}$ aryl group (e.g., phenyl), a 5-membered monocyclic aromatic heterocyclic group (e.g., pyrazolyl, oxazolyl, thiazolyl, isothiazolyl, thienyl, furyl, imidazolyl) optionally having one substituent, an optionally substituted 6- or 7-membered (preferably 6-membered) monocyclic aromatic heterocyclic group (e.g., pyridyl, pyrimidinyl, pyrazinyl, pyridazinyl) or an optionally substituted 8- to 12-membered fused aromatic heterocyclic group (e.g., imidazopyridyl).

$R^3$ is more preferably
(1) a hydrogen atom,
(2) a halogen atom (e.g., a bromine atom), (3) a $C_{6-12}$ aryl group (e.g., phenyl) optionally substituted by 1 to 3 halogen atoms (e.g., a fluorine atom), (4) a 5-membered monocyclic aromatic heterocyclic group (e.g., pyrazolyl, oxazolyl, thiazolyl, isothiazolyl, thienyl, furyl, imidazolyl) optionally substituted by one substituent selected from the following Substituent Group C, (5) a 6-membered monocyclic aromatic heterocyclic group (e.g., pyridyl, pyrimidinyl, pyrazinyl, pyridazinyl) optionally substituted by 1 to 3 substituents selected from following Substituent Group C, or (6) a 8- to 12-membered fused aromatic heterocyclic group (e.g., imidazopyridyl) optionally substituted by 1 to 3 substituents selected from following Substituent Group C.

Substituent Group C:

(a) a $C_{1-6}$ alkyl group (e.g., methyl, ethyl, isopropyl) optionally substituted by 1 to 3 substituents selected from
  (i) a hydroxy group,
  (ii) a $C_{1-6}$ alkoxy group (e.g., methoxy),
  (iii) a $C_{1-6}$ alkylsulfonyl group (e.g., methylsulfonyl),
  (iv) an amino group optionally mono- or di-substituted by substituent(s) selected from
    (A) a $C_{1-6}$ alkyl-carbonyl group (e.g., acetyl),
    (B) a formyl group, and
    (C) a $C_{1-6}$ alkyl group (e.g., methyl),
  (v) a cyano group,
  (vi) a 3- to 8-membered monocyclic non-aromatic heterocyclic group (e.g., pyrrolidinyl, morpholinyl, piperazinyl) optionally substituted by 1 to 3 $C_{1-6}$ alkyl groups (e.g., methyl)
  (vii) a 3- to 8-membered monocyclic non-aromatic heterocyclylcarbonyl group (e.g., morpholinylcarbonyl, piperidylcarbonyl) optionally substituted by 1 to 3 hydroxy groups, and
  (viii) a carbamoyl group optionally mono- or di-substituted by substituent(s) selected from
    (A) a 3- to 8-membered monocyclic non-aromatic heterocyclic group (e.g., oxetanyl), and
    (B) a $C_{1-6}$ alkyl group (e.g., methyl), (b) a cyano group, (c) an amino group optionally mono- or di-substituted by substituent(s) selected from
  (i) a formyl group,
  (ii) a $C_{1-6}$ alkyl group (e.g., ethyl) optionally substituted by 1 to 3 amino groups optionally mono- or di-substituted by $C_{1-6}$ alkyl group(s) (e.g., methyl), and
  (iii) a $C_{1-6}$ alkyl-carbonyl group (e.g., acetyl), (d) a carbamoyl group optionally mono- or di-substituted by substituent(s) selected from
  (i) a $C_{1-6}$ alkyl group (e.g., methyl, ethyl) optionally substituted by 1 to 3 substituents selected from
    (A) a hydroxy group, and
    (B) a $C_{1-6}$ alkoxy group (e.g., methoxy), and
  (ii) a 3- to 8-membered monocyclic non-aromatic heterocyclic group (e.g., tetrahydropyranyl), (e) a $C_{1-6}$ alkoxy-carbonyl group (e.g., ethoxycarbonyl), (f) a $C_{1-6}$ alkoxy group (e.g., methoxy, ethoxy, isopropoxy, isobutoxy, neo-pentyloxy) optionally substituted by 1 to 3 substituents selected from
  (i) a $C_{1-6}$ alkoxy group (e.g., methoxy),
  (ii) an amino group optionally mono- or di-substituted by substituent(s) selected from
    (A) a $C_{1-6}$ alkyl group (e.g., methyl), and
    (B) a $C_{1-6}$ alkyl-carbonyl group (e.g., acetyl),
  (iii) a carbamoyl group optionally mono- or di-substituted by $C_{1-5}$ alkyl group(s) (e.g., methyl),
  (iv) a 3- to 8-membered monocyclic non-aromatic heterocyclic group (e.g., pyrrolidinyl) optionally substituted by oxo group(s),
  (v) a hydroxy group, and
  (vi) a $C_{6-14}$ aryl group (e.g., phenyl) optionally substituted by 1 to 3 $C_{1-6}$ alkoxy groups (e.g., methoxy), (g) a 3- to 8-membered monocyclic non-aromatic heterocyclic group (e.g., azetidinyl, piperazinyl, piperidyl, morpholinyl, tetrahydropyranyl, 1,1-dioxidothiomorpholinyl) optionally substituted by 1 to 3 substituents selected from
  (i) a $C_{1-6}$ alkyl group (e.g., methyl, ethyl) optionally substituted by 1 to 3 hydroxy groups,
  (ii) a $C_{1-6}$ alkoxy group (e.g., methoxy),
  (iii) a $C_{1-6}$ alkyl-carbonyl group (e.g., acetyl),
  (iv) an oxo group,
  (v) a hydroxy group, and
  (vi) a halogen atom (e.g., a fluorine atom), (h) a 3- to 8-membered monocyclic non-aromatic heterocyclylcarbonyl group (e.g., pyrrolidinylcarbonyl, morpholinylcarbonyl), (i) a 3- to 8-membered monocyclic non-aromatic heterocyclyloxy group (e.g., tetrahydropyranyloxy), (j) a $C_{3-8}$ cycloalkyloxy group (e.g., cyclopentyloxy), and (k) a hydroxy group.

$R^3$ is further more preferably (1) a hydrogen atom, (2) a halogen atom (e.g., a bromine atom), (3) a $C_{6-12}$ aryl group (e.g., phenyl) optionally substituted by 1 to 3 halogen atoms (e.g., a fluorine atom), (4) a 5-membered monocyclic aromatic heterocyclic group (e.g., pyrazolyl, oxazolyl, thiazolyl, isothiazolyl, thienyl, furyl, imidazolyl) optionally substituted by one substituent selected from
  (a) a $C_{1-6}$ alkyl group (e.g., methyl, ethyl) optionally substituted by 1 to 3 substituents selected from
    (i) a hydroxy group,
    (ii) a $C_{1-6}$ alkoxy group (e.g., methoxy),
    (iii) a $C_{1-6}$ alkylsulfonyl group (e.g., methylsulfonyl),
    (iv) an amino group optionally mono- or di-substituted by substituent(s) selected from
      (A) a $C_{1-6}$ alkyl-carbonyl group (e.g., acetyl), and
      (B) a $C_{1-6}$ alkyl group (e.g., methyl),
    (v) a cyano group, and
    (vi) a 3- to 8-membered monocyclic non-aromatic heterocyclic group (e.g., pyrrolidinyl),
  (b) a carbamoyl group optionally mono- or di-substituted by $C_{1-6}$ alkyl group(s) (e.g., methyl, ethyl) optionally substituted by 1 to 3 $C_{1-6}$ alkoxy groups (e.g., methoxy),
  (c) a $C_{1-6}$ alkoxy-carbonyl group (e.g., ethoxycarbonyl), and
  (d) a 3- to 8-membered monocyclic non-aromatic heterocyclylcarbonyl group (e.g., morpholinylcarbonyl), (5) a 6-membered monocyclic aromatic heterocyclic group (e.g., pyridyl, pyrimidinyl, pyrazinyl, pyridazinyl) optionally substituted by 1 to 3 substituents selected from
  (a) a $C_{1-6}$ alkyl group (e.g., methyl, ethyl, isopropyl) optionally substituted by 1 to 3 substituents selected from
    (i) a hydroxy group,
    (ii) an amino group optionally mono- or di-substituted by substituent(s) selected from
      (A) a $C_{1-6}$ alkyl-carbonyl group (e.g., acetyl),
      (B) a formyl group, and
      (C) a $C_{1-6}$ alkyl group (e.g., methyl),
    (iii) a cyano group, (iv) a 3- to 8-membered monocyclic non-aromatic heterocyclic group (e.g., pyrrolidinyl, morpholinyl, piperazinyl) optionally substituted by 1 to 3 $C_{1-6}$ alkyl groups (e.g., methyl),
(v) a 3- to 8-membered monocyclic non-aromatic heterocyclylcarbonyl group (e.g., morpholinylcarbonyl, piperidylcarbonyl) optionally substituted by 1 to 3 hydroxy groups, and
(vi) a carbamoyl group optionally mono- or di-substituted by substituent(s) selected from
(A) a 3- to 8-membered monocyclic non-aromatic heterocyclic group (e.g., oxetanyl), and
(B) a $C_{1-6}$ alkyl group (e.g., methyl),
(b) a cyano group,
(c) an amino group optionally mono- or di-substituted by substituent(s) selected from
(i) a formyl group,
(ii) a $C_{1-6}$ alkyl group (e.g., ethyl) optionally substituted by 1 to 3 amino groups optionally mono- or di-substituted by $C_{1-6}$ alkyl group(s) (e.g., methyl), and
(iii) a $C_{1-6}$ alkyl-carbonyl group (e.g., acetyl),
(d) a carbamoyl group optionally mono- or di-substituted by substituent(s) selected from
(i) a $C_{1-6}$ alkyl group (e.g., methyl, ethyl) optionally substituted by 1 to 3 hydroxy groups, and
(ii) a 3- to 8-membered monocyclic non-aromatic heterocyclic group (e.g., tetrahydropyranyl),
(e) a $C_{1-6}$ alkoxy group (e.g., methoxy, ethoxy, isopropoxy, isobutoxy, neo-pentyloxy) optionally substituted by 1 to 3 substituents selected from
(i) a $C_{1-6}$ alkoxy group (e.g., methoxy),
(ii) an amino group optionally mono- or di-substituted by substituent(s) selected from
(A) a $C_{1-6}$ alkyl group (e.g., methyl), and
(B) a $C_{1-6}$ alkyl-carbonyl group (e.g., acetyl),
(iii) a carbamoyl group optionally mono- or di-substituted by $C_{1-6}$ alkyl group(s) (e.g., methyl),
(iv) a 3- to 8-membered monocyclic non-aromatic heterocyclic group (e.g., pyrrolidinyl) optionally substituted by oxo group(s),
(v) a hydroxy group, and
(vi) a $C_{6-14}$ aryl group (e.g., phenyl) optionally substituted by 1 to 3 $C_{1-6}$ alkoxy groups (e.g., methoxy),
(f) a 3- to 8-membered monocyclic non-aromatic heterocyclic group (e.g., azetidinyl, piperazinyl, piperidyl, morpholinyl, tetrahydropyranyl, 1,1-dioxidothiomorpholinyl) optionally substituted by 1 to 3 substituents selected from
(i) a $C_{1-6}$ alkyl group (e.g., methyl, ethyl) optionally substituted by 1 to 3 hydroxy groups,
(ii) a $C_{1-6}$ alkoxy group (e.g., methoxy),
(iii) a $C_{1-6}$ alkyl-carbonyl group (e.g., acetyl),
(iv) an oxo group,
(v) a hydroxy group, and
(vi) a halogen atom (e.g., a fluorine atom),
(g) a 3- to 8-membered monocyclic non-aromatic heterocyclylcarbonyl group (e.g., pyrrolidinylcarbonyl, morpholinylcarbonyl),
(h) a 3- to 8-membered monocyclic non-aromatic heterocyclyloxy group (e.g., tetrahydropyranyloxy),
(i) a $C_{3-8}$ cycloalkyloxy group (e.g., cyclopentyloxy), and
(j) a hydroxy group, or
(6) a 8- to 12-membered fused aromatic heterocyclic group (e.g., imidazopyridyl).
$R^3$ is still more preferably
(1) a halogen atom (e.g., a bromine atom),
(2) a $C_{6-12}$ aryl group (e.g., phenyl) optionally substituted by 1 to 3 halogen atoms (e.g., a fluorine atom),
(3) a 5-membered monocyclic aromatic heterocyclic group (e.g., pyrazolyl, oxazolyl, thiazolyl, isothiazolyl, thienyl, furyl, imidazolyl) optionally substituted by one substituent selected from
(a) a $C_{1-6}$ alkyl group (e.g., methyl, ethyl) optionally substituted by 1 to 3 substituents selected from
(i) a hydroxy group,
(ii) a $C_{1-6}$ alkoxy group (e.g., methoxy),
(iii) a $C_{1-6}$ alkylsulfonyl group (e.g., methylsulfonyl),
(iv) an amino group optionally mono- or di-substituted by substituent(s) selected from
(A) a $C_{1-6}$ alkyl-carbonyl group (e.g., acetyl), and
(B) a $C_{1-6}$ alkyl group (e.g., methyl),
(v) a cyano group, and
(vi) a 3- to 8-membered monocyclic non-aromatic heterocyclic group (e.g., pyrrolidinyl),
(b) a carbamoyl group optionally mono- or di-substituted by $C_{1-6}$ alkyl group(s) (e.g., methyl, ethyl) optionally substituted by 1 to 3 $C_{1-6}$ alkoxy groups (e.g., methoxy),
(c) a $C_{1-6}$ alkoxy-carbonyl group (e.g., ethoxycarbonyl), and
(d) a 3- to 8-membered monocyclic non-aromatic heterocyclylcarbonyl group (e.g., morpholinylcarbonyl),
(4) a 6-membered monocyclic aromatic heterocyclic group (e.g., pyridyl, pyrimidinyl, pyrazinyl, pyridazinyl) optionally substituted by 1 to 3 substituents selected from
(a) a $C_{1-6}$ alkyl group (e.g., methyl, ethyl, isopropyl) optionally substituted by 1 to 3 substituents selected from
(i) a hydroxy group,
(ii) an amino group optionally mono- or di-substituted by substituent(s) selected from
(A) a $C_{1-6}$ alkyl-carbonyl group (e.g., acetyl),
(B) a formyl group, and
(C) a $C_{1-6}$ alkyl group (e.g., methyl),
(iii) a cyano group,
(iv) a 3- to 8-membered monocyclic non-aromatic heterocyclic group (e.g., pyrrolidinyl, morpholinyl, piperazinyl) optionally substituted by 1 to 3 $C_{1-6}$ alkyl groups (e.g., methyl),
(v) a 3- to 8-membered monocyclic non-aromatic heterocyclylcarbonyl group (e.g., morpholinylcarbonyl, piperidylcarbonyl) optionally substituted by 1 to 3 hydroxy groups, and
(vi) a carbamoyl group optionally mono- or di-substituted by substituent(s) selected from
(A) a 3- to 8-membered monocyclic non-aromatic heterocyclic group (e.g., oxetanyl), and
(B) a $C_{1-6}$ alkyl group (e.g., methyl),
(b) a cyano group,
(c) an amino group optionally mono- or di-substituted by substituent(s) selected from
(i) a formyl group,
(ii) a $C_{1-6}$ alkyl group (e.g., ethyl) optionally substituted by 1 to 3 amino groups optionally mono- or di-substituted by $C_{1-6}$ alkyl group(s) (e.g., methyl), and
(iii) a $C_{1-6}$ alkyl-carbonyl group (e.g., acetyl),
(d) a carbamoyl group optionally mono- or di-substituted by substituent(s) selected from
(i) a $C_{1-6}$ alkyl group (e.g., methyl, ethyl) optionally substituted by 1 to 3 hydroxy groups, and
(ii) a 3- to 8-membered monocyclic non-aromatic heterocyclic group (e.g., tetrahydropyranyl),
(e) a $C_{1-6}$ alkoxy group (e.g., methoxy, ethoxy, isopropoxy, isobutoxy, neo-pentyloxy) optionally substituted by 1 to 3 substituents selected from
(i) a $C_{1-6}$ alkoxy group (e.g., methoxy),
(ii) an amino group optionally mono- or di-substituted by substituent(s) selected from
(A) a $C_{1-6}$ alkyl group (e.g., methyl), and
(B) a $C_{1-6}$ alkyl-carbonyl group (e.g., acetyl), (iii) a carbamoyl group optionally mono- or di-substituted by $C_{1-6}$ alkyl group(s) (e.g., methyl),
(iv) a 3- to 8-membered monocyclic non-aromatic heterocyclic group (e.g., pyrrolidinyl) optionally substituted by oxo group(s),
(v) a hydroxy group, and
(vi) a $C_{6-14}$ aryl group (e.g., phenyl) optionally substituted by 1 to 3 $C_{1-6}$ alkoxy groups (e.g., methoxy),
(f) a 3- to 8-membered monocyclic non-aromatic heterocyclic group (e.g., azetidinyl, piperazinyl, piperidyl, morpholinyl, tetrahydropyranyl, 1,1-dioxidothiomorpholinyl) optionally substituted by 1 to 3 substituents selected from
(i) a $C_{1-6}$ alkyl group (e.g., methyl, ethyl) optionally substituted by 1 to 3 hydroxy groups,
(ii) a $C_{1-6}$ alkoxy group (e.g., methoxy),
(iii) a $C_{1-6}$ alkyl-carbonyl group (e.g., acetyl),
(iv) an oxo group,
(v) a hydroxy group, and
(vi) a halogen atom (e.g., a fluorine atom),
(g) a 3- to 8-membered monocyclic non-aromatic heterocyclylcarbonyl group (e.g., pyrrolidinylcarbonyl, morpholinylcarbonyl),
(h) a 3- to 8-membered monocyclic non-aromatic heterocyclyloxy group (e.g., tetrahydropyranyloxy),
(i) a $C_{3-8}$ cycloalkyloxy group (e.g., cyclopentyloxy), and
(j) a hydroxy group, or
(5) a 8- to 12-membered fused aromatic heterocyclic group (e.g., imidazopyridyl).

Preferable examples of compound (I) include the following compounds.

[Compound A-1]
Compound (I) wherein
$R^1$ is an optionally substituted $C_{1-6}$ alkyl group, an optionally substituted $C_{3-10}$ cycloalkyl group or an optionally substituted $C_{6-14}$ aryl group;
$R^2$ is a hydrogen atom or a cyano group; and
$R^3$ is a hydrogen atom, a halogen atom, an optionally substituted $C_{6-14}$ aryl group or an optionally substituted 5- to 7-membered (preferably 5- or 6-membered) monocyclic aromatic heterocyclic group (e.g., pyrazolyl, oxazolyl, thiazolyl, isothiazolyl, thienyl, furyl, pyridyl, pyrimidinyl, pyrazinyl).

[Compound A-2]
Compound (I) wherein
$R^1$ is an optionally substituted $C_{1-6}$ alkyl group, an optionally substituted $C_{3-10}$ cycloalkyl group, an optionally substituted $C_{6-14}$ aryl group, an optionally substituted 3- to 8-membered monocyclic non-aromatic heterocyclic group or an optionally substituted 5- or 6-membered monocyclic aromatic heterocyclic group;
$R^2$ is a hydrogen atom or a cyano group; and
$R^3$ is a hydrogen atom, a halogen atom (e.g., a bromine atom), an optionally substituted $C_{6-12}$ aryl group (e.g., phenyl), a 5-membered monocyclic aromatic heterocyclic group (e.g., pyrazolyl, oxazolyl, thiazolyl, isothiazolyl, thienyl, furyl, imidazolyl) optionally having one substituent, an optionally substituted 6- or 7-membered (preferably 6-membered) monocyclic aromatic heterocyclic group (e.g., pyridyl, pyrimidinyl, pyrazinyl, pyridazinyl) or an optionally substituted 8- to 12-membered fused aromatic heterocyclic group (e.g., imidazopyridyl).

[Compound B-1]
Compound (I) wherein
$R^1$ is
1) a $C_{1-6}$ alkyl group (e.g., propyl, isopropyl, 1,2-dimethylpropyl) optionally substituted by 1 to 3 halogen atoms (e.g., a fluorine atom),
(2) a $C_{3-10}$ cycloalkyl group (e.g., cyclohexyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
(a) a halogen atom (e.g., a fluorine atom, a chlorine atom),
(b) a $C_{1-6}$ alkyl group (e.g., methyl) optionally substituted by 1 to 3 halogen atoms (e.g., a fluorine atom), and
(c) a cyano group;
$R^2$ is a hydrogen atom or a cyano group; and
$R^3$ is
(1) a hydrogen atom,
(2) a halogen atom (e.g., a bromine atom),
(3) a $C_{6-14}$ aryl group (e.g., phenyl) optionally substituted by 1 to 3 halogen atoms (e.g., a fluorine atom), or
(4) a 5- to 7-membered (preferably 5- or 6-membered) monocyclic aromatic heterocyclic group (e.g., pyrazolyl, oxazolyl, thiazolyl, isothiazolyl, thienyl, furyl, pyridyl, pyrimidinyl, pyrazinyl) optionally substituted by 1 to 3 substituents selected from
(a) a $C_{1-6}$ alkyl group (e.g., methyl, ethyl) optionally substituted by 1 to 3 substituents selected from
(i) a hydroxy group,
(ii) a $C_{1-6}$ alkoxy group (e.g., methoxy),
(iii) a $C_{1-6}$ alkylsulfonyl group (e.g., methylsulfonyl),
(iv) an amino group optionally mono- or di-substituted by $C_{1-6}$ alkyl-carbonyl group(s) (e.g., acetyl) or $C_{1-6}$ alkyl group(s) (e.g., methyl),
(v) a cyano group, and
(vi) a 3- to 8-membered monocyclic non-aromatic heterocyclic group (e.g., pyrrolidinyl),
(b) a cyano group,
(c) an amino group,
(d) an carbamoyl group,
(e) a $C_{1-6}$ alkoxy-carbonyl group (e.g., ethoxycarbonyl), and
(f) a 3- to 8-membered monocyclic non-aromatic heterocyclic group (e.g., piperazinyl, piperidyl) optionally substituted by 1 to 3 $C_{1-6}$ alkyl groups (e.g., ethyl) optionally substituted by 1 to 3 hydroxy groups.

[Compound B-2]
Compound (I) wherein
$R^1$ is
(1) a $C_{1-6}$ alkyl group (e.g., ethyl, propyl, 1,2-dimethylpropyl, isobutyl, sec-butyl, 1-methylbutyl, 1-ethyl-2-methylpropyl) optionally substituted by 1 to 3 substituents selected from
(a) a halogen atom (e.g., a fluorine atom), and
(b) a $C_{3-8}$ cycloalkyl group (e.g., cyclopropyl, cyclobutyl),
(2) a $C_{3-10}$ cycloalkyl group (e.g., cyclopentyl, cyclohexyl) optionally substituted by 1 to 3 substituents selected from
(a) a halogen atom (e.g., a fluorine atom), and
(b) a $C_{1-6}$ alkyl group (e.g., methyl),
(3) a $C_{6-14}$ aryl group (e.g., phenyl) optionally substituted by 1 to 3 substituents selected from
(a) a halogen atom (e.g., a fluorine atom, a chlorine atom),
(b) a $C_{1-6}$ alkyl group (e.g., methyl) optionally substituted by 1 to 3 halogen atoms (e.g., a fluorine atom),
(c) a cyano group,
(d) an amino group optionally mono- or di-substituted by $C_{1-6}$ alkyl-carbonyl group(s) (e.g., acetyl), and
(e) a $C_{1-6}$ alkoxy group (e.g., methoxy),
(4) a 3- to 8-membered monocyclic non-aromatic heterocyclic group (e.g., 1,1-dioxidotetrahydrothiopyranyl), or
(5) a 5- or 6-membered monocyclic aromatic heterocyclic group (e.g., pyridyl) optionally substituted by 1 to 3 substituents selected from
(a) a halogen atom (e.g., a chlorine atom), and
(b) a cyano group;
$R^2$ is a hydrogen atom or a cyano group; and R³ is
(1) a hydrogen atom,
(2) a halogen atom (e.g., a bromine atom),
(3) a $C_{6-12}$ aryl group (e.g., phenyl) optionally substituted by 1 to 3 halogen atoms (e.g., a fluorine atom),
(4) a 5-membered monocyclic aromatic heterocyclic group (e.g., pyrazolyl, oxazolyl, thiazolyl, isothiazolyl, thienyl, furyl, imidazolyl) optionally substituted by one substituent selected from the above-mentioned Substituent Croup C,
(5) a 6-membered monocyclic aromatic heterocyclic group (e.g., pyridyl, pyrimidinyl, pyrazinyl, pyridazinyl) optionally substituted by 1 to 3 substituents selected from the above-mentioned Substituent Group C, or
(6) a 8- to 12-membered fused aromatic heterocyclic group (e.g., imidazopyridyl) optionally substituted by 1 to 3 substituents selected from the above-mentioned Substituent Group C.

[Compound C]
Compound (I) wherein
R¹ is
(1) a $C_{1-6}$ alkyl group (e.g., ethyl, propyl, 1,2-dimethylpropyl, isobutyl, sec-butyl, 1-methylbutyl, 1-ethyl-2-methylpropyl) optionally substituted by 1 to 3 substituents selected from
  (a) a halogen atom (e.g., a fluorine atom), and
  (b) a $C_{3-8}$ cycloalkyl group (e.g., cyclopropyl, cyclobutyl),
(2) a $C_{3-10}$ cycloalkyl group (e.g., cyclopentyl, cyclohexyl) optionally substituted by 1 to 3 substituents selected from
  (a) a halogen atom (e.g., a fluorine atom), and
  (b) a $C_{1-6}$ alkyl group (e.g., methyl),
(3) a $C_{5-14}$ aryl group (e.g., phenyl) optionally substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a cyano group,
  (d) an amino group optionally mono- or di-substituted by $C_{1-6}$ alkyl-carbonyl group(s) (e.g., acetyl), and
  (e) a alkoxy group (e.g., methoxy),
(4) a 3- to 8-membered monocyclic non-aromatic heterocyclic group (e.g., 1,1-dioxidotetrahydrothiopyranyl), or
(5) a 5- or 6-membered monocyclic aromatic heterocyclic group (e.g., pyridyl) optionally substituted by 1 to 3 substituents selected from
  (a) a halogen atom (e.g., a chlorine atom), and
  (b) a cyano group;
R² is a hydrogen atom or a cyano group; and
R³ is
(1) a hydrogen atom,
(2) a halogen atom (e.g., a bromine atom),
(3) a $C_{6-12}$ aryl group (e.g., phenyl) optionally substituted by 1 to 3 halogen atoms (e.g., a fluorine atom),
(4) a 5-membered monocyclic aromatic heterocyclic group (e.g., pyrazolyl, oxazolyl, thiazolyl, isothiazolyl, thienyl, furyl, imidazolyl) optionally substituted by one substituent selected from
  (a) a $C_{1-6}$ alkyl group (e.g., methyl, ethyl) optionally substituted by 1 to 3 substituents selected from
    (i) a hydroxy group,
    (ii) a $C_{1-6}$ alkoxy group (e.g., methoxy),
    (iii) a $C_{1-6}$ alkylsulfonyl group (e.g., methylsulfonyl),
    (iv) an amino group optionally mono- or di-substituted by substituent(s) selected from
      (A) a $C_{1-6}$ alkyl-carbonyl group (e.g., acetyl), and
      (B) a $C_{1-6}$ alkyl group (e.g., methyl),
    (v) a cyano group, and
    (vi) a 3- to 8-membered monocyclic non-aromatic heterocyclic group (e.g., pyrrolidinyl),
  (b) a carbamoyl group optionally mono- or di-substituted by $C_{1-6}$ alkyl group(s) (e.g., methyl, ethyl) optionally substituted by 1 to 3 $C_{1-6}$ alkoxy groups (e.g., methoxy),
  (c) a $C_{1-6}$ alkoxy-carbonyl group (e.g., ethoxycarbonyl), and
  (d) a 3- to 8-membered monocyclic non-aromatic heterocyclylcarbonyl group (e.g., morpholinylcarbonyl),
(5) a 6-membered monocyclic aromatic heterocyclic group (e.g., pyridyl, pyrimidinyl, pyrazinyl, pyridazinyl) optionally substituted by 1 to 3 substituents selected from
  (a) a $C_{1-6}$ alkyl group (e.g., methyl, ethyl, isopropyl) optionally substituted by 1 to 3 substituents selected from
    (i) a hydroxy group,
    (ii) an amino group optionally mono- or di-substituted by substituent(s) selected from
      (A) a $C_{1-6}$ alkyl-carbonyl group (e.g., acetyl),
      (B) a formyl group, and
      (C) a $C_{1-6}$ alkyl group (e.g., methyl),
    (iii) a cyano group,
    (iv) a 3- to 8-membered monocyclic non-aromatic heterocyclic group (e.g., pyrrolidinyl, morpholinyl, piperazinyl) optionally substituted by 1 to 3 $C_{1-6}$ alkyl groups (e.g., methyl),
    (v) a 3- to 8-membered monocyclic non-aromatic heterocyclylcarbonyl group (e.g., morpholinylcarbonyl, piperidylcarbonyl) optionally substituted by 1 to 3 hydroxy groups, and
    (vi) a carbamoyl group optionally mono- or di-substituted by substituent(s) selected from
      (A) a 3- to 8-membered monocyclic non-aromatic heterocyclic group (e.g., oxetanyl), and
      (B) a $C_{1-6}$ alkyl group (e.g., methyl),
  (b) a cyano group,
  (c) an amino group optionally mono- or di-substituted by substituent(s) selected from
    (i) a formyl group,
    (ii) a $C_{1-6}$ alkyl group (e.g., ethyl) optionally substituted by 1 to 3 amino groups optionally mono- or di-substituted by $C_{1-6}$ alkyl group(s) (e.g., methyl), and
    (iii) a $C_{1-6}$ alkyl-carbonyl group (e.g., acetyl),
  (d) a carbamoyl group optionally mono- or di-substituted by substituent(s) selected from
    (i) a $C_{1-6}$ alkyl group (e.g., methyl, ethyl) optionally substituted by 1 to 3 hydroxy groups, and
    (ii) a 3- to 8-membered monocyclic non-aromatic heterocyclic group (e.g., tetrahydropyranyl),
  (e) a $C_{1-6}$ alkoxy group (e.g., methoxy, ethoxy, isopropoxy, isobutoxy, neo-pentyloxy) optionally substituted by 1 to 3 substituents selected from
    (i) a $C_{1-6}$ alkoxy group (e.g., methoxy),
    (ii) an amino group optionally mono- or di-substituted by substituent(s) selected from
      (A) a $C_{1-6}$ alkyl group (e.g., methyl), and
      (B) a $C_{1-6}$ alkyl-carbonyl group (e.g., acetyl),
    (iii) a carbamoyl group optionally mono- or di-substituted by $C_{1-6}$ alkyl group(s) (e.g., methyl),
    (iv) a 3- to 8-membered monocyclic non-aromatic heterocyclic group (e.g., pyrrolidinyl) optionally substituted by oxo group(s),
    (v) a hydroxy group, and
    (vi) a $C_{6-14}$ aryl group (e.g., phenyl) optionally substituted by 1 to 3 $C_{1-6}$ alkoxy groups (e.g., methoxy), (f) a 3- to 8-membered monocyclic non-aromatic heterocyclic group (e.g., azetidinyl, piperazinyl, piperidyl, morpholinyl, tetrahydropyranyl, 1,1-dioxidothiomorpholinyl) optionally substituted by 1 to 3 substituents selected from
   (i) a $C_{1-6}$ alkyl group (e.g., methyl, ethyl) optionally substituted by 1 to 3 hydroxy groups,
   (ii) a $C_{1-6}$ alkoxy group (e.g., methoxy),
   (iii) a $C_{1-6}$ alkyl-carbonyl group (e.g., acetyl),
   (iv) an oxo group,
   (v) a hydroxy group, and
   (vi) a halogen atom (e.g., a fluorine atom),
(g) a 3- to 8-membered monocyclic non-aromatic heterocyclylcarbonyl group (e.g., pyrrolidinylcarbonyl, morpholinylcarbonyl),
(h) a 3- to 8-membered monocyclic non-aromatic heterocyclyloxy group (e.g., tetrahydropyranyloxy),
(i) a $C_{3-8}$ cycloalkyloxy group (e.g., cyclopentyloxy), and
(j) a hydroxy group, or
(6) a 8- to 12-membered fused aromatic heterocyclic group (e.g., imidazopyridyl).

[Compound D]
Compound (I) wherein
$R^1$ is
(1) a $C_{1-6}$ alkyl group (e.g., ethyl, propyl, 1,2-dimethylpropyl, isobutyl, sec-butyl, 1-methylbutyl, 1-ethyl-2-methylpropyl) optionally substituted by 1 to 3 substituents selected from
   (a) a halogen atom (e.g., a fluorine atom), and
   (b) a $C_{3-8}$ cycloalkyl group (e.g., cyclopropyl, cyclobutyl),
(2) a $C_{3-10}$ cycloalkyl group (e.g., cyclopentyl, cyclohexyl) optionally substituted by 1 to 3 substituents selected from
   (a) a halogen atom (e.g., a fluorine atom), and
   (b) a $C_{1-6}$ alkyl group (e.g., methyl),
(3) a $C_{6-14}$ aryl group (e.g., phenyl) optionally substituted by 1 to 3 substituents selected from
   (a) a halogen atom (e.g., a fluorine atom, a chlorine atom),
   (b) a $C_{1-6}$ alkyl group (e.g., methyl) optionally substituted by 1 to 3 halogen atoms (e.g., a fluorine atom),
   (c) a cyano group,
   (d) an amino group optionally mono- or di-substituted by $C_{1-6}$ alkyl-carbonyl group(s) (e.g., acetyl), and
   (e) a $C_{1-6}$ alkoxy group (e.g., methoxy),
(4) a 3- to 8-membered monocyclic non-aromatic heterocyclic group (e.g., 1,1-dioxidotetrahydrothiopyranyl), or
(5) a 5- or 6-membered monocyclic aromatic heterocyclic group (e.g., pyridyl) optionally substituted by 1 to 3 substituents selected from
   (a) a halogen atom (e.g., a chlorine atom), and
   (b) a cyano group;
$R^2$ is a hydrogen atom; and
$R^3$ is
(1) a halogen atom (e.g., a bromine atom),
(2) a $C_{6-12}$ aryl group (e.g., phenyl) optionally substituted by 1 to 3 halogen atoms (e.g., a fluorine atom),
(3) a 5-membered monocyclic aromatic heterocyclic group (e.g., pyrazolyl, oxazolyl, thiazolyl, isothiazolyl, thienyl, furyl, imidazolyl) optionally substituted by one substituent selected from
   (a) a $C_{1-6}$ alkyl group (e.g., methyl, ethyl) optionally substituted by 1 to 3 substituents selected from
      (i) a hydroxy group,
      (ii) a $C_{1-6}$ alkoxy group (e.g., methoxy),
      (iii) a $C_{1-6}$ alkylsulfonyl group (e.g., methylsulfonyl),
      (iv) an amino group optionally mono- or di-substituted by substituent(s) selected from
         (A) a $C_{1-6}$ alkyl-carbonyl group (e.g., acetyl), and
         (B) a $C_{1-6}$ alkyl group (e.g., methyl),
      (v) a cyano group, and
      (vi) a 3- to 8-membered monocyclic non-aromatic heterocyclic group (e.g., pyrrolidinyl),
   (b) a carbamoyl group optionally mono- or di-substituted by $C_{1-6}$ alkyl group(s) (e.g., methyl, ethyl) optionally substituted by 1 to 3 $C_{1-6}$ alkoxy groups (e.g., methoxy),
   (c) a $C_{1-6}$ alkoxy-carbonyl group (e.g., ethoxycarbonyl), and
   (d) a 3- to 8-membered monocyclic non-aromatic heterocyclylcarbonyl group (e.g., morpholinylcarbonyl),
(4) a 6-membered monocyclic aromatic heterocyclic group (e.g., pyridyl, pyrimidinyl, pyrazinyl, pyridazinyl) optionally substituted by 1 to 3 substituents selected from
   (a) a $C_{1-6}$ alkyl group (e.g., methyl, ethyl, isopropyl) optionally substituted by 1 to 3 substituents selected from
      (i) a hydroxy group,
      (ii) an amino group optionally mono- or di-substituted by substituent(s) selected from
         (A) a $C_{1-6}$ alkyl-carbonyl group (e.g., acetyl),
         (B) a formyl group, and
         (C) a $C_{1-6}$ alkyl group (e.g., methyl),
      (iii) a cyano group,
      (iv) a 3- to 8-membered monocyclic non-aromatic heterocyclic group (e.g., pyrrolidinyl, morpholinyl, piperazinyl) optionally substituted by 1 to 3 $C_{1-6}$ alkyl groups (e.g., methyl),
      (v) a 3- to 8-membered monocyclic non-aromatic heterocyclylcarbonyl group (e.g., morpholinylcarbonyl, piperidylcarbonyl) optionally substituted by 1 to 3 hydroxy groups, and
      (vi) a carbamoyl group optionally mono- or di-substituted by substituent(s) selected from
         (A) a 3- to 8-membered monocyclic non-aromatic heterocyclic group (e.g., oxetanyl), and
         (B) a $C_{1-6}$ alkyl group (e.g., methyl),
   (b) a cyano group,
   (c) an amino group optionally mono- or di-substituted by substituent(s) selected from
      (i) a formyl group,
      (ii) a $C_{1-6}$ alkyl group (e.g., ethyl) optionally substituted by 1 to 3 amino groups optionally mono- or di-substituted by $C_{1-6}$ alkyl group(s) (e.g., methyl), and
      (iii) a $C_{1-6}$ alkyl-carbonyl group (e.g., acetyl),
   (d) a carbamoyl group optionally mono- or di-substituted by substituent(s) selected from
      (i) a $C_{1-6}$ alkyl group (e.g., methyl, ethyl) optionally substituted by 1 to 3 hydroxy groups, and
      (ii) a 3- to 8-membered monocyclic non-aromatic heterocyclic group (e.g., tetrahydropyranyl),
   (e) a $C_{1-6}$ alkoxy group (e.g., methoxy, ethoxy, isopropoxy, isobutoxy, neo-pentyloxy) optionally substituted by 1 to 3 substituents selected from
      (i) a $C_{1-6}$ alkoxy group (e.g., methoxy),
      (ii) an amino group optionally mono- or di-substituted by substituent(s) selected from
         (A) a $C_{1-6}$ alkyl group (e.g., methyl), and
         (B) a $C_{1-6}$ alkyl-carbonyl group (e.g., acetyl),
      (iii) a carbamoyl group optionally mono- or di-substituted by $C_{1-6}$ alkyl group(s) (e.g., methyl),
      (iv) a 3- to 8-membered monocyclic non-aromatic heterocyclic group (e.g., pyrrolidinyl) optionally substituted by oxo group(s),
      (v) a hydroxy group, and
      (vi) a $C_{6-14}$ aryl group (e.g., phenyl) optionally substituted by 1 to 3 $C_{1-6}$ alkoxy groups (e.g., methoxy), (f) a 3- to 8-membered monocyclic non-aromatic heterocyclic group (e.g., azetidinyl, piperazinyl, piperidyl, morpholinyl, tetrahydropyranyl, 1,1-dioxidothiomorpholinyl) optionally substituted by 1 to 3 substituents selected from
  (i) a $C_{1-6}$ alkyl group (e.g., methyl, ethyl) optionally substituted by 1 to 3 hydroxy groups,
  (ii) a $C_{1-6}$ alkoxy group (e.g., methoxy),
  (iii) a $C_{1-6}$ alkyl-carbonyl group (e.g., acetyl),
  (iv) an oxo group,
  (v) a hydroxy group, and
  (vi) a halogen atom (e.g., a fluorine atom),
(g) a 3- to 8-membered monocyclic non-aromatic heterocyclylcarbonyl group (e.g., pyrrolidinylcarbonyl, morpholinylcarbonyl),
(h) a 3- to 8-membered monocyclic non-aromatic heterocyclyloxy group (e.g., tetrahydropyranyloxy),
(i) a $C_{3-8}$ cycloalkyloxy group (e.g., cyclopentyloxy), and
(j) a hydroxy group, or
(5) a 8- to 12-membered fused aromatic heterocyclic group (e.g., imidazopyridyl).

[Compound E]
3-amino-5-(2,6-difluorophenyl)-7-(1-methyl-1H-pyrazol-3-yl)-1,5-dihydro-4H-pyrazolo[4,3-c]pyridin-4-one;
2-(3-amino-7-(1-methyl-1H-pyrazol-3-yl)-4-oxo-1,4-dihydro-5H-pyrazolo[4,3-c]pyridin-5-yl)-3-fluorobenzonitrile;
3-amino-5-(1-cyclopropylethyl)-7-(1-methyl-1H-pyrazol-3-yl)-1,5-dihydro-4H-pyrazolo[4,3-c]pyridin-4-one;
or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]
The production method of compound (I) or a salt thereof of the present invention are explained in the followings.

The compound (I) and the starting compounds can be produced according to a method known per se, for example, method shown in the following scheme and the like. In each step in the following production method, the "room temperature" generally means 10-30° C. and, unless otherwise specified, each symbol in the chemical formulas described in the schemes is as defined above. In the compounds in the formulas, each compound includes salts, and examples of such salt include those similar to the salts of compound (I) and the like.

In each reaction, when the starting compound or intermediate has an amino group, a carboxyl group or a hydroxy group as a substituent, these groups may be protected by a protecting group generally used in peptide chemistry and the like. By removing the protecting group as necessary after the reaction, the objective compound can be obtained. The introduction and removal of the protecting group can be performed according to a method known per se, for example, the method described in "Protective Groups in Organic Synthesis, 4th Ed", Wiley-Interscience, Inc. (2006) (Theodora W. Greene, Peter G. M. Wuts).

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl etc.), a $C_{7-12}$ aralkyloxy-carbonyl group (e.g., benzyloxycarbonyl, 9-fluorenylmethoxycarbonyl etc.), a trityl group, a phthaloyl group, an N,N-dimethylaminomethylene group, a silyl group optionally substituted by $C_{1-6}$ alkyl group(s) (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like. These groups are optionally substituted by 1 to 3 substituents selected from a halogen atom, $C_{1-6}$ alkoxy group and a nitro group.

Examples of the carboxyl-protecting group include a $C_{1-6}$ alkyl group, a $C_{7-12}$ aralkyl group (e.g., benzyl etc.), a phenyl group, a trityl group, a silyl group optionally substituted by $C_{1-6}$ alkyl group(s) (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like.

Examples of the hydroxyl-protecting group include a $C_{1-6}$ alkyl group, a phenyl group, a trityl group, a $C_{7-12}$ aralkyl group (e.g., benzyl etc.), a formyl group, a $C_{1-6}$ alkyl-carbonyl group, a benzoyl group, a $C_{7-12}$ aralkyl-carbonyl group (e.g., benzylcarbonyl etc.), a 2-tetrahydropyranyl group, a 2-tetrahydrofuranyl group, a silyl group optionally substituted by $C_{1-6}$ alkyl group(s) (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like.

These groups are optionally substituted by 1 to 3 substituents selected from a halogen atom, a $C_{1-6}$ alkyl group, a $C_{1-6}$ alkoxy group and a nitro group.

These protecting groups can be removed according to a method known per se, for example, the method described in "Protective Groups in Organic Synthesis, $4^{th}$ Ed." Wiley-Interscience, Inc. (2006) (Theodora W. Greene, Peter G. M. Wuts) or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

Where necessary, the reaction in each step can also be carried out under microwave irradiation using microwave irradiation apparatus (e.g., INITIATOR, manufactured by Biotage, etc.) and the like.

The compound obtained in each step can be used directly for the next step as the reaction mixture or a crude product, or can be isolated from the reaction mixture according to a conventional means, and can be easily purified according to a separation means such as recrystallization, distillation, chromatography and the like.

Compound (I) can be produced, for example, according to the following Method A, Method B, Method C, Method D, Method E, Method F, Method G, Method H, Method I or a method analogous thereto. The starting compound in each method may be a commercially available product, or can also be produced according to a method known per se or a method analogous thereto.

Among compound (I), a compound represented by the formula (I-A)

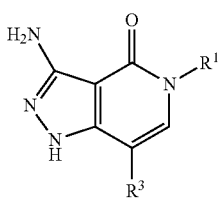

wherein each symbol in the formulas is as defined above, (hereinafter, to be abbreviated as compound (I-A)) can be produced according to the following Method A, Method B, Method C or a method analogous thereto. In each step in the production methods, the starting compound may be in the form of a salt. Examples of the salt include those similar to the salt of compound (I).

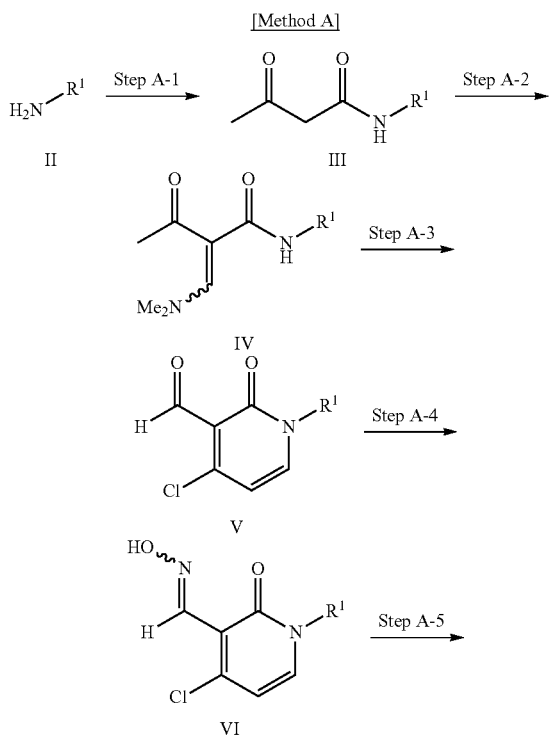

wherein G is —B(OH)$_2$ or —B(OR)(OR') wherein R and R' are each independently a $C_{1-6}$ alkyl group; or the adjacent R and R' are optionally bonded to form, for example, a 4,4,5,5-tetramethyl-1,3,2-dioxaboran-2-yl group, X is a halogen atom, and the other symbols are as defined above.

In this method, compound (II) and compound (IX) used as starting materials may be a commercially available product, or can also be produced according to a method known per se or a method analogous thereto.

(Step A-1)

This step is a step of subjecting compound (II) to an acylation reaction with an acylating agent to convert compound (II) to compound (III).

This step can be performed, where necessary, in the presence of a base, in a solvent that does not adversely influence the reaction.

Examples of the acylating agent used in this step include 2,2,6-trimethyl-4H-1,3-didioxin-4-one, diketene, acid chlorides, anhydrides, active esters and the like. Among them, 2,2,6-trimethyl-4H-1,3-didioxin-4-one and diketene are preferable.

The amount of the acylating agent to be used is about 1 mol-about 100 mol, preferably about 1 mol-about 10 mol, per 1 mol of compound (II).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, alkali metal salts such as sodium acetate potassium acetate and the like are preferable.

The amount of the base to be used is about 0.1 mol-about 100 mol, preferably about 1 mol-about 10 mol, per 1 mol of compound (II).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 100° C. The reaction time in this step is generally about 0.1 hr-about 100 hr.

The thus-obtained compound (III) can be isolated and purified by a known separation and purification means, for example, concentration, concentrated under reduced pressure, solvent extraction, crystallization, recrystallization, phase transfer, chromatography and the like. In addition, compound (III) may be directly used without isolation for the next reaction.

(Step A-2)

This step is a step of reacting compound (III) with an olefinating agent to convert compound (III) to compound (IV).

This step can be performed, where necessary, in a solvent that does not adversely influence the reaction.

Examples of the olefinating agent include 1,1-dimethoxy-N,N-dimethylmethanamine, 1,1-diethoxy-N,N-dimethylmethanamine and the like.

The amount of the olefinating agent to be used is about 1 mol-about 100 mol, preferably about 1 mol-about 10 mol, per 1 mol of compound (III).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 100° C. The reaction time in this step is generally about 0.1 hr-about 100 hr.

The thus-obtained compound (IV) can be isolated and purified by a known separation and purification means, for example, concentration, concentrated under reduced pressure, solvent extraction, crystallization, recrystallization, phase transfer, chromatography and the like. In addition, compound (IV) may be directly used without isolation for the next reaction.

(Step A-3)

This step is a step of reacting compound (IV) with the Vilsmeier reagent to convert compound (IV) to compound (V).

This step can be performed, where necessary, in a solvent that does not adversely influence the reaction.

The Vilsmeier reagent can be prepared from N,N-dimethylformamide and a chlorinating agent (e.g., phosphorus oxychloride, phosphorus pentachloride, phosgene etc.) or may be a commercially available product.

The amount of the Vilsmeier reagent to be used is about 1 mol-about 100 mol, preferably about 1 mol-about 10 mol, per 1 mol of compound (IV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (V) can be isolated and purified by a known separation and purification means, for example, concentration, concentrated under reduced pressure, solvent extraction, crystallization, recrystallization, phase transfer, chromatography and the like. In addition, compound (V) may be directly used without isolation for the next reaction.

(Step A-4)

This step is a step of subjecting compound (V) to an oximation reaction with hydroxylamine or a salt thereof to convert compound (V) to compound (VI).

This step can be performed, where necessary, in the presence of an acid or a base, in a solvent that does not adversely influence the reaction.

The amount of the hydroxylamine or a salt thereof to be used is about 1 mol-about 100 mol, preferably about 1 mol-about 10 mol, per 1 mol of compound (V).

Examples of the acid to be used include hydrochloric acid, hydrobromic acid, sulfuric acid, trifluoroacetic acid, trifluoromethanesulfonic acid, hydrogen chloride and the like.

The amount of the acid to be used is about 0.1 mol-about 100 mol per 1 mol of compound (V).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.) and the like. Among them, alkali metal salts such as sodium acetate, potassium acetate and the like are preferable.

The amount of the base to be used is about 0.1 mol-about 100 mol, preferably about 1 mol-about 10 mol, per 1 mol of compound (V).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (VI) can be isolated and purified by a known separation and purification means, for example, concentration, concentrated under reduced pressure, solvent extraction, crystallization, recrystallization, phase transfer, chromatography and the like. In addition, compound (VI) may be directly used without isolation for the next reaction.

(Step A-5)

This step is a step of reacting compound (VI) with a dehydrating agent to convert compound (VI) to compound (VII).

This step can be performed, where necessary, in a solvent that does not adversely influence the reaction.

Examples of the dehydrating agent to be used include phosphorus oxychloride, thionyl chloride, oxalyl chloride, acetic anhydride, acetyl chloride, trichloroacetyl chloride and the like.

The amount of the dehydrating agent to be used is about 0.1 mol-about 100 mol, per 1 mol of compound (VI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (VII) can be isolated and purified by a known separation and purification means, for example, concentration, concentrated under reduced pressure, solvent extraction, crystallization, recrystallization, phase transfer, chromatography and the like. In addition, compound (VII) may be directly used without isolation for the next reaction.

(Step A-6)

This step is a step of subjecting compound (VII) to a substitution reaction with a halogenating agent to convert compound (VII) to compound (VIII).

This step can be performed, where necessary, in a solvent that does not adversely influence the reaction.

Examples of the halogenating agent to be used include bromine, iodine, N-bromosuccinimide, N-iodosuccinimide and the like. Where necessary, an acid (hydrobromic acid, hydrochloric acid, trifluoroacetic acid etc.) may be added.

The amount of the halogenating agent to be used is about 0.1 mol-about 100 mol, per 1 mol of compound (VII). The amount of the acid to be used is about 0.000001 mol-about 100 mol per 1 mol of compound (VII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (VIII) can be isolated and purified by a known separation and purification means, for example, concentration, concentrated under reduced pressure, solvent extraction, crystallization, recrystallization, phase transfer, chromatography and the like. In addition, compound (VIII) may be directly used without isolation for the next reaction.

(Step A-7)

This step is a step of subjecting compound (VIII) to a coupling reaction with compound (IX) and a transition metal catalyst to convert compound (VIII) to compound (X).

The reaction with a transition metal catalyst can be carried out according to a known method per se [e.g., Chemical Reviews, 1995, vol. 95, page 2457, and the like], for example, in the presence of a transition metal catalyst and a base, in a solvent that does not adversely influence the reaction.

The amount of compound (IX) to be used is about 1 mol-about 100 mol, preferably about 1 mol-about 10 mol, per 1 mol of compound (VIII).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol—about 1 mol, preferably about 0.01 mol-about 0.5 mol, per 1 mol of compound (VIII). The amount of the ligand or cocatalyst to be used is generally about 0.0001 mol -about 4 mol, preferably about 0.01 mol-about 2 mol, per 1 mol of compound (VIII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (VIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2- dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (X) can be isolated and purified by a known separation and purification means, for example, concentration, concentrated under reduced pressure, solvent extraction, crystallization, recrystallization, phase transfer, chromatography and the like. In addition, compound (X) may be directly used without isolation for the next reaction.

(Step A-8)

This step is a step of reacting compound (X) with hydrazine or a salt thereof or a hydrate thereof to convert compound (X) to compound (I-A).

This step can be performed, where necessary, in a solvent that does not adversely influence the reaction.

The amount of the hydrazine or a salt thereof or a hydrate thereof to be used is about 1 mol-about 100 mol per 1 mol of compound (X).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-A) can be isolated and purified by a known separation and purification means, for example, concentration, concentrated under reduced pressure, solvent extraction, crystallization, recrystallization, phase transfer, chromatography and the like.

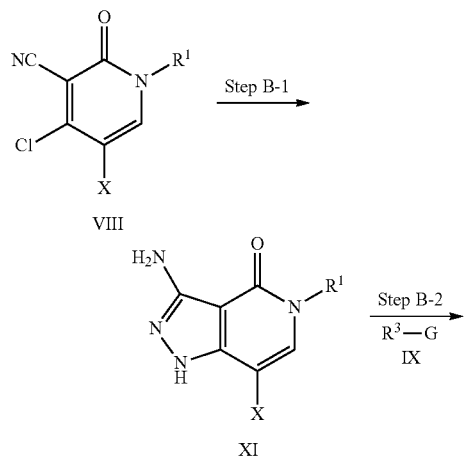

[Method B]

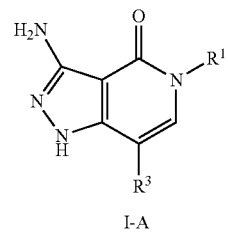

I-A wherein each symbol in the formulas is as defined above.

In this method, compound (IX) used as a starting material may be a commercially available product, or can also be produced according to a method known per se or a method analogous thereto.

(Step B-1)

This step is a step of reacting compound (VIII) obtained according to Method A or a method analogous thereto with hydrazine or a salt thereof or a hydrate thereof to convert compound (VIII) to compound (XI).

This step can be performed, where necessary, in a solvent that does not adversely influence the reaction.

Examples of the halogen atom for X include a bromine atom, an iodine atom and the like.

The amount of the hydrazine or a salt thereof or a hydrate thereof to be used is about 1 mol-about 100 mol per 1 mol of compound (VIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XI) can be isolated and purified by a known separation and purification means, for example, concentration, concentrated under reduced pressure, solvent extraction, crystallization, recrystallization, phase transfer, chromatography and the like. In addition, compound (XI) may be directly used without isolation for the next reaction.

(Step B-2)

This step is a step of subjecting compound (XI) to a coupling reaction with compound (IX) and a transition metal catalyst to convert compound (XI) to compound (I-A).

The reaction with a transition metal catalyst can be carried out according to a known method per se [e.g., Chemical Reviews, 1995, vol. 95, page 2457 and the like], for example, in the presence of a transition metal catalyst and a base, in a solvent that does not adversely influence the reaction.

The amount of compound (IX) to be used is about 1 mol-about 100 mol, preferably about 1 mol-about 10 mol, per 1 mol of compound (XI).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol-about 1 mol, preferably about 0.01 mol-about 0.5 mol, per 1 mol of compound (XI). The amount of the ligand or cocatalyst to be used is generally about 0.0001 mol-about 4 mol, preferably about 0.01 mol-about 2 mol, per 1 mol of compound (XI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-A) can be isolated and purified by a known separation and purification means, for example, concentration, concentrated under reduced pressure, solvent extraction, crystallization, recrystallization, phase transfer, chromatography and the like.

[Method C]

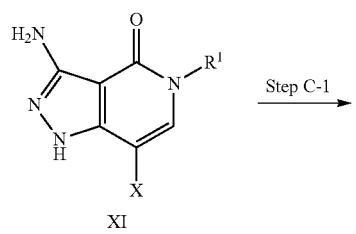

XI

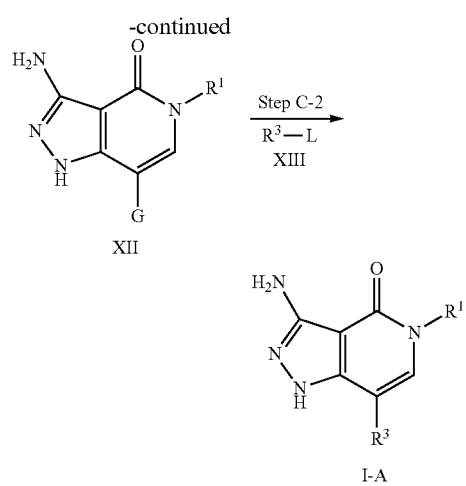

wherein L is a leaving group, and the other symbols are as defined above.

Examples of the leaving group for L include halogen atoms (e.g., a fluorine atom, a chlorine atom, a bromine atom, iodine atom etc.), optionally substituted sulfonyloxy groups (e.g., $C_{1-6}$ alkylsulfonyloxy groups optionally substituted by 1 to 3 halogen atoms (e.g., a chlorine atom, a bromine atom, iodine atom etc.) (e.g., a methanesulfonyloxy group, an ethanesulfonyloxy group, a trifluoromethanesulfonyloxy group etc.); $C_{6-14}$ arylsulfonyloxy groups (e.g., a benzenesulfonyloxy group, a p-toluenesulfonyloxy group etc.); and $C_{7-16}$ aralkylsulfonyloxy groups (e.g., a benzylsulfonyloxy group etc.) etc.). halogen atoms are is particularly preferable.

In this method, compound (XIII) used as a starting material may be a commercially available product, or can also be produced according to a method known per se or a method analogous thereto.

(Step C-1)

This step is a step of subjecting compound (XI) obtained according to Method B or a method analogous thereto to a substitution reaction in the presence of a transition metal catalyst to convert compound (XI) to compound (XII).

The reaction with a transition metal catalyst can be carried out according to a known method per se [e.g., Chemical Reviews, 1995, vol. 95, page 2457 and the like], for example, using 4,4,4',4',5,5,5',5'-octamethyl-2,2'-bi-1,3,2-dioxaborolane in the presence of a transition metal catalyst and a base, in a solvent that does not adversely influence the reaction.

The amount of the 4,4,4',4',5,5,5',5'-octamethyl-2,2'-bi-1,3,2-dioxaborolane to be used is about 1 mol-about 100 mol, preferably about 1 mol-about 10 mol, per 1 mol of compound (XI).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol-about 1 mol, preferably about 0.01 mol-about 0.5 mol, per 1 mol of compound (XI). The amount of the ligand or cocatalyst to be used is generally about 0.0001 mol-about 4 mol, preferably about 0.01 mol-about 2 mol, per 1 mol of compound (XI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XII) can be isolated and purified by a known separation and purification means, for example, concentration, concentrated under reduced pressure, solvent extraction, crystallization, recrystallization, phase transfer, chromatography and the like. In addition, compound (XII) may be directly used without isolation for the next reaction.

(Step C-2)

This step is a step of subjecting compound (XII) to a coupling reaction with compound (XIII) and a transition metal to convert compound (XII) to compound (I-A).

The reaction with a transition metal catalyst can be carried out according to a known method per se [e.g., Chemical Reviews, 1995, vol. 95, page 2457 and the like], for example, in the presence of a transition metal catalyst and a base, in a solvent that does not adversely influence the reaction.

The amount of the compound (XIII) to be used is about 1 mol-about 100 mol, preferably about 1 mol-about 10 mol, per 1 mol of compound (XII).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol-about 1 mol, preferably about 0.01 mol-about 0.5 mol, per 1 mol of compound (XII). The amount of the ligand or cocatalyst to be used is generally about 0.0001 mol-about 4 mol, preferably about 0.01 mol-about 2 mol, per 1 mol of compound (XII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-A) can be isolated and purified by a known separation and purification means, for example, concentration, concentrated under reduced pressure, solvent extraction, crystallization, recrystallization, phase transfer, chromatography and the like.

Among compound (I), a compound represented by the formula (I-D)

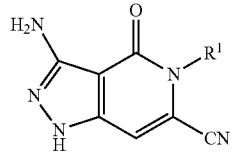

wherein each symbol in the formulas is as defined above, (hereinafter, to be abbreviated as compound (I-D)) can be produced according to the following Method D or a method analogous thereto. In each step in the production methods, the starting compound may be in the form of a salt. Examples of the salt include those similar to the salt of compound (I).

[Method D]

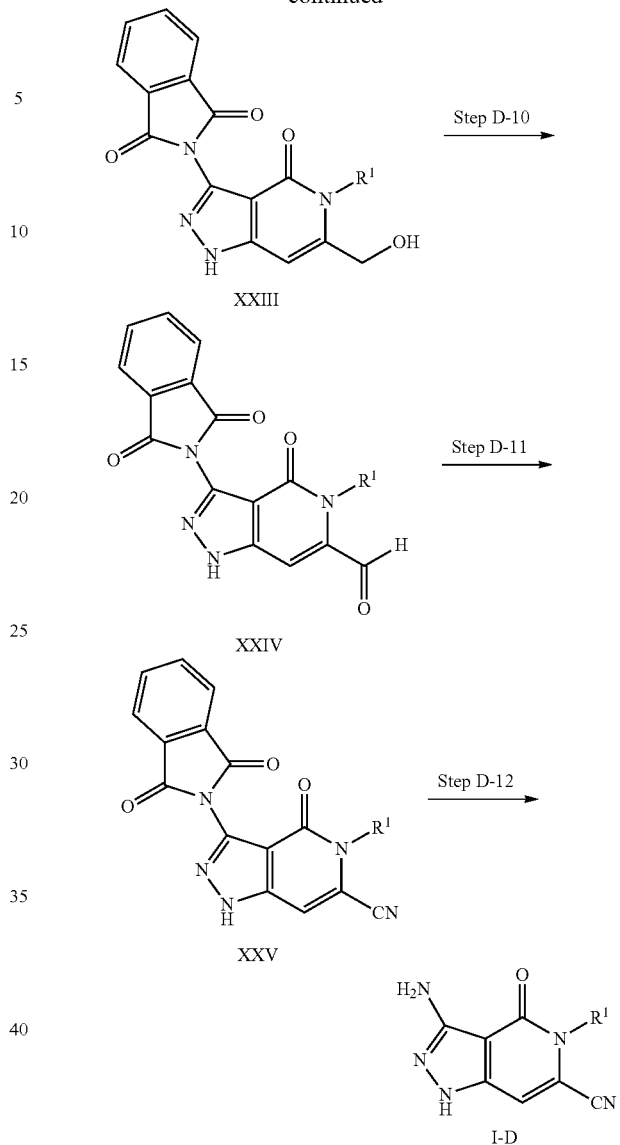

wherein each symbol in the formulas is as defined above.

In this method, compound (XIV) and compound (II) used as starting materials may be a commercially available product, or can also be produced according to a method known per se or a method analogous thereto.

(Step D-1)

This step is a step of reacting compound (XIV) with compound (II) to convert compound (XIV) to compound (XV).

This step can be performed in the presence of a base, where necessary, in a solvent that does not adversely influence the reaction.

The amount of compound (II) to be used is about 1 mol-about 100 mol, preferably about 1 mol-about 10 mol, per 1 mol of compound (XIV).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XIV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 200° C. The reaction time in this step is generally about 0.1 hr-about 100 hr.

The thus-obtained compound (XV) can be isolated and purified by a known separation and purification means, for example, concentration, concentrated under reduced pressure, solvent extraction, crystallization, recrystallization, phase transfer, chromatography and the like. In addition, compound (XV) may be directly used without isolation for the next reaction.

(Step D-2)

This step is a step of reacting compound (XV) with a formylating agent to convert compound (XV) to compound (XVI).

This step is where necessary, for example in the presence of a base, in a solvent that does not adversely influence the reaction.

Examples of the formylating agent include chloroform, the Vilsmeier reagent and the like.

The Vilsmeier reagent can be prepared from N,N-dimethylformamide and a chlorinating agent (e.g., phosphorus oxychloride, phosphorus pentachloride, phosgene etc.) or may be a commercially available product.

The amount of the formylating agent to be used is about 1 mol-about 100 mol, preferably about 1 mol-about 10 mol, per 1 mol of compound (XV).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali disilazides (e.g., lithium disilazide, sodium disilazide, potassium disilazide etc.) and the like. Among them, alkali metal salts (sodium hydroxide, potassium hydroxide etc.) are preferable.

The amount of the base to be used is about 0.1 mol-about 100 mol, preferably about 1 mol-about 10 mol, per 1 mol of compound (XV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XVI) can be isolated and purified by a known separation and purification means, for example, concentration, concentrated under reduced pressure, solvent extraction, crystallization, recrystallization, phase transfer, chromatography and the like. In addition, compound (XVI) may be directly used without isolation for the next reaction.

(Step D-3)

This step is a step of subjecting compound (XVI) to an oximation reaction with hydroxylamine or a salt thereof to convert compound (XVI) to compound (XVII).

This step can be performed, where necessary, in the presence of an acid or a base, in a solvent that does not adversely influence the reaction.

The amount of the hydroxylamine or a salt thereof to be used is about 1 mol-about 100 mol, preferably about 1 mol-about 10 mol, per 1 mol of compound (XVI).

Examples of the acid to be used include hydrochloric acid, hydrobromic acid, sulfuric acid, trifluoroacetic acid, trifluoromethanesulfonic acid, hydrogen chloride and the like.

The amount of the acid to be used is about 0.1 mol-about 100 mol, per 1 mol of compound (XVI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.) and the like. Among them, alkali metal salts such as sodium acetate, potassium acetate and the like are preferable.

The amount of the base to be used is about 0.1-about 100 mol, preferably about 1-about 10 mol, per 1 mol of compound (XVI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XVII) can be isolated and purified by a known separation and purification means, for example, concentration, concentrated under reduced pressure, solvent extraction, crystallization, recrystallization, phase transfer, chromatography and the like. In addition, compound (XVII) may be directly used without isolation for the next reaction.

(Step D-4)

This step is a step of reacting compound (XVII) with a dehydrating agent to convert compound (XVII) to compound (XVIII).

This step can be performed, where necessary, in a solvent that does not adversely influence the reaction.

Examples of the dehydrating agent to be used include acetic acid, phosphorus oxychloride, thionyl chloride, oxalyl chloride, acetic anhydride, acetyl chloride, trichloroacetyl chloride and the like.

The amount of the dehydrating agent to be used is about 0.1 mol-about 100 mol per 1 mol of compound (XVII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XVIII) can be isolated and purified by a known separation and purification means, for example, concentration, concentrated under reduced pressure, solvent extraction, crystallization, recrystallization, phase transfer, chromatography and the like. In addition, compound (XVIII) may be directly used without isolation for the next reaction.

(Step D-5)

This step is a step of reacting compound (XVIII) with the Vilsmeier reagent to convert compound (XVIII) to compound (XIX).

This step can be performed, where necessary, in a solvent that does not adversely influence the reaction.

The Vilsmeier reagent can be prepared from N,N-dimethylformamide and a chlorinating agent (e.g., phosphorus oxychloride, phosphorus pentachloride, phosgene etc.) or may be a commercially available product.

The amount of the Vilsmeier reagent to be used is about 1 mol-about 100 mol, preferably about 1 mol-about 10 mol, per 1 mol of compound (XVIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XIX) can be isolated and purified by a known separation and purification means, for example, concentration, concentrated under reduced pressure, solvent extraction, crystallization, recrystallization, phase transfer, chromatography and the like. In addition, compound (XIX) may be directly used without isolation for the next reaction.

(Step D-6)

This step is a step of subjecting compound (XIX) to a substitution reaction with a halogenating agent to convert compound (XIX) to compound (XX).

This step can be performed, where necessary, in the presence of a radical initiator, in a solvent that does not adversely influence the reaction.

Examples of the halogenating agent to be used include chlorine, bromine, iodine, N-chlorosuccinimide, N-bromosuccinimide, N-iodosuccinimide and the like.

The amount of the halogenating agent to be used is about 0.1 mol-about 100 mol per 1 mol of compound (XIX).

Examples of the radical initiator include azobis(isobutyronitrile) and the like.

The amount of the radical initiator to be used is about 0.01 mol-about 10 mol per 1 mol of compound (XIX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane, carbon tetrachloride etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XX) can be isolated and purified by a known separation and purification means, for example, concentration, concentrated under reduced pressure, solvent extraction, crystallization, recrystallization, phase transfer, chromatography and the like. In addition, compound (XX) may be directly used without isolation for the next reaction.

(Step D-7)

This step is a step of reacting compound (XX) with an alkali metal acetate to convert compound (XX) to compound (XXI).

This step can be performed, where necessary, in a solvent that does not adversely influence the reaction.

Examples of the alkali metal acetate to be used include sodium acetate, potassium acetate and the like.

The amount of the alkali metal acetate to be used is about 1 mol-about 100 mol per 1 mol of compound (XX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXI) can be isolated and purified by a known separation and purification means, for example, concentration, concentrated under reduced pressure, solvent extraction, crystallization, recrystallization, phase transfer, chromatography and the like. In addition, compound (XXI) may be directly used without isolation for the next reaction.

(Step D-8)

This step is a step of reacting compound (XXI) with hydrazine or a salt thereof or a hydrate thereof to convert compound (XXI) to compound (XXII).

This step can be performed, where necessary, in a solvent that does not adversely influence the reaction.

The amount of the hydrazine or a salt thereof or a hydrate thereof to be used is about 1 mol-about 100 mol per 1 mol of compound (XXI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXII) can be isolated and purified by a known separation and purification means, for example, concentration, concentrated under reduced pressure, solvent extraction, crystallization, recrystallization, phase transfer, chromatography and the like. In addition, compound (XXII) may be directly used without isolation for the next reaction.

(Step D-9)

This step is a step of reacting compound (XXII) with phthalic anhydride to convert compound (XXII) to compound (XXIII).

This step can be performed, where necessary, in a solvent that does not adversely influence the reaction.

The amount of the phthalic anhydride to be used is about 1 mol-about 100 mol, preferably about 1 mol-about 10 mol, per 1 mol of compound (XXII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXIII) can be isolated and purified by a known separation and purification means, for example, concentration, concentrated under reduced pressure, solvent extraction, crystallization, recrystallization, phase transfer, chromatography and the like. In addition, compound (XXIII) may be directly used without isolation for the next reaction.

(Step D-10)

This step is a step of subjecting compound (XXIII) to an oxidation reaction with an oxidizing agent to convert compound (XXIII) to compound (XXIV).

This step can be performed, where necessary, in a solvent that does not adversely influence the reaction.

Examples of the oxidizing agent to be used include hydrogen peroxide, m-chloroperbenzoic acid, Oxone (registered trademark), Dess-Martin periodinane, manganese dioxide, potassium permanganate and the like. Among them m-chloroperbenzoic acid, Oxone (registered trademark), Dess-Martin periodinane are preferable.

The amount of the oxidizing agent to be used is about 0.5 mol-about 100 mol, preferably about 0.5 mol-about 10 mol, per 1 mol of compound (XXIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water etc.) and mixtures thereof.

The reaction temperature in this step is generally about −50-about 200° C., preferably about −10° C.-about 100° C. The reaction time in this step is generally about 0.1 hr-about 100 hr.

The thus-obtained compound (XXIV) can be isolated and purified by a known separation and purification means, for example, concentration, concentrated under reduced pressure, solvent extraction, crystallization, recrystallization, phase transfer, chromatography and the like. In addition, compound (XXIV) may be directly used without isolation for the next reaction.

(Step D-11)

This step is a step of reacting compound (XXIV) with a cyanating agent to convert compound (XXIV) to compound (XXV).

This step is where necessary, for example in the presence of a base, in a solvent that does not adversely influence the reaction.

Examples of the cyanating agent to be used include 2,2,2-trifluoro-N-(2,2,2-trifluoroacetoxyl)acetamide and the like.

The amount of the cyanating agent to be used is about 1 mol-about 100 mol, preferably about 1 mol-about 10 mol, per 1 mol of compound (XXIV).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXIV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXV) can be isolated and purified by a known separation and purification means, for example, concentration, concentrated under reduced pressure, solvent extraction, crystallization, recrystallization, phase transfer, chromatography and the like. In addition, compound (XXV) may be directly used without isolation for the next reaction.

(Step D-12)

This step is a step of reacting compound (XXV) with hydrazine or a salt thereof or a hydrate thereof to convert compound (XXV) to compound (I-D).

This step can be performed, where necessary, in a solvent that does not adversely influence the reaction.

The amount of the hydrazine or a salt thereof or a hydrate thereof to be used is about 1 mol-about 100 mol per 1 mol of compound (XXV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-D) can be isolated and purified by a known separation and purification means, for example, concentration, concentrated under reduced pressure, solvent extraction, crystallization, recrystallization, phase transfer, chromatography and the like.

Alternatively, compound (VIII) can also be produced according to the following Method E.

[Method E]

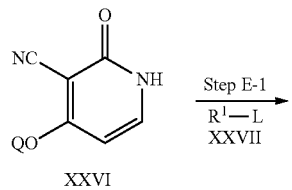

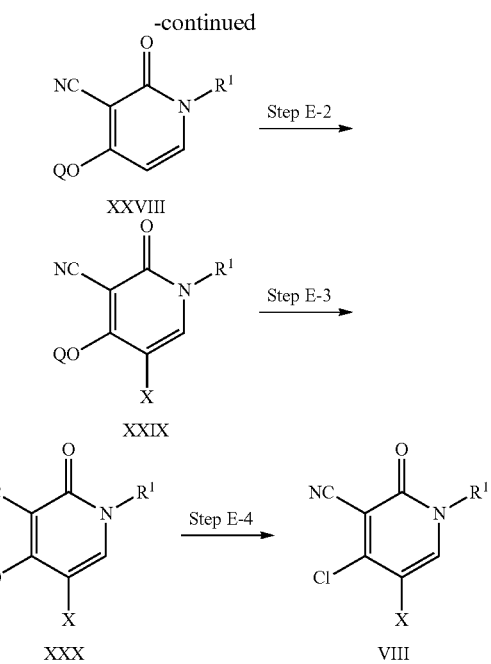

wherein Q is a $C_{1-3}$ alkyl group, and the other symbols are as defined above.

Examples of the $C_{1-3}$ alkyl group for Q include methyl, ethyl and the like.

In this method, compound (XXVI) and compound (XXVII) used as starting materials may be a commercially available product, or can also be produced according to a method known per se or a method analogous thereto. In each step in the production methods, the starting compound may be in the form of a salt. Examples of the salt include those similar to the salt of compound (I).

(Step E-1)

This step is a step of reacting compound (XXVI) with compound (XXVII) to convert compound (XXVI) to compound (XXVIII).

This step can be performed in the presence of a base, where necessary, in a solvent that does not adversely influence the reaction. Where necessary, potassium iodide, sodium iodide and the like may be added.

The amount of compound (XXVII) to be used is about 1 mol-about 100 mol, preferably about 1 mol-about 10 mol, per 1 mol of compound (XXVI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXVI).

The amount of the potassium iodide or sodium iodide to be used is about 0.01 mol-about 100 mol, per 1 mol of compound (XXVI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXVIII) can be isolated and purified by a known separation and purification means, for example, concentration, concentrated under reduced pressure, solvent extraction, crystallization, recrystallization, phase transfer, chromatography and the like. In addition, compound (XXVIII) may be directly used without isolation for the next reaction.

(Step E-2)

This step is a step of subjecting compound (XXVIII) to a substitution reaction with a halogenating agent to convert compound (XXVIII) to compound (XXIX).

This step can be performed, where necessary, in a solvent that does not adversely influence the reaction.

Examples of the halogenating agent to be used include bromine, iodine, N-bromosuccinimide, N-iodosuccinimide and the like. Where necessary, an acid (hydrobromic acid, hydrochloric acid, trifluoroacetic acid etc.) may be added.

The amount of the halogenating agent to be used is about 0.1 mol-about 100 mol per 1 mol of compound (XXVIII). The amount of the acid to be used is about 0.000001 mol-about 100 mol per 1 mol of compound (XXVIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXIX) can be isolated and purified by a known separation and purification means, for example, concentration, concentrated under reduced pressure, solvent extraction, crystallization, recrystallization, phase transfer, chromatography and the like. In addition, compound (XXIX) may be directly used without isolation for the next reaction.

(Step E-3)

This step is a step of subjecting compound (XXIX) to a hydrolysis reaction with a base to convert compound (XXIX) to compound (XXX).

This step can be performed, where necessary, in a solvent that does not adversely influence the reaction.

Examples of the base to be used include alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.) and the like.

The amount of the base to be used is about 0.1 mol-about 100 mol, preferably about 1 mol-about 10 mol, per 1 mol of compound (XXIX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXX) can be isolated and purified by a known separation and purification means, for example, concentration, concentrated under reduced pressure, solvent extraction, crystallization, recrystallization, phase transfer, chromatography and the like. In addition, compound (XXX) may be directly used without isolation for the next reaction.

(Step E-4)

This step is a step of reacting compound (XXX) with a chlorinating agent to convert compound (XXX) to compound (VIII).

This step can be performed, where necessary, in a solvent that does not adversely influence the reaction.

Examples of the chlorinating agent to be used include phosphorus oxychloride, thionyl chloride and the like.

The amount of the chlorinating agent to be used is about 0.1 mol-about 100 mol, preferably about 1 mol-about 10 mol, per 1 mol of compound (XXX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (VIII) can be isolated and purified by a known separation and purification means, for example, concentration, concentrated under reduced pressure, solvent extraction, crystallization, recrystallization, phase transfer, chromatography and the like. In addition, compound (VIII) may be directly used without isolation for the next reaction.

Compounds (XXVIII), (XXIX), (XXX) and (VIII) obtained according to the above-mentioned Method E can also be modified by subjecting to a known reaction such as condensation reaction (e.g. various acylation reaction, alkylation reaction etc.), Sandmeyer reaction, oxidation reaction, reduction reaction and the like. Such reaction can be carried out according to a known method per se.

Among compound (I), a compound represented by the formula (I-F)

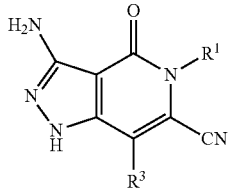

wherein each symbol in the formulas is as defined above, (hereinafter, to be abbreviated as compound (I-F)) can be produced according to the following Method F, Method G or a method analogous thereto. In each step in the production methods, the starting compound may be in the form of a salt. Examples of the salt include those similar to the salt of compound (I).

[Method F]

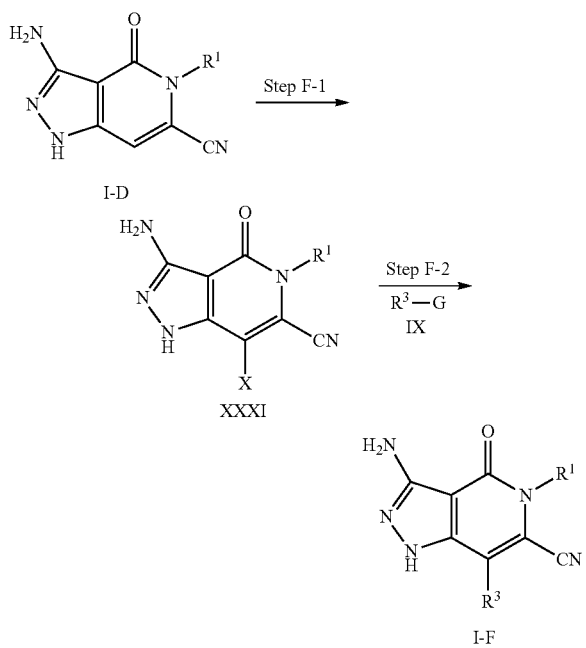

wherein each symbol in the formulas is as defined above.

In this method, compound (IX) used as a starting material may be a commercially available product, or can also be produced according to a method known per se or a method analogous thereto.

(Step F-1)

This step is a step of subjecting compound (I-D) obtained according to Method D or a method analogous thereto to a substitution reaction with a halogenating agent to convert compound (I-D) to compound (XXXI).

This step can be performed, where necessary, in a solvent that does not adversely influence the reaction.

Examples of the halogenating agent to be used include bromine, iodine, N-bromosuccinimide, N-iodosuccinimide and the like. Where necessary, an acid (hydrobromic acid, hydrochloric acid, trifluoroacetic acid etc.) may be added.

The amount of the halogenating agent to be used is about 0.1 mol-about 100 mol per 1 mol of compound (I-D). The amount of the acid to be used is about 0.000001 mol-about 100 mol per 1 mol of compound (I-D).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXXI) can be isolated and purified by a known separation and purification means, for example, concentration, concentrated under reduced pressure, solvent extraction, crystallization, recrystallization, phase transfer, chromatography and the like. In addition, compound (XXXI) may be directly used without isolation for the next reaction.

(Step F-2)

This step is a step of subjecting compound (XXXI) to a coupling reaction with compound (IX) and a transition metal catalyst to convert compound (XXXI) to compound (I-F).

The reaction with a transition metal catalyst can be carried out according to a known method per se [e.g., Chemical Reviews, 1995, vol. 95, page 2457 and the like], for example, in the presence of a transition metal catalyst and a base, in a solvent that does not adversely influence the reaction.

The amount of compound (IX) to be used is about 1 mol-about 100 mol, preferably about 1 mol-about 10 mol, per 1 mol of compound (XXXI).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol-about 1 mol, preferably about 0.01 mol-about 0.5 mol, per 1 mol of compound (XXXI). The amount of the ligand or cocatalyst to be used is generally about 0.0001 mol-about 4 mol, preferably about 0.01 mol-about 2 mol, per 1 mol of compound (XXXI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like.

Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XXXI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-F) can be isolated and purified by a known separation and purification means, for example, concentration, concentrated under reduced pressure, solvent extraction, crystallization, recrystallization, phase transfer, chromatography and the like.

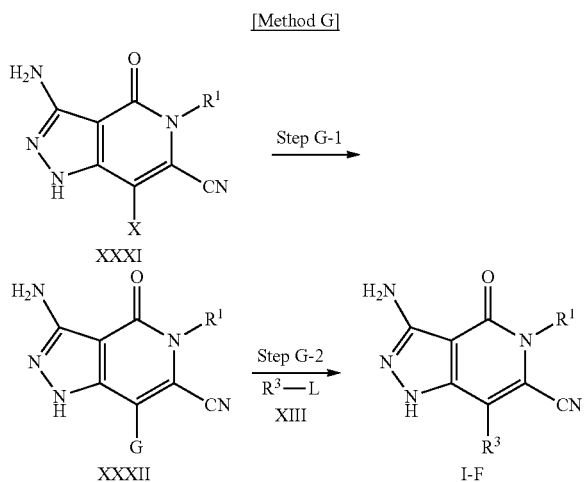

[Method G]

wherein each symbol in the formulas is as defined above.

In this method, compound (XIII) used as a starting material may be a commercially available product, or can also be produced according to a method known per se or a method analogous thereto.

(Step G-1)

This step is a step of subjecting compound (XXXI) obtained according to Method F or a method analogous thereto to a substitution reaction in the presence of a transition metal catalyst to convert compound (XXXI) to compound (XXXII).

The reaction with a transition metal catalyst can be carried out according to a known method per se [e.g., Chemical Reviews, 1995, vol. 95, page 2457 and the like], for example, using 4,4,4',4',5,5,5',5'-octamethyl-2,2'-bi-1,3,2-dioxaborolane, in the presence of a transition metal catalyst and a base, in a solvent that does not adversely influence the reaction.

The amount of the 4,4,4',4',5,5,5',5'-octamethyl-2,2'-bi-1,3,2-dioxaborolane to be used is about 1 mol-about 100 mol, preferably about 1 mol-about 10 mol, per 1 mol of compound (XXXI).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst.

While the amount of the catalyst to be used varies depending on the kind of the transition metal catalyst, it is generally about 0.0001 mol-about 1 mol, preferably about 0.01 mol-about 0.5 mol, per 1 mol of compound (XXXI). The amount of the ligand or cocatalyst to be used is generally about 0.0001 mol-about 4 mol, preferably about 0.01 mol-about 2 mol, per 1 mol of compound (XXXI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XXXI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXXII) can be isolated and purified by a known separation and purification means, for example, concentration, concentrated under reduced pressure, solvent extraction, crystallization, recrystallization, phase transfer, chromatography and the like. In addition, compound (XXXII) may be directly used without isolation for the next reaction.

(Step G-2)

This step is a step of subjecting compound (XXXII) to a coupling reaction with compound (XIII) and a transition metal catalyst to convert compound (XXXII) to compound (I-F).

The reaction with a transition metal catalyst can be carried out according to a known method per se [e.g., Chemical Reviews, 1995, vol. 95, page 2457 and the like], for example, in the presence of a transition metal catalyst and a base, in a solvent that does not adversely influence the reaction.

The amount of compound (XIII) to be used is about 1 mol-about 100 mol, preferably about 1 mol-about 10 mol, per 1 mol of compound (XXXII).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II) etc.), nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol-about 1 mol, preferably about 0.01 mol-about 0.5 mol, per 1 mol of compound (XXXII). The amount of the ligand or cocatalyst to be used is generally about 0.0001 mol-about 4 mol, preferably about 0.01 mol-about 2 mol, per 1 mol of compound (XXXII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XXXII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-F) can be isolated and purified by a known separation and purification means, for example, concentration, concentrated under reduced pressure, solvent extraction, crystallization, recrystallization, phase transfer, chromatography and the like.

Alternatively, compound (I-A) can also be produced according to the following Method H.

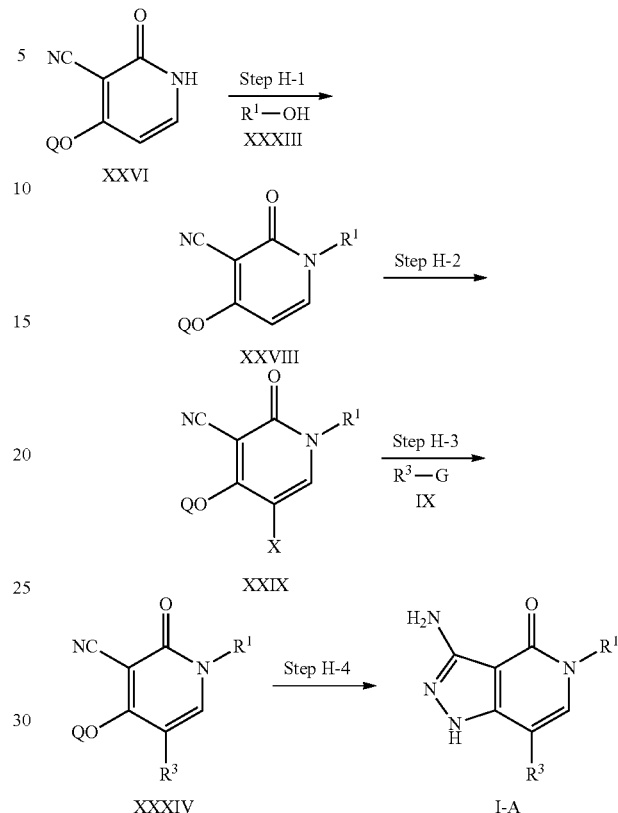

wherein each symbol in the formulas is as defined above.

In this method, compound (XXVI) and compound (XXXIII) used as starting materials may be a commercially available product, or can also be produced according to a method known per se or a method analogous thereto. In each step in the production methods, the starting compound may be in the form of a salt. Examples of the salt include those similar to the salt of compound (I).

(Step H-1)

This step is a step of reacting compound (XXVI) with compound (XXXIII) to convert compound (XXVI) to compound (XXVIII). This reaction can be carried out according to a method known per se, for example, a method described in Synthesis, page 1 (1981) and the like, or method analogous thereto. To be specific, this reaction is carried out in the presence of an organophosphorous compound and an electrophilic agent, in a solvent that does not adversely influence the reaction.

Examples of the organophosphorous compound include triphenylphosphine, tributylphosphine and the like.

Examples of the electrophilic agent include diethyl azodicarboxylate, diisopropyl azodicarboxylate, azodicarbonyldipiperazine, bis(2-methoxyethyl) azodicarboxylate and the like.

The amount of the organophosphorous compound and electrophilic agent to be used is each about 0.1 mol-about 100 mol, preferably about 1 mol-about 10 mol, relative to compound (XXVI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXVIII) can be isolated and purified by a known separation and purification means, for example, concentration, concentrated under reduced pressure, solvent extraction, crystallization, recrystallization, phase transfer, chromatography and the like. In addition, compound (XXVIII) may be directly used without isolation for the next reaction.

(Step H-2)

This step is a step of subjecting compound (XXVIII) to a substitution reaction with a halogenating agent to convert compound (XXVIII) to compound (XXIX).

This step can be performed, where necessary, in a solvent that does not adversely influence the reaction.

Examples of the halogenating agent to be used include bromine, iodine, N-bromosuccinimide, N-iodosuccinimide and the like. Where necessary, an acid (hydrobromic acid, hydrochloric acid, trifluoroacetic acid etc.) may be added.

The amount of the halogenating agent to be used is about 0.1 mol-about 100 mol per 1 mol of compound (XXVIII). The amount of the acid to be used is about 0.000001 mol-about 100 mol per 1 mol of compound (XXVIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXIX) can be isolated and purified by a known separation and purification means, for example, concentration, concentrated under reduced pressure, solvent extraction, crystallization, recrystallization, phase transfer, chromatography and the like. In addition, compound (XXIX) may be directly used without isolation for the next reaction.

(Step H-3)

This step is a step of subjecting compound (XXIX) to a coupling reaction with compound (IX) and a transition metal catalyst to convert compound (XXIX) to compound (XXXIV).

The reaction with a transition metal catalyst can be carried out according to a known method per se [e.g., Chemical Reviews, 1995, vol. 95, page 2457 and the like], for example, in the presence of a transition metal catalyst and a base, in a solvent that does not adversely influence the reaction.

The amount of compound (IX) to be used is about 1 mol-about 100 mol, preferably about 1 mol-about 10 mol, per 1 mol of compound (XXIX).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II)) and the like, nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, and a metal oxide (e.g., copper oxide, silver oxide etc.) may be used as a co-catalyst. While the amount of the transition metal catalyst to be used varies depending on the kinds of the catalyst, it is generally about 0.0001 mol-about 1 mol, preferably about 0.01 mol-about 0.5 mol, per 1 mol of compound (XXIX). The amount of the ligand or cocatalyst to be used is generally about 0.0001 mol-about 4 mol, preferably about 0.01 mol-about 2 mol, per 1 mol of compound (XXIX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium-tert-butoxide, potassium-tert-butoxide etc.), alkali disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XXIX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXXIV) can be isolated and purified by a known separation and purification means, for example, concentration, concentrated under reduced pressure, solvent extraction, crystallization, recrystallization, phase transfer, chromatography and the like. In addition, compound (XXXIV) may be directly used without isolation for the next reaction.

(Step H-4)

This step is a step of reacting compound (XXXIV) with hydrazine or a salt thereof or a hydrate thereof to convert compound (XXXIV) to compound (I-A).

This step can be performed, where necessary, in a solvent that does not adversely influence the reaction.

The amount of the hydrazine or a salt thereof or a hydrate thereof to be used is about 1 mol-about 100 mol, preferably about 1 mol-about 10 mol, per 1 mol of compound (XXXIV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I-A) can be isolated and purified by a known separation and purification means, for example, concentration, concentrated under reduced pressure, solvent extraction, crystallization, recrystallization, phase transfer, chromatography and the like.

Compounds (XXVIII), (XXIX) and (XXIV) obtained according to the above-mentioned Method H can also be modified by subjecting to a known reaction such as condensation reaction (e.g. various acylation reaction, alkylation reaction etc.), Sandmeyer reaction, oxidation reaction, reduction reaction and the like. Such reaction can be carried out according to a known method per se.

Alternatively, compound (XI) can also be produced according to the following Method I.

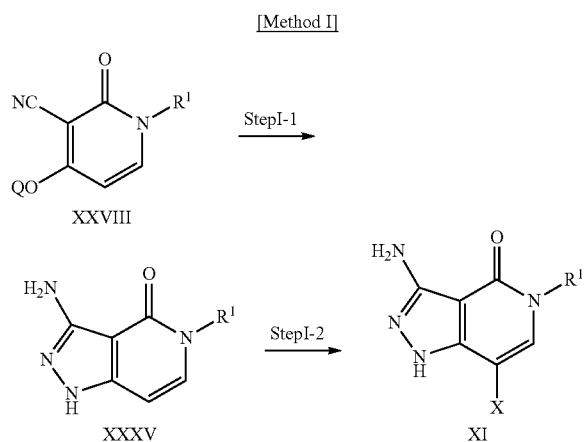

[Method I]

wherein each symbol in the formulas is as defined above.

In this method, compound (XXVIII) used as a starting material may be a commercially available product, or can also be produced according to a method known per se or a method analogous thereto. In each step in the production methods, the starting compound may be in the form of a salt. Examples of the salt include those similar to the salt of compound (I).

(Step I-1)

This step is a step of reacting compound (XXVIII) obtained according to Method H or a method analogous thereto with hydrazine or a salt thereof or a hydrate thereof to convert compound (XXVIII) to compound (XXXV).

This step can be performed, where necessary, in a solvent that does not adversely influence the reaction.

The amount of the hydrazine or a salt thereof or a hydrate thereof to be used is about 1 mol-about 100 mol, preferably about 1 mol-about 10 mol, per 1 mol of compound (XXVIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XXXV) can be isolated and purified by a known separation and purification means, for example, concentration, concentrated under reduced pressure, solvent extraction, crystallization, recrystallization, phase transfer, chromatography and the like. In addition, compound (XXXV) may be directly used without isolation for the next reaction.

(Step I-2)

This step is a step of subjecting compound (XXXV) to a substitution with a halogenating agent to convert compound (XXXV) to compound (XI).

Examples of the halogen atom for X include a bromine atom, an iodine atom and the like.

This step can be performed, where necessary, in a solvent that does not adversely influence the reaction.

Examples of the halogenating agent to be used include bromine, iodine, N-bromosuccinimide, N-iodosuccinimide and the like. Where necessary, an acid (hydrobromic acid, hydrochloric acid, trifluoroacetic acid etc.) may be added.

The amount of the halogenating agent to be used is about 0.1 mol-about 100 mol per 1 mol of compound (XXXV). The amount of the acid to be used is about 0.000001 mol-about 100 mol per 1 mol of compound (XXXV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoroamide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (XI) can be isolated and purified by a known separation and purification means, for example, concentration, concentrated under reduced pressure, solvent extraction, crystallization, recrystallization, phase transfer, chromatography and the like. In addition, compound (XI) may be directly used without isolation for the next reaction.

Compounds (I-A), (VII) and (X) obtained according to the above-mentioned Method A, compound (XI) obtained according to the above-mentioned Method B, compounds (I-D) and (XXV) obtained according to the above-mentioned Method D, and compound (I-F) obtained according to the above-mentioned Method F or the above-mentioned Method G can also be modified by subjecting to a known reaction such as condensation reaction (e.g. various acylation reaction, alkylation reaction etc.), oxidation reaction, reduction reaction and the like. Such reaction can be carried out according to a known method per se.

The compound (I) obtained according to the above-mentioned Methods can be isolated and purified by a known separation means such as recrystallization, distillation, chromatography and the like.

When compound (I) has an optical isomer, a stereoisomer, a regioisomer or a rotamer, these are also encompassed in compound (I), and can be obtained as a single product according to a synthesis method and separation method known per se (e.g., concentration, solvent extraction, column chromatography, recrystallization etc.). For example, when compound (I) has an optical isomer, the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0-50° C., preferably 0-20° C.) not higher than the dissolution-temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a medicament.

In the present specification, specific optical rotation ([α]D) means a specific optical rotation measured using, for example, polarimeter (JASCO, P-1030 Polarimeter (No.AP-2)) and the like.

In the present specification, the melting point means a melting point measured using, for example, a micro melting point determination apparatus (YANACO, MP-500D), a DSC (differential scanning calorimetry) apparatus (SEIKO, EXSTAR6000) or the like.

Compound (I) may be used as a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include
(1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation or cyclopropylcarbonylation, and the like);
(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);
(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like)
and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

Compound (I) also encompasses a compound labeled with an isotope (e.g., $^3H$, $^{14}C$, $^{35}S$, $^{125}I$ etc.) and the like.

Compound (I) also encompasses a deuterium conversion form wherein $^1H$ is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

Since the compound of the present invention have superior Tyk2 inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for Tyk2 associated diseases, more specifically, the diseases described in (1)-(4) (especially, (2)) below.

(1) inflammatory diseases (e.g., acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis etc.),
(2) autoimmune diseases (e.g., psoriasis, rheumatoid arthritis, inflammatory bowel disease (e.g., Crohn's disease, ulcerative colitis etc.), Sjogren's syndrome, Behcet's disease, multiple sclerosis, systemic lupus erythematosus, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, graft versus host disease, Addison's disease, abnormal immunoresponse, arthritis, dermatitis, radiodermatitis etc.)(especially, psoriasis, rheumatoid arthritis, inflammatory bowel disease, Sjogren's syndrome, Behcet's disease, multiple sclerosis and systemic lupus erythematosus),
(3) osteoarticular degenerative disease (e.g., rheumatoid arthritis, osteoporosis, osteoarthritis etc.),
(4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., mucinous adenocarcinoma, adenosquamous carcinoma etc.), papillary adenocarcinoma, breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary).

The medicament of the present invention can be preferably used as an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.), inflammatory disease, osteoarticular degenerative disease or neoplastic disease, Particularly preferably psoriasis, rheumatoid arthritis, inflammatory bowel disease (preferably Crohn's disease or ulcerative colitis), Sjogren's syndrome, Behcet's disease, multiple sclerosis, or systemic lupus erythematosus.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. The dose varies depending on administration subject, administration route, disease and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (compound (I)) can be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, bin ding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as a Tyk2 inhibitor, IL-12 or IL-23 inhibitor, it can be used in combination with the following drugs.

(1) Non-Steroidal Anti-Inflammatory Drug (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

(ii) cyclooxygenase inhibitor (COX-1 selective inhibitor, COX-2 selective inhibitor etc.)
salicylic acid derivatives (e.g., celecoxib, aspirin), etoricoxib, valdecoxib, diclofenac, indomethacin, loxoprofen and the like.

(iii) nitric oxide-releasing NSAIDs.
(iv) JAR inhibitor
tofacitinib, ruxolitinib and the like.

(2) Disease-Modifying Anti-Rheumatic Drugs (DMARDs)
(i) Gold preparation
auranofin and the like.
(ii) penicillamine
D-penicillamine and the like.
(iii) aminosalicylic acid preparation
sulfasalazine, mesalazine, olsalazine, balsalazide and the like.
(iv) antimalarial drug
chloroquine and the like.
(v) pyrimidine synthesis inhibitor
leflunomide and the like.
(vi) prograf (3) Anti-Cytokine Drug
(I) Protein Drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.

(II) Non-Protein Drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.

(4) Integrin Inhibitor
natalizumab, vedolizumab, AJM300, TRK-170, E-6007 and the like.

(5) Immunomodulator (Immunosuppressant)
methotrexate, cyclophosphamide, MX-68, atiprimod dihydrochloride, BMS-188667, CKD-461, rimexolone, cyclosporine, tacrolimus, gusperimus, azathioprine, anti-lymphocyte serum, freeze-dried sulfonated normal immunoglobulin, erythropoietin, colony stimulating factor, interleukin, interferon and the like.

(6) Steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.

(7) Angiotensin Converting Enzyme Inhibitor
enalapril, captopril, ramipril, lisinopril, cilazapril, perindopril and the like.

(8) Angiotensin II Receptor Antagonist
candesartan, candesartan cilexetil, azilsartan, azilsartan medoxomil, valsartan, irbesartan, olmesartan, eprosartan and the like.

(9) Diuretic Drug
hydrochlorothiazide, spironolactone, furosemide, indapamide, bendrofluazide, cyclopenthiazide and the like.

(10) Cardiotonic Drug
digoxin, dobutamine and the like.

(11) β Receptor Antagonist
carvedilol, metoprolol, atenolol and the like.

(12) Ca Sensitizer
MCC-135 and the like.

(13) Ca Channel Antagonist
nifedipine, diltiazem, verapamil and the like.

(14) Anti-Platelet Drug, Anticoagulator
  heparin, aspirin, warfarin and the like.
(15) HMG-CoA Reductase Inhibitor
  atorvastatin, simvastatin and the like.
(16) Contraceptive
(i) sex hormone or derivatives thereof
  gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
  ormeloxifene, mifepristone, Org-33628 and the like.
(iii) spermatocide
  ushercell and the like.
(17) Others
(i) T cell inhibitors
(ii) inosine monophosphate dehydrogenase (IMPDH) inhibitor
  mycophenolate mofetil and the like.
(iii) adhesion molecule inhibitor
  ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
  V-85546 and the like.
(vii) glucose-6-phosphate dehydrogenase inhibitor
(viii) Dihydroorotate dehydrogenase (DHODH) inhibitor
(ix) phosphodiesterase IV(PDE IV) inhibitor
  roflumilast, CG-1088 and the like.
(x) phospholipase $A_2$ inhibitor
(xi) iNOS inhibitor
  VAS-203 and the like.
(xii) microtubule stimulating drug
  paclitaxel and the like.
(xiii) microtuble inhibitor
  reumacon and the like.
(xiv) MHC class II antagonist
(xv) prostacyclin agonist
  iloprost and the like.
(xvi) CD4 antagonist
  zanolimumab and the like.
(xvii) CD23 antagonist
(xviii) LTB4 receptor antagonist
  DW-1305 and the like.
(xix) 5-lipoxygenase inhibitor
  zileuton and the like.
(xx) cholinesterase inhibitor
  galanthamine and the like.
(xxi) tyrosine kinase inhibitor
  Tyk2 inhibitor (WO2010142752) and the like.
(xxii) cathepsin B inhibitor
(xxiii) adenosine deaminase inhibitor
  pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
  synvisc (hylan G-F 20), orthovisc and the like.
(xxix) glucosamine sulfate
(xxx) amiprilose
(xxxi) CD-20 inhibitor
  rituximab, ibritumomab, tositumomab, ofatumumab and the like.
(xxxii) BAFF inhibitor
  belimumab, tabalumab, atacicept, A-623 and the like.
(xxxiii) CD52 inhibitor
  alemtuzumab and the like.
(xxxiv) IL-17 inhibitor
  secukinumab (AIN-457), LY-2439821, AMG827 and the like Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, antipruritic drug, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent
(i) sulfa drug
  sulfamethizole, sulfisoxazole, sulfamonomethoxine, sulfamethizole, salazosulfapyridine, silver sulfadiazine and the like.
(ii) quinolone antibacterial agent
  nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
  isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
  diaphenylsulfone, rifampicin and the like.
(v) antiviral drug
  idoxuridine, acyclovir, vidarabine, gancyclovir and the like.
(vi) anti-HIV agent
  zidovudine, didanosine, zalcitabine, indinavir sulfate ethanolate, ritonavir and the like.
(vii) antispirochetele
(viii) antibiotic
  tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxyl)phenyl]-3(2H,4H)-1,2,4-triazolone, fluconazole, itraconazole and the like] and the like.

(2) Antifungal Agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) Antiprotozoal Agent
metronidazole, tinidazole, diethylcarbamazine citrate, quinine hydrochloride, quinine sulfate and the like.

(4) Antitussive and Expectorant Drug
ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative
chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic
(6-1) Local Anesthetic
cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.
(6-2) General Anesthetic
(i) inhalation anesthetic (e.g., ether, halothane, nitrous oxide, isoflurane, enflurane),
(ii) intravenous anesthetic (e.g., ketamine hydrochloride, droperidol, thiopental sodium, thiamylal sodium, pentobarbital) and the like.

(7) Antiulcer Drug
histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) Antiarrhythmic Agent
(i) sodium channel blocker (e.g., quinidine, procainamide, disopyramide, ajmaline, lidocaine, mexiletine, phenytoin),
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone),
(iv) calcium channel blacker (e.g., verapamil, diltiazem) and the like.

(9) Hypotensive Diuretic Drug
hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant
heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer
diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic
chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug
6-O-(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug
clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) Muscle Relaxant
pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug
phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) Antidepressant
imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac Stimulants trans-π-oxocamphor, terephyllol, aminophylline, etilefrine, dopamine, dobutamine, denopamine, aminophylline, vesnarinone, amrinone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine denopamine and the like.

(22) Hypotensive Diuretic hexamethonium bromide, pentolinium, mecamylamine, ecarazine, clonidine, diltiazem, nifedipine and the like.

(23) Therapeutic Drug for Diabetes tolbutamide, chlorpropamide, acetohexamide, glibenclamide, tolazamide, acarbose, epalrestat, troglitazone, glucagon, glymidine, glipuzide, phenformin, buformin, metformin and the like.

(24) Antinarcotic levallorphan, nalorphine, naloxone or a salt thereof and the like.

(25) Liposoluble Vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) Vitamin Derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranikast hydrate, seratrodast, dexamethasone, prednisolone, hydrocortisone, hydrocortisone sodium succinate, beclometasone dipropionate and the like.

(28) Therapeutic Agent for Pollakisuria/Anischuria flavoxate hydrochloride and the like.

(29) Therapeutic Agent for Atopic Dermatitis sodium cromoglicate and the like.

(30) Therapeutic Agent for Allergic Rhinitis sodium cromoglicate, chlorpheniramine maleate, alimemazine tartrate, clemastine fumarate, homochlorcyclizine hydrochloride, fexofenadine, mequitazine and the like.

(31) Hypertensor dopamine, dobutamine, denopamine, digitoxin, digoxin, methyldigoxin, lanatoside C, G-strophanthin and the like.

(32) Others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with inflammatory bowel disease (IBD), about 0.1 mg/kg body weight-about 30 mg/kg body weight, preferably about 1 mg/kg body weight-20 mg/kg body weight, of compound (I) can be administered once to several portions per day.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Reference Examples, Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, basic silica gel means use of aminopropylsilane-bound silica gel. In HPLC (high performance liquid chromatography), C18 means use of octadecyl-bound silica gel. The ratios of elution solvents are volume mixing ratios, unless otherwise specified.

In Examples and Experimental Examples, the following abbreviations are used.
BSA: bovine serum albumin
DMSO: dimethyl sulfoxide
DTT: dithiothreitol
EDTA: ethylenediaminetetraacetic acid
EGTA: glycoletherdiaminetetraacetic acid
HEPES: 4-(2-hydroxyethyl)-1-piperazine ethanesulfonic acid
TsOH: p-toluenesulfonic acid (tosyl acid)
M: mol concentration $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As ionization method, ESI (Electro Spray Ionization) method or APCI (Atomospheric Pressure Chemical Ionization) method was used. The data indicates those found. Generally, a molecular ion peak is observed. In the case of a salt, a molecular ion peak or fragment ion peak of free form is generally observed.

Reference Example 1

2-bromo-5-(3-methoxyazetidin-1-yl)pyridine

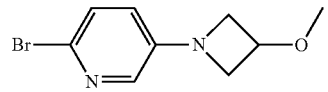

A mixture of 2-bromo-5-iodopyridine (1.00 g), 3-methoxyazetidine hydrochloride (0.435 g), tris(dibenzylideneacetone)dipalladium(0) (0.106 g), 4,5-bis(diphenylphosphino)-9,9-dimethylxanthene (0.204 g), sodium tert-butoxide (0.846 g), 1,8-diazabicyclo[5.4.0]undec-7-ene (0.531 mL) and toluene (30 mL) was stirred at room temperature for 3 days under argon atmosphere. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (basic silica gel, ethyl acetate/hexane) to give the title compound (625.1 mg).

MS(ESI+): [M+H]$^+$243.1.

Reference Example 2

4-(6-bromopyridin-3-yl)thiomorpholine 1,1-dioxide

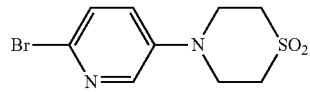 [SMILES: O=S1(=O)CCN(c2ccc(Br)nc2)CC1]

The title compound was obtained from 2-bromo-5-iodopyridine and thiomorpholine 1,1-dioxide in the same manner as in Reference Example 1.

MS(ESI+): [M+H]$^+$290.9.

Reference Example 3

2-bromo-5-(4-methoxypiperidin-1-yl)pyridine

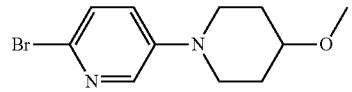

The title compound was obtained from 2-bromo-5-iodopyridine and 4-methoxypiperidine in the same manner as in Reference Example 1.

MS(ESI+): [M+H]$^+$271.1.

Reference Example 4 tert-butyl(2-((6-bromopyridin-3-yl)oxy)ethyl)carbamate

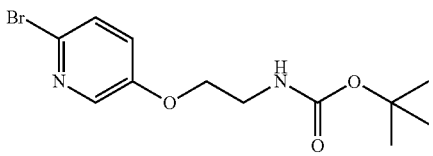 [SMILES: CC(C)(C)OC(=O)NCCOc1ccc(Br)nc1]

A mixture of 6-bromopyridin-3-ol (1.50 g), tert-butyl(2-bromoethyl)carbamate (2.32 g), cesium carbonate (3.65) and N,N-dimethylformamide (30 mL) was stirred at 40° C. for 20 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (2.47 g).

MS(ESI+): [M+H]$^+$317.2.

Reference Example 5

2-((6-bromopyridin-3-yl)oxy)ethanamine dihydrochloride

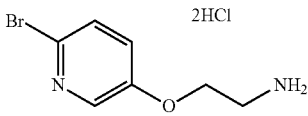 [SMILES: NCCOc1ccc(Br)nc1]

To a solution of tert-butyl(2-((6-bromopyridin-3-yl)oxy) ethyl)carbamate obtained in Reference Example 4 (1.20 g) in ethanol (25 mL) was added a 4M solution of hydrogen chloride in ethyl acetate (10 mL) at room temperature. The mixture was stirred at room temperature for 3 days, and the solvent was evaporated under reduced pressure. To the residue was added ethanol, the solvent was evaporated under reduced pressure, and the precipitated solid was collected by filtration to give the title compound (1.09 g).

MS(ESI+): [M+H]$^+$217.1.

Reference Example 6

N-(2-((6-bromopyridin-3-yl)oxy)ethyl)acetamide

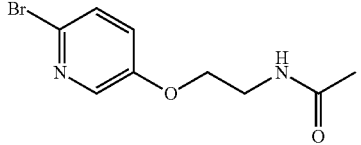

To a mixture of 2-((6-bromopyridin-3-yl)oxy)ethanamine dihydrochloride obtained in Reference Example 5 (1.00 g), pyridine (1.12 mL) and tetrahydrofuran (20 mL) was added dropwise acetyl chloride (0.368 mL) at 0° C. The reaction mixture was stirred at room temperature for 5 hr, aqueous sodium hydrogen carbonate solution was added thereto, and the mixture was extracted with ethyl acetate. The extract was washed with water and saturated brine, and dried over anhydrous sodium sulfate, and the solvent was evaporated under reduced pressure. The precipitated solid was collected by filtration, and washed with diisopropyl ether to give the title compound (0.792 g).

MS(ESI+): [M+H]$^+$259.0.

Reference Example 7

(3S)-4-(6-bromopyridin-3-yl)-3-methylmorpholine

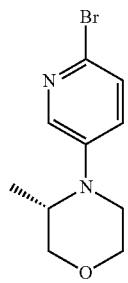

A mixture of 2-bromo-5-iodopyridine (500 mg), (3S)-methylmorpholine tosylate (534 mg), sodium tert-butoxide (599 mg), tris(dibenzylideneacetone)dipalladium(0) (49 mg) and 4,5-bis(diphenylphosphino)-9,9-dimethylxanthene (105 mg) in toluene (15 mL) was stirred at room temperature for 19 hr. Sodium tert-butoxide (85 mg), tris(dibenzylideneacetone)dipalladium(0) (49 mg) and 4,5-bis(diphenylphosphino)-9,9-dimethylxanthene (105 mg) were added thereto, and the mixture was stirred at 80° C. for 31.5 hr. To the reaction mixture was added water, and the mixture was extracted with ethyl acetate. The obtained organic layer was washed with saturated brine, and dried over anhydrous sodium sulfate, and the solvent was evaporated under reduced pressure. The residue was purified by silica gel column chromatography (hexane/ethyl acetate) to give the title compound (148 mg).

MS(ESI+): [M+H]$^+$256.9.

Reference Example 8

(3R)-4-(6-bromopyridin-3-yl)-3-methylmorpholine

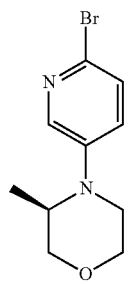

A mixture of 2-bromo-5-iodopyridine (490 mg), (3R)-methylmorpholine tosylate (496 mg), sodium tert-butoxide (666 mg), tris(dibenzylideneacetone)dipalladium(0) (49 mg) and 4,5-bis(diphenylphosphino)-9,9-dimethylxanthene (103 mg) in toluene (20 mL) was stirred at 70° C. for 5.5 hr. To the reaction mixture was added water, and the mixture was extracted with ethyl acetate. The obtained organic layer was washed with saturated brine, and dried over anhydrous sodium sulfate, and the solvent was evaporated under reduced pressure. The residue was purified by silica gel column chromatography (hexane/ethyl acetate) to give the title compound (289 mg).

MS(ESI+): [M+H]$^+$256.9.

Reference Example 9

1-((6-bromopyridin-3-yl)oxy)-2-methylpropan-2-ol

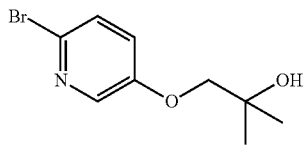

The title compound was obtained from 6-bromopyridin-3-ol and 2,2-dimethyloxirane in the same manner as in Reference Example 4.

MS(ESI+): [M+H]$^+$246.1.

Reference Example 10

4-(6-bromopyridin-3-yl)tetrahydro-2H-pyran-4-ol

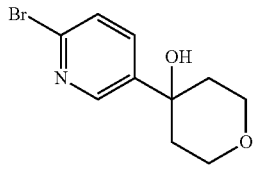 [SMILES: OC1(c2ccc(Br)nc2)CCOCC1]

To a suspension of 2-bromo-5-iodopyridine (2.00 g) in tetrahydrofuran (20 mL) and diethyl ether (10 mL) was added dropwise 1.6M n-butyllithium hexane solution (4.40 mL) at −78° C. The mixture was stirred at −78° C. for 30 min under argon atmosphere, and a solution of tetrahydro-4H-pyran-4-one (0.651 mL) in tetrahydrofuran (10 mL) was added dropwise thereto at −78° C. The reaction mixture was slowly warmed to −50° C., aqueous ammonium chloride solution was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (ethyl acetate/hexane) to give the title compound (0.932 g).

MS(ESI+): [M+H]$^+$258.1.

Reference Example 11

2-(2-chloropyridin-4-yl)-1-(morpholin-4-yl)ethanone

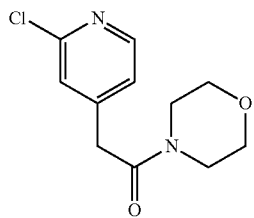 [SMILES: O=C(Cc1ccnc(Cl)c1)N1CCOCC1]

A solution of (2-chloropyridin-4-yl)acetic acid (300 mg), 1-hydroxybenzotriazole (284 mg), triethylamine (0.487 mL), morpholine (0.183 mL) and 1-ethyl-3-(3-dimethylaminopropyl)carbodiimide hydrochloride (469 mg) in N,N-dimethylformamide (10 mL) was stirred at room temperature for 18 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (239 mg).

MS(ESI+): [M+H]$^+$241.2.

Reference Example 12

2-(2-chloropyridin-4-yl)-1-(4-hydroxypiperidin-1-yl)ethanone

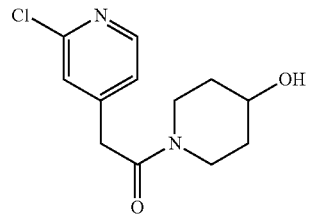 [SMILES: O=C(Cc1ccnc(Cl)c1)N1CCC(O)CC1]

The title compound was obtained from (2-chloropyridin-4-yl)acetic acid and piperidin-4-ol in the same manner as in Reference Example 11.

MS (ESI+): [M+H]$^+$255.2.

Reference Example 13

2-(2-chloropyridin-4-yl)-N-(oxetan-3-yl)acetamide

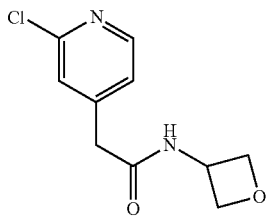 [SMILES: O=C(Cc1ccnc(Cl)c1)NC1COC1]

The title compound was obtained from (2-chloropyridin-4-yl)acetic acid and oxetan-3-amine in the same manner as in Reference Example 11.

MS (ESI+): [M+H]$^+$227.2.

Reference Example 14

2-(2-chloropyridin-4-yl)-N,N-dimethylacetamide

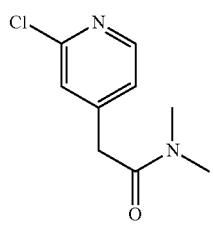

The title compound was obtained from (2-chloropyridin-4-yl)acetic acid and dimethylamine hydrochloride in the same manner as in Reference Example 11.

MS (ESI+): [M+H]$^+$199.2.

Reference Example 15

1-(2-((2-chloropyridin-4-yl)oxy)ethyl)pyrrolidin-2-one

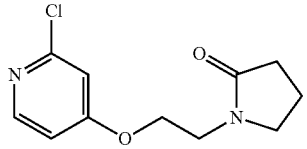 [SMILES: O=C1CCCN1CCOc1ccnc(Cl)c1]

The title compound was obtained from 2-chloropyridin-4-ol and 1-(2-hydroxyethyl)pyrrolidin-2-one in the same manner as in Step A of Example 163.

MS (ESI+): [M+H]$^+$241.1.

Reference Example 16

1-((2-chloropyridin-4-yl)oxy)-2-methylpropan-2-ol

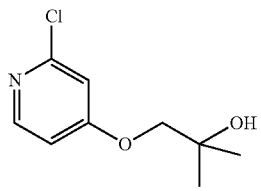

The title compound was obtained from 2-chloropyridin-4-ol and 2,2-dimethyloxirane in the same manner as in Reference Example 4.

MS (ESI+): [M+H]$^+$202.2.

Reference Example 17

4-(2-chloropyridin-4-yl)tetrahydro-2H-pyran-4-ol

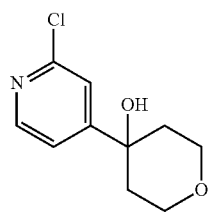 [SMILES: OC1(c2ccnc(Cl)c2)CCOCC1]

The title compound was obtained from 2-chloro-4-iodopyridine and tetrahydro-4H-pyran-4-one in the same manner as in Step A of Reference Example 10.

MS (ESI+): [M+H]$^+$214.1.

Reference Example 18

N-(6-bromopyridin-2-yl)formamide

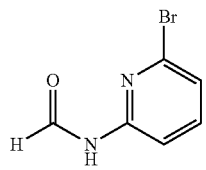

To acetic anhydride (1.5 mL) was added dropwise formic acid (0.73 mL) under ice-cooling, and the mixture was stirred at 55° C. for 45 min. The mixture was allowed to be warmed to room temperature, tetrahydrofuran (20 mL) was added thereto, and a solution of 6-bromopyridin-2-amine (1.00 g) in tetrahydrofuran (10 mL) was added dropwise thereto over 3 min under ice-cooling. The reaction mixture was stirred at room temperature for 1.5 hr. The reaction solution was concentrated under reduced pressure, and the obtained white solid was subjected to azeotropy with toluene, and washed with hexane to give the title compound (1.1 g).

MS (ESI+): [M+H]$^+$201.1.

Reference Example 19

1-(6-bromopyridin-2-yl)-N-(2,4-dimethoxybenzyl)methanamine

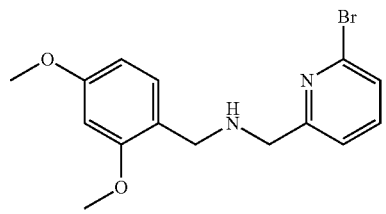 [SMILES: COc1ccc(CNCc2cccc(Br)n2)c(OC)c1]

6-Bromopicoline aldehyde (0.520 g) and 2,4-dimethoxybenzylamine (0.504 mL) were dissolved in tetrahydrofuran (25 mL), acetic acid (0.176 mL) was added thereto, and the mixture was stirred at room temperature for 1 hr. Sodium triacetoxyborohydride (889 mg) was added thereto, and the mixture was stirred in a second straight night at room temperature. To the reaction mixture was added saturated aqueous sodium hydrogen carbonate solution, and the mixture was extracted with ethyl acetate. The organic layer was washed with saturated brine, and dried over anhydrous magnesium sulfate, and the solvent was evaporated under reduced pressure. The residue was purified by silica gel column chromatography (hexane/ethyl acetate) to give the title compound (930 mg).

MS (ESI+): [M+H]$^+$337.1.

Reference Example 20

N-((6-bromopyridin-2-yl)methyl)-N-(2,4-dimethoxybenzyl)formamide

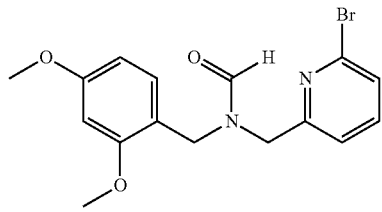 [SMILES: COc1ccc(CN(C=O)Cc2cccc(Br)n2)c(OC)c1]

To acetic anhydride (0.703 mL) was added dropwise formic acid (0.349 mL) under ice-cooling, and the mixture was stirred at 55° C. for 45 min. The mixture was allowed to be cooled to room temperature, and tetrahydrofuran (10 mL) was added thereto. A solution of 1-(6-bromopyridin-2-yl)-N-(2,4-dimethoxybenzyl)methanamine obtained in Reference Example 19 (930 mg) in tetrahydrofuran (10 mL) was added dropwise thereto over 3 min under ice-cooling, and the reaction mixture was stirred at room temperature for 30 min. The reaction solution was concentrated under reduced pressure, the obtained colorless oil was subjected to azeotropy with toluene, and the residue was purified by silica gel column chromatography (hexane/ethyl acetate) to give the title compound (932 mg).

NMR (300 MHz, CDCl$_3$) δppm 3.70 (s, 0.75 H), 3.77 (s, 2.25 H), 3.79 (s, 0.75 H), 3.80 (s, 2.25 H), 4.37 (s, 1.5 H), 4.43 (s, 0.5 H), 4.49 (s, 0.5 H), 4.51 (s, 1.5 H), 6.33-6.47 (m, 2 H), 7.06 (d, J=8.1 Hz, 1 H), 7.11-7.21 (m, 1 H), 7.29-7.39 (m, 1 H), 7.40-7.55 (m, 1 H), 8.32 (s, 0.25 H), 8.42 (s, 0.75 H).

Reference Example 21

N-((6-bromopyridin-2-yl)methyl)formamide

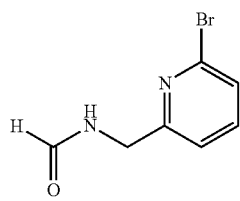 [SMILES: O=CNCc1cccc(Br)n1]

N-((6-Bromopyridin-2-yl)methyl)-N-(2,4-dimethoxybenzyl)formamide obtained in Reference Example 20 (830 mg) and anisole (1.0 mL) were dissolved in formic acid (20 mL), and the solution was stirred at 100% for 8 hr. The mixture was allowed to be cooled to room temperature, and concentrated under reduced pressure. The residue was subjected to azeotropy with toluene, to the residue was added saturated aqueous sodium hydrogen carbonate solution, and the mixture was extracted with ethyl acetate. The organic layer was washed with saturated brine, and dried over anhydrous magnesium sulfate, and the solvent was evaporated under reduced pressure. The obtained residue was purified by silica gel column chromatography (basic silica gel, hexane/ethyl acetate) to give the title compound (279 mg).

MS (ESI+): 215.0.

Reference Example 22

1-(2-((6-chloropyrimidin-4-yl)oxy)ethyl)pyrrolidin-2-one

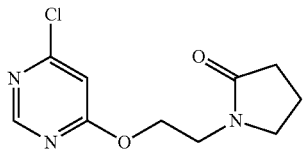

To a solution of 4,6-dichloropyrimidine (600 mg) and 1-(2-hydroxyethyl)-2-pyrrolidinone (0.728 mL) in N,N-dimethylformamide (2 mL) was added sodium hydride (60% oil, 209 mg) under ice-cooling, and the mixture was stirred for 30 min. The reaction mixture was poured into saturated aqueous ammonium chloride solution (10 mL), water (5 mL) was added thereto, and the mixture was extracted with ethyl acetate. The organic layer was washed with, water (10 mL, threetimes) and saturated brine, and dried over anhydrous magnesium sulfate, and the solvent was evaporated under reduced pressure. The obtained pale-yellow oil was purified by silica gel chromatography (hexane/ethyl acetate) to give the title compound (634 mg).

MS(ESI+): [M+H]$^+$242.2.

Reference Example 23

2-bromo-5-((4-methoxybenzyl)oxy)pyrazine

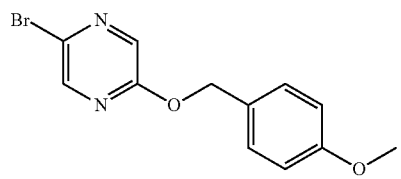 [SMILES: COc1ccc(COc2cnc(Br)cn2)cc1]

The title compound was obtained from 2,5-dibromopyrazine and 4-methoxybenzyl alcohol in the same manner as in Step A of Reference Example 22.

MS (ESI−), found: 173.0.

Reference Example 24

2-chloro-3-((4-methoxybenzyl)oxy)pyrazine

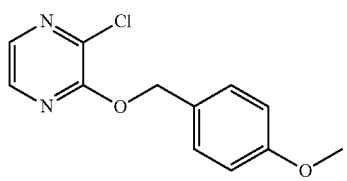 [SMILES: COc1ccc(COc2nccnc2Cl)cc1]

The title compound was obtained from 2,3-dichloropyrazine and 4-methoxybenzyl alcohol in the same manner as in Step A of Reference Example 22.

MS (ESI−), found: 129.1.

Reference Example 25

6-hydroxy-3-(tetrahydro-2H-pyran-4-yl)pyrimidin-4(3H)-one

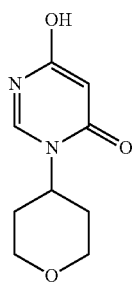 [SMILES: O=c1cc(O)ncn1C1CCOCC1]

A mixture of ethyl formimidate hydrochloride (1.00 g), tetrahydropyran-4-ylamine (1.02 g) and ethanol (10.0 mL) was heated with reflux for 1 hr, and allowed to be cooled to room temperature. The solvent was evaporated under reduced pressure, and the residue was dried. The obtained residue (1.50 g) was dissolved in methanol (15.0 mL). To the solution were added sodium methoxide methanol solution (28%, 3.86 g) and diethyl malonate (1.43 mL) at room temperature, and the mixture was stirred at 40° C. for 14 hr.

The reaction solution was allowed to be cooled to room temperature, and the solvent was evaporated under reduced pressure to give a white residue. The white residue was dissolved in water (10 mL), the solution was acidified with 2M hydrochloric acid, and sodium chloride was added thereto until the solution became saturated. The solution was extracted with a mixed solvent of tetrahydrofuran/ethyl acetate (1:1), and then with a mixed solvent of methanol/ethyl acetate (1:4). The organic layer was washed with saturated brine, and dried over anhydrous magnesium sulfate, and the solvent was evaporated under reduced pressure, and the residue was dried to give the title compound (230 mg).

MS(ESI+): [M+H]$^+$197.2.

Reference Example 26

6-chloro-3-(tetrahydro-2H-pyran-4-yl)pyrimidin-4(3H)-one

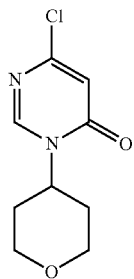

A mixture of 6-hydroxy-3-(tetrahydro-2H-pyran-4-yl)pyrimidin-4(3H)-one obtained in Reference Example 25 (210 mg) and phosphorus oxychloride (6 mL) was stirred at 100° C. for 2 hr. The mixture was allowed to be cooled to room temperature, the solvent was evaporated under reduced pressure, and the residue was subjected to azeotropy with toluene to give a residue. The residue was dissolved in water (10 mL), and the solution was basified with saturated aqueous sodium hydrogen carbonate solution (30 mL) under ice-cooling. The mixture was extracted with ethyl acetate, and the organic layer was washed with saturated brine, and dried over anhydrous magnesium sulfate, and the solvent was evaporated under reduced pressure to give a residue. The residue was purified by chromatography (hexane/ethyl acetate) to give the title compound (125 mg).

MS(ESI+): [M+H]$^+$215.0.

Reference Example 27

4-chloro-6-((4-methoxybenzyl)oxy)pyrimidine

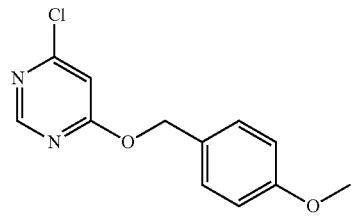 [SMILES: COc1ccc(COc2cc(Cl)ncn2)cc1]

The title compound was obtained from 2,4-dichloropyrimidine and 4-methoxybenzyl alcohol in the same manner as in Step A of Reference Example 22.

MS (ESI−), found: 129.1.

Reference Example 28

2-bromo-5-(4,4-difluoropiperidin-1-yl)pyrazine

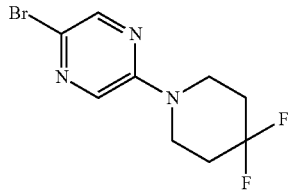 [SMILES: FC1(F)CCN(c2cnc(Br)cn2)CC1]

A solution of 2,5-dibromopyrazine (200 mg), 4,4-difluoropiperidine hydrochloride (132 mg) and cesium carbonate (603 mg) in dimethyl sulfoxide (5 mL) was stirred overnight at 90° C. under nitrogen atmosphere. To the reaction mixture was added water, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (89 mg).

MS(ESI+): [M+H]$^+$277.8.

Reference Example 29

2-chloro-5-((4-methylpiperazin-1-yl)methyl)pyrazine

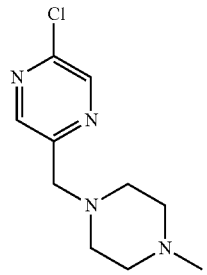

Sodium triacetoxyborohydride (870 mg) was added to a solution of 5-chloropyrazine-2-carbaldehyde (390 mg) and 1-methylpiperazine (0.335 mL) in acetonitrile (10 mL) at 0° C. The reaction mixture was stirred at room temperature for 4 hr. To the reaction mixture was added saturated aqueous sodium hydrogen carbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (basic silica gel, hexane/ethyl acetate) to give the title compound (285 mg).
MS(ESI+): [M+H]$^+$226.8.

Reference Example 30

2-bromo-N-(2-methoxyethyl)-N-methyl-1,3-thiazole-5-carboxamide

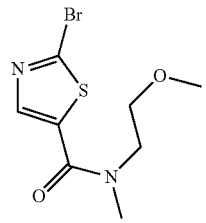

The title compound was obtained from 2-bromo-1,3-thiazole-5-carboxylic acid and 2-methoxy-N-methylethanamine in the same manner as in Step A of Reference Example 11.
MS (ESI+): [M+H]$^+$278.7.

Example 1

3-amino-7-bromo-5-(2-methylphenyl)-1,5-dihydro-4H-pyrazolo[4,3-c]pyridin-4-one

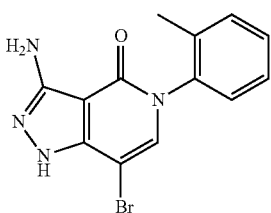 [SMILES: Cc1ccccc1-n1cc(Br)c2[nH]nc(N)c2c1=O]

A) 2-((dimethylamino)methylene)-N-(2-methylphenyl)-3-oxobutanamide

To a mixture of N-(2-methylphenyl)-3-oxobutanamide (10.0 g), potassium carbonate (7.23 g) and N,N-dimethylformamide (130 mL) was added dropwise 1,1-dimethoxy-N,N-dimethylmethanamine (12.5 g) over 30 min at room temperature, and the reaction mixture was stirred at room temperature for 2 hr. The reaction mixture was slowly poured into water, and the mixture was extracted with dichloromethane. The extract was washed with water, and dried over anhydrous magnesium sulfate, and the solvent was evaporated under reduced pressure. The residue was purified by silica gel column chromatography (ethyl acetate/hexane) to give the title compound (10.2 g).
$^1$H NMR (400 MHz, CDCl$_3$) δ 2.32 (3H, s), 2.38 (3H, s), 3.22 (6H, brs), 6.99 (1H, dd, J=7.6, 7.2 Hz), 7.17-7.21 (2H, m), 7.72 (1H, s), 8.13 (1H, d, J=8.0 Hz), 10.60 (1H, brs).

B) 4-chloro-1-(2-methylphenyl)-2-oxo-1,2-dihydropyridine-3-carbaldehyde

Phosphorus oxychloride (15.4 mL) was slowly added to N,N-dimethylformamide (12.8 mL) under ice-cooling, and the reaction mixture was stirred under ice-cooling for 15 min. To the reaction mixture was added a solution of 2-((dimethylamino)methylene)-N-(2-methylphenyl)-3-oxobutanamide obtained in Step A (10.2 g) in N,N-dimethylformamide (100 mL) under ice-cooling, and the mixture was heated at 125° C. for 30 min. The reaction mixture was cooled to room temperature, saturated brine was added thereto, and the mixture was extracted with dichloromethane. The extract was washed with water, and dried over anhydrous sodium sulfate, and the solvent was evaporated under reduced pressure. To the residue were added ethyl acetate and diethyl ether, and the resulting solid was collected by filtration, and washed with diethyl ether to give the title compound (6.00 g).
$^1$H NMR (400 MHz, CDCl$_3$) δ 2.20 (3H, s), 6.41 (1H, d, J=7.6 Hz), 7.18 (1H, d, J=8.0 Hz), 7.33-7.44 (4H, m), 10.40 (1H, s).

C) 4-chloro-3-((hydroxyimino)methyl)-1-(2-methylphenyl)pyridin-2(1H)-one

A mixture of 4-chloro-1-(2-methylphenyl)-2-oxo-1,2-dihydropyridine-3-carbaldehyde obtained in Step B (6.00 g), hydroxylamine hydrochloride (2.53 g), conc. hydrochloric acid (0.0740 mL) and 2-propanol (60 mL) was heated at 100° C. for 2 hr, and the mixture was cooled to room temperature, and concentrated under reduced pressure. To the residue was added ethyl acetate, and the mixture was washed with water and saturated brine, and dried over anhydrous sodium sulfate, and the solvent was evaporated under reduced pressure to give the title compound (6.02 g).
$^1$H NMR (400 MHz, CDCl$_3$) δ 2.15 (3H, s), 6.42 (1H, d, J=7.2 Hz), 7.15 (1H, d, J=8.0 Hz), 7.21 (1H, d, J=7.2 Hz), 7.29-7.42 (3H, m), 8.50 (1H, s).

D) 4-chloro-1-(2-methylphenyl)-2-oxo-1,2-dihydropyridine-3-carbonitrile

To a solution of 4-chloro-3-((hydroxyimino)methyl)-1-(2-methylphenyl)pyridin-2(1H)-one obtained in Step C (6.36 g) in acetonitrile (60 mL) was added phosphorus oxychloride (2.93 mL) at room temperature. The reaction mixture was heated at 90° C. for 1 hr, cooled to room temperature, and poured into ice water. The resulting solid was collected by filtration to give the title compound (3.15 g).

¹H NMR (400 MHz, CDCl₃) δ 2.17 (3H, s), 6.45 (1H, d, = 7.2 Hz), 7.13-7.15 (1H, m), 7.32-7.44 (4H, m).

E) 3-amino-5-(2-methylphenyl)-1,5-dihydro-4H-pyrazolo[4,3-c]pyridin-4-one

To a solution of 4-chloro-1-(2-methylphenyl)-2-oxo-1,2-dihydropyridine-3-carbonitrile obtained in Step D (3.15 g) in ethanol (10 mL) was added hydrazine monohydrate (1.58 mL) at room temperature. The reaction mixture was heated overnight at 90° C., and cooled to room temperature. The reaction mixture was concentrated under reduced pressure, to the residue was added water, and the mixture was extracted with ethyl acetate. The extract was washed with saturated aqueous sodium hydrogen carbonate solution, and dried over anhydrous sodium sulfate, and the solvent was evaporated under reduced pressure to give the title compound (3.14 g).

¹H NMR (400 MHz, CDCl₃) δ 2.18 (3H, s), 4.77 (2H, brs), 6.29 (1H, d, J=7.6 Hz), 6.99 (1H, d, J=7.6 Hz), 7.22 (1H, d, = 7.2 Hz), 7.24-7.36 (3H, m).

F) 3-amino-7-bromo-5-(2-methylphenyl)-1,5-dihydro-4H-pyrazolo[4,3-c]pyridin-4-one To a mixture of 3-amino-5-(2-methylphenyl)-1,5-dihydro-4H-pyrazolo[4,3-c]pyridin-4-one obtained in Step E (200 mg) and acetonitrile (6 mL) was slowly added a solution of N-bromosuccinimide (163 mg) in acetonitrile (2 mL) under ice-cooling. The reaction mixture was stirred overnight at room temperature, and the resulting solid was collected by filtration, and washed with acetonitrile. The obtained solid was purified by silica gel chromatography (methanol/dichloromethane) to give the title compound (127 mg).

MS (ESI+): [M+H]⁺319.2.

Example 2

3-amino-5-(2-methylphenyl)-7-phenyl-1,5-dihydro-4H-pyrazolo[4,3-c]pyridin-4-one

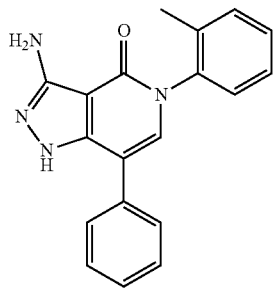 [SMILES: Cc1ccccc1-n1cc(-c2ccccc2)c2[nH]nc(N)c2c1=O]

A) 5-bromo-4-chloro-1-(2-methylphenyl)-2-oxo-1,2-dihydropyridine-3-carbonitrile

To a solution of 4-chloro-1-(2-methylphenyl)-2-oxo-1,2-dihydropyridine-3-carbonitrile obtained in Step D of Example 1 (4.00 g) in N,N-dimethylformamide (33 mL) was added N-bromosuccinimide (3.49 g) at 50° C. The reaction mixture was heated at 50° C. for 6 hr, cooled to room temperature, and diluted with water. The resulting solid was collected by filtration, and washed with acetonitrile. The solid was purified by silica gel column chromatography (ethyl acetate/hexane) to give the title compound (4.30 g).

¹H NMR (400 MHz, CDCl₃) δ 2.19 (3H, s), 7.14-7.16 (1H, m), 7.33-7.45 (3H, m), 7.76 (1H, s).

B) 4-chloro-1-(2-methylphenyl)-2-oxo-5-phenyl-1,2-dihydropyridine-3-carbonitrile A mixture of 5-bromo-4-chloro-1-(2-methylphenyl)-2-oxo-1,2-dihydropyridine-3-carbonitrile obtained in Step A (400 mg), phenylboronic acid (211 mg), tetrakis(triphenylphosphine)palladium(0) (143 mg), aqueous sodium carbonate solution (2 M, 1.24 mL) and 1,2-dimethoxyethane (4.0 mL) was heated with microwave irradiation at 90° C. for 1 hr. The reaction mixture was cooled to room temperature, and water was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (255 mg).

MS (ESI+): [M+H]⁺321.1.

C) 3-amino-5-(2-methylphenyl)-7-phenyl-1,5-dihydro-4H-pyrazolo[4,3-c]pyridin-4-one To a solution of 4-chloro-1-(2-methylphenyl)-2-oxo-5-phenyl-1,2-dihydropyridine-3-carbonitrile obtained in Step B (255 mg) in ethanol (1.6 mL) was added hydrazine monohydrate (59.7 mg) at room temperature. The reaction mixture was heated at 70° C. for 2 hr, and cooled to room temperature, water was added thereto, and the mixture was extracted with ethyl acetate. The extract was dried over anhydrous magnesium sulfate, and the solvent was evaporated under reduced pressure. The residue was purified by thin layer silica gel chromatography (methanol/dichloromethane) to give the title compound (67.0 mg).

MS (ESI+): [M+H]⁺317.3.

Example 3

3-amino-5-(2-methylphenyl)-7-(pyridin-2-yl)-1,5-dihydro-4H-pyrazolo[4,3-c]pyridin-4-one

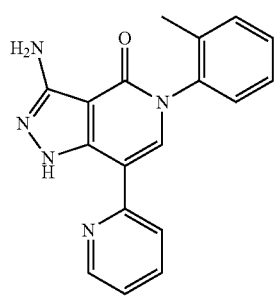 [SMILES: Cc1ccccc1-n1cc(-c2ccccn2)c2[nH]nc(N)c2c1=O]

A mixture of 3-amino-7-bromo-5-(2-methylphenyl)-1,5-dihydro-4H-pyrazolo[4,3-c]pyridin-4-one obtained in Step F of Example 1 (130 mg), 4,4,4',4',5,5,5',5'-octamethyl-2,2'-bi-1,3,2-dioxaborolane (114 mg), (1,1'-bis(diphenylphosphino)ferrocene)dichloropalladium(II) (14.9 mg), potassium acetate (80.0 mg) and N,N-dimethylformamide (2.0 mL) was heated with microwave irradiation at 110° C. for 7 hr. The reaction mixture was cooled to room temperature, and 2-bromopyridine (111 mg), aqueous sodium carbonate solution (2 M, 0.350 mL) and tetrakis(triphenylphosphine)palladium(0) (40.4 mg) were added thereto. The reaction mixture was heated with microwave irradiation at 140° C. for 1 hr. The reaction mixture was cooled to room temperature, water was added thereto, and the mixture was extracted with ethyl acetate. The extract was washed with water, and dried over anhydrous sodium sulfate, and the solvent was evaporated under reduced pressure. The residue was purified by thin layer silica gel chromatography (methanol/dichloromethane) to give the title compound (15.0 mg).

MS (ESI+): [M+H]+318.3.

Example 4

3-amino-5-(2-methylphenyl)-7-(1-methyl-1H-pyrazol-4-yl)-1,5-dihydro-4H-pyrazolo[4,3-c]pyridin-4-one

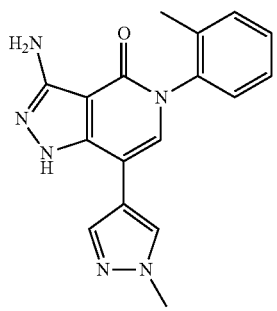 [SMILES: Cc1ccccc1-n1cc(-c2cnn(C)c2)c2[nH]nc(N)c2c1=O]

A mixture of 3-amino-7-bromo-5-(2-methylphenyl)-1,5-dihydro-4H-pyrazolo[4,3-c]pyridin-4-one obtained in Step F of Example 1 (200 mg), 1-methyl-4-(4,4,5,5-tetramethyl-1,3,2-dioxaborolan-2-yl)-1H-pyrazole (196 mg), tetrakis(triphenylphosphine)palladium(0) (72.4 mg), aqueous sodium carbonate solution (2 M, 0.630 mL) and N,N-dimethylformamide (3.0 mL) was heated with microwave irradiation at 140° C. for 3 hr. The reaction mixture was cooled to room temperature, and poured into water, and the mixture was extracted with ethyl acetate. The extract was washed with water, and dried over anhydrous sodium sulfate, and the solvent was evaporated under reduced pressure. The residue was purified by silica gel chromatography (methanol/dichloromethane) to give the title compound (23.0 mg).

MS (ESI+): [M+H]+321.3.

Example 5

3-amino-5-(2-methylphenyl)-7-(1-methyl-1H-pyrazol-3-yl)-1,5-dihydro-4H-pyrazolo[4,3-c]pyridin-4-one

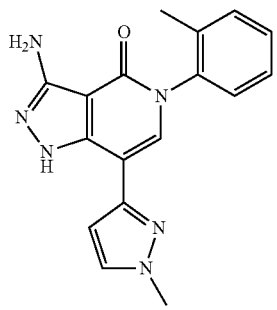 [SMILES: Cc1ccccc1-n1cc(-c2ccn(C)n2)c2[nH]nc(N)c2c1=O]

A) 3-bromo-1-methyl-1H-pyrazole

To a solution of 1-methyl-1H-pyrazol-3-amine (2.00 g) in hydrobromic acid (14.0 mL) was slowly added an aqueous solution (2.06 mL) of sodium nitrite (1.56 g) under ice-cooling. The reaction mixture was stirred under ice-cooling for 30 min, and a solution of copper(I) bromide (7.39 g) in hydrobromic acid (14.0 mL) was slowly added thereto. The reaction mixture was stirred under ice-cooling for 30 hr, neutralized with saturated aqueous sodium hydrogen carbonate solution, and diluted with dichloromethane. The insoluble substance was removed by filtration, the filtrate was washed with water and saturated brine, and dried over anhydrous magnesium sulfate, and the solvent was evaporated under reduced pressure. The residue was purified by silica gel column chromatography (ethyl acetate/hexane) to give the title compound (818 mg).

$^1$H NMR (400 MHz, CDCl$_3$) δ 3.88 (3H, s), 6.25 (1H, d, J=2.4 Hz), 7.25 (1H, d, J=2.0 Hz).

B) 1-methyl-3-(4,4,5,5-tetramethyl-1,3,2-dioxaborolan-2-yl)-1H-pyrazole

A mixture of 3-bromo-1-methyl-1H-pyrazole obtained in Step A (400 mg), 4,4,4',4',5,5,5',5'-octamethyl-2,2'-bi-1,3,2-dioxaborolane (694 mg), (1,1'-bis(diphenylphosphino)ferrocene)dichloropalladium(II) (101 mg), potassium acetate (488 mg) and 1,4-dioxane (5.0 mL) was heated with microwave irradiation at 120° C. for 3 hr. The insoluble substance was removed by filtration, and the solvent was evaporated under reduced pressure to give the title compound as a crude product.

$^1$H NMR (400 MHz, CDCl$_3$) δ 1.27 (12H, s), 3.98 (3H, s), 6.66 (1H, d, J=2.0 Hz), 7.38 (1H, d, J=2.0 Hz).

C) 3-amino-5-(2-methylphenyl)-7-(1-methyl-1H-pyrazol-3-yl)-1,5-dihydro-4H-pyrazolo[4,3-c]pyridin-4-one The title compound was obtained from 3-amino-7-bromo-5-(2-methylphenyl)-1,5-dihydro-4H-pyrazolo[4,3-c]pyridin-4-one obtained in Step F of Example 1 and the crude 1-methyl-3-(4,4,5,5-tetramethyl-1,3,2-dioxaborolan-2-yl)-1H-pyrazole obtained in Step B in the same manner as in Step A of Example 4.

MS (ESI+): [M+H]+321.3.

Example 6

3-amino-7-(1-(2-hydroxyethyl)-1H-pyrazol-3-yl)-5-(2-methylphenyl)-1,5-dihydro-4H-pyrazolo[4,3-c]pyridin-4-one

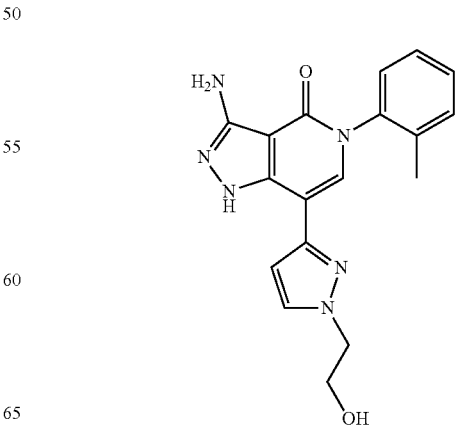

A) N,N-dimethyl-1H-pyrazole-1-sulfonamide

To a solution of 1H-pyrazole (5.00 g) in toluene (67.0 mL) were added dimethylsulfamoyl chloride (7.89 mL) and triethylamine (13.3 mL) at room temperature, and the reaction mixture was stirred at room temperature for 18 hr. The resulting solid was removed by filtration, and the solvent was evaporated under reduced pressure. The residue was purified by silica gel column chromatography (ethyl acetate/hexane) to give the title compound (6.24 g).
$^1$H NMR (400 MHz, CDCl$_3$) δ 2.91 (6H, s), 6.38 (1H, dd, J=2.6, 1.8 Hz), 7.72 (1H, d, J=1.2 Hz), 7.96 (1H, d, J=2.4 Hz).

B) 3-bromo-N,N-dimethyl-1H-pyrazole-1-sulfonamide

To a solution of N,N-dimethyl-1H-pyrazole-1-sulfonamide obtained in Step A (6.74 g) in tetrahydrofuran (75 mL) was added dropwise n-butyllithium hexane solution (1.3 M, 31.1 mL) over 15 min at −78° C. The reaction mixture was stirred at −78° C. for 15 min, and a solution of 1,2-dibromo-1,1,2,2-tetrachloroethane (13.8 g) in tetrahydrofuran (25 mL) was added dropwise thereto over 10 min. The reaction mixture was stirred at −78° C. for 15 min, and then at room temperature for 1 hr. The reaction mixture was poured into water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (8.03 g).
$^1$H NMR (400 MHz, CDCl$_3$) δ 3.06 (6H, s), 6.42 (1H, d, J=1.6 Hz), 7.60 (1H, d, J=1.6 Hz).

C) 3-bromo-1H-pyrazole

A mixture of 3-bromo-N,N-dimethyl-1H-pyrazole-1-sulfonamide obtained in Step B (5.63 g) and trifluoroacetic acid (9.0 mL) was stirred at room temperature for 2 hr. To the reaction mixture was added ethyl acetate, and the mixture was neutralized with saturated aqueous sodium hydrogen carbonate solution, and washed with saturated brine. The organic layer was dried over anhydrous sodium sulfate, and the solvent was evaporated under reduced pressure. The residue was purified by silica gel column chromatography (ethyl acetate/hexane) to give the title compound (2.92 g).
$^1$H NMR (400 MHz, CDCl$_3$) δ 6.37 (1H, d, J=2.4 Hz), 7.57 (1H, d, J=2.4 Hz).

D) 2-(3-bromo-1H-pyrazol-1-yl)ethanol

To a solution of 3-bromo-1H-pyrazole obtained in Step C (1.20 g) in N,N-dimethylformamide (82 mL) was added potassium tert-butoxide tetrahydrofuran solution (1 M, 12.3 mL) at room temperature. The reaction mixture was stirred at room temperature for 10 min, 1,3,2-dioxathiolane 2,2-dioxide (1.52 g) was added thereto at room temperature, and the mixture was stirred for 1 hr. conc. Hydrochloric acid (7.5 mL) was added thereto at room temperature, and the reaction mixture was stirred at room temperature for 18 hr. To the reaction mixture was added ethyl acetate, and the mixture was neutralized with saturated aqueous sodium hydrogen carbonate solution, and washed with saturated brine. The organic layer was dried over anhydrous sodium sulfate, and the solvent was evaporated under reduced pressure. The residue was purified by silica gel column chromatography (ethyl acetate/hexane) to give the title compound (880 mg).
$^1$H NMR (400 MHz, CDCl$_3$) δ 3.99 (2H, t, J=4.8 Hz), 4.21 (2H, t, J=4.8 Hz), 6.27 (1H, d, J=2.4 Hz), 7.36 (1H, d, J=2.4 Hz).

E) 3-amino-7-(1-(2-hydroxyethyl)-1H-pyrazol-3-yl)-5-(2-methylphenyl)-1,5-dihydro-4H-pyrazolo[4,3-c]pyridin-4-one The title compound was obtained from 3-amino-7-bromo-5-(2-methylphenyl)-1,5-dihydro-4H-pyrazolo[4,3-c]pyridin-4-one obtained in Step F of Example 1 and 2-(3-bromo-1H-pyrazol-1-yl)ethanol obtained in Step D in the same manner as in Step A of Example 3.
MS (ESI+): [M+H]$^+$351.3.

Example 7

3-amino-7-(1-(2-methoxyethyl)-1H-pyrazol-3-yl)-5-(2-methylphenyl)-1,5-dihydro-4H-pyrazolo[4,3-c]pyridin-4-one

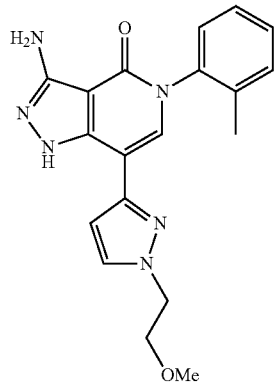 [SMILES: COCCn1ccc(-c2cn(-c3ccccc3C)c(=O)c3c(N)n[nH]c23)n1]

A) 3-bromo-1-(2-methoxyethyl)-1H-pyrazole

To a solution of 2-(3-bromo-1H-pyrazol-1-yl)ethanol obtained in Step D of Example 6 (300 mg) in N,N-dimethylformamide (16 mL) were added sodium hydride (55%, 137 mg) and iodomethane (196 μL) under ice-cooling. The reaction mixture was stirred under ice-cooling for 2 hr, water was added thereto, and the mixture was extracted with ethyl acetate. The extract was dried over anhydrous sodium sulfate, and the solvent was evaporated under reduced pressure. The residue was purified by silica gel column chromatography (ethyl acetate/hexane) to give the title compound (150 mg).
$^1$H NMR (400 MHz, CDCl$_3$) δ 3.32 (3H, s), 3.71 (2H, t, J=5.2 Hz), 4.24 (2H, t, J=5.2 Hz), 6.25 (1H, d, J=2.4 Hz), 7.36 (1H, d, J=2.4 Hz).

B) 3-amino-7-(1-(2-methoxyethyl)-1H-pyrazol-3-yl)-5-(2-methylphenyl)-1,5-dihydro-4H-pyrazolo[4,3-c]pyridin-4-one The title compound was obtained from 3-amino-7-bromo-5-(2-methylphenyl)-1,5-dihydro-4H-pyrazolo[4,3-c]pyridin-4-one obtained in Step F of Example 1 and 3-bromo-1-(2-methoxyethyl)-1H-pyrazole obtained in Step A in the same manner as in Step A of Example 3.
MS (ESI+): [M+H]$^+$365.3.

Example 8

3-amino-5-(2-methylphenyl)-7-(1-(2-(methylsulfonyl)ethyl)-1H-pyrazol-3-yl)-1,5-dihydro-4H-pyrazolo[4,3-c]pyridin-4-one

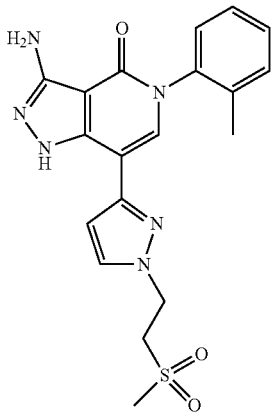 [SMILES: Cc1ccccc1-n1cc(-c2ccn(CCS(C)(=O)=O)n2)c2[nH]nc(N)c2c1=O]

A) 1-chloro-2-(methylsulfonyl)ethane

To a solution of 1-chloro-2-(methylsulfanyl)ethane (2.00 g) in methanol (20 mL) was added a solution of Oxone (registered trademark) (22.2 g) in water (10 mL). The reaction mixture was stirred at room temperature for 18 hr, and concentrated under reduced pressure. The residue was diluted with dichloromethane, and the mixture was washed successively with 1M aqueous sodium carbonate solution, water and saturated brine, and dried over anhydrous sodium sulfate, and the solvent was evaporated under reduced pressure to give the title compound (1.84 g).
$^1$H NMR (400 MHz, CDCl$_3$) δ 3.04 (3H, s), 3.45 (2H, t, J=6.8 Hz), 3.93 (2H, t, J=6.6 Hz).

B) 3-bromo-1-(2-(methylsulfonyl)ethyl)-1H-pyrazole

To a solution of 3-bromo-1H-pyrazole obtained in Step C of Example 6 (600 mg) in N,N-dimethylformamide (40 mL) was added potassium tert-butoxide tetrahydrofuran solution (1 M, 6.12 mL) at room temperature, and the mixture was stirred for 10 min. To the reaction mixture was added 1-chloro-2-(methylsulfonyl)ethane obtained in Step A (873 mg) at room temperature, and the mixture was stirred for 2 hr. To the reaction mixture was added ethyl acetate, and the mixture was washed with water and saturated brine, and dried over anhydrous sodium sulfate, and the solvent was evaporated under reduced pressure. The residue was purified by silica gel column chromatography (ethyl acetate/hexane) to give the title compound (730 mg).
$^1$H NMR (400 MHz, CDCl$_3$) δ 2.57 (3H, s), 3.63 (2H, t, J=6.2 Hz), 4.58 (2H, t, J=6.2 Hz), 6.30 (1H, d, J=2.0 Hz), 7.43 (1H, d, J=2.0 Hz).

C) 3-amino-5-(2-methylphenyl)-7-(1-(2-(methylsulfonyl)ethyl)-1H-pyrazol-3-yl)-1,5-dihydro-4H-pyrazolo[4,3-c]pyridin-4-one The title compound was obtained from 3-amino-7-bromo-5-(2-methylphenyl)-1,5-dihydro-4H-pyrazolo[4,3-c]pyridin-4-one obtained in Step F of Example 1 and 3-bromo-1-(2-(methylsulfonyl)ethyl)-1H-pyrazole obtained in Step B in the same manner as in Step A of Example 3.
MS (ESI+): [M+H]$^+$413.2.

Example 9

N-(2-(3-(3-amino-5-(2-methylphenyl)-4-oxo-4,5-dihydro-1H-pyrazolo[4,3-c]pyridin-7-yl)-1H-pyrazol-1-yl)ethyl)acetamide

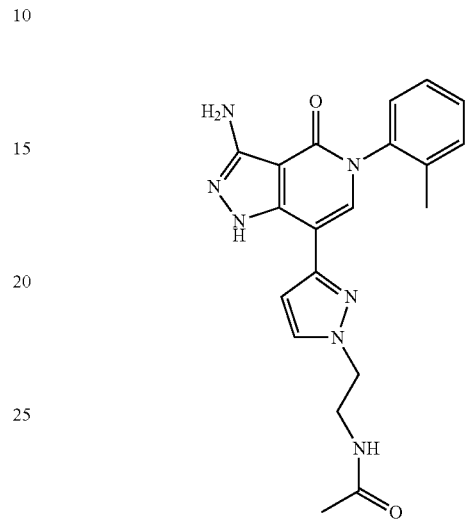

A) 2-bromo-N-tritylethanamine

To a solution of 2-bromoethanamine (5.00 g) and trityl chloride (6.80 g) in dichloromethane (24 mL) was slowly added triethylamine (7.48 mL) under ice-cooling, and the reaction mixture was stirred under ice-cooling for 2 hr. The resulting solid was removed by filtration, the filtrate was poured into water, and the mixture was extracted with dichloromethane. The extract was washed with water and saturated brine, and dried over anhydrous sodium sulfate, and the solvent was evaporated under reduced pressure. The residue was recrystallized from dichloromethane/cyclohexane to give the title compound (5.60 g).
$^1$H NMR (400 MHz, CDCl$_3$) δ 2.55-2.57 (2H, m), 3.51 (2H, t, J=5.8 Hz), 7.17-7.23 (3H, m), 7.27-7.30 (6H, m), 7.46-7.49 (6H, m).

B) 2-(3-bromo-1H-pyrazol-1-yl)-N-tritylethanamine

The title compound was obtained from 3-bromo-1H-pyrazole obtained in Step C of Example 6 and 2-bromo-N-tritylethanamine obtained in Step A in the same manner as in Step B of Example 8.
$^1$H NMR (400 MHz, CDCl$_3$) 52.57 (2H, t, J=5.6 Hz), 4.14 (2H, t, J=5.8 Hz), 6.29 (1H, d, J=2.0 Hz), 7.15-7.19 (2H, m), 7.23-7.27 (7H, m), 7.32-7.37 (7H, m).

C) N-(2-(3-bromo-1H-pyrazol-1-yl)ethyl)acetamide

To a solution of 2-(3-bromo-1H-pyrazol-1-yl)-N-tritylethanamine obtained in Step B (100 mg) and triethylsilane (38.8 μL) in dichloromethane (1.2 mL) was slowly added trifluoroacetic acid (1.2 mL) under ice-cooling. The reaction mixture was warmed to room temperature, stirred for 3 hr, and concentrated under reduced pressure. To a solution of the obtained residue and acetic anhydride (32.7 μL) in dichloromethane (2.0 mL) was added triethylamine (97.0 μL) under ice-cooling, and the mixture was stirred for 2 hr. To the reaction mixture was added dichloromethane, and the mixture was washed with water and saturated brine, and dried over anhydrous sodium sulfate, and the solvent was evaporated under reduced pressure. The residue was purified by silica gel column chromatography (ethyl acetate) to give the title compound (40.0 mg).
$^1$H NMR (400 MHz, CDCl$_3$) δ1.95 (3H, s), 3.66 (2H, q, J=5.6 Hz), 4.20 (2H, t, J=5.6 Hz), 6.06 (1H, brs), 6.25 (1H, d, J=2.4 Hz), 7.28 (1H, d, J=2.4 Hz).

D) N-(2-(3-(3-amino-5-(2-methylphenyl)-4-oxo-4,5-dihydro-1H-pyrazolo[4,3-c]pyridin-7-yl)-1H-pyrazol-1-yl)ethyl)acetamide The title compound was obtained from 3-amino-7-bromo-5-(2-methylphenyl)-1,5-dihydro-4H-pyrazolo[4,3-c]pyridin-4-one obtained in Step F of Example 1 and N-(2-(3-bromo-1H-pyrazol-1-yl)ethyl)acetamide obtained in Step C in the same manner as in Step A of Example 3.
MS (ESI+): [M+H]$^+$392.2.

Example 10

3-amino-5-(2-methylphenyl)-7-(1,3-thiazol-2-yl)-1,5-dihydro-4H-pyrazolo[4,3-c]pyridin-4-one

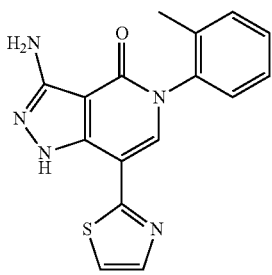 [SMILES: Cc1ccccc1-n1cc(-c2nccs2)c2[nH]nc(N)c2c1=O]

The title compound was obtained from 3-amino-7-bromo-5-(2-methylphenyl)-1,5-dihydro-4H-pyrazolo[4,3-c]pyridin-4-one obtained in Step F of Example 1 and 2-bromo-1,3-thiazole in the same manner as in Step A of Example 3.
MS (ESI+): [M+H]$^+$324.2.

Example 11 ethyl 2-(3-amino-5-(2-methylphenyl)-4-oxo-4,5-dihydro-1H-pyrazolo[4,3-c]pyridin-7-yl)-1,3-oxazole-4-carboxylate

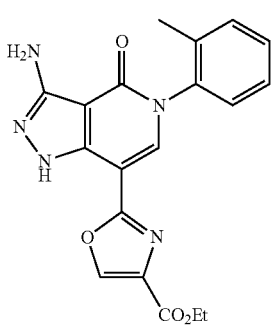 [SMILES: CCOC(=O)c1coc(-c2cn(-c3ccccc3C)c(=O)c3c(N)n[nH]c23)n1]

A) ethyl 2-amino-1,3-oxazole-4-carboxylate

A mixture of ethyl bromopyruvate (5.00 g), urea (2.31 g) and ethanol (51 mL) was refluxed overnight. The reaction mixture was cooled to room temperature, and the solvent was evaporated under reduced pressure. To the residue was added water, and the mixture was extracted with ethyl acetate. The extract was washed with saturated brine, and dried over anhydrous magnesium sulfate, and the solvent was evaporated under reduced pressure to give the title compound (2.87 g).
$^1$H NMR (400 MHz, CDCl$_3$) δ 1.36 (3H, t, J=7.2 Hz), 4.33 (2H, q, J=7.2 Hz), 5.30 (2H, brs), 7.72 (1H, s).

B) ethyl 2-chloro-1,3-oxazole-4-carboxylate

To a mixture of tert-butyl nitrate (2.86 mL), copper(II) chloride (3.23 g) and acetonitrile (64 mL) was added ethyl 2-amino-1,3-oxazole-4-carboxylate obtained in Step A (2.50 g) at 60° C. The reaction mixture was heated at 80° C. for 3 hr, and cooled to room temperature. The reaction mixture was poured into 1 M hydrochloric acid, and the mixture was extracted with dichloromethane. The extract was washed with saturated brine, and dried over anhydrous magnesium sulfate, and the solvent was evaporated under reduced pressure. The residue was purified by silica gel column chromatography (ethyl acetate/hexane) to give the title compound (1.90 g).
$^1$H NMR (400 MHz, CDCl$_3$) δ 1.39 (3H, t, J=7.2 Hz), 4.40 (2H, q, J=7.2 Hz), 8.19 (1H, s).

C) ethyl 2-(3-amino-5-(2-methylphenyl)-4-oxo-4,5-dihydro-1H-pyrazolo[4,3-c]pyridin-7-yl)-1,3-oxazole-4-carboxylate The title compound was obtained from 3-amino-7-bromo-5-(2-methylphenyl)-1,5-dihydro-4H-pyrazolo[4,3-c]pyridin-4-one obtained in Step F of Example 1 and ethyl 2-chloro-1,3-oxazole-4-carboxylate obtained in Step B in the same manner as in Step A of Example 3.
MS (ESI+): [M+H]$^+$380.2.

Example 12

3-amino-7-(6-(4-(2-hydroxyethyl)piperazin-1-yl)-2-methylpyrimidin-4-yl)-5-(2-methylphenyl)-1,5-dihydro-4H-pyrazolo[4,3-c]pyridin-4-one

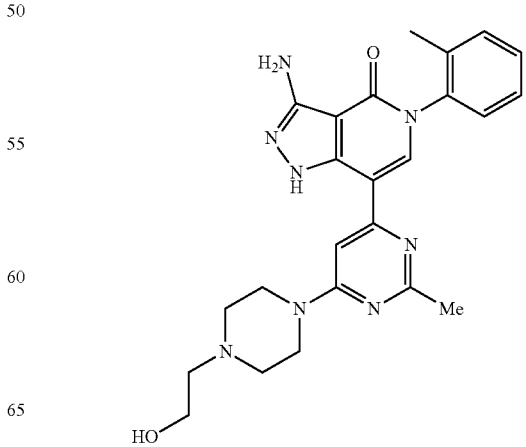

A) 2-(4-(6-chloro-2-methylpyrimidin-4-yl)piperazin-1-yl)ethanol

To a solution of 4,6-dichloro-2-methylpyrimidine (3.00 g) in dichloromethane (35 mL) was added 2-(piperazin-1-yl)ethanol (4.51 mL) at room temperature, and the mixture was stirred for 4 hr. To the reaction mixture was added triethylamine (0.513 mL) at room temperature, and the reaction mixture was stirred overnight. The resulting solid was collected by filtration, washed with dichloromethane, and dried under reduced pressure to give the title compound (4.08 g).

$^1$H NMR (400 MHz, CDCl$_3$) δ 2.48 (3H, s), 2.55-2.63 (6H, m), 3.63-3.73 (6H, m), 6.34 (1H, s).

B) 4-(4-(2-((tert-butyl(dimethyl)silyl)oxy)ethyl)piperazin-1-yl)-6-chloro-2-methylpyrimidine To a solution of 2-(4-(6-chloro-2-methylpyrimidin-4-yl)piperazin-1-yl)ethanol obtained in Step A (1.00 g) and imidazole (0.636 g) in N,N-dimethylformamide (13 mL) was added tert-butyl(chloro)dimethylsilane (0.793 g) at room temperature, and the mixture was stirred for 2 hr. The reaction mixture was poured into water, and the mixture was extracted with ethyl acetate. The extract was washed with water and saturated brine, and dried over anhydrous sodium sulfate, and the solvent was evaporated under reduced pressure to give the title compound (1.42 g).

$^1$H NMR (400 MHz, CDCl$_3$) δ 0.06 (6H, s), 0.90 (9H, s), 2.47 (3H, s), 2.55-2.60 (6H, m), 3.63 (4H, brs), 3.78 (2H, t, J=6.0 Hz), 6.32 (1H, s).

C) 3-amino-7-(6-(4-(2-((tert-butyl(dimethyl)silyl)oxy)ethyl)piperazin-1-yl)-2-methylpyrimidin-4-yl)-5-(2-methylphenyl)-1,5-dihydro-4H-pyrazolo[4,3-c]pyridin-4-one The title compound was obtained from 3-amino-7-bromo-5-(2-methylphenyl)-1,5-dihydro-4H-pyrazolo[4,3-c]pyridin-4-one obtained in Step F of Example 1 and 4-(4-(2-((tert-butyl(dimethyl)silyl)oxy)ethyl)piperazin-1-yl)-6-chloro-2-methylpyrimidine obtained in Step B in the same manner as in Step A of Example 3.

$^1$H NMR (400 MHz, CDCl$_3$) δ 0.06 (6H, s), 0.89 (9H, s), 2.21 (3H, s), 2.54-2.61 (9H, m), 3.66 (4H, t, J=4.8 Hz), 3.78 (2H, t, J=6.0 Hz), 4.75 (2H, brs), 6.43 (1H, s), 7.28 (1H, d, J=7.2 Hz), 7.34-7.44 (3H, m), 7.62 (1H, s).

D) 3-amino-7-(6-(4-(2-hydroxyethyl)piperazin-1-yl)-2-methylpyrimidin-4-yl)-5-(2-methylphenyl)-1,5-dihydro-4H-pyrazolo[4,3-c]pyridin-4-one To a solution of 3-amino-7-(6-(4-(2-((tert-butyl(dimethyl)silyl)oxy)ethyl)piperazin-1-yl)-2-methylpyrimidin-4-yl)-5-(2-methylphenyl)-1,5-dihydro-4H-pyrazolo[4,3-c]pyridin-4-one obtained in Step C (195 mg) in tetrahydrofuran (2.0 mL) was added tetrabutylammonium fluoride tetrahydrofuran solution (1 M, 0.679 mL) at room temperature, and the mixture was stirred overnight. The reaction mixture was poured into water, and the mixture was extracted with ethyl acetate. The extract was washed with water and saturated brine, and dried over anhydrous sodium sulfate, and the solvent was evaporated under reduced pressure. The residue was purified by thin layer silica gel chromatography (methanol/dichloromethane), and then HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and concentrated under reduced pressure to give the title compound (50.0 mg).

MS (ESI+): [M+H]$^+$461.4.

Example 13

3-amino-5-(3-methylbutan-2-yl)-7-(1-methyl-1H-pyrazol-3-yl)-1,5-dihydro-4H-pyrazolo[4,3-c]pyridin-4-one

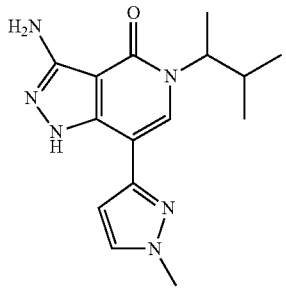

A) N-(3-methylbutan-2-yl)-3-oxobutanamide

To a mixture of 3-methylbutan-2-amine (1.00 g), 2,2,6-trimethyl-4H-1,3-didioxin-4-one (2.12 g) and tetrahydrofuran (3.0 mL) was added sodium acetate (941 mg) at room temperature. The reaction mixture was refluxed overnight, and cooled to room temperature. The reaction mixture was poured into water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (1.46 g).

$^1$H NMR (400 MHz, CDCl$_3$) δ 0.90 (6H, dd, J=6.8, 4.0 Hz), 1.09 (3H, d, J=6.8 Hz), 1.67-1.76 (1H, m), 2.27 (3H, s), 3.41 (2H, s), 3.83-3.92 (1H, m), 6.82 (1H, brs).

B) 2-((dimethylamino)methylene)-N-(3-methylbutan-2-yl)-3-oxobutanamide

To a solution of N-(3-methylbutan-2-yl)-3-oxobutanamide obtained in Step A (500 mg) in N,N-dimethylformamide (6.0 mL) was added dropwise 1,1-dimethoxy-N,N-dimethylmethanamine (696 mg) over 5 min at room temperature, and the reaction mixture was stirred overnight at room temperature. The solvent was evaporated under reduced pressure, and the residue was purified by silica gel column chromatography (methanol/ethyl acetate) to give the title compound (630 mg).

$^1$H NMR (400 MHz, CDCl$_3$) δ 0.93 (6H, m), 1.11 (3H, d, J=6.8 Hz), 1.71-1.79 (1H, m), 2.22 (3H, s), 3.11 (6H, m), 3.89-3.97 (1H, m), 7.50 (1H, brs), 7.61 (1H, brs).

C) 4-chloro-1-(3-methylbutan-2-yl)-2-oxo-1,2-dihydropyridine-3-carbaldehyde

Phosphorus oxychloride (1.04 mL) was slowly added to N,N-dimethylformamide (4.0 mL) under ice-cooling, and the mixture was stirred for 15 min. To the reaction mixture was added a solution of 2-((dimethylamino)methylene)-N-(3-methylbutan-2-yl)-3-oxobutanamide obtained in Step B (630 mg) in N,N-dimethylformamide (5.3 mL) under ice-cooling, and the reaction mixture was heated at 100° C. for 30 min. The reaction mixture was cooled to room temperature, and poured into ice water. The reaction mixture was neutralized with saturated aqueous sodium hydrogen carbonate solution, and extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (400 mg).
$^1$H NMR (400 MHz, CDCl$_3$) δ 0.85 (3H, d, J=6.8 Hz), 1.04 (3H, d, J=6.8 Hz), 1.36 (3H, d, J=7.2 Hz), 1.88-1.97 (1H, m), 4.82-4.90 (1H, m), 6.34 (1H, d, J=7.6 Hz), 7.38 (1H, d, J=7.2 Hz), 10.40 (1H, s).

D) 4-chloro-3-((hydroxyimino)methyl)-1-(3-methylbutan-2-yl)pyridin-2(1H)-one

A mixture of 4-chloro-1-(3-methylbutan-2-yl)-2-oxo-1,2-dihydropyridine-3-carbaldehyde obtained in Step C (400 mg), hydroxylamine hydrochloride (244 mg) and sodium acetate (288 mg) in methanol/water (4:1, 6.0 mL) was heated at 75° C. for 1 hr, and cooled to room temperature. The reaction mixture was poured into ice water, and the resulting solid was collected by filtration, washed with water, and dried under reduced pressure to give the title compound (328 mg).
$^1$H NMR (400 MHz, CDCl$_3$) δ 0.84 (3H, d, J=6.8 Hz), 1.02 (3H, d, J=6.4 Hz), 1.32 (3H, d, J=6.8 Hz), 1.85-1.94 (1H, m), 4.95-4.99 (1H, m), 6.34 (1H, d, J=7.6 Hz), 7.19 (1H, d, J=7.2 Hz), 8.51 (1H, s), 10.89 (1H, brs).

E) 4-chloro-1-(3-methylbutan-2-yl)-2-oxo-1,2-dihydropyridine-3-carbonitrile

To a solution of 4-chloro-3-((hydroxyimino)methyl)-1-(3-methylbutan-2-yl)pyridin-2(1H)-one obtained in Step D (328 mg) in acetonitrile (3.0 mL) was added phosphorus oxychloride (0.126 mL) at room temperature. The reaction mixture was heated at 90° C. for 30 min, and cooled to room temperature. The reaction mixture was poured into ice water, and the mixture was neutralized with saturated aqueous sodium hydrogen carbonate solution, and extracted with ethyl acetate. The extract was washed with water, and dried over anhydrous sodium sulfate, and the solvent was evaporated under reduced pressure to give the title compound (305 mg).
$^1$H NMR (400 MHz, CDCl$_3$) δ 0.83 (3H, d, J=6.4 Hz), 1.03 (3H, d, J=6.4 Hz), 1.36 (3H, d, J=7.2 Hz), 1.87-1.96 (1H, m), 4.77-4.84 (1H, m), 6.39 (1H, d, J=7.2 Hz), 7.42 (1H, d, J=7.6 Hz).

F) 5-bromo-4-chloro-1-(3-methylbutan-2-yl)-2-oxo-1,2-dihydropyridine-3-carbonitrile To a solution of 4-chloro-1-(3-methylbutan-2-yl)-2-oxo-1,2-dihydropyridine-3-carbonitrile obtained in Step E (305 mg) in N,N-dimethylformamide (3.0 mL) was added N-bromosuccinimide (296 mg) at room temperature. The reaction mixture was heated at 50° C. for 4 hr, and cooled to room temperature. The reaction mixture was poured into water, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (386 mg).
$^1$H NMR (400 MHz, CDCl$_3$) δ 0.85 (3H, d, J=6.8 Hz), 1.03 (3H, d, J=6.8 Hz), 1.38 (3H, d, J=6.8 Hz), 1.87-1.96 (1H, m), 4.77-4.84 (1H, m), 7.66 (1H, s).

G) 3-amino-7-bromo-5-(3-methylbutan-2-yl)-1,5-dihydro-4H-pyrazolo[4,3-c]pyridin-4-one To a solution of 5-bromo-4-chloro-1-(3-methylbutan-2-yl)-2-oxo-1,2-dihydropyridine-3-carbonitrile obtained in Step F (386 mg) in ethanol (6.0 mL) was added hydrazine monohydrate (0.094 mL) at room temperature. The reaction mixture was heated at 90° C. for 1 hr, and cooled to room temperature. The reaction mixture was poured into ice water, and the mixture was neutralized with saturated aqueous sodium hydrogen carbonate solution, and extracted with dichloromethane. The extract was dried over anhydrous sodium sulfate, and the solvent was evaporated under reduced pressure to give the title compound (332 mg).
$^1$H NMR (400 MHz, CDCl$_3$) δ 0.81 (3H, d, J=6.4 Hz), 1.05 (3H, d, J=6.4 Hz), 1.34 (3H, d, J=7.2 Hz), 1.81-1.90 (1H, m), 4.78-4.84 (1H, m), 4.89 (2H, brs), 7.11 (1H, s), 9.58 (1H, brs).

H) 3-amino-5-(3-methylbutan-2-yl)-7-(1-methyl-1H-pyrazol-3-yl)-1,5-dihydro-4H-pyrazolo[4,3-c]pyridin-4-one A mixture of 3-amino-7-bromo-5-(3-methylbutan-2-yl)-1,5-dihydro-4H-pyrazolo[4,3-c]pyridin-4-one obtained in Step G (332 mg), 1-methyl-3-(4,4,5,5-tetramethyl-1,3,2-dioxaborolan-2-yl)-1H-pyrazole (347 mg), tetrakis(triphenylphosphine)palladium(0) (128 mg), aqueous sodium carbonate solution (2 M, 1.11 ml) and N,N-dimethylformamide (6.0 mL) was heated with microwave irradiation at 120° C. for 1 hr. The reaction mixture was cooled to room temperature, and poured into water, and the mixture was extracted with ethyl acetate. The extract was washed with water and saturated brine, and dried over anhydrous sodium sulfate, and the solvent was evaporated under reduced pressure. The residue was purified by silica gel column chromatography (methanol/ethyl acetate), and then HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and concentrated under reduced pressure to give the title compound (36.0 mg).
$^1$H NMR (400 MHz, CDCl$_3$) δ 0.82 (3H, d, J=6.8 Hz), 1.08 (3H, d, J=6.8 Hz), 1.39 (3H, d, J=6.8 Hz), 1.88-1.97 (1H, m), 3.96 (3H, s), 4.77 (2H, brs), 4.84-4.94 (1H, m), 6.42 (1H, d, J=2.4 Hz), 7.31 (1H, s), 7.39 (1H, d, J=2.4 Hz), 10.44 (1H, brs).
MS (ESI+): [M+H]$^+$301.2.

Example 14

3-amino-5-(2-methylcyclohexyl)-7-(1-methyl-1H-pyrazol-3-yl)-1,5-dihydro-4H-pyrazolo[4,3-c]pyridin-4-one

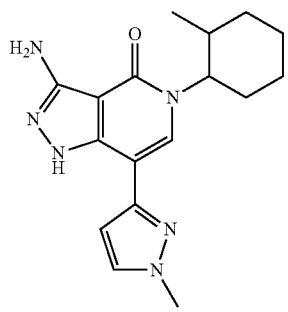 [SMILES: CC1CCCCC1n1cc(-c2ccn(C)n2)c2[nH]nc(N)c2c1=O]

A) N-(2-methylcyclohexyl)-3-oxobutanamide

To a mixture of 2-methylcyclohexanamine (2.00 g), 2,2,6-trimethyl-4H-1,3-didioxin-4-one (3.26 g) and tetrahydrofuran (5.0 mL) was added sodium acetate (1.45 g) at room temperature. The reaction mixture was refluxed overnight, and cooled to room temperature. The reaction mixture was poured into water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (1.99 g).

$^1$H NMR (400 MHz, CDCl$_3$) δ 0.85-0.92 (3H, m), 1.06-1.95 (9H, m), 2.27-2.28 (3H, m), 3.41-3.44 (2H, m), 3.46-4.10 (1H, m), 6.63-7.19 (1H, m).

B) 2-((dimethylamino)methylene)-N-(2-methylcyclohexyl)-3-oxobutanamide

To a solution of N-(2-methylcyclohexyl)-3-oxobutanamide obtained in Step A (1.99 g) in N,N-dimethylformamide (20 mL) was added dropwise 1,1-dimethoxy-N,N-dimethylmethanamine (2.41 g) over 10 min at room temperature, and the reaction mixture was stirred overnight at room temperature. The solvent was evaporated under reduced pressure, and the residue was purified by silica gel column chromatography (methanol/dichloromethane) to give the title compound (1.94 g).

$^1$H NMR (400 MHz, CDCl$_3$) δ 0.89-0.97 (3H, m), 1.04-2.02 (9H, m), 2.22-2.24 (3H, m), 3.10 (6H, s), 3.49-4.15 (1H, m), 7.42-7.99 (2H, brs).

C) 4-chloro-1-(2-methylcyclohexyl)-2-oxo-1,2-dihydropyridine-3-carbaldehyde

Phosphorus oxychloride (2.86 mL) was slowly added to N,N-dimethylformamide (16 mL) under ice-cooling, and the mixture was stirred for 15 min. To the reaction mixture was added a solution of 2-((dimethylamino)methylene)-N-(2-methylcyclohexyl)-3-oxobutanamide obtained in Step B (1.94 g) in N,N-dimethylformamide (10 mL) under ice-cooling, and the reaction mixture was heated at 100° C. for 30 min. The reaction mixture was cooled to room temperature, and poured into ice water. The reaction mixture was neutralized with saturated aqueous sodium hydrogen carbonate solution, and extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (1.22 g).

$^1$H NMR (400 MHz, CDCl$_3$) δ 0.79-0.81 (3H, m), 1.24-2.05 (9H, m), 4.68 (1H, brs), 6.30-6.35 (1H, m), 7.39-7.43 (1H, m), 10.40 (1H, brs).

D) 4-chloro-3-((hydroxyimino)methyl)-1-(2-methylcyclohexyl)pyridin-2(1H)-one A mixture of 4-chloro-1-(2-methylcyclohexyl)-2-oxo-1,2-dihydropyridine-3-carbaldehyde obtained in Step C (1.22 g), hydroxylamine hydrochloride (667 mg) and sodium acetate (787 mg) in methanol/water (4:1, 6.0 mL) was heated at 75° C. for 1 hr, and cooled to room temperature. The reaction mixture was poured into ice water, and the resulting solid was collected by filtration, washed with water, and dried under reduced pressure to give the title compound (1.19 g).

$^1$H NMR (400 MHz, DMSO-d$_6$) δ 0.61-0.76 (3H, m), 1.11-1.84 (9H, m), 4.47 (1H, brs), 6.4-6.47 (1H, m), 7.63-7.80 (1H, m), 8.12 (1H, s), 11.50-11.51 (1H, m).

E) 4-chloro-1-(2-methylcyclohexyl)-2-oxo-1,2-dihydropyridine-3-carbonitrile

To a solution of 4-chloro-3-((hydroxyimino)methyl)-1-(2-methylcyclohexyl)pyridin-2(1H)-one obtained in Step D (1.19 g) in acetonitrile (9.0 mL) was added phosphorus oxychloride (0.412 mL) at room temperature. The reaction mixture was heated at 90° C. for 30 min, and cooled to room temperature. The reaction mixture was poured into ice water, and the mixture was neutralized with saturated aqueous sodium hydrogen carbonate solution, and extracted with ethyl acetate. The extract was washed with water, and dried over anhydrous sodium sulfate, and the solvent was evaporated under reduced pressure to give the title compound (1.14 g).

$^1$H NMR (400 MHz, CDCl$_3$) δ 0.77-0.80 (3H, m), 1.23-1.92 (9H, m), 4.63 (1H, brs), 6.35-6.41 (1H, m), 7.42-7.46 (1H, m).

F) 5-bromo-4-chloro-1-(2-methylcyclohexyl)-2-oxo-1,2-dihydropyridine-3-carbonitrile To a solution of 4-chloro-1-(2-methylcyclohexyl)-2-oxo-1,2-dihydropyridine-3-carbonitrile obtained in Step E (1.14 g) in N,N-dimethylformamide (9.0 mL) was added N-bromosuccinimide (993 mg) at room temperature. The reaction mixture was heated at 50° C. for 3 hr, and cooled to room temperature. The reaction mixture was poured into water, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (1.29 g).

$^1$H NMR (400 MHz, CDCl$_3$) δ 0.79-0.82 (3H, m), 1.20-1.94 (9H, m), 4.63 (1H, brs), 7.66-7.68 (1H, m).

G) 3-amino-7-bromo-5-(2-methylcyclohexyl)-1,5-dihydro-4H-pyrazolo[4,3-c]pyridin-4-one To a solution of 5-bromo-4-chloro-1-(2-methylcyclohexyl)-2-oxo-1,2-dihydropyridine-3-carbonitrile obtained in Step F (1.29 g) in ethanol (20 mL) was added hydrazine monohydrate (0.288 mL) at room temperature. The reaction mixture was heated at 90° C. for 2 hr, and cooled to room temperature. The reaction mixture was poured into ice water, and the mixture was neutralized with saturated aqueous sodium hydrogen carbonate solution under ice-cooling, and extracted with dichloromethane. The extract was dried over anhydrous sodium sulfate, and the solvent was evaporated under reduced pressure. The residue was purified by silica gel column chromatography (ethyl acetate/hexane) to give the title compound (1.21 g).

$^1$H NMR (400 MHz, CDCl$_3$) δ 0.77-0.85 (3H, m), 1.21-1.90 (9H, m), 4.64 (1H, brs), 4.97 (2H, brs), 7.14-7.15 (1H, m).

H) 3-amino-5-(2-methylcyclohexyl)-7-(1-methyl-1H-pyrazol-3-yl)-1,5-dihydro-4H-pyrazolo[4,3-c]pyridin-4-one A mixture of 3-amino-7-bromo-5-(2-methylcyclohexyl)-1,5-dihydro-4H-pyrazolo[4,3-c]pyridin-4-one obtained in Step G (200 mg), 4,4,4',4',5,5,5',5'-octamethyl-2,2'-bi-1,3,2-dioxaborolane (861 mg), (1,1'-bis(diphenylphosphino)ferrocene)dichloropalladium(II) (22.0 mg), potassium acetate (121 mg) and N,N-dimethylformamide (3.0 mL) was heated with microwave irradiation at 110° C. for 5 hr. The reaction mixture was cooled to room temperature, and 3-iodo-1-methyl-1H-pyrazole (384 mg), aqueous sodium carbonate solution (2 M, 0.610 mL) and tetrakis(triphenylphosphine)palladium(0) (71.0 mg) were added thereto at room temperature. The reaction mixture was heated with microwave irradiation at 140° C. for 1 hr. The reaction mixture was cooled to room temperature, and poured into water, and the mixture was extracted with ethyl acetate. The extract was washed with water, and dried over anhydrous sodium sulfate, and the solvent was evaporated under reduced pressure. The residue was purified by silica gel column chromatography (methanol/dichloromethane) to give the title compound (51.0 mg).

$^1$H NMR (400 MHz, CDCl$_3$) δ 0.78-0.88 (3H, m), 1.24-2.04 (9H, m), 3.96 (3H, brs), 4.74-4.77 (2H, m), 6.40-6.45 (1H, m), 7.33-7.37 (1H, m), 7.39-7.40 (1H, m), 10.45 (1H, brs).

MS (ESI+): [M+H]$^+$327.3.

Example 15

3-amino-5-(2,6-difluorophenyl)-7-(1-methyl-1H-pyrazol-3-yl)-1,5-dihydro-4H-pyrazolo[4,3-c]pyridin-4-one

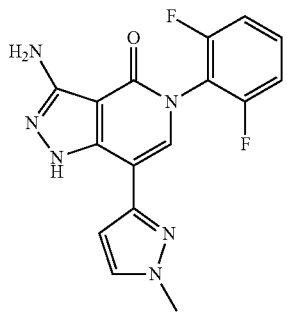 [SMILES: Cn1ccc(-c2cn(-c3c(F)cccc3F)c(=O)c3c(N)n[nH]c23)n1]

A) N-(2,6-difluorophenyl)-3-oxobutanamide

To a mixture of 2,6-difluoroaniline (5.00 g), 2,2,6-trimethyl-4H-1,3-didioxin-4-one (7.16 g) and tetrahydrofuran (13 mL) was added sodium acetate (3.18 g) at room temperature. The reaction mixture was refluxed overnight, and cooled to room temperature. The reaction mixture was poured into water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (5.04 g).

$^1$H NMR (400 MHz, CDCl$_3$) δ 2.35 (3H, s), 3.67 (2H, s), 6.93-6.99 (2H, m), 7.18-7.24 (1H, m), 8.77 (1H, brs).

B) N-(2,6-difluorophenyl)-2-((dimethylamino)methylene)-3-oxobutanamide

To a mixture of N-(2,6-difluorophenyl)-3-oxobutanamide obtained in Step A (5.00 g) and N,N-dimethylformamide (20 mL) was added dropwise 1,1-dimethoxy-N,N-dimethylmethanamine (6.32 mL) over 20 min at room temperature, and the reaction mixture was stirred overnight at room temperature. The solvent was evaporated under reduced pressure, and the residue was purified by silica gel column chromatography (methanol/ethyl acetate) to give the title compound (3.70 g).

$^1$H NMR (400 MHz, CDCl$_3$) δ 2.32 (3H, s), 3.20 (6H, s), 6.89-6.96 (2H, m), 7.09-7.16 (1H, m), 7.71 (1H, s), 10.37 (1H, s).

C) 4-chloro-1-(2,6-difluorophenyl)-2-oxo-1,2-dihydropyridine-3-carbaldehyde

Phosphorus oxychloride (5.14 mL) was slowly added to N,N-dimethylformamide (4.27 mL) under ice-cooling, and the mixture was stirred for 15 min. To the reaction mixture was added a solution of N-(2,6-difluorophenyl)-2-((dimethylamino)methylene)-3-oxobutanamide obtained in Step B (3.70 g) in N,N-dimethylformamide (30 mL) under ice-cooling, and the reaction mixture was heated at 125° C. for 30 min. The reaction mixture was cooled to room temperature, ice/saturated brine was added thereto, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (1.07 g).

$^1$H NMR (400 MHz, CDCl$_3$) δ 6.44 (1H, d, J=7.6 Hz), 7.10-7.16 (2H, m), 7.36 (1H, d, J=7.2 Hz), 7.45-7.53 (1H, m), 10.38 (1H, s).

D) 4-chloro-1-(2,6-difluorophenyl)-3-((hydroxyimino)methyl)pyridin-2(1H)-one

A mixture of 4-chloro-1-(2,6-difluorophenyl)-2-oxo-1,2-dihydropyridine-3-carbaldehyde obtained in Step C (1.07 g), hydroxylamine hydrochloride (414 mg), conc. hydrochloric acid (0.0120 mL) and 2-propanol (10 mL) was heated at 100° C. for 2 hr, and cooled to room temperature. The resulting solid was collected by filtration, and dried under reduced pressure to give the title compound (800 mg).

$^1$H NMR (400 MHz, CDCl$_3$) δ 6.43 (1H, d, J=7.2 Hz), 6.99-7.11 (2H, m), 7.16 (1H, d, J=7.6 Hz), 7.40-7.48 (1H, m), 8.45 (1H, s).

E) 4-chloro-1-(2,6-difluorophenyl)-2-oxo-1,2-dihydropyridine-3-carbonitrile

To a solution of 4-chloro-1-(2,6-difluorophenyl)-3-((hydroxyimino)methyl)pyridin-2(1H)-one obtained in Step D (800 mg) in acetonitrile (7.0 mL) was added phosphorus oxychloride (0.341 mL) at room temperature. The reaction mixture was heated at 100° C. for 1 hr, cooled to room temperature, and poured into ice water. The resulting solid was collected by filtration, and dried under reduced pressure to give the title compound (600 mg).

$^1$H NMR (400 MHz, CDCl$_3$) δ 6.49 (1H, d, J=7.2 Hz), 7.10-7.15 (2H, m), 7.40 (1H, d, J=7.2 Hz), 7.46-7.54 (1H, m).

F) 5-bromo-4-chloro-1-(2,6-difluorophenyl)-2-oxo-1,2-dihydropyridine-3-carbonitrile To a solution of 4-chloro-1-(2,6-difluorophenyl)-2-oxo-1,2-dihydropyridine-3-carbonitrile obtained in Step E (670 mg) in N,N-dimethylformamide (5.0 mL) was added N-bromosuccinimide (548 mg) at room temperature. The reaction mixture was heated at 50° C. for 4 hr, and cooled to room temperature. To the reaction mixture was added water, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (380 mg).

¹H NMR (400 MHz, CDCl₃) δ 7.11-7.16 (2H, m), 7.48-7.56 (1H, m), 7.73 (1H, s).

G) 3-amino-7-bromo-5-(2,6-difluorophenyl)-1,5-dihydro-4H-pyrazolo[4,3-c]pyridin-4-one To a solution of 5-bromo-4-chloro-1-(2,6-difluorophenyl)-2-oxo-1,2-dihydropyridine-3-carbonitrile obtained in Step F (270 mg) in ethanol (10 mL) was added hydrazine monohydrate (0.135 mL) at room temperature. The reaction mixture was heated overnight at 90° C., and cooled to room temperature. The reaction mixture was concentrated under reduced pressure, to the residue was added water, and the mixture was extracted with ethyl acetate. The extract was dried over anhydrous sodium sulfate, and the solvent was evaporated under reduced pressure to give the title compound (332 mg).
¹H NMR (400 MHz, CDCl₃) δ 7.05-7.12 (2H, m), 7.14 (1H, s), 7.39-7.47 (1H, m).

H) 3-amino-5-(2,6-difluorophenyl)-7-(1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one obtained in Step G (270 mg), 4,4,4',4',5,5,5',5'-octamethyl-2,2'-bi-1,3,2-dioxaborolane (281 mg), (1,1'-bis(diphenylphosphino)ferrocene)dichloropalladium(II) (29.0 mg), potassium acetate (155 mg) and N,N-dimethylformamide (4.0 mL) was heated with microwave irradiation at 110° C. for 5 hr. The reaction mixture was cooled to room temperature, and 1-methyl-3-iodopyrazole (329 mg), aqueous sodium carbonate solution (2 M, 0.792 mL) and tetrakis(triphenylphosphine)palladium(0) (91.0 mg) were added thereto at room temperature. The reaction mixture was heated with microwave irradiation at 120° C. for 4 hr. The reaction mixture was cooled to room temperature, water was added thereto, and the mixture was extracted with ethyl acetate. The extract was washed with water and saturated brine, and dried over anhydrous sodium sulfate, and the solvent was evaporated under reduced pressure. The residue was purified by thin layer silica gel chromatography (methanol/dichloromethane) to give the title compound (110 mg).
¹H NMR (400 MHz, CDCl₃) δ 3.97 (3H, s), 4.75 (2H, s), 6.38 (1H, d, J=2.4 Hz), 7.07-7.13 (2H, m), 7.29 (1H, s), 7.38 (1H, d, J=2.4 Hz), 7.39-7.47 (1H, m), 10.68 (1H, brs).
MS (ESI+): [M+H]⁺343.3.

Example 16

3-amino-5-(2-chlorophenyl)-4-oxo-4,5-dihydro-1H-pyrazolo[4,3-c]pyridine-6-carbonitrile

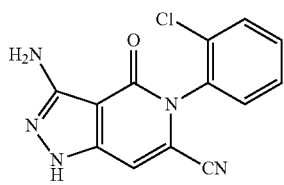 [SMILES: N#Cc1cc2[nH]nc(N)c2c(=O)n1-c1ccccc1Cl]

A) 1-(2-chlorophenyl)-4-hydroxy-6-methylpyridin-2(1H)-one

To a mixture of 4-hydroxy-6-methyl-2H-pyran-2-one (10.0 g) and 1,2-dichlorobenzene (9.91 mL) was added 2-chloroaniline (10.1 g) over 10 min at 165° C., and the reaction mixture was stirred at 165° C. for 30 min, and cooled to room temperature. The resulting solid was collected by filtration, and washed with dichloromethane to give the title compound (5.19 g).
¹H NMR (400 MHz, DMSO-d₆) δ 1.80 (3H, s), 5.55 (1H, d, J=2.4 Hz), 5.93 (1H, d, J=1.6 Hz), 7.37-7.41 (1H, m), 7.45-7.51 (2H, m), 7.63-7.67 (1H, m), 10.70 (1H, brs).

B) 1-(2-chlorophenyl)-4-hydroxy-6-methyl-2-oxo-1,2-dihydropyridine-3-carbaldehyde 1-(2-Chlorophenyl)-4-hydroxy-6-methylpyridin-2(1H)-one obtained in Step A (9.25 g) was added to a solution of sodium hydroxide' (54.9 g) in water/ethanol (1:2, 157 mL) at room temperature, and the mixture was heated at 70° C. Chloroform (34.8 mL) was slowly added to the reaction mixture at 70° C., and the mixture was stirred for 2 hr, and cooled to room temperature. The reaction mixture was concentrated under reduced pressure, and the residue was extracted with ethyl acetate. The extract was washed with water, and dried over anhydrous magnesium sulfate, and the solvent was evaporated under reduced pressure. The residue was suspended in dichloromethane, the solid was removed by filtration, and the filtrate was concentrated under reduced pressure. The residue was purified by silica gel column chromatography (ethyl acetate/hexane), and recrystallized from diethyl ether to give the title compound (3.95 g).
¹H NMR (400 MHz, DMSO-d₆) δ 1.93 (3H, s), 6.27 (1H, s), 7.55-7.59 (3H, m), 7.69-7.74 (1H, m), 9.88 (1H, s), 13.59 (1H, brs).

C) 1-(2-chlorophenyl)-4-hydroxy-3-((hydroxyimino)methyl)-6-methylpyridin-2(1H)-one A mixture of 1-(2-chlorophenyl)-4-hydroxy-6-methyl-2-oxo-1,2-dihydropyridine-3-carbaldehyde obtained in Step B (3.95 g), hydroxylamine hydrochloride (2.08 g) and sodium acetate (2.46 g) in methanol/water (4:1, 75.0 mL) was heated at 70° C. for 2 hr, cooled to room temperature, and poured into ice water. The resulting solid was collected by filtration, washed with water, and dried under reduced pressure to give the title compound (3.88 g).
¹H NMR (400 MHz, DMSO-d₆) δ 1.87 (3H, s), 6.21 (1H, s), 7.46-7.55 (3H, m), 7.66-7.71 (1H, m), 8.23 (1H, s), 11.46 (1H, s), 11.88 (1H, brs).

D) 1-(2-chlorophenyl)-4-hydroxy-6-methyl-2-oxo-1,2-dihydropyridine-3-carbonitrile A mixture of 1-(2-chlorophenyl)-4-hydroxy-3-((hydroxyimino)methyl)-6-methylpyridin-2(1H)-one obtained in Step C (3.88 g) and acetic acid (46.4 mL) was stirred at 120° C. for 2 hr, cooled to room temperature, and poured into ice water. The resulting solid was collected by filtration, washed with water, and dried under reduced pressure to give the title compound (2.90 g).
¹H NMR (400 MHz, DMSO-d₆) δ 1.89 (3H, s), 6.15 (1H, s), 7.49-7.57 (3H, m), 7.67-7.73 (1H, m), 12.93 (1H, brs).

E) 4-chloro-1-(2-chlorophenyl)-6-methyl-2-oxo-1,2-dihydropyridine-3-carbonitrile Phosphorus oxychloride (2.59 mL) was slowly added to N,N-dimethylformamide (17.8 mL) under ice-cooling, and the mixture was stirred for 15 min. To the reaction mixture was added a solution of 1-(2-chlorophenyl)-4-hydroxy-6-methyl-2-oxo-1,2-dihydropyridine-3-carbonitrile obtained in Step D (2.90 g) in N,N-dimethylformamide (4.50 mL) under ice-cooling, and the reaction mixture was heated overnight at 80° C. The reaction mixture was cooled to room temperature, and poured into ice water, and the mixture was neutralized with saturated aqueous sodium hydrogen carbonate solution, and extracted with ethyl acetate. The extract was washed with water, and dried over anhydrous magnesium sulfate, and the solvent was evaporated under reduced pressure. The residue was recrystallized from ethyl acetate/hexane to give the title compound (2.50 g).

$^1$H NMR (400 MHz, CDCl$_3$) δ 2.05 (3H, s), 6.37 (1H, s), 7.24-7.28 (1H, m), 7.45-7.52 (2H, m), 7.59-7.63 (1H, m).

F) 6-(bromomethyl)-4-chloro-1-(2-chlorophenyl)-2-oxo-1,2-dihydropyridine-3-carbonitrile To a solution of 4-chloro-1-(2-chlorophenyl)-6-methyl-2-oxo-1,2-dihydropyridine-3-carbonitrile obtained in Step E (1.55 g) in carbon tetrachloride (69.4 mL) were added N-bromosuccinimide (1.19 g) and 2,2'-azobis(isobutyronitrile) (0.0910 g) at room temperature. The reaction mixture was refluxed for 3 hr, and cooled to room temperature. The reaction mixture was diluted with dichloromethane, and the mixture was washed with saturated brine, and dried over anhydrous magnesium sulfate, and the solvent was evaporated under reduced pressure. The residue was purified by silica gel column chromatography (ethyl acetate/hexane) to give the title compound (1.23 g).

$^1$H NMR (400 MHz, CDCl$_3$) δ 3.74 (1H, d, J=11.6 Hz), 4.08 (1H, d, J=11.6 Hz), 6.62 (1H, s), 7.44 (1H, dd, J=7.6, 2.0 Hz), 7.49-7.56 (2H, m), 7.62 (1H, dd, J=7.6, 2.0 Hz).

G) (4-chloro-1-(2-chlorophenyl)-5-cyano-6-oxo-1,6-dihydropyridin-2-yl)methyl acetate To a solution of 6-(bromomethyl)-4-chloro-1-(2-chlorophenyl)-2-oxo-1,2-dihydropyridine-3-carbonitrile obtained in Step F (1.53 g) in acetone (42.7 mL) was added sodium acetate (1.75 g) at room temperature. The reaction mixture was stirred at 70° C. for 8 hr, and cooled to room temperature. To the reaction mixture was added water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (670 mg).

$^1$H NMR (400 MHz, CDCl$_3$) δ 2.11 (3H, s), 4.54 (1H, d, J=15.6 Hz), 4.62 (1H, d, J=15.6 Hz), 6.54 (1H, s), 7.29 (1H, dd, J=7.6, 1.6 Hz), 7.46-7.54 (2H, m), 7.60-7.63 (1H, m).

H) 3-amino-5-(2-chlorophenyl)-6-(hydroxymethyl)-1,5-dihydro-4H-pyrazolo[4,3-c]pyridin-4-one To a solution of (4-chloro-1-(2-chlorophenyl)-5-cyano-6-oxo-1,6-dihydropyridin-2-yl)methyl acetate obtained in Step G (670 mg) in ethanol (3.97 mL) was added hydrazine monohydrate (398 mg) at room temperature. The reaction mixture was stirred at room temperature for 5 hr. The resulting solid was collected by filtration, washed with water, and dried under reduced pressure to give the title compound (500 mg).

$^1$H NMR (400 MHz, DMSO-d$_6$) δ 3.61 (1H, dd, J=16.1, 4.3 Hz), 3.84 (1H, dd, J=16.1, 5.3 Hz), 4.70 (2H, brs), 5.70 (1H, brs), 6.80 (1H, s), 7.42-7.53 (3H, m), 7.64-7.67 (1H, m), 8.84 (1H, brs).

I) 2-(5-(2-chlorophenyl)-6-(hydroxymethyl)-4-oxo-4,5-dihydro-1H-pyrazolo[4,3-c]pyridin-3-yl)-1H-isoindole-1,3(2H)-dione A mixture of 3-amino-5-(2-chlorophenyl)-6-(hydroxymethyl)-1,5-dihydro-4H-pyrazolo[4,3-c]pyridin-4-one obtained in Step H (450 mg), phthalic anhydride (321 mg) and 1,4-dioxane (5.20 mL) was refluxed overnight, and cooled to room temperature. The resulting solid was collected by filtration, and washed with ethyl acetate to give the title compound (320 mg).

$^1$H NMR (400 MHz, DMSO-d$_6$) δ 3.77 (1H, dd, J=15.9, 5.7 Hz), 3.94 (1H, dd, J=15.9, 5.9 Hz), 5.71 (1H, t, J=6.0 Hz), 6.78 (1H, s), 7.45-7.52 (3H, m), 7.63 (1H, d, J=7.2 Hz), 7.93-8.02 (4H, m), 13.79 (1H, brs).

J) 5-(2-chlorophenyl)-3-(1,3-dioxo-1,3-dihydro-2H-isoindol-2-yl)-4-oxo-4,5-dihydro-1H-pyrazolo[4,3-c]pyridine-6-carbaldehyde A mixture of 2-(5-(2-chlorophenyl)-6-(hydroxymethyl)-4-oxo-4,5-dihydro-1H-pyrazolo[4,3-c]pyridin-3-yl)-1H-isoindole-1,3(2H)-dione obtained in Step I (317 mg), Dess-Martin periodinane (351 mg) and dichloromethane (7.53 mL) was stirred at room temperature for 1 hr. To the reaction mixture was added saturated aqueous sodium hydrogen carbonate solution, and the mixture was extracted with ethyl acetate. The extract was washed with water and saturated brine, and dried over anhydrous magnesium sulfate, and the solvent was evaporated under reduced pressure. to give the title compound (311 mg).

$^1$H NMR (400 MHz, CDCl$_3$) δ 7.28 (1H, s), 7.34-7.37 (1H, m), 7.38-7.44 (2H, m), 7.49-7.54 (1H, m), 7.73-7.79 (2H, m), 7.93-7.97 (2H, m), 9.29 (1H, s), 11.40 (1H, brs).

K) 5-(2-chlorophenyl)-3-(1,3-dioxo-1,3-dihydro-2H-isoindol-2-yl)-4-oxo-4,5-dihydro-1H-pyrazolo[4,3-c]pyridine-6-carbonitrile A mixture of 5-(2-chlorophenyl)-3-(1,3-dioxo-1,3-dihydro-2H-isoindol-2-yl)-4-oxo-4,5-dihydro-1H-pyrazolo[4,3-c]pyridine-6-carbaldehyde obtained in Step J (260 mg), 2,2,2-trifluoro-N-(2,2,2-trifluoroacetoxyl)acetamide (140 mg), pyridine (0.100 mL) and benzene (3.10 mL) was refluxed for 1 hr, and cooled to room temperature. To the reaction mixture was added water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (203 mg).

$^1$H NMR (400 MHz, CDCl$_3$) δ 7.16 (1H, s), 7.40-7.49 (3H, m), 7.58 (1H, dd, J=7.2, 2.0 Hz), 7.78-7.82 (2H, m), 7.96-8.01 (2H, m), 11.75 (1H, brs).

L) 3-amino-5-(2-chlorophenyl)-4-oxo-4,5-dihydro-1H-pyrazolo[4,3-c]pyridine-6-carbonitrile To a solution of 5-(2-chlorophenyl)-3-(1,3-dioxo-1,3-dihydro-2H-isoindol-2-yl)-4-oxo-4,5-dihydro-1H-pyrazolo[4,3-c]pyridine-6-carbonitrile obtained in Step K (203 mg) in ethanol (1.63 mL) was added hydrazine monohydrate (29.3 mg) at room temperature. The reaction mixture was stirred at 50° C. for 20 min, and cooled to room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (methanol/dichloromethane) to give the title compound (105 mg).

MS (ESI+): [M+H]$^+$286.2.

Example 17

3-amino-5-(2-chlorophenyl)-1,5-dihydro-4H-pyrazolo[4,3-c]pyridin-4-one

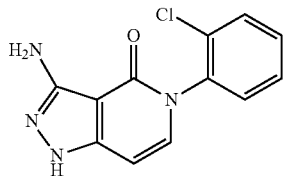 [SMILES: Nc1n[nH]c2ccn(-c3ccccc3Cl)c(=O)c12]

A) N-(2-chlorophenyl)-2-((dimethylamino)methylene)-3-oxobutanamide

To a mixture of N-(2-chlorophenyl)-3-oxobutanamide (2.63 g), potassium carbonate (1.72 g) and N,N-dimethylformamide (31.0 mL) was added dropwise 1,1-dimethoxy-N,N-dimethylmethanamine (3.30 mL) over 30 min at room temperature, and the reaction mixture was stirred at room temperature for 2 hr. The reaction mixture was slowly poured into water, and the mixture was extracted with dichloromethane. The extract was washed with water, and dried over anhydrous magnesium sulfate, and the solvent was evaporated under reduced pressure. The residue was purified by silica gel column chromatography (ethyl acetate/hexane) to give the title compound (2.30 g).

$^1$H NMR (400 MHz, CDCl$_3$) δ 2.32 (3H, s), 3.21 (6H, s), 6.95-7.00 (1H, m), 7.21-7.26 (1H, m), 7.37 (1H, dd, J=8.0, 1.6 Hz), 7.73 (1H, s), 8.48 (1H, dd, J=8.0, 1.6 Hz), 11.04 (1H, brs).

B) 4-chloro-1-(2-chlorophenyl)-2-oxo-1,2-dihydropyridine-3-carbaldehyde

Phosphorus oxychloride (2.35 mL) was slowly added to N,N-dimethylformamide (12.6 mL) under ice-cooling, and the mixture was stirred for 15 min. To the reaction mixture was added a solution of N-(2-chlorophenyl)-2-((dimethylamino)methylene)-3-oxobutanamide obtained in Step A (1.68 g) in N,N-dimethylformamide (50.0 mL) under ice-cooling, and the reaction mixture was heated at 100° C. for 30 min. The reaction mixture was cooled to room temperature, and poured into ice water, and the mixture was neutralized with saturated aqueous sodium hydrogen carbonate solution, and extracted with ethyl acetate. The extract was washed with water, and dried over anhydrous magnesium sulfate, and the solvent was evaporated under reduced pressure. The residue was recrystallized from 2-propanol to give the title compound (995 mg).

$^1$H NMR (400 MHz, CDCl$_3$) δ 6.43 (1H, d, J=7.2 Hz), 7.36 (1H, d, J=7.2 Hz), 7.37-7.39 (1H, m), 7.43-7.52 (2H, m), 7.59-7.62 (1H, m), 10.39 (1H, s).

C) 4-chloro-1-(2-chlorophenyl)-3-((hydroxyimino)methyl)pyridin-2(1H)-one

A mixture of 4-chloro-1-(2-chlorophenyl)-2-oxo-1,2-dihydropyridine-3-carbaldehyde obtained in Step B (995 mg), hydroxylamine hydrochloride (516 mg) and sodium acetate (609 mg) in methanol/water (4:1, 12.4 mL) was heated at 75° C. for 2 hr, cooled to room temperature, and poured into ice water. The resulting solid was collected by filtration, washed with water, and dried under reduced pressure to give the title compound (968 mg).

$^1$H NMR (400 MHz, CDCl$_3$) δ 6.41 (1H, d, J=7.2 Hz), 7.14 (1H, d, J=7.2 Hz), 7.34-7.44 (3H, m), 7.54-7.56 (1H, m), 8.46 (1H, s).

D) 4-chloro-1-(2-chlorophenyl)-2-oxo-1,2-dihydropyridine-3-carbonitrile

To a solution of 4-chloro-1-(2-chlorophenyl)-3-((hydroxyimino)methyl)pyridin-2(1H)-one obtained in Step C (968 mg) in acetonitrile (6.80 mL) was added phosphorus oxychloride (0.319 mL) at room temperature. The reaction mixture was heated at 90° C. for 1 hr, cooled to room temperature, and poured into ice water, and the mixture was neutralized with saturated aqueous sodium hydrogen carbonate solution under ice-cooling. The aqueous layer was extracted with ethyl acetate. The extract was washed with water, and dried over anhydrous magnesium sulfate, and the solvent was evaporated under reduced pressure to give the title compound (891 mg). $^1$H NMR (400 MHz, CDCl$_3$) δ 6.47 (1H, d, J=7.6 Hz), 7.35 (1H, dd, J=7.6, 1.6 Hz), 7.39 (1H, d, J=7.6 Hz), 7.42-7.50 (2H, m), 7.60 (1H, dd, J=7.6, 1.6 Hz).

E) 3-amino-5-(2-chlorophenyl)-1,5-dihydro-4H-pyrazolo[4,3-c]pyridin-4-one

To a solution of 4-chloro-1-(2-chlorophenyl)-2-oxo-1,2-dihydropyridine-3-carbonitrile obtained in Step D (891 mg) in ethanol (6.72 mL) was added hydrazine monohydrate (252 mg) at room temperature. The reaction mixture was heated at 90° C. for 5 hr, and cooled to room temperature. The reaction mixture was concentrated under reduced pressure, to the residue was added water, and the mixture was extracted with ethyl acetate. The extract was dried over anhydrous sodium sulfate, and the solvent was evaporated under reduced pressure to give the title compound (854 mg).

MS (ESI+): [M+H]$^+$261.2.

Example 18

3-amino-7-bromo-5-(2-chlorophenyl)-1,5-dihydro-4H-pyrazolo[4,3-c]pyridin-4-one

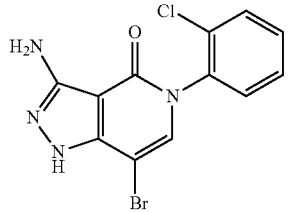 [SMILES: Nc1n[nH]c2c(Br)cn(-c3ccccc3Cl)c(=O)c12]

A) 5-bromo-4-chloro-1-(2-chlorophenyl)-2-oxo-1,2-dihydropyridine-3-carbonitrile To a mixture of 4-chloro-1-(2-chlorophenyl)-2-oxo-1,2-dihydropyridine-3-carbonitrile obtained in Step D of Example (16.4 g) and N,N-dimethylformamide (124 mL) was added N-bromosuccinimide (16.5 g) at 60° C., and the mixture was stirred for 40 hr. The reaction mixture was cooled to room temperature, and poured into water. The resulting solid was collected by filtration, and washed with water to give the title compound (20.9 g).
¹H NMR (400 MHz, CDCl₃) δ 7.36 (1H, dd, J=7.6, 1.6 Hz), 7.43-7.52 (2H, m), 7.61 (1H, dd, J=8.0, 1.6 Hz), 7.73 (1H, s).

B) 3-amino-7-bromo-5-(2-chlorophenyl)-1,5-dihydro-4H-pyrazolo[4,3-c]pyridin-4-one To a solution of 5-bromo-4-chloro-1-(2-chlorophenyl)-2-oxo-1,2-dihydropyridine-3-carbonitrile obtained in Step A (20.9 g) in ethanol (122 mL) was added hydrazine monohydrate (6.08 g) at room temperature. The reaction mixture was heated at 70° C. for 2 hr. The reaction mixture was cooled to room temperature, and poured into water. The resulting solid was collected by filtration, and washed with water to give the title compound (16.9 g).
MS (ESI+): [M+H]⁺339.2.

Example 19

3-amino-5-(2-chlorophenyl)-7-(1-methyl-1H-pyrazol-3-yl)-1,5-dihydro-4H-pyrazolo[4,3-c]pyridin-4-one

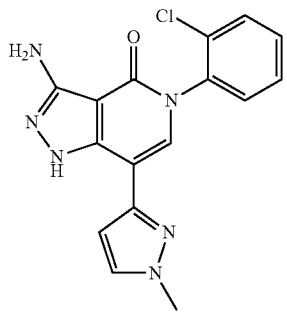 [SMILES: Cn1ccc(-c2cn(-c3ccccc3Cl)c(=O)c3c(N)n[nH]c23)n1]

The title compound was obtained from 3-amino-7-bromo-5-(2-chlorophenyl)-1,5-dihydro-4H-pyrazolo[4,3-c]pyridin-4-one obtained in Step B of Example 18 and 3-iodo-1-methyl-1H-pyrazole in the same manner as in Step A of Example 3.
MS (ESI+): [M+H]⁺341.2.

Example 20

3-amino-5-(2-chlorophenyl)-7-(pyrazin-2-yl)-1,5-dihydro-4H-pyrazolo[4,3-c]pyridin-4-one

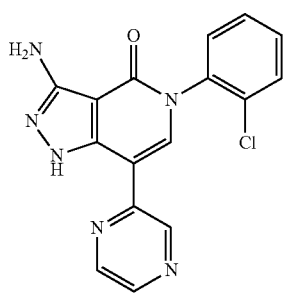

The title compound was obtained from 3-amino-7-bromo-5-(2-chlorophenyl)-1,5-dihydro-4H-pyrazolo[4,3-c]pyridin-4-one obtained in Step B of Example 18 and 2-bromopyrazine in the same manner as in Step A of Example 3.
MS (ESI+): [M+H]⁺339.1.

Example 21

3-amino-5-(2-chlorophenyl)-7-(2-fluorophenyl)-1,5-dihydro-4H-pyrazolo[4,3-c]pyridin-4-one

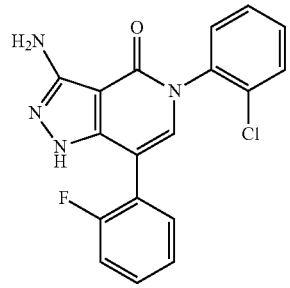 [SMILES: Nc1n[nH]c2c(-c3ccccc3F)cn(-c3ccccc3Cl)c(=O)c12]

A mixture of 3-amino-7-bromo-5-(2-chlorophenyl)-1,5-dihydro-4H-pyrazolo[4,3-c]pyridin-4-one obtained in Step B of Example 18 (150 mg), 2-fluorophenylboronic acid (93 mg), tetrakis(triphenylphosphine)palladium(0) (51 mg), potassium carbonate (122 mg), 1,2-dimethoxyethane (5.0 mL) and water (0.5 mL) was stirred overnight at 90° C. under argon atmosphere. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (basic silica gel, methanol/ethyl acetate) to give the title compound (38.3 mg).
MS (ESI+): [M+H]⁺355.0.

Example 22

3-amino-5-(2-chlorophenyl)-7-(pyrimidin-2-yl)-1,5-dihydro-4H-pyrazolo[4,3-c]pyridin-4-one

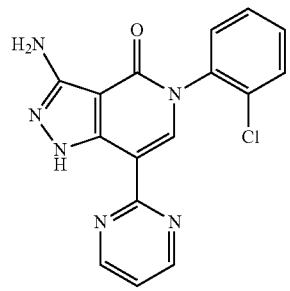 [SMILES: Nc1n[nH]c2c(-c3ncccn3)cn(-c3ccccc3Cl)c(=O)c12]

A mixture of 3-amino-7-bromo-5-(2-chlorophenyl)-1,5-dihydro-4H-pyrazolo[4,3-c]pyridin-4-one obtained in Step B of Example 18 (200 mg), 4,4,4',4',5,5,5',5'-octamethyl-2,2'-bi-1,3,2-dioxaborolane (179 mg), (1,1'-bis(diphenylphosphino)ferrocene)dichloropalladium(II) (21.6 mg), potassium acetate (116 mg) and N,N-dimethylformamide (3.0 mL) was stirred overnight at 110° C. under argon atmosphere. The reaction mixture was cooled to room temperature, water was added thereto, and the mixture was extracted with ethyl acetate. The extract was washed with water and saturated brine, and dried over anhydrous sodium sulfate, and the solvent was evaporated under reduced pressure to give 3-amino-5-(2-chlorophenyl)-7-(4,4,5,5-tetramethyl-1,3,2-dioxaborolan-2-yl)-1,5-dihydro-4H-pyrazolo[4,3-c]pyridin-4-one (277 mg). A mixture of 3-amino-5-(2-chlorophenyl)-7-(4,4,5,5-tetramethyl-1,3,2-dioxaborolan-2-yl)-1,5-dihydro-4H-pyrazolo[4,3-c]pyridin-4-one (277 mg), 2-chloropyrimidine (131 mg), tripotassium phosphate (365 mg), tetrakis(triphenylphosphine)palladium(0) (99.0 mg), toluene (5.0 mL), ethanol (1.0 mL) and water (1.0 mL) was stirred overnight at 120° C. under argon atmosphere. The reaction mixture was cooled to room temperature, water was added thereto, and the mixture was extracted with ethyl acetate. The extract was washed with water and saturated brine, and dried over anhydrous sodium sulfate, and the solvent was evaporated under reduced pressure. The residue was purified by silica gel chromatography (basic silica gel, methanol/ethyl acetate) to give the title compound (47.0 mg).

MS (ESI+): [M+H]⁺339.1.

Example 23

3-amino-5-(2-chlorophenyl)-7-(1,3-thiazol-4-yl)-1,5-dihydro-4H-pyrazolo[4,3-c]pyridin-4-one

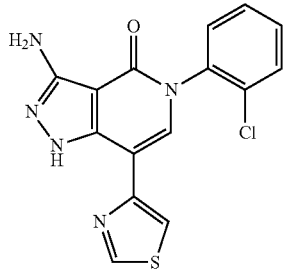 [SMILES: Nc1n[nH]c2c(-c3cscn3)cn(-c3ccccc3Cl)c(=O)c12]

A mixture of 3-amino-7-bromo-5-(2-chlorophenyl)-1,5-dihydro-4H-pyrazolo[4,3-c]pyridin-4-one obtained in Step B of Example 18 (200 mg), 4,4,4',4',5,5,5',5'-octamethyl-2,2'-bi-1,3,2-dioxaborolane (179 mg), (1,1'-bis(diphenylphosphino)ferrocene)dichloropalladium(II) (21.6 mg), potassium acetate (116 mg) and N,N-dimethylformamide (3.0 mL) was stirred overnight at 110° C. under argon atmosphere. The reaction mixture was cooled to room temperature, 4-bromo-1,3-thiazole (0.105 mL), aqueous sodium carbonate solution (2 M, 0.589 mL) and tetrakis(triphenylphosphine)palladium (0) (68.1 mg) were added thereto, and the reaction mixture was stirred overnight at 120° C. under argon atmosphere. The reaction mixture was cooled to room temperature, water was added thereto, and the mixture was extracted with ethyl acetate. The extract was washed with water and saturated brine, and dried over anhydrous sodium sulfate, and the solvent was evaporated under reduced pressure. The residue was purified by silica gel chromatography (basic silica gel, methanol/ethyl acetate) to give the title compound (20.0 mg).

MS (ESI+): [M+H]⁺344.0.

Examples 24 to 30

In Examples 24 to 30, the title compound was obtained from 3-amino-7-bromo-5-(2-chlorophenyl)-1,5-dihydro-4H-pyrazolo[4,3-c]pyridin-4-one obtained in Step B of Example 18 and a 5- or 6-membered monocyclic aromatic heterocycle (e.g., isothiazole, pyridine, pyrimidine) optionally substituted by 1 to 3 substituents selected from a halogen atom, a cyano group and an amino group, which corresponds to the compounds of Examples 24 to 30, in the same manner as in Example 23. MS in the tables means actual measured value.

TABLE 1

| Example number | IUPAC name | Structure | MS |
|---|---|---|---|
| 24 | 3-amino-5-(2-chlorophenyl)-7-(pyridin- 2-yl)-1,5-dihydro-4H-pyrazolo[4,3-c]pyridin-4-one | 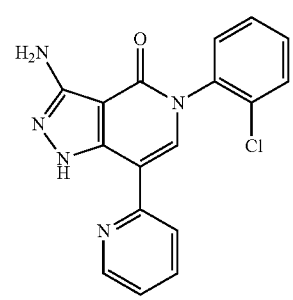 [SMILES: Nc1n[nH]c2c(-c3ccccn3)cn(-c3ccccc3Cl)c(=O)c12] | 338.2 |
| 25 | 3-amino-5-(2-chlorophenyl)-7-(1,2-thiazol-4-yl)-1,5-dihydro-4H-pyrazolo[4,3-c]pyridin-4-one | 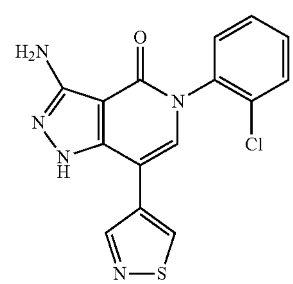 | 344.1 |

TABLE 1-continued

| Example number | IUPAC name | Structure | MS |
|---|---|---|---|
| 26 | 3-amino-7-(2-amino pyrimidin-4-yl)-5-(2-chlorophenyl)-1,5-dihydro-4H-pyrazolo[4,3-c]pyridin-4-one | 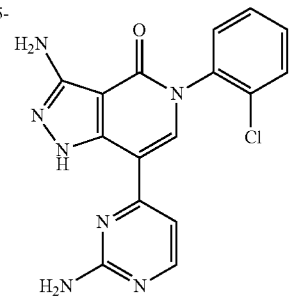 | 354.1 |
| 27 | 3-amino-7-(4-aminopyrimidin-2-yl)-5-(2-chlorophenyl)-1,5-dihydro-4H-pyrazolo[4,3-c]pyridin-4-one | 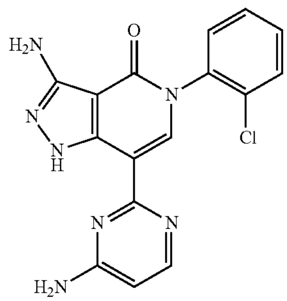 [SMILES: Nc1ccnc(-c2cn(-c3ccccc3Cl)c(=O)c3c(N)n[nH]c23)n1] | 354.1 |
| 28 | 2-(3-amino-5-(2-chlorophenyl)-4-oxo-4,5-dihydro-1H-pyrazolo[4,3-c]pyridin-7-yl)isonicotinonitrile | 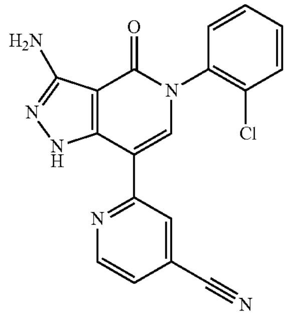 [SMILES: N#Cc1ccnc(-c2cn(-c3ccccc3Cl)c(=O)c3c(N)n[nH]c23)c1] | 363.1 |
| 29 | 6-(3-amino-5-(2-chlorophenyl)-4-oxo-4,5-dihydro-1H-pyrazolo[4,3-c]pyridin-7-yl)pyridine-2-carbonitrile | 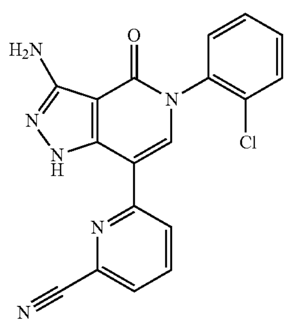 [SMILES: N#Cc1cccc(-c2cn(-c3ccccc3Cl)c(=O)c3c(N)n[nH]c23)n1] | 363.1 |
| 30 | 6-(3-amino-5-(2-chlorophenyl)-4-oxo-4,5-dihydro-1H-pyrazolo[4,3-c]pyridin-7-yl)pyridine-2-carboxamide | 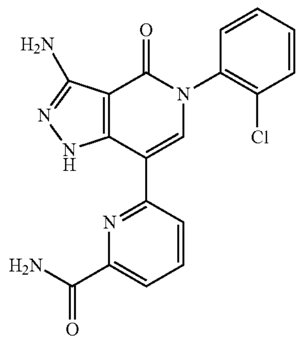 [SMILES: NC(=O)c1cccc(-c2cn(-c3ccccc3Cl)c(=O)c3c(N)n[nH]c23)n1] | 381.1 |

Example 31

3-amino-5-(2-chlorophenyl)-7-(2-(piperidin-1-yl)pyrimidin-4-yl)-1,5-dihydro-4H-pyrazolo[4,3-c]pyridin-4-one

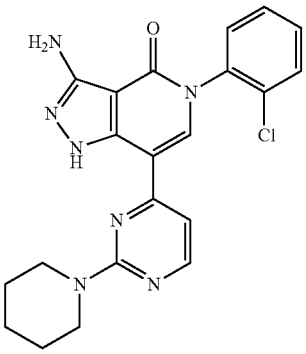 [SMILES: Nc1n[nH]c2c(-c3ccnc(N4CCCCC4)n3)cn(-c3ccccc3Cl)c(=O)c12]

A) 4-chloro-2-(piperidin-1-yl)pyrimidine

A mixture of 2,4-dichloropyrimidine (1.0 g), 1-ethylpiperidine (1.099 mL) and 1,2-dimethoxyethane (10 mL) was refluxed for 6 hr. The solvent was evaporated under reduced pressure, and the residue was purified by silica gel column chromatography (ethyl acetate/hexane) to give the title compound (553.1 mg).

MS (ESI+): [M+H]$^+$198.1.

B) 3-amino-5-(2-chlorophenyl)-7-(2-(piperidin-1-yl)pyrimidin-4-yl)-1,5-dihydro-4H-pyrazolo[4,3-c]pyridin-4-one The title compound was obtained from 3-amino-7-bromo-5-(2-chlorophenyl)-1,5-dihydro-4H-pyrazolo[4,3-c]pyridin-4-one obtained in Step B of Example 18 and 4-chloro-2-(piperidin-1-yl)pyrimidine obtained in Step A in the same manner as in Example 23.

MS (ESI+): [M+H]$^+$422.2.

Example 32

3-amino-7-(6-aminopyrimidin-4-yl)-5-(2-chlorophenyl)-1,5-dihydro-4H-pyrazolo[4,3-c]pyridin-4-one

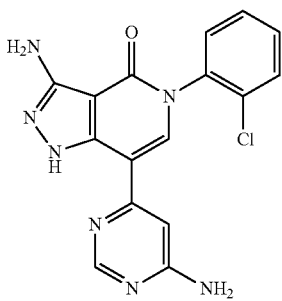 [SMILES: Nc1cc(-c2cn(-c3ccccc3Cl)c(=O)c3c(N)n[nH]c23)ncn1]

A) di-tert-butyl(6-chloropyrimidin-4-yl)imidedicarbonate

To a solution of 6-chloropyrimidin-4-amine (500 mg) and N,N-dimethylaminopyridine (47.2 mg) in acetonitrile (5.0 mL) was added di-tert-butyl dicarbonate (2.24 mL) at room temperature. The reaction mixture was stirred at room temperature for 3 days, and the solvent was evaporated under reduced pressure. The residue was purified by silica gel column chromatography (ethyl acetate/hexane) to give the title compound (1.13 g).

MS (ESI+): [M+H]$^+$330.2.

B) 3-amino-7-(6-aminopyrimidin-4-yl)-5-(2-chlorophenyl)-1,5-dihydro-4H-pyrazolo[4,3-c]pyridin-4-one The title compound was obtained from 3-amino-7-bromo-5-(2-chlorophenyl)-1,5-dihydro-4H-pyrazolo[4,3-c]pyridin-4-one obtained in Step B of Example 18 and di-tert-butyl(6-chloropyrimidin-4-yl)imidedicarbonate obtained in Step A in the same manner as in Example 23.

MS (ESI+): [M+H]$^+$354.1.

Example 33

(6-(3-amino-5-(2-chlorophenyl)-4-oxo-4,5-dihydro-1H-pyrazolo[4,3-c]pyridin-7-yl)pyridin-2-yl)acetonitrile

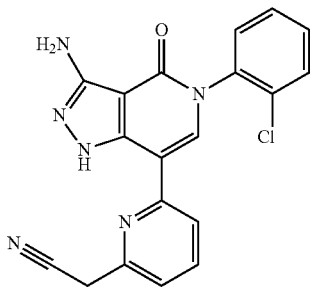 [SMILES: N#CCc1cccc(-c2cn(-c3ccccc3Cl)c(=O)c3c(N)n[nH]c23)n1]

A) 2-(6-chloropyridin-2-yl)acetonitrile

To a solution of acetonitrile (2.77 mL) in tetrahydrofuran (80 mL) was added dropwise n-butyl lithium hexane solution (1.6 M, 29.6 mL) at −78° C., and the reaction mixture was stirred at −78° C. for 1 hr under argon atmosphere. A solution of 2,6-dichloropyridine (2.0 g) in tetrahydrofuran (10 mL) was added dropwise thereto at −78° C., and the reaction mixture was stirred at −78° C. for 2 hr under argon atmosphere, and allowed to be warmed to room temperature. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (1.91 g).

$^1$H NMR (300 MHz, CDCl$_3$) δ 3.93 (2H, s), 7.33 (1H, dd, J=8.1, 0.6 Hz), 7.43 (1H, dd, J=7.5, 0.6 Hz), 7.73 (1H, t, J=7.8 Hz).

B) (6-(3-amino-5-(2-chlorophenyl)-4-oxo-4,5-dihydro-1H-pyrazolo[4,3-c]pyridin-7-yl)pyridin-2-yl)acetonitrile The title compound was obtained from 3-amino-7-bromo-5-(2-chlorophenyl)-1,5-dihydro-4H-pyrazolo[4,3-c]pyridin-4-one obtained in Step B of Example 18 and 2-(6-chloropyridin-2-yl)acetonitrile obtained in Step A in the same manner as in Example 23.

MS (ESI+): [M+H]⁺377.2.

Example 34

3-amino-5-(2-chlorophenyl)-7-(4-(pyrrolidin-1-ylmethyl)pyridin-2-yl)-1,5-dihydro-4H-pyrazolo[4,3-c]pyridin-4-one

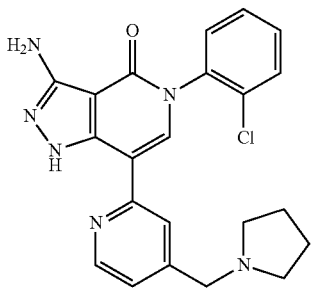 [SMILES: Nc1n[nH]c2c(-c3cc(CN4CCCC4)ccn3)cn(-c3ccccc3Cl)c(=O)c12]

A) 2-bromo-4-(pyrrolidin-1-ylmethyl)pyridine

To a solution of 2-bromoisonicotinaldehyde (400 mg) and pyrrolidine (0.197 mL) in acetonitrile (16 mL) was added sodium triacetoxyborohydride (547 mg) at room temperature, and the mixture was stirred at room temperature for 2 hr. To the reaction mixture was added saturated aqueous sodium hydrogen carbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (445 mg).

MS (ESI+): [M+H]⁺241.1.

B) 3-amino-5-(2-chlorophenyl)-7-(4-(pyrrolidin-1-ylmethyl)pyridin-2-yl)-1,5-dihydro-4H-pyrazolo[4,3-c]pyridin-4-one The title compound was obtained from 3-amino-7-bromo-5-(2-chlorophenyl)-1,5-dihydro-4H-pyrazolo[4,3-c]pyridin-4-one obtained in Step B of Example 18 and 2-bromo-4-(pyrrolidin-1-ylmethyl)pyridine obtained in Step A in the same manner as in Example 23.

MS (ESI+): [M+H]⁺421.1.

Example 35

(4-(3-amino-5-(2-chlorophenyl)-4-oxo-4,5-dihydro-1H-pyrazolo[4,3-c]pyridin-7-yl)-2-thienyl)acetonitrile

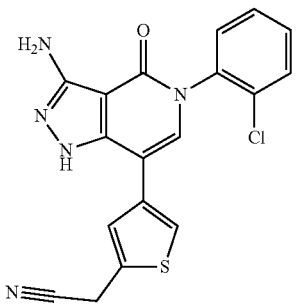 [SMILES: N#CCc1cc(-c2cn(-c3ccccc3Cl)c(=O)c3c(N)n[nH]c23)cs1]

A mixture of 3-amino-7-bromo-5-(2-chlorophenyl)-1,5-dihydro-4H-pyrazolo[4,3-c]pyridin-4-one obtained in Step B of Example 18 (200 mg), 2-(4-(4,4,5,5-tetramethyl-1,3,2-dioxaborolan-2-yl)thiophen-2-yl)acetonitrile (220 mg), tetrakis(triphenylphosphine)palladium(0) (68.1 mg), aqueous sodium carbonate solution (2 M, 0.589 mL) and N,N-dimethylformamide (3.0 mL) was stirred overnight at 120° C. under argon atmosphere. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (basic silica gel, methanol/ethyl acetate) to give the title compound (83.6 mg).

MS (ESI+): [M+H]⁺382.1.

Example 36

3-amino-5-(2-chlorophenyl)-7-(3-thienyl)-1,5-dihydro-4H-pyrazolo[4,3-c]pyridin-4-one

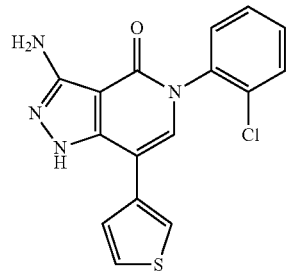 [SMILES: Nc1n[nH]c2c(-c3ccsc3)cn(-c3ccccc3Cl)c(=O)c12]

The title compound was obtained from 3-amino-7-bromo-5-(2-chlorophenyl)-1,5-dihydro-4H-pyrazolo[4,3-c]pyridin-4-one obtained in Step 3 of Example 18 and 3-thiopheneboronic acid in the same manner as in Example 35.

MS (ESI+): [M+H]⁺343.0.

Example 37

3-amino-5-(2-chlorophenyl)-7-(2-furyl)-1,5-dihydro-4H-pyrazolo[4,3-c]pyridin-4-one

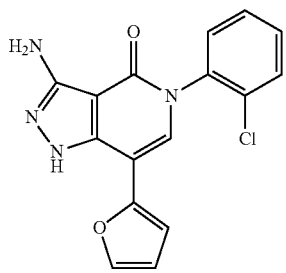 [SMILES: Nc1n[nH]c2c(-c3ccco3)cn(-c3ccccc3Cl)c(=O)c12]

The title compound was obtained from 3-amino-7-bromo-5-(2-chlorophenyl)-1,5-dihydro-4H-pyrazolo[4,3-c]pyridin-4-one obtained in Step B of Example 18 and 2-furanboronic acid in the same manner as in Example 35.
MS (ESI+): [M+H]$^+$327.1.

Example 38

3-amino-5-(2-chlorophenyl)-7-(5-(pyrrolidin-1-ylmethyl)-3-thienyl)-1,5-dihydro-4H-pyrazolo[4,3-c]pyridin-4-one

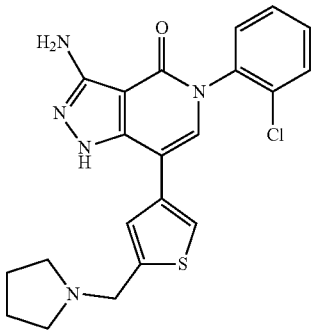 [SMILES: Nc1n[nH]c2c(-c3csc(CN4CCCC4)c3)cn(-c3ccccc3Cl)c(=O)c12]

A) 4-(3-amino-5-(2-chlorophenyl)-4-oxo-4,5-dihydro-1H-pyrazolo[4,3-c]pyridin-7-yl)thiophene-2-carbaldehyde The title compound was obtained from 3-amino-7-bromo-5-(2-chlorophenyl)-1,5-dihydro-4H-pyrazolo[4,3-c]pyridin-4-one obtained in Step B of Example 18 and (5-formylthiophen-3-yl)boronic acid in the same manner as in Example 35.
MS (ESI+): [M+H]$^+$371.0.

B) 3-amino-5-(2-chlorophenyl)-7-(5-(pyrrolidin-1-ylmethyl)-3-thienyl)-1,5-dihydro-4H-pyrazolo[4,3-c]pyridin-4-one To a solution of 4-(3-amino-5-(2-chlorophenyl)-4-oxo-4,5-dihydro-1H-pyrazolo[4,3-c]pyridin-7-yl)thiophene-2-carbaldehyde obtained in Step A (100 mg) and pyrrolidine (0.053 mL) in acetonitrile (10 mL) was added sodium triacetoxyborohydride (89 mg) at room temperature, and the mixture was stirred at room temperature 3 hr. To the reaction mixture was added saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (basic silica gel, methanol/ethyl acetate) to give the title compound (63.1 mg).
MS (ESI+): [M+H]$^+$426.1.

Example 39

3-amino-5-(2-chlorophenyl)-7-(5-((dimethylamino)methyl)-3-thienyl)-1,5-dihydro-4H-pyrazolo[4,3-c]pyridin-4-one

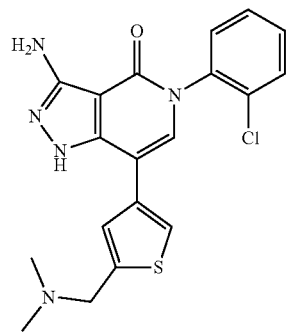 [SMILES: CN(C)Cc1cc(-c2cn(-c3ccccc3Cl)c(=O)c3c(N)n[nH]c23)cs1]

The title compound was obtained from 4-(3-amino-5-(2-chlorophenyl)-4-oxo-4,5-dihydro-1H-pyrazolo[4,3-c]pyridin-7-yl)thiophene-2-carbaldehyde obtained in Step A of Example 38 and dimethylamine in the same manner as in Step B of Example 38.
MS (ESI+): [M+H]$^+$400.1.

Example 40

3-amino-5-(2-chlorophenyl)-7-(5-((methylamino)methyl)-3-thienyl)-1,5-dihydro-4H-pyrazolo[4,3-c]pyridin-4-one

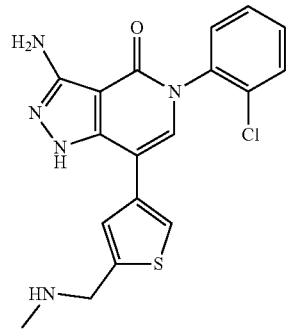 [SMILES: CNCc1cc(-c2cn(-c3ccccc3Cl)c(=O)c3c(N)n[nH]c23)cs1]

The title compound was obtained from 4-(3-amino-5-(2-chlorophenyl)-4-oxo-4,5-dihydro-1H-pyrazolo[4,3-c]pyridin-7-yl)thiophene-2-carbaldehyde obtained in Step A of Example 38 and methylamine in the same manner as in Step B of Example 38.
MS (ESI+): [M+H]$^+$386.0.

Examples 41 to 50

In Examples 41 to 50, the title compound was obtained from aniline optionally substituted by 1 to 3 substituents selected from (a) a halogen atom (e.g., a fluorine atom, a chlorine atom), (b) a $C_{1-6}$ alkyl group (e.g., methyl) optionally substituted by 1 to 3 halogen atoms (e.g., a fluorine atom) and (c) a cyano group, which corresponds to the compounds of Examples 41 to 50, in the same manner as in Example 13. MS in the tables means actual measured value.

TABLE 2-1

| Example number | IUPAC name | Structure | MS |
|---|---|---|---|
| 41 | 3-amino-5-(2,3-difluorophenyl)-7-(1-methyl-1H-pyrazol-3-yl)-1,5-dihydro-4H-pyrazolo[4,3-c]pyridin-4-one | 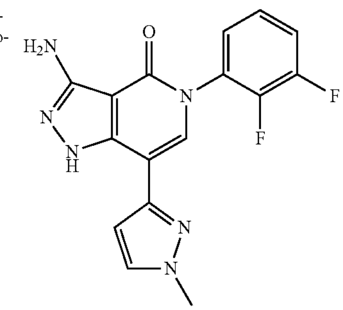 | 343.1 |
| 42 | 3-amino-5-(5-chloro-2-fluorophenyl)-7-(1-methyl-1H-pyrazol-3-yl)-1,5-dihydro-4H-pyrazolo[4,3-c]pyridin-4-one | 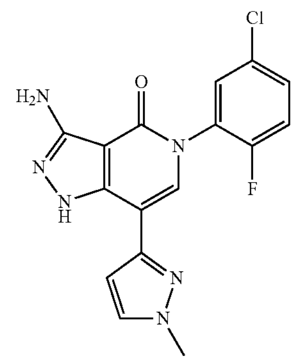 [SMILES: Cn1ccc(-c2cn(-c3cc(Cl)ccc3F)c(=O)c3c(N)n[nH]c23)n1] | 359.2 |
| 43 | 3-amino-7-(1-methyl-1H-pyrazol-3-yl)-5-(2-(trifluoromethyl)phenyl)-1,5-dihydro-4H-pyrazolo[4,3-c]pyridin-4-one | 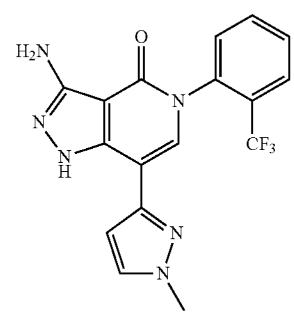 | 375.2 |
| 44 | 3-amino-5-(2,6-dichlorophenyl)-7-(1-methyl-1H-pyrazol-3-yl)-1,5-dihydro-4H-pyrazolo[4,3-c]pyridin-4-one | 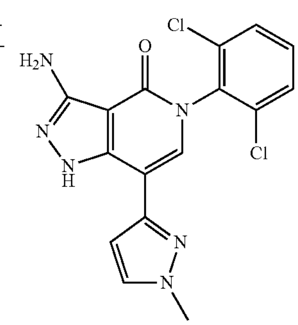 | 375.1 |

TABLE 2-1-continued

| Example number | IUPAC name | Structure | MS |
|---|---|---|---|
| 45 | 3-amino-5-(2-chloro-6-fluorophenyl)-7-(1-methyl-1H-pyrazol-3-yl)-1,5-dihydro-4H-pyrazolo[4,3-c]pyridin-4-one | 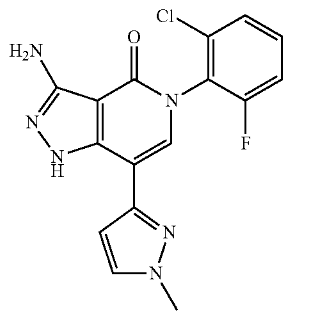 | 359.2 |
| 46 | 3-amino-7-(1-methyl-1H-pyrazol-3-yl)-5-(2,4,6-trifluorophenyl)-1,5-dihydro-4H-pyrazolo[4,3-c]pyridin-4-one | 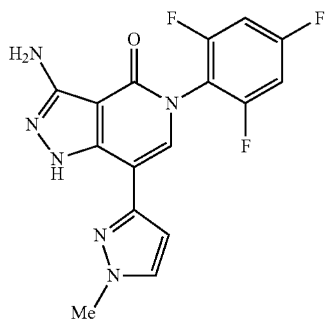 [SMILES: Cn1ccc(-c2cn(-c3c(F)cc(F)cc3F)c(=O)c3c(N)n[nH]c23)n1] | 361.2 |
| 47 | 3-amino-5-(2--chloro-3-fluorophenyl)-7-(1-methyl-1H-pyrazol-3-yl)-1,5-dihydro-4H-pyrazolo[4,3-c]pyridin-4-one | 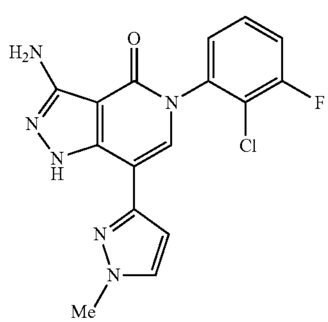 [SMILES: Cn1ccc(-c2cn(-c3cccc(F)c3Cl)c(=O)c3c(N)n[nH]c23)n1] | 359.2 |
| 48 | 3-amino-5-(2-chloro-5-fluorophenyl)-7-(1-methyl-1H-pyrazol-3-yl)-1,5-dihydro-4H-pyrazolo[4,3-c]pyridin-4-one | 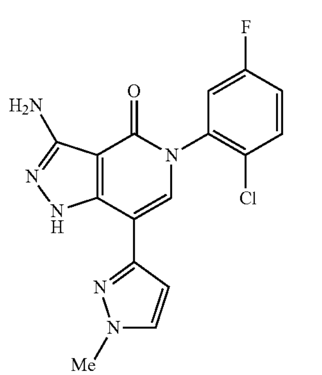 [SMILES: Cn1ccc(-c2cn(-c3cc(F)ccc3Cl)c(=O)c3c(N)n[nH]c23)n1] | 359.2 |

TABLE 2-2

| Example number | IUPAC name | Structure | MS |
|---|---|---|---|
| 49 | 2-(3-amino-7-(1-methyl-1H-pyrazol-3-yl)-4-oxo-1,4-dihydro-5H-pyrazolo[4,3-c]pyridin-5-yl)benzonitrile | 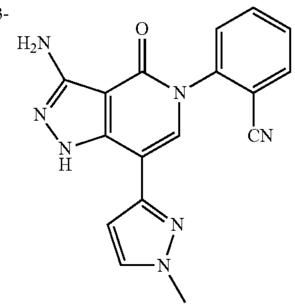 | 331.9 |
| 50 | 3-amino-5-(2,6-dimethylphenyl)-7-(1-methyl-1H-pyrazol-3-yl)-1,5-dihydro-4H-pyrazolo[4,3-c]pyridin-4-one | 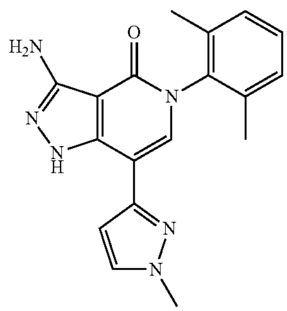 [SMILES: Cc1cccc(C)c1-n1cc(-c2ccn(C)n2)c2[nH]nc(N)c2c1=O] | 335.1 |

Example 52

3-amino-7-(1-methyl-1H-pyrazol-3-yl)-5-(3,3,3-trifluoropropyl)-1,5-dihydro-4H-pyrazolo[4,3-c]pyridin-4-one

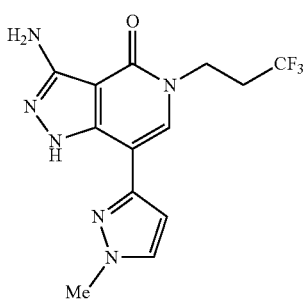 [SMILES: Cn1ccc(-c2cn(CCC(F)(F)F)c(=O)c3c(N)n[nH]c23)n1]

The title compound was obtained from 4-methoxy-2-oxo-1,2-dihydropyridine-3-carbonitrile and 1,1,1-trifluoro-3-iodopropane in the same manner as in Example 51.

MS (ESI+): [M+H]⁺327.3.

Example 53

3-amino-5-(2-chlorophenyl)-7-(5-(morpholin-4-yl)pyridin-2-yl)-1,5-dihydro-4H-pyrazolo[4,3-c]pyridin-4-one

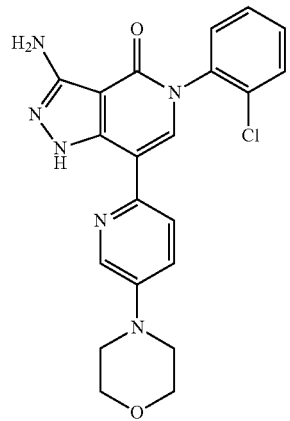 [SMILES: Nc1n[nH]c2c(-c3ccc(N4CCOCC4)cn3)cn(-c3ccccc3Cl)c(=O)c12]

A mixture of 3-amino-7-bromo-5-(2-chlorophenyl)-1,5-dihydro-4H-pyrazolo[4,3-c]pyridin-4-one obtained in Step B of Example 18 (300 mg), 4,4,4',4',5,5,5',5'-octamethyl-2,2'-bi-1,3,2-dioxaborolane (269 mg), (1,1'-bis(diphenylphosphino)ferrocene)dichloropalladium(II) (21.5 mg), potassium acetate (173 mg) and N,N-dimethylformamide (4.0 mL) was stirred overnight at 110° C. under argon atmosphere. The reaction mixture was cooled to room temperature, 4-(6-bromopyridin-3-yl)morpholine (430 mg), aqueous sodium carbonate solution (2 M, 0.883 mL) and tetrakis(triphenylphosphine)palladium(0) (102 mg) were added thereto, and the reaction mixture was stirred at 120° C. for 5 hr under argon atmosphere. The reaction mixture was cooled to room temperature, water was added thereto, and the mixture was extracted with ethyl acetate. The extract was washed with water and saturated brine, and dried over anhydrous magnesium sulfate, and the solvent was evaporated under reduced pressure. The residue was purified by silica gel chromatography (basic silica gel, methanol/ethyl acetate). The obtained rough-purified product was crystallized from methanol/ethyl acetate/hexane to give the title compound (18.0 mg).

MS (ESI+): [M+H]$^+$423.2.

Examples 54 to 103

In Examples 54 to 103, the title compound was obtained from 3-amino-7-bromo-5-(2,6-difluorophenyl)-1,5-dihydro-4H-pyrazolo[4,3-c]pyridin-4-one obtained in Step G of Example 15 and the reagent corresponding to the compounds of Examples 54 to 103, in the same manner as in Step H of Example 15, or Example 23, or a method analogous thereto. MS in the tables means actual measured value.

TABLE 3-1

| Example number | IUPAC name | Structure | MS |
|---|---|---|---|
| 54 | 3-amino-5-(2,6-difluorophenyl)-7-(5-(morpholin-4-yl)pyridin-2-yl)-1,5-dihydro-4H-pyrazolo[4,3-c]pyridin-4-one | 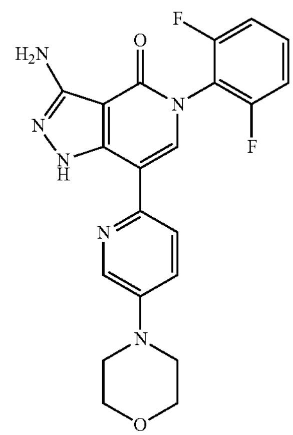 [SMILES: Nc1n[nH]c2c(-c3ccc(N4CCOCC4)cn3)cn(-c3c(F)cccc3F)c(=O)c12] | 425.2 |
| 55 | 3-amino-5-(2,6-difluorophenyl)-7-(1-isopropyl-6-oxo-1,6-dihydropyrimidin-4-yl)-1,5-dihydro-4H-pyrazolo[4,3-c]pyridin-4-one | 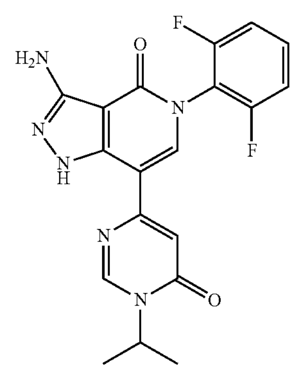 [SMILES: CC(C)n1cnc(-c2cn(-c3c(F)cccc3F)c(=O)c3c(N)n[nH]c23)cc1=O] | 399.0 |
| 56 | (6-(3-amino-5-(2,6-difluorophenyl)-4-oxo-4,5-dihydro-1H-pyrazolo[4,3-c]pyridin-7-yl)pyridin-3-yl)acetonitrile | 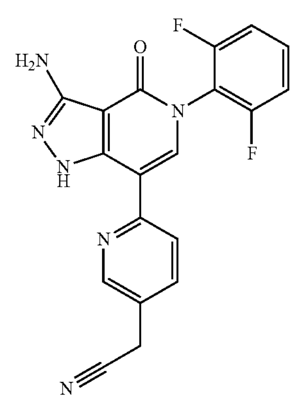 [SMILES: N#CCc1ccc(-c2cn(-c3c(F)cccc3F)c(=O)c3c(N)n[nH]c23)nc1] | 379.1 |

TABLE 3-1-continued

| Example number | IUPAC name | Structure | MS |
|---|---|---|---|
| 57 | 3-amino-5-(2,6-difluorophenyl)-7-(5-(morpholin-4-ylmethyl)pyridin-2-yl)-1,5-dihydro-4H-pyrazolo[4,3-c]pyridin-4-one | 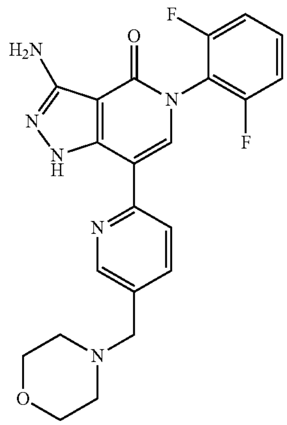 [SMILES: Nc1n[nH]c2c(-c3ccc(CN4CCOCC4)cn3)cn(-c3c(F)cccc3F)c(=O)c12] | 439.1 |
| 58 | 3-amino-5-(2,6-difluorophenyl)-7-(5-(2-methoxyethoxy)pyridin-2-yl)-1,5-dihydro-4H-pyrazolo[4,3-c]pyridin-4-one | 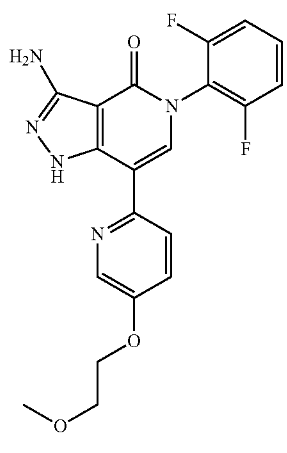 [SMILES: COCCOc1ccc(-c2cn(-c3c(F)cccc3F)c(=O)c3c(N)n[nH]c23)nc1] | 414.2 |
| 59 | 3-amino-5-(2,6-difluorophenyl)-7-(5-(2-(dimethylamino)ethoxy)pyridin-2-yl)-1,5-dihydro-4H-pyrazolo[4,3-c]pyridin-4-one | 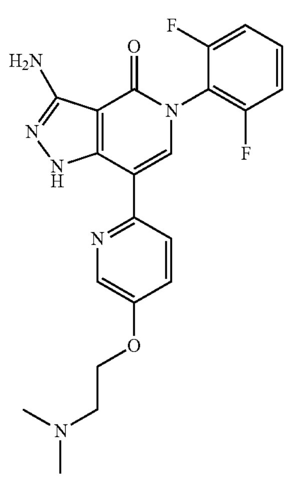 [SMILES: CN(C)CCOc1ccc(-c2cn(-c3c(F)cccc3F)c(=O)c3c(N)n[nH]c23)nc1] | 427.1 |

TABLE 3-1-continued

| Example number | IUPAC name | Structure | MS |
|---|---|---|---|
| 60 | 3-amino-5-(2,6-difluorophenyl)-7-(5-(morpholin-4-ylcarbonyl)pyridin-2-yl)-1,5-dihydro-4H-pyrazolo[4,3-c]pyridin-4-one | 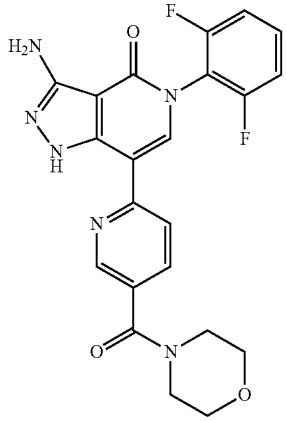 [SMILES: Nc1n[nH]c2c(-c3ccc(C(=O)N4CCOCC4)cn3)cn(-c3c(F)cccc3F)c(=O)c12] | 453.1 |
| 61 | 7-(5-(4-acetylpiperazin-1-yl)pyridin-2-yl)-3-amino-5-(2,6-difluorophenyl)-1,5-dihydro-4H-pyrazolo[4,3-c]pyridin-4-one | 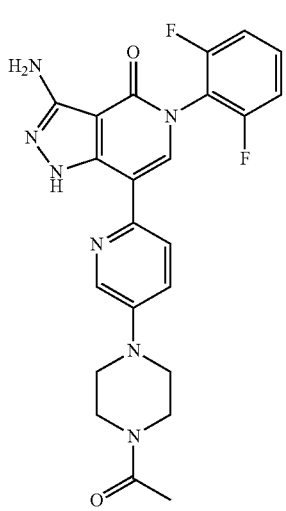 [SMILES: CC(=O)N1CCN(c2ccc(-c3cn(-c4c(F)cccc4F)c(=O)c4c(N)n[nH]c34)nc2)CC1] | 466.1 |

TABLE 3-2

| Example number | IUPAC name | Structure | MS |
|---|---|---|---|
| 62 | 2-((6-(3-amino-6-(2,6-difluorophenyl)-4-oxo-4,5-dihydro-1H-pyrazolo[4,3-c]pyridin-7-yl)pyridin-3-yl)oxy)-N-methylacetamide | 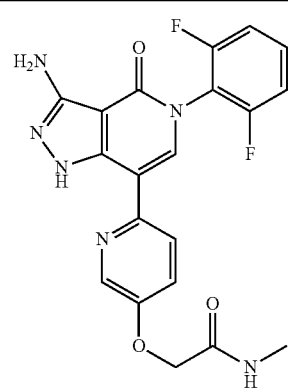 | 427.1 |

TABLE 3-2-continued

| Example number | IUPAC name | Structure | MS |
|---|---|---|---|
| 63 | 3-amino-5-(2,6-difluorophenyl)-7-(5-(morpholin-4-yl)pyrazin-2-yl)-1,5-dihydro-4H-pyrazolo[4,3-c]pyridin-4-one | 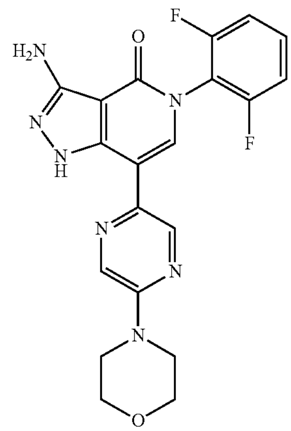 [SMILES: Nc1n[nH]c2c(-c3cnc(N4CCOCC4)cn3)cn(-c3c(F)cccc3F)c(=O)c12] | 426.1 |
| 64 | 6-(3-amino-5-(2,6-difluorophenyl)-4-oxo-4,5-dihydro-1H-pyrazolo[4,3-c]pyridin-7-yl)-N-methylnicotinamide | 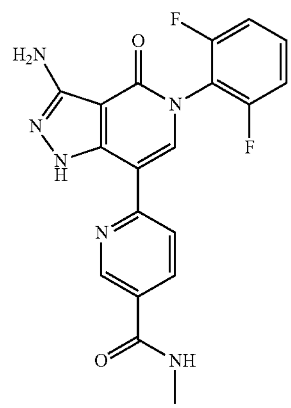 [SMILES: CNC(=O)c1ccc(-c2cn(-c3c(F)cccc3F)c(=O)c3c(N)n[nH]c23)nc1] | 397.1 |
| 65 | 3-amino-5-(2,6-difluorophenyl)-7-(6-(morpholin-4-yl)pyridazin-3-yl)-1,5-dihydro-4H-pyrazolo[4,3-c]pyridin-4-one | 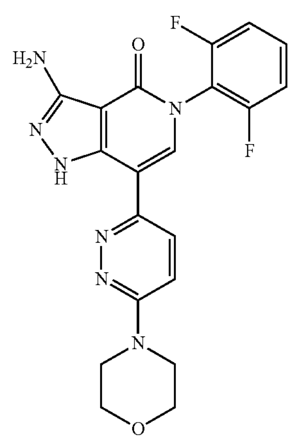 [SMILES: Nc1n[nH]c2c(-c3ccc(N4CCOCC4)nn3)cn(-c3c(F)cccc3F)c(=O)c12] | 426.1 |

TABLE 3-2-continued

| Example number | IUPAC name | Structure | MS |
|---|---|---|---|
| 66 | 2-(3-amino-5-(2,6-difluorophenyl)-4-oxo-4,5-dihydro-1H-pyrazolo[4,3-c]pyridin-7-yl)-N-methyl-1,3-thiazole-5-carboxamide | 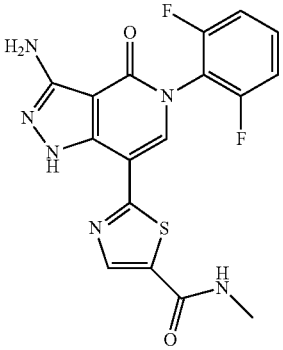 [SMILES: CNC(=O)c1cnc(-c2cn(-c3c(F)cccc3F)c(=O)c3c(N)n[nH]c23)s1] | 403.1 |
| 67 | 3-amino-5-(2,6-difluorophenyl)-7-(6-(morpholin-4-yl)pyridin-3-yl)-1,5-dihydro-4H-pyrazolo[4,3-c]pyridin-4-one | 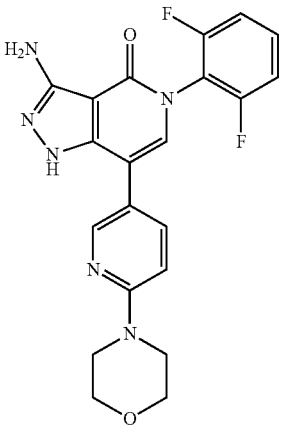 [SMILES: Nc1n[nH]c2c(-c3ccc(N4CCOCC4)nc3)cn(-c3c(F)cccc3F)c(=O)c12] | 425.4 |
| 68 | 3-amino-5-(2,6-difluorophenyl)-7-(pyridin-2-yl)-1,5-dihydro-4H-pyrazolo[4,3-c]pyridin-4-one | 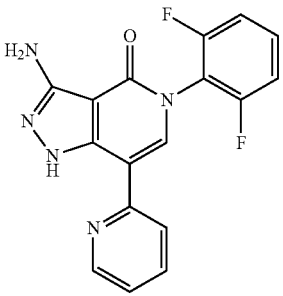 [SMILES: Nc1n[nH]c2c(-c3ccccn3)cn(-c3c(F)cccc3F)c(=O)c12] | 340.3 |
| 69 | 3-amino-5-(2,6-difluorophenyl)-7-(4-((dimethylamino)methyl)pyridin-2-yl)-1,5-dihydro-4H-pyrazolo[4,3-c]pyridin-4-one | 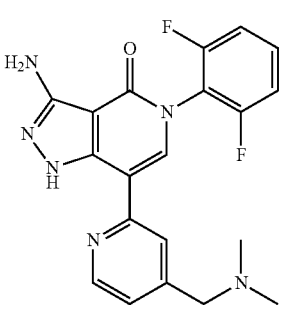 [SMILES: CN(C)Cc1ccnc(-c2cn(-c3c(F)cccc3F)c(=O)c3c(N)n[nH]c23)c1] | 397.1 |

TABLE 3-2-continued

| Example number | IUPAC name | Structure | MS |
|---|---|---|---|
| 70 | 3-amino-5-(2,6-difluorophenyl)-7-(4-(pyrrolidin-1-ylmethyl)pyridin-2-yl)-1,5-dihydro-4H-pyrazolo[4,3-c]pyridin-4-one | 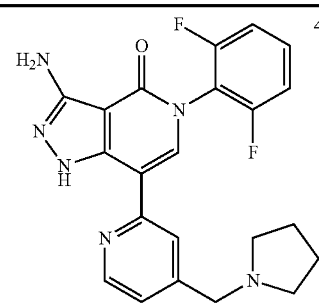 | 423.4 |

TABLE 3-3

| Example number | IUPAC name | Structure | MS |
|---|---|---|---|
| 71 | N-((2-(3-amino-5-(2,6-difluorophenyl)-4-oxo-4,5-dihydro-1H-pyrazolo[4,3-c]pyridin-7-yl)pyridin-4-yl)methyl)acetamide | 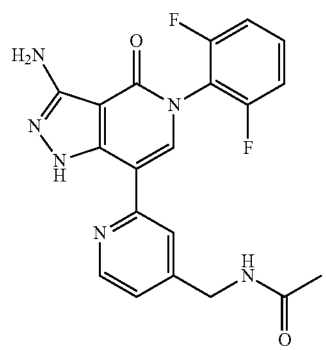 [SMILES: CC(=O)NCc1ccnc(-c2cn(-c3c(F)cccc3F)c(=O)c3c(N)n[nH]c23)c1] | 411.3 |
| 72 | 2-(3-amino-5-(2,6-difluorophenyl)-4-oxo-4,5-dihydro-1H-pyrazolo[4,3-c]pyridin-7-yl)isonicotinonitrile | 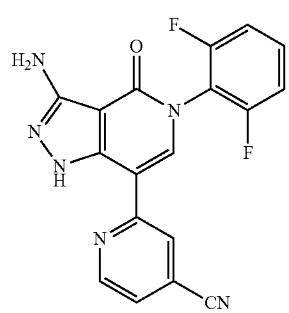 [SMILES: N#Cc1ccnc(-c2cn(-c3c(F)cccc3F)c(=O)c3c(N)n[nH]c23)c1] | 365.3 |
| 73 | 3-amino-5-(2,6-difluorophenyl)-7-(pyrimidin-4-yl)-1,5-dihydro-4H-pyrazolo[4,3-c]pyridin-4-one | 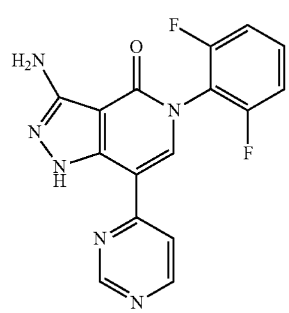 [SMILES: Nc1n[nH]c2c(-c3ccncn3)cn(-c3c(F)cccc3F)c(=O)c12] | 341.1 |

TABLE 3-3-continued

| Example number | IUPAC name | Structure | MS |
|---|---|---|---|
| 74 | 3-amino-5-(2,6-difluorophenyl)-7-(5-(piperidin-1-yl)pyridin-2-yl)-1,5-dihydro-4H-pyrazolo[4,3-c]pyridin-4-one | 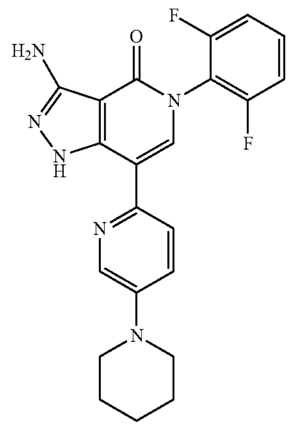 [SMILES: Nc1n[nH]c2c(-c3ccc(N4CCCCC4)cn3)cn(-c3c(F)cccc3F)c(=O)c12] | 423.0 |
| 75 | 3-amino-5-(2,6-difluorophenyl)-7-(6-(hydroxymethyl)pyrimidin-4-yl)-1,5-dihydro-4H-pyrazolo[4,3-c]pyridin-4-one | 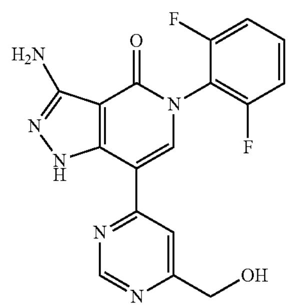 [SMILES: Nc1n[nH]c2c(-c3cc(CO)ncn3)cn(-c3c(F)cccc3F)c(=O)c12] | 371.4 |
| 76 | 3-amino-5-(2,6-difluorophenyl)-7-(2-methyl-1H-imidazol-4-yl)-1,5-dihydro-4H-pyrazolo[4,3-c]pyridin-4-one | 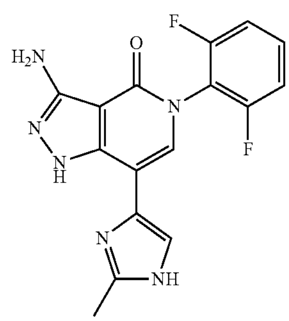 [SMILES: Cc1nc(-c2cn(-c3c(F)cccc3F)c(=O)c3c(N)n[nH]c23)c[nH]1] | 343.1 |
| 77 | 3-amino-5-(2,6-difluorophenyl)-7-(5-(3-oxomorpholin-4-yl)pyridin-2-yl)-1,5-dihydro-4H-pyrazolo[4,3-c]pyridin-4-one | 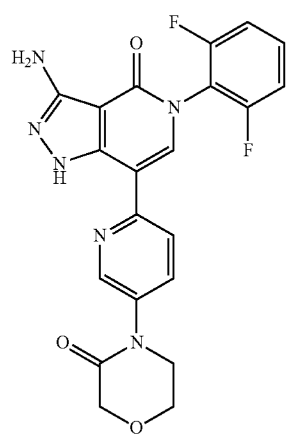 [SMILES: Nc1n[nH]c2c(-c3ccc(N4CCOCC4=O)cn3)cn(-c3c(F)cccc3F)c(=O)c12] | 439.0 |

TABLE 3-3-continued

| Example number | IUPAC name | Structure | MS |
|---|---|---|---|
| 78 | 2-(3-amino-5-(2,6-difluorophenyl)-4-oxo-4,5-dihydro-1H-pyrazolo[4,3-c]pyridin-7-yl)-N-methylisonicotinamide | 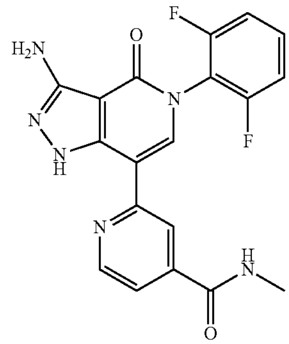 [SMILES: CNC(=O)c1ccnc(-c2cn(-c3c(F)cccc3F)c(=O)c3c(N)n[nH]c23)c1] | 397.1 |
| 79 | 3-amino-5-(2,6-difluorophenyl)-7-(4-(morpholin-4-ylcarbonyl)pyridin-2-yl)-1,5-dihydro-4H-pyrazolo[4,3-c]pyridin-4-one | 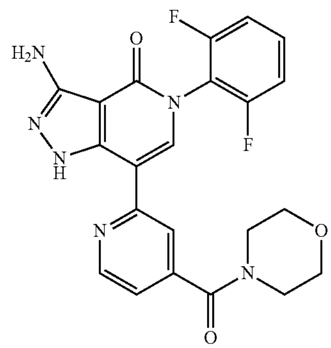 [SMILES: Nc1n[nH]c2c(-c3cc(C(=O)N4CCOCC4)ccn3)cn(-c3c(F)cccc3F)c(=O)c12] | 453.4 |

TABLE 3-4

| Example number | IUPAC name | Structure | MS |
|---|---|---|---|
| 80 | 3-amino-5-(2,6-difluorophenyl)-7-(6-(morpholin-4-yl)pyrimidin-4-yl)-1,5-dihydro-4H-pyrazolo[4,3-c]pyridin-4-one | 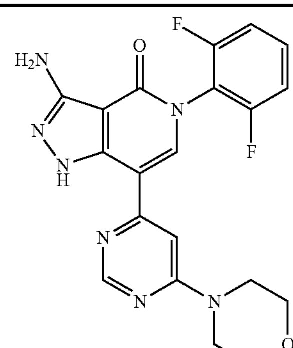 | 426.2 |
| 81 | 3-amino-5-(2,6-difluorophenyl)-7-(6-(4-(2-hydroxyethyl)piperazin-1-yl)pyrimidin-4-yl)-1,5-dihydro-4H-pyrazolo[4,3-c]pyridin-4-one | 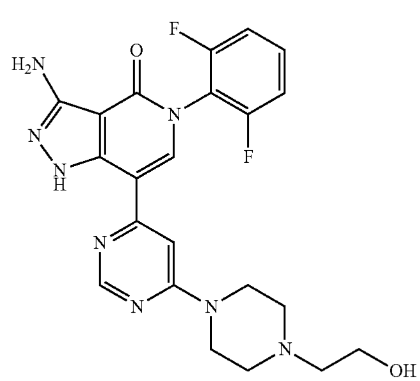 [SMILES: Nc1n[nH]c2c(-c3cc(N4CCN(CCO)CC4)ncn3)cn(-c3c(F)cccc3F)c(=O)c12] | 469.1 |

TABLE 3-4-continued

| Example number | IUPAC name | Structure | MS |
|---|---|---|---|
| 82 | 2-(3-amino-5-(2,6-difluorophenyl)-4-oxo-4,5-dihydro-1H-pyrazolo[4,3-c]pyridin-7-yl)-N-(2-hydroxyethyl)isonicotinamide | 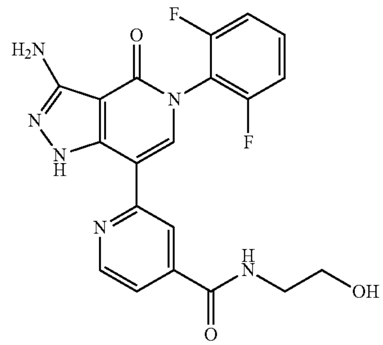 [SMILES: Nc1n[nH]c2c(-c3cc(C(=O)NCCO)ccn3)cn(-c3c(F)cccc3F)c(=O)c12] | 427.1 |
| 83 | 3-amino-7-(6-(cyclopentyloxy)pyrimidin-4-yl)-5-(2,6-difluorophenyl)-1,5-dihydro-4H-pyrazolo[4,3-c]pyridin-4-one | 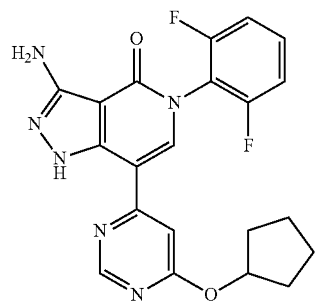 [SMILES: Nc1n[nH]c2c(-c3cc(OC4CCCC4)ncn3)cn(-c3c(F)cccc3F)c(=O)c12] | 425.2 |
| 84 | 3-amino-5-(2,6-difluorophenyl)-7-(2-furyl)-1,5-dihydro-4H-pyrazolo[4,3-c]pyridin-4-one | 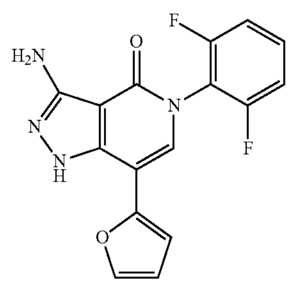 [SMILES: Nc1n[nH]c2c(-c3ccco3)cn(-c3c(F)cccc3F)c(=O)c12] | 329.1 |
| 85 | 3-amino-5-(2,6-difluorophenyl)-7-(4-(pyrrolidin-1-ylcarbonyl)pyridin-2-yl)-1,5-dihydro-4H-pyrazolo[4,3-c]pyridin-4-one | 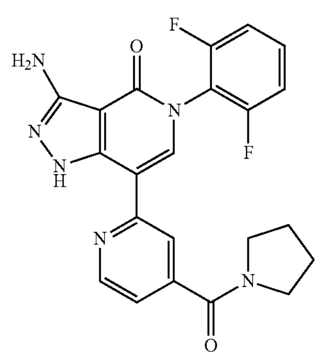 [SMILES: Nc1n[nH]c2c(-c3cc(C(=O)N4CCCC4)ccn3)cn(-c3c(F)cccc3F)c(=O)c12] | 437.2 |

TABLE 3-4-continued

| Example number | IUPAC name | Structure | MS |
|---|---|---|---|
| 86 | 3-amino-5-(2,6-difluorophenyl)-7-(4-(2-(dimethylamino)ethyl)pyridin-2-yl)-1,5-dihydro-4H-pyrazolo[4,3-c]pyridin-4-one | 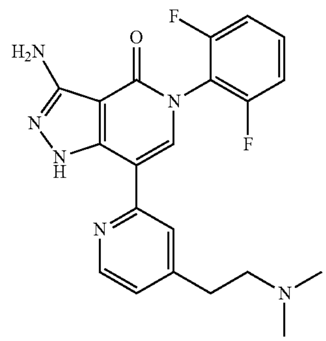 [SMILES: CN(C)CCc1ccnc(-c2cn(-c3c(F)cccc3F)c(=O)c3c(N)n[nH]c23)c1] | 411.2 |
| 87 | 5-(3-amino-5-(2,6-difluorophenyl)-4-oxo-4,5-dihydro-1H-pyrazolo[4,3-c]pyridin-7-yl)-N-methyl-2-furancarboxamide | 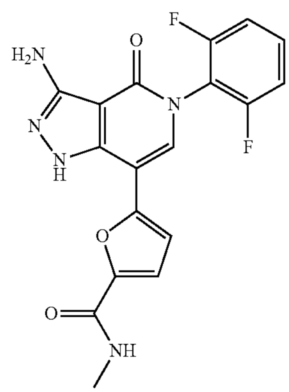 [SMILES: CNC(=O)c1ccc(-c2cn(-c3c(F)cccc3F)c(=O)c3c(N)n[nH]c23)o1] | 386 |
| 88 | 5-(3-amino-5-(2,6-difluorophenyl)-4-oxo-4,5-dihydro-1H-pyrazolo[4,3-c]pyridin-7-yl)-N-methyl-3-furancarboxamide | 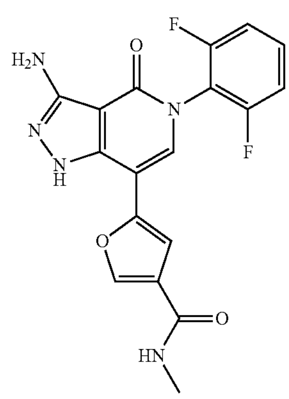 [SMILES: CNC(=O)c1coc(-c2cn(-c3c(F)cccc3F)c(=O)c3c(N)n[nH]c23)c1] | 386.2 |

TABLE 3-5

| Example number | IUPAC name | Structure | MS |
|---|---|---|---|
| 89 | 2-(3-amino-5-(2,6-difluorophenyl)-4-oxo-4,5-dihydro-1H-pyrazolo[4,3-c]pyridin-7-yl)-N-(tetrahydro-2H-pyran-4-yl)isonicotinamide | 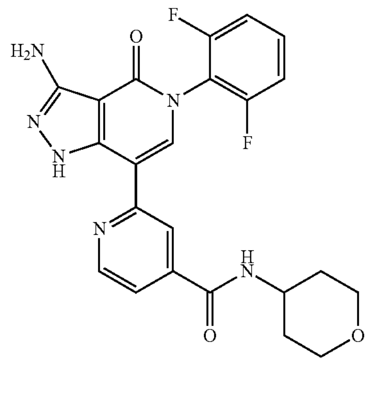 [SMILES: Nc1n[nH]c2c(-c3cc(C(=O)NC4CCOCC4)ccn3)cn(-c3c(F)cccc3F)c(=O)c12] | 467.2 |
| 90 | 3-amino-5-(2,6-difluorophenyl)-7-(4-(morpholin-4-ylcarbonyl)-2-furyl)-1,5-dihydro-4H-pyrazolo[4,3-c]pyridin-4-one | 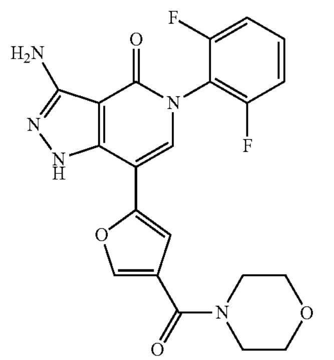 [SMILES: Nc1n[nH]c2c(-c3cc(C(=O)N4CCOCC4)co3)cn(-c3c(F)cccc3F)c(=O)c12] | 442.1 |
| 91 | 3-amino-5-(2,6-difluorophenyl)-7-(4-(morpholin-4-yl)pyridin-2-yl)-1,5-dihydro-4H-pyrazolo[4,3-c]pyridin-4-one | 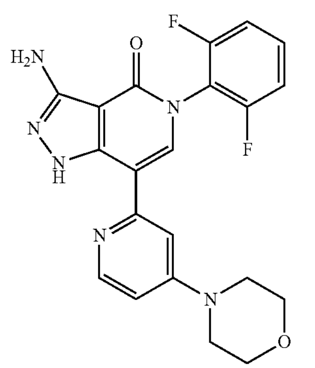 [SMILES: Nc1n[nH]c2c(-c3cc(N4CCOCC4)ccn3)cn(-c3c(F)cccc3F)c(=O)c12] | 425.3 |
| 92 | 3-amino-5-(2,6-difluorophenyl)-7-(4-(2-(dimethylamino)ethoxy)pyridin-2-yl)-1,5-dihydro-4H-pyrazolo[4,2-c]pyridin-4-one | 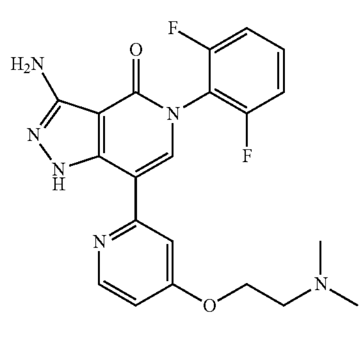 [SMILES: CN(C)CCOc1ccnc(-c2cn(-c3c(F)cccc3F)c(=O)c3c(N)n[nH]c23)c1] | 427.3 |

TABLE 3-5-continued

| Example number | IUPAC name | Structure | MS |
|---|---|---|---|
| 93 | 3-amino-5-(2,6-difluorophenyl)-7-(4-(2-methoxyethoxy)pyridin-2-yl)-1,5-dihydro-4H-pyrazolo[4,3-c]pyridin-4-one | 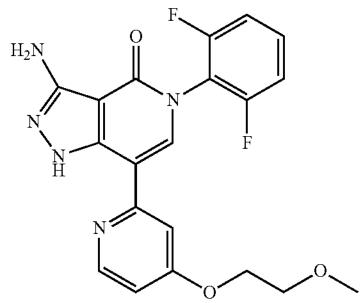 [SMILES: COCCOc1ccnc(-c2cn(-c3c(F)cccc3F)c(=O)c3c(N)n[nH]c23)c1] | 414.3 |
| 94 | 3-amino-5-(2,6-difluorophenyl)-7-(4-(tetrahydro-2H-pyran-4-yloxo)pyridin-2-yl)-1,5-dihydro-4H-pyrazolo[4,3-c]pyridin-4-one | 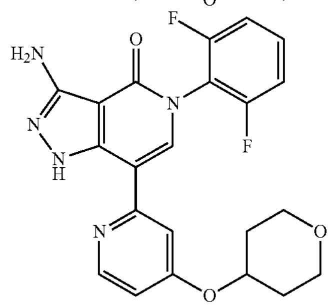 | 440.3 |
| 95 | 3-amino-5-(2,6-difluorophenyl)-7-(6-(4-(2-hydroxyethyl)piperazin-1-yl)-2-methylpyrimidin-4-yl)-1,5-dihydro-4H-pyrazolo[4,3-c]pyridin-4-one | 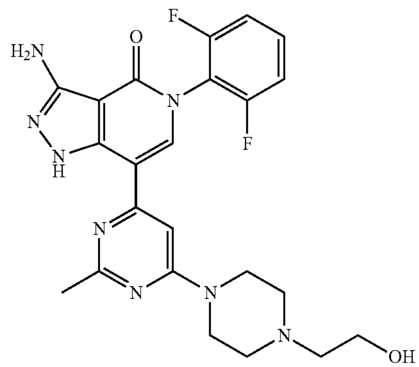 [SMILES: Cc1nc(-c2cn(-c3c(F)cccc3F)c(=O)c3c(N)n[nH]c23)cc(N2CCN(CCO)CC2)n1] | 483.2 |
| 96 | 3-amino-5-(2,6-difluorophenyl)-7-(6-(hydroxymethyl)pyridin-2-yl)-1,5-dihydro-4H-pyrazolo[4,3-c]pyridin-4-one | 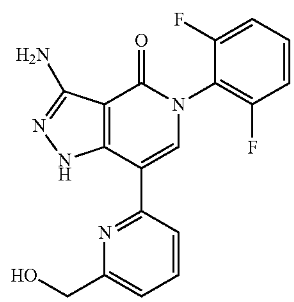 [SMILES: Nc1n[nH]c2c(-c3cccc(CO)n3)cn(-c3c(F)cccc3F)c(=O)c12] | 370.1 |
| 97 | N-(6-(3-amino-5-(2,6-difluorophenyl)-4-oxo-4,5-dihydro-1H-pyrazolo[4,3-c]pyridin-7-yl)pyridin-2-yl)acetamide | 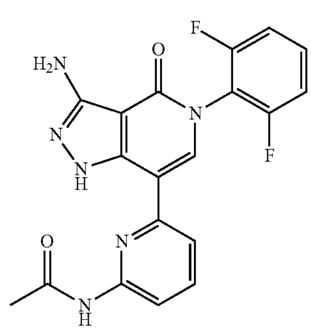 [SMILES: CC(=O)Nc1cccc(-c2cn(-c3c(F)cccc3F)c(=O)c3c(N)n[nH]c23)n1] | 397.2 |

TABLE 3-6

| Example number | IUPAC name | Structure | MS |
|---|---|---|---|
| 98 | 3-amino-5-(2,6-difluorophenyl)-7-(6-(2,2-dimethylpropoxy)pyrimidin-4-yl)-1,5-dihydro-4H-pyrazolo[4,3-c]pyridin-4-one | 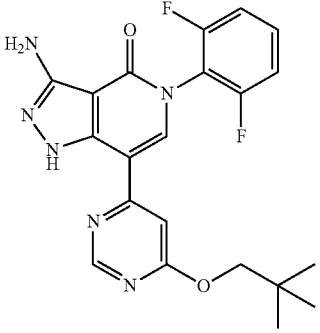 [SMILES: CC(C)(C)COc1cc(-c2cn(-c3c(F)cccc3F)c(=O)c3c(N)n[nH]c23)ncn1] | 427.1 |
| 99 | N-((6-(3-amino-5-(2,6-difluorophenyl)-4-oxo-4,5-dihydro-1H-pyrazolo[4,3-c]pyridin-7-yl)pyridin-2-yl)methyl)acetamide | 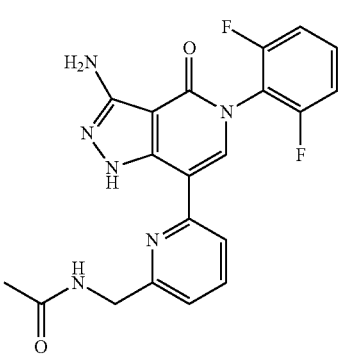 [SMILES: CC(=O)NCc1cccc(-c2cn(-c3c(F)cccc3F)c(=O)c3c(N)n[nH]c23)n1] | 411.1 |
| 100 | 3-amino-5-(2,6-difluorophenyl)-7-(6-(2-(dimethylamino)ethoxy)pyrimidin-4-yl)-1,5-dihydro-4H-pyrazolo[4,3-c]pyridin-4-one | 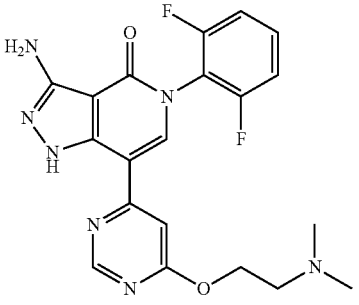 [SMILES: CN(C)CCOc1cc(-c2cn(-c3c(F)cccc3F)c(=O)c3c(N)n[nH]c23)ncn1] | 428.2 |
| 101 | 3-amino-5-(2,6-difluorophenyl)-7-(6-((2-(dimethylamino)ethyl)amino)pyrimidin-4-yl)-1,5-dihydro-4H-pyrazolo[4,3-c]pyridin-4-one | 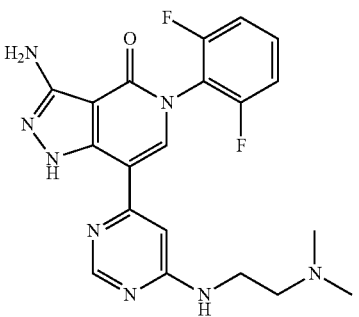 [SMILES: CN(C)CCNc1cc(-c2cn(-c3c(F)cccc3F)c(=O)c3c(N)n[nH]c23)ncn1] | 427.1 |

TABLE 3-6-continued

| Example number | IUPAC name | Structure | MS |
|---|---|---|---|
| 102 | 3-amino-5-(2,6-difluorophenyl)-7-(6-(4-methylpiperazin-1-yl)pyrimidin-4-yl)-1,5-dihydro-4H-pyrazolo[4,3-c]pyridin-4-one | 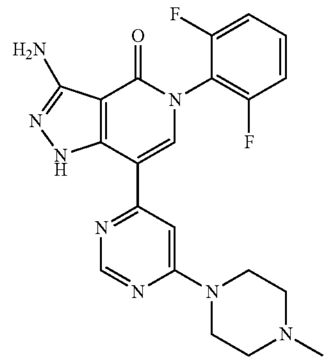 [SMILES: CN1CCN(c2cc(-c3cn(-c4c(F)cccc4F)c(=O)c4c(N)n[nH]c34)ncn2)CC1] | 439.1 |
| 103 | N-(6-(3-amino-5-(2,6-difluorophenyl)-4-oxo-4,5-dihydro-1H-pyrazolo[4,3-c]pyridin-7-yl)pyrimidin-4-yl)acetamide | 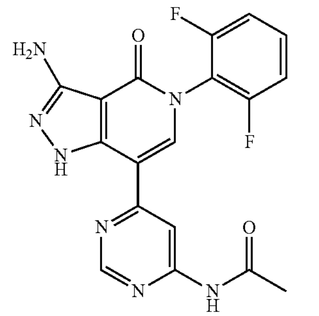 [SMILES: CC(=O)Nc1cc(-c2cn(-c3c(F)cccc3F)c(=O)c3c(N)n[nH]c23)ncn1] | 398.2 |

Example 104

2-(3-amino-7-(1-methyl-1H-pyrazol-3-yl)-4-oxo-1,4-dihydro-5H-pyrazolo[4,3-c]pyridin-5-yl)-3-fluorobenzonitrile

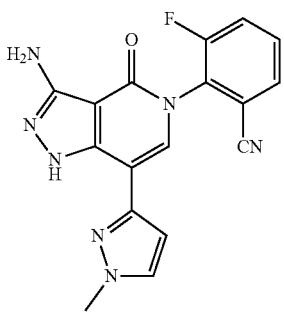 [SMILES: Cn1ccc(-c2cn(-c3c(F)cccc3C#N)c(=O)c3c(N)n[nH]c23)n1]

A) N-(2-cyano-6-fluorophenyl)-3-oxobutanamide

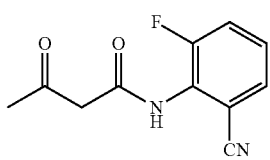 [SMILES: CC(=O)CC(=O)Nc1c(F)cccc1C#N]

To a mixture of 2-amino-3-fluorobenzonitrile (41.9 g), sodium acetate (30.3 g) and toluene (200 mL) was added diketene (28.2 mL) over 10 min at 0° C. The reaction mixture was stirred at room temperature for 7 hr. To the reaction mixture were added toluene (150 mL) and diketene (4.7 mL) at room temperature, and the mixture was stirred at room temperature for 16 hr. The reaction mixture was poured into water, and the mixture was extracted with ethyl acetate. The extract was washed successively with water and saturated brine, and dried over anhydrous magnesium sulfate, and the solvent was evaporated under reduced pressure. The residue was recrystallized from diisopropyl ether/ethanol to give the title compound (48.64 g).

MS (ESI+): [M+H]$^+$221.2.

B) N-(2-cyano-6-fluorophenyl)-2-((dimethylamino)methylene)-3-oxobutanamide

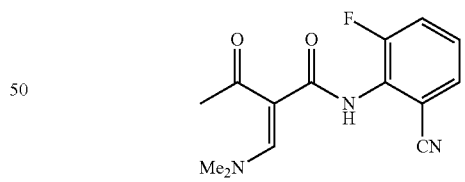

To a mixture of N-(2-cyano-6-fluorophenyl)-3-oxobutanamide obtained in Step A (48.60 g) and N,N-dimethylformamide (200 mL) was added dropwise 1,1-dimethoxy-N,N-dimethylmethanamine (52.6 g) over 10 min at 0° C. The reaction mixture was stirred at room temperature 3 hr. The solvent was evaporated under reduced pressure, to the residue was added water, and the mixture was extracted with ethyl acetate. The extract was dried over anhydrous magnesium sulfate, and the solvent was evaporated under reduced pressure. The residue was recrystallized from ethyl acetate, and collected by filtration. The obtained solid was washed with ethyl acetate/diisopropyl ether, and then diisopropyl ether to give the title compound (26.16 g).

MS (ESI+): [M+H]$^+$276.1.

C) 2-(4-chloro-3-formyl-2-oxopyridin-1(2H)-yl)-3-fluorobenzonitrile

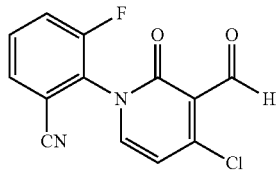 [SMILES: N#Cc1cccc(F)c1-n1ccc(Cl)c(C=O)c1=O]

To a solution of N-(2-cyano-6-fluorophenyl)-2-((dimethylamino)methylene)-3-oxobutanamide obtained in Step B (11.00 g) in N,N-dimethylformamide (150 mL) was added (chloromethylene)dimethylammonium chloride (24.9 g) under ice-cooling, and the reaction mixture was heated at 100° C. for 30 min. The reaction mixture was cooled to room temperature, and poured into ice water, and the mixture was extracted with ethyl acetate. The extract was dried over anhydrous magnesium sulfate, and the solvent was evaporated under reduced pressure. The residue was purified by silica gel column chromatography (ethyl acetate/hexane) to give an orange oil. The obtained oil was crystallized from diisopropyl ether/hexane to give the title compound (2.81 g).
MS (ESI+): [M+H]$^+$277.1.

D) 2-(4-chloro-3-((hydroxyimino)methyl)-2-oxopyridin-1(2H)-yl)-3-fluorobenzonitrile

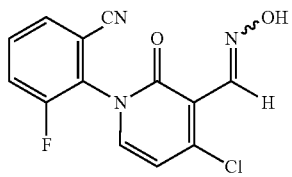

A mixture of 2-(4-chloro-3-formyl-2-oxopyridin-1(2H)-yl)-3-fluorobenzonitrile obtained in Step C (2.70 g), hydroxylamine hydrochloride (814 mg), sodium acetate (1.60 g) and methanol (60 mL)/water (15 mL) was stirred at room temperature for 1 hr. The reaction solution was poured into ice water. The resulting solid was collected by filtration, and washed successively with water, 2-propanol and diethyl ether to give the title compound (2.39 g).
MS (ESI+): [M+H]$^+$292.0.

E) 4-chloro-1-(2-cyano-6-fluorophenyl)-2-oxo-1,2-dihydropyridine-3-carbonitrile

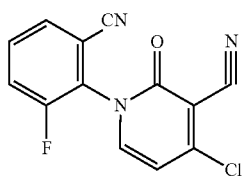

To a solution of 2-(4-chloro-3-((hydroxyimino)methyl)-2-oxopyridin-1(2H)-yl)-3-fluorobenzonitrile obtained in Step D (8.0 g) in acetonitrile (180 mL) was added thionyl chloride (3.98 mL) at room temperature. The reaction mixture was stirred at room temperature for 1 hr. The solvent was evaporated under reduced pressure, and the residue was crystallized from diisopropyl ether/methanol. The obtained solid was collected by filtration to give the title compound (7.05 g).
MS (ESI+): [M+H]$^+$274.2.

F) 5-bromo-4-chloro-1-(2-cyano-6-fluorophenyl)-2-oxo-1,2-dihydropyridine-3-carbonitrile

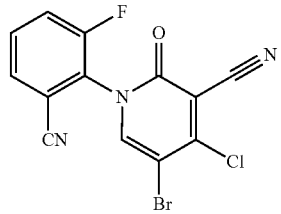 [SMILES: N#Cc1cccc(F)c1-n1cc(Br)c(Cl)c(C#N)c1=O]

To a solution of 4-chloro-1-(2-cyano-6-fluorophenyl)-2-oxo-1,2-dihydropyridine-3-carbonitrile obtained in Step E (4.0 g) in N,N-dimethylformamide (40 mL) was added N-bromosuccinimide (3.90 g) at room temperature. The reaction mixture was heated at 50° C. for 16 hr. To the reaction mixture was added water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (1.10 g).
MS (ESI+): [M+H]$^+$352.1.

G) 2-(3-amino-7-bromo-4-oxo-1,4-dihydro-5H-pyrazolo[4,3-c]pyridin-5-yl)-3-fluorobenzonitrile

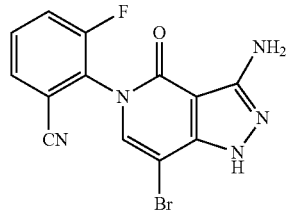 [SMILES: N#Cc1cccc(F)c1-n1cc(Br)c2[nH]nc(N)c2c1=O]

A solution of 5-bromo-4-chloro-1-(2-cyano-6-fluorophenyl)-2-oxo-1,2-dihydropyridine-3-carbonitrile obtained in Step F (4.35 g) and hydrazine monohydrate (0.658 mL) in ethanol (32 mL)/tetrahydrofuran (64 mL) was heated at 90° C. for 1 hr. To the reaction mixture was added hydrazine monohydrate (0.5 mL), and the mixture was heated at 90° C. for 30 min. The solvent was evaporated under reduced pressure, to the reaction mixture was added water, and the mixture was extracted with ethyl acetate. The extract was washed with saturated brine, dried over anhydrous magnesium sulfate, and concentrated under reduced pressure. The residue was purified by silica gel column chromatography (ethyl acetate/hexane) to give the title compound (4.12 g).
$^1$H NMR (400 MHz, CDCl$_3$) δ 5.08 (2H, brs), 7.12 (1H, s), 7.45-7.65 (3H, m), 10.46 (1H, brs).

H) 2-(3-amino-7-(1-methyl-1H-pyrazol-3-yl)-4-oxo-1,4-dihydro-5H-pyrazolo[4,3-c]pyridin-5-yl)-3-fluorobenzonitrile A mixture of 2-(3-amino-7-bromo-4-oxo-1,4-dihydro-5H-pyrazolo[4,3-c]pyridin-5-yl)-3-fluorobenzonitrile obtained in Step G (160 mg), 1-methyl-3-(4,4,5,5-tetramethyl-1,3,2-dioxaborolan-2-yl)-1H-pyrazole (191 mg), tetrakis(triphenylphosphine)palladium(0) (53 mg), aqueous sodium carbonate solution (2 M, 0.460 mL) and N,N-dimethylformamide (10 mL) was heated with microwave irradiation at 130° C. for 90 min under argon atmosphere. To the reaction mixture was added water, and the mixture was extracted with ethyl acetate/tetrahydrofuran. The extract was washed with saturated brine, and dried over anhydrous magnesium sulfate, and the solvent was evaporated under reduced pressure. The residue was purified by silica gel chromatography (basic silica gel, methanol/ethyl acetate) to give a crude product. The crude product was crystallized from ethyl acetate/diethyl ether to give the title compound (44 mg).

MS (ESI+): [M+H]$^+$350.2.

$^1$H NMR (400 MHz, CDCl$_3$) δ 3.98 (3H, s), 4.75 (2H, s), 6.39 (1H, d, J=2.4 Hz), 7.29 (1H, s), 7.39 (1H, d, J=2.4 Hz), 7.51-7.68 (3H, m), 10.75 (1H, brs).

Examples 105 to 111

In Examples 105 to 111, the title compound was obtained from 2-(3-amino-7-bromo-4-oxo-1,4-dihydro-5H-pyrazolo[4,3-c]pyridin-5-yl)-3-fluorobenzonitrile obtained in Step G of Example 104 and the reagent corresponding to the compounds of Examples 105 to 111, in the same manner as in Example 23 or a method analogous thereto. MS in the tables means actual measured value.

TABLE 4

| Example number | IUPAC name | Structure | MS |
|---|---|---|---|
| 105 | 2-(3-amino-7-(5-(morpholin-4-yl)pyridin-2-yl)-4-oxo-1,4-dihydro-5H-pyrazolo[4,3-c]pyridin-5-yl)-3-fluorobenzonitrile | 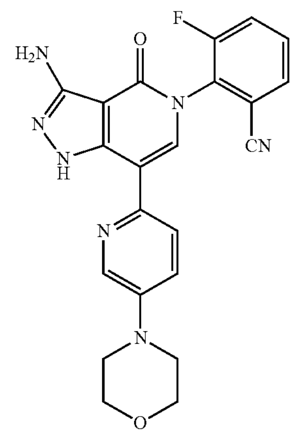 [SMILES: N#Cc1cccc(F)c1-n1cc(-c2ccc(N3CCOCC3)cn2)c2[nH]nc(N)c2c1=O] | 432.2 |
| 106 | 2-(3-amino-7-(4-(morpholin-4-yl)pyridin-2-yl)-4-oxo-1,4-dihydro-5H-pyrazolo[4,3-c]pyridin-5-yl)-3-fluorobenzonitrile | 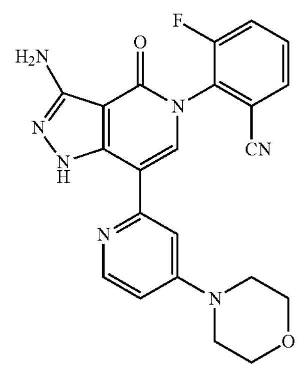 [SMILES: N#Cc1cccc(F)c1-n1cc(-c2cc(N3CCOCC3)ccn2)c2[nH]nc(N)c2c1=O] | 432.3 |
| 107 | 2-(3-amino-7-(5-(morpholin-4-yl)pyrazin-2-yl)-4-oxo-1,4-dihydro-5H-pyrazolo[4,3-c]pyridin-5-yl)-3-fluorobenzonitrile | 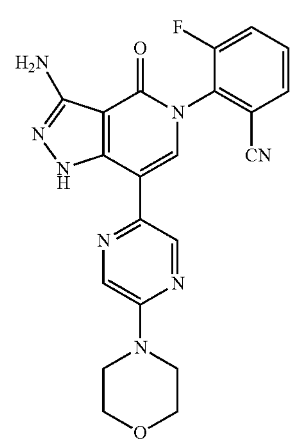 [SMILES: N#Cc1cccc(F)c1-n1cc(-c2cnc(N3CCOCC3)cn2)c2[nH]nc(N)c2c1=O] | 433.3 |

TABLE 4-continued

| Example number | IUPAC name | Structure | MS |
|---|---|---|---|
| 108 | 2-(3-amino-7-(5-isopropoxypyrazin-2-yl)-4-oxo-1,4-dihydro-5H-pyrazolo[4,3-c]pyridin-5-yl)-3-fluorobenzonitrile | 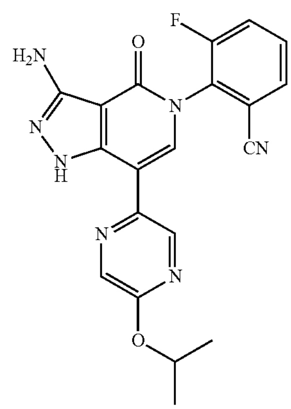 [SMILES: CC(C)Oc1cnc(-c2cn(-c3c(F)cccc3C#N)c(=O)c3c(N)n[nH]c23)cn1] | 406.3 |
| 109 | 2-(3-amino-7-(5-(4-methylpiperazin-1-yl)pyrazin-2-yl)-4-oxo-1,4-dihydro-5H-pyrazolo[4,3-c]pyridin-5-yl)-3-fluorobenzonitrile | 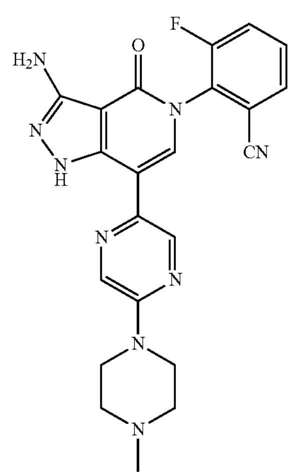 [SMILES: CN1CCN(c2cnc(-c3cn(-c4c(F)cccc4C#N)c(=O)c4c(N)n[nH]c34)cn2)CC1] | 446.3 |
| 110 | 2-(3-amino-7-(5-(2-(dimethylamino)ethoxy)pyridin-2-yl)-4-oxo-1,4-dihydro-5H-pyrazolo[4,3-c]pyridin-5-yl)-3-fluorobenzonitrile | 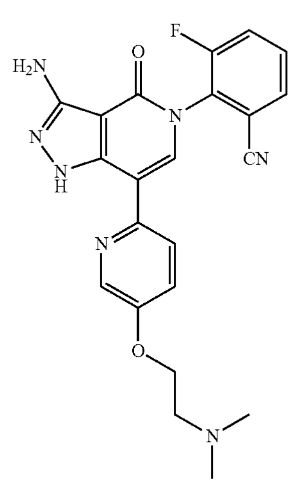 [SMILES: CN(C)CCOc1ccc(-c2cn(-c3c(F)cccc3C#N)c(=O)c3c(N)n[nH]c23)nc1] | 434.2 |

TABLE 4-continued

| Example number | IUPAC name | Structure | MS |
|---|---|---|---|
| 111 | 2-(3-amino-7-(5-(morpholin-4-ylmethyl)pyrazin-2-yl)-4-oxo-1,4-dihydro-5H-pyrazolo[4,3-c]pyridin-5-yl)-3-fluorobenzonitrile | 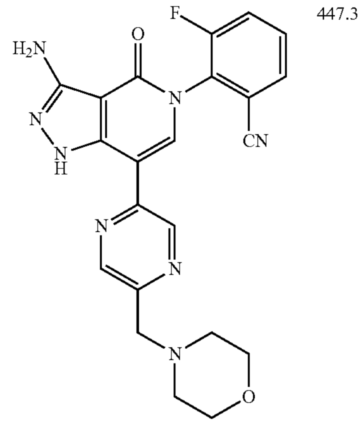 | 447.3 |

Example 112

3-amino-7-bromo-5-((2S)-3-methylbutan-2-yl)-1,5-dihydro-4H-pyrazolo[4,3-c]pyridin-4-one

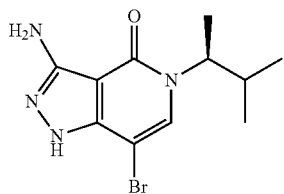 [SMILES: CC(C)[C@H](C)n1cc(Br)c2[nH]nc(N)c2c1=O]

Racemic 3-amino-7-bromo-5-(3-methylbutan-2-yl)-1,5-dihydro-4H-pyrazolo[4,3-c]pyridin-4-one obtained in Step G of Example 13 (7.89 g) was resolved by HPLC (column: CHIRALPAK AD, 50 mmID×500 mmL, manufactured by Daicel Chemical Industries, mobile phase: hexane/ethanol=600/400(v/v)) to give the title compound (3.751 g) having a shorter retention time.

MS (ESI+): [M+H]$^+$299.1.

>99.9% ee (HPLC (column: CHIRALPAK AD, 4.6 mmID×250 mmL, manufactured by Daicel Chemical Industries, mobile phase: hexane/ethanol=600/400(v/v), flow rate: 0.5 mL/min, retention time: 9.88 min))

Example 113

3-amino-7-bromo-5-((2R)-3-methylbutan-2-yl)-1,5-dihydro-4H-pyrazolo[4,3-c]pyridin-4-one

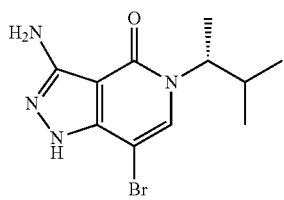 [SMILES: CC(C)[C@@H](C)n1cc(Br)c2[nH]nc(N)c2c1=O]

Racemic 3-amino-7-bromo-5-(3-methylbutan-2-yl)-1,5-dihydro-4H-pyrazolo[4,3-c]pyridin-4-one obtained in Step G of Example 13 (7.89 g) was resolved by HPLC (column: CHIRALPAK AD, 50 mmID×500 mmL, manufactured by Daicel Chemical Industries, mobile phase: hexane/ethanol=600/400(v/v)) to give the title compound (3.479 g) having a longer retention time.

MS (ESI+): [M+H]$^+$299.1.

>99.9% ee (HPLC (column: CHIRALPAK AD, 4.6 mmID×250 mmL, manufactured by Daicel Chemical Industries, mobile phase: hexane/ethanol=600/400(v/v), flow rate: 0.5 mL/min, retention time: 12.14 min))

Examples 114 to 117

In Examples 114 to 117, the title compound was obtained from 3-amino-7-bromo-5-(3-methylbutan-2-yl)-1,5-dihydro-4H-pyrazolo[4,3-c]pyridin-4-one obtained in Step G of Example 13 and the reagent corresponding to the compounds of Examples 114 to 117, in the same manner as in Example 23 or a method analogous thereto. MS in the tables means actual measured value.

TABLE 5

| Example number | IUPAC name | Structure | MS |
|---|---|---|---|
| 114 | 3-amino-5-(3-methylbutan-2-yl)-7-(6-(morpholin-4-yl)pyrimidin-4-yl)-1,5-dihydro-4H-pyrazolo[4,3-c]pyridin-4-one | 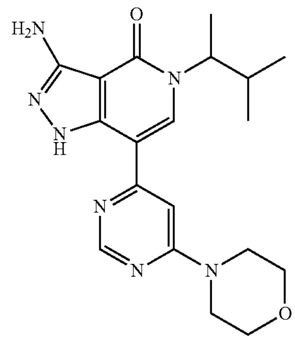 [SMILES: CC(C)C(C)n1cc(-c2cc(N3CCOCC3)ncn2)c2[nH]nc(N)c2c1=O] | 384.2 |
| 115 | 3-amino-7-(5-(2-(dimethylamino)ethoxy)pyridin-2-yl)-5-(3-methylbutan-2-yl)-1,5-dihydro-4H-pyrazolo[4,3-c]pyridin-4-one | 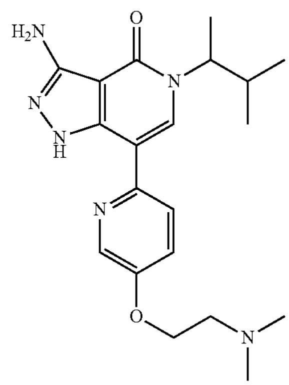 [SMILES: CC(C)C(C)n1cc(-c2ccc(OCCN(C)C)cn2)c2[nH]nc(N)c2c1=O] | 385.3 |
| 116 | 3-amino-5-(3-methylbutan-2-yl)-7-(5-(morpholin-4-yl)pyridin-2-yl)-1,5-dihydro-4H-pyrazolo[4,3-c]pyridin-4-one | 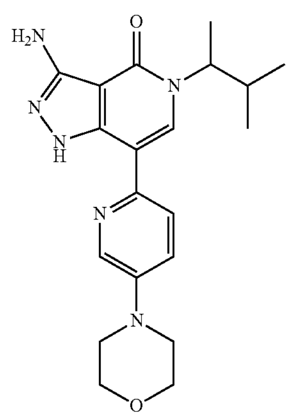 | 383.4 |
| 117 | 3-amino-5-(3-methylbutan-2-yl)-7-(5-(tetrahydro-2H-pyran-4-yloxy)pyridin-2-yl)-1,5-dihydro-4H-pyrazolo[4,3-c]pyridin-4-one | 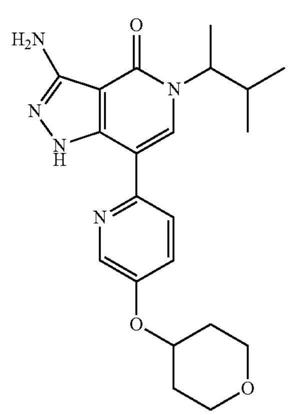 [SMILES: CC(C)C(C)n1cc(-c2ccc(OC3CCOCC3)cn2)c2[nH]nc(N)c2c1=O] | 398.2 |

Example 118

3-amino-5-((2S)-3-methylbutan-2-yl)-7-(5-(morpholin-4-yl)pyrazin-2-yl)-1,5-dihydro-4H-pyrazolo[4,3-c]pyridin-4-one

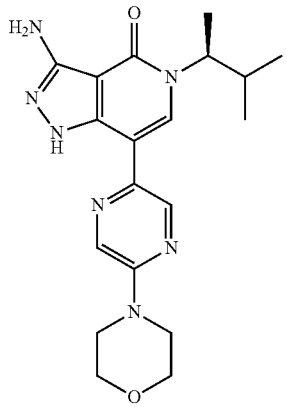 [SMILES: CC(C)[C@H](C)n1cc(-c2cnc(N3CCOCC3)cn2)c2[nH]nc(N)c2c1=O]

The title compound was obtained from 3-amino-7-bromo-5-((2S)-3-methylbutan-2-yl)-1,5-dihydro-4H-pyrazolo[4,3-c]pyridin-4-one obtained in Example 112 and 4-(5-bromopyrazin-2-yl)morpholine in the same manner as in Example 23.
MS (ESI+): [M+H]$^+$384.4.

Example 119

3-amino-5-((2R)-3-methylbutan-2-yl)-7-(5-(morpholin-4-yl)pyridin-2-yl)-1,5-dihydro-4H-pyrazolo[4,3-c]pyridin-4-one

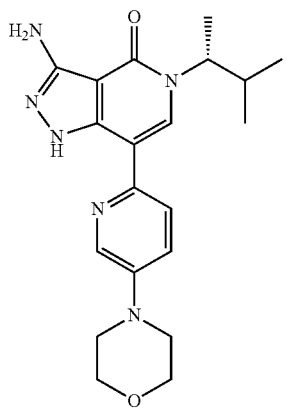 [SMILES: CC(C)[C@@H](C)n1cc(-c2ccc(N3CCOCC3)cn2)c2[nH]nc(N)c2c1=O]

Racemic 3-amino-5-(3-methylbutan-2-yl)-7-(5-(morpholin-4-yl)pyridin-2-yl)-1,5-dihydro-4H-pyrazolo[4,3-c]pyridin-4-one obtained in Example 116 (90 mg) was resolved by HPLC (column: CHIRALCEL OJ, 50 mmID×500 mmL, manufactured by Daicel Chemical Industries, mobile phase: hexane/ethanol/diethylamine=700/300/1(v/v/v)) to give the title compound (43 mg) having a shorter retention time.
>99.9% ee (HPLC (column: CHIRALCEL OJ3, 4.6 mmID×250 mmL, manufactured by Daicel Chemical Industries, mobile phase: hexane/ethanol/diethylamine=700/300/1 (v/v/v), flow rate: 1.0 mL/min, retention time: 12.71 min))
MS (ESI+): [M+H]$^+$383.3.

Example 120

3-amino-5-((2S)-3-methylbutan-2-yl)-7-(5-(morpholin-4-yl)pyridin-2-yl)-1,5-dihydro-4H-pyrazolo[4,3-c]pyridin-4-one

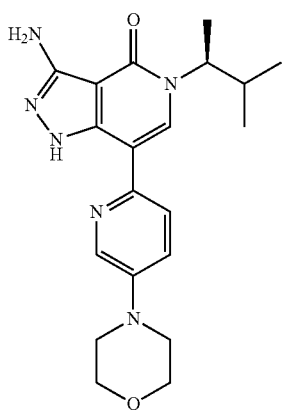 [SMILES: CC(C)[C@H](C)n1cc(-c2ccc(N3CCOCC3)cn2)c2[nH]nc(N)c2c1=O]

Racemic 3-amino-5-(3-methylbutan-2-yl)-7-(5-(morpholin-4-yl)pyridin-2-yl)-1,5-dihydro-4H-pyrazolo[4,3-c]pyridin-4-one obtained in Example 116 (90 mg) was resolved by HPLC (column: CHIRALCEL OJ, 50 mmID×500 mmL, manufactured by Daicel Chemical Industries, mobile phase: hexane/ethanol/diethylamine=700/300/1(v/v/v)) to give the title compound (40 mg) having a longer retention time. 99.2% ee (HPLC (column: CHIRALCEL OJ3, 4.6 mmID×250 mmL, manufactured by Daicel Chemical Industries, mobile phase: hexane/ethanol/diethylamine=700/300/1(v/v/v), flow rate: 1.0 mL/min, retention time: 16.41 min))
MS (ESI+): [M+H]$^+$383.2.

Examples 121 to 132

In Examples 121 to 132, the title compound was obtained from aniline derivative corresponding to the compounds of Examples 121 to 132, in the same manner as in Example 13 and Example 23 or a method analogous thereto. MS in the tables means actual measured value.

TABLE 6-1

| Example number | IUPAC name | Structure | MS |
|---|---|---|---|
| 121 | 3-amino-7-(5-(2-(dimethylamino)ethoxy)pyridin-2-yl)-5-(2-fluoro-6-methylphenyl)-1,5-dihydro-4H-pyrazolo[4,3-c]pyridin-4-one | 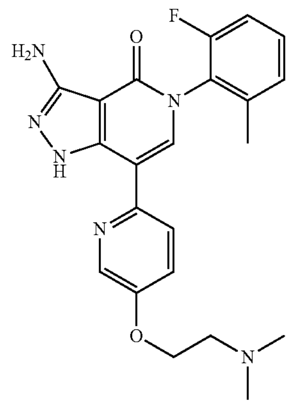 [SMILES: Cc1cccc(F)c1-n1cc(-c2ccc(OCCN(C)C)cn2)c2[nH]nc(N)c2c1=O] | 423.2 |
| 122 | 3-amino-7-(1-methyl-1H-pyrazol-3-yl)-5-(2,3,6-trifluorophenyl)-1,5-dihydro-4H-pyrazolo[4,3-c]pyridin-4-one | 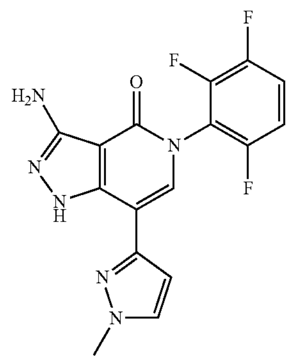 [SMILES: Cn1ccc(-c2cn(-c3c(F)ccc(F)c3F)c(=O)c3c(N)n[nH]c23)n1] | 361.3 |
| 123 | 3-amino-7-(5-(morpholin-4-yl)pyridin-2-yl)-5-(2,3,6-trifluorophenyl)-1,5-dihydro-4H-pyrazolo[4,3-c]pyridin-4-one | 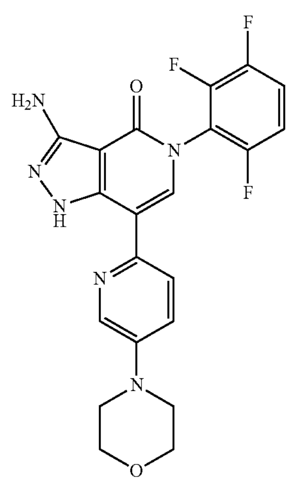 [SMILES: Nc1n[nH]c2c(-c3ccc(N4CCOCC4)cn3)cn(-c3c(F)ccc(F)c3F)c(=O)c12] | 443.3 |
| 124 | 3-amino-5-(2-fluoro-6-methoxyphenyl)-7-(1-methyl-1H-pyrazol-3-yl)-1,5-dihydro-4H-pyrazolo[4,3-c]pyridin-4-one | 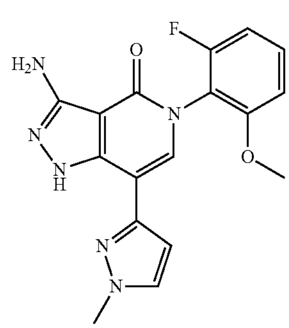 [SMILES: COc1cccc(F)c1-n1cc(-c2ccn(C)n2)c2[nH]nc(N)c2c1=O] | 355.1 |

TABLE 6-1-continued

| Example number | IUPAC name | Structure | MS |
|---|---|---|---|
| 125 | 3-amino-5-(2-fluoro-6-methoxyphenyl)-7-(5-(morpholin-4-yl)pyridin-2-yl)-1,5-dihydro-4H-pyrazolo[4,3-c]pyridin-4-one | 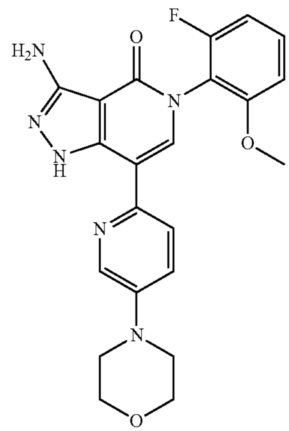 [SMILES: COc1cccc(F)c1-n1cc(-c2ccc(N3CCOCC3)cn2)c2[nH]nc(N)c2c1=O] | 437.2 |
| 126 | 3-amino-5-(2-fluoro-6-(trifluoromethyl)phenyl)-7-(5-(morpholin-4-yl)pyridin-2-yl)-1,5-dihydro-4H-pyrazolo[4,3-c]pyridin-4-one | 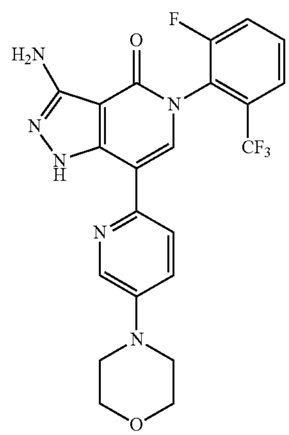 | 475.1 |
| 127 | 3-amino-5-(2-fluoro-6-methylphenyl)-7-(1-methyl-1H-pyrazol-3-yl)-1,5-dihydro-4H-pyrazolo[4,3-c]pyridin-4-one | 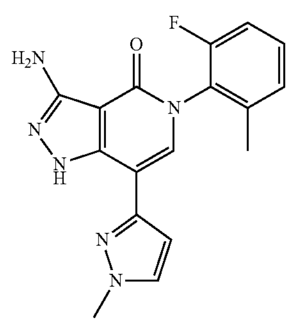 [SMILES: Cc1cccc(F)c1-n1cc(-c2ccn(C)n2)c2[nH]nc(N)c2c1=O] | 339.2 |
| 128 | 2-(3-amino-7-(5-(morpholin-4-yl)pyridin-2-yl)-4-oxo-1,4-dihydro-5H-pyrazolo[4,3-c]pyridin-5-yl)benzonitrile | 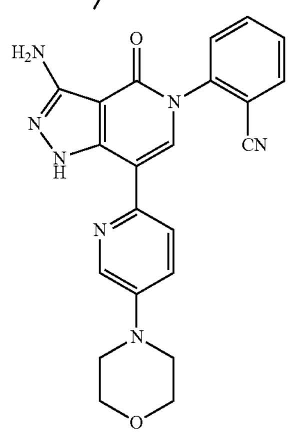 | 414.2 |

TABLE 6-2

| Example number | IUPAC name | Structure | MS |
|---|---|---|---|
| 129 | 3-amino-5-(2-fluoro-6-methylphenyl)-7-(5-(morpholin-4-yl)pyridin-2-yl)-1,5-dihydro-4H-pyrazolo[4,3-c]pyridin-4-one | 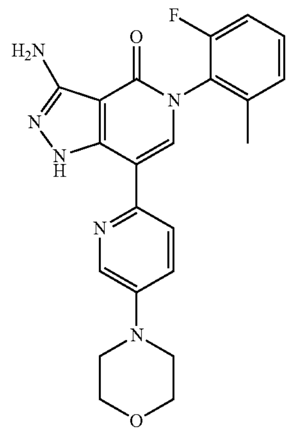 [SMILES: Cc1cccc(F)c1-n1cc(-c2ccc(N3CCOCC3)cn2)c2[nH]nc(N)c2c1=O] | 421.1 |
| 130 | 3-amino-5-(2-fluoro-6-(trifluoromethyl)phenyl)-7-(1-methyl-1H-pyrazol-3-yl)-1,5-dihydro-4H-pyrazolo[4,3-c]pyridin-4-one | 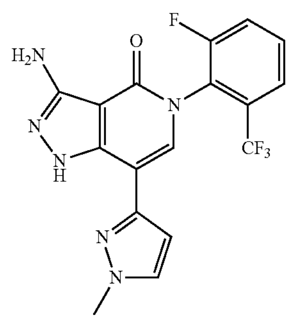 [SMILES: Cn1ccc(-c2cn(-c3c(F)cccc3C(F)(F)F)c(=O)c3c(N)n[nH]c23)n1] | 393.1 |
| 131 | 3-amino-5-(2-fluorophenyl)-7-(1-methyl-1H-pyrazol-3-yl)-1,5-dihydro-4H-pyrazolo[4,3-c]pyridin-4-one | 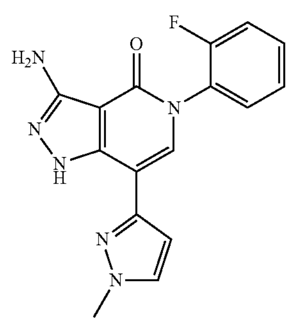 [SMILES: Cn1ccc(-c2cn(-c3ccccc3F)c(=O)c3c(N)n[nH]c23)n1] | 325.0 |
| 132 | 3-amino-7-(5-(morpholin-4-yl)pyridin-2-yl)-5-(2,4,6-trifluorophenyl)-1,5-dihydro-4H-pyrazolo[4,3-c]pyridin-4-one | 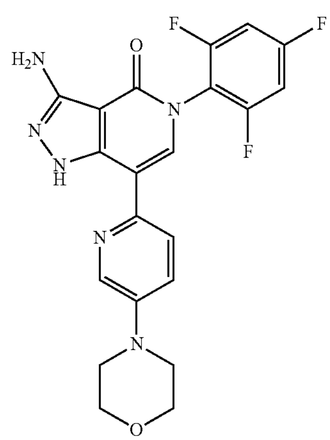 [SMILES: Nc1n[nH]c2c(-c3ccc(N4CCOCC4)cn3)cn(-c3c(F)cc(F)cc3F)c(=O)c12] | 443.3 |

Examples 133 to 151

In Examples 133 to 151, the title compound was obtained from 3-amino-7-bromo-5-(2,6-difluorophenyl)-1,5-dihydro-4H-pyrazolo[4,3-c]pyridin-4-one obtained in Step G of Example 15 and a halide compound corresponding to the compounds of Examples 133 to 151, in the same manner as in Example 23 or a method analogous thereto. MS in the tables means actual measured value. The halide compounds used for synthesis in Example 133 to 151 was synthesized according to the method described in Reference Examples 1 to 23, or a method analogous thereto.

TABLE 7-1

| Example number | IUPAC name | Structure | MS |
|---|---|---|---|
| 133 | 3-amino-5-(2,6-difluorophenyl)-7-(5-(3-methoxyazetidin-1-yl)pyridin-2-yl)-1,5-dihydro-4H-pyrazolo[4,3-c]pyridin-4-one | 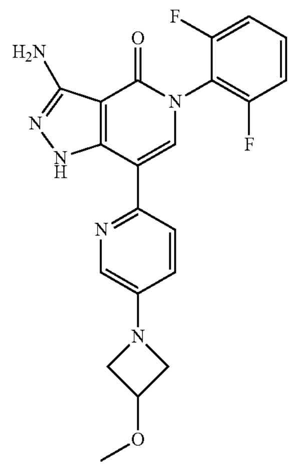 [SMILES: COC1CN(c2ccc(-c3cn(-c4c(F)cccc4F)c(=O)c4c(N)n[nH]c34)nc2)C1] | 425.2 |
| 134 | 3-amino-5-(2,6-difluorophenyl)-7-(5-(1,1-dioxidethiomorpholin-4-yl)pyridin-2-yl)-1,5-dihydro-4H-pyrazolo[4,3-c]pyridin-4-one | 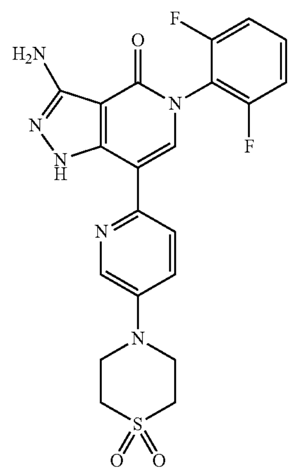 [SMILES: Nc1n[nH]c2c(-c3ccc(N4CCS(=O)(=O)CC4)cn3)cn(-c3c(F)cccc3F)c(=O)c12] | 473.2 |
| 135 | 3-amino-5-(2,6-difluorophenyl)-7-(5-(4-methoxypiperidin-1-yl)pyridin-2-yl)-1,5-dihydro-4H-pyrazolo[4,3-c]pyridin-4-one | 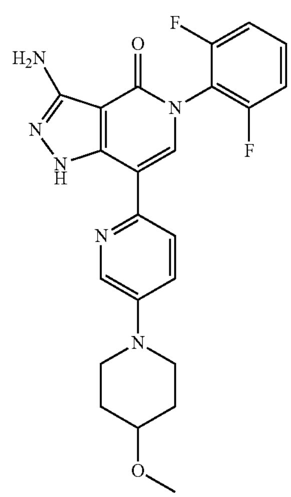 [SMILES: COC1CCN(c2ccc(-c3cn(-c4c(F)cccc4F)c(=O)c4c(N)n[nH]c34)nc2)CC1] | 453.2 |

TABLE 7-1-continued
| Example number | IUPAC name | Structure | MS |
|---|---|---|---|
| 136 | 3-amino-5-(2,6-difluorophenyl)-7-(5-((3S)-3-methylmorpholin-4-yl)pyridin-2-yl)-1,5-dihydro-4H-pyrazolo[4,3-c]pyridin-4-one | 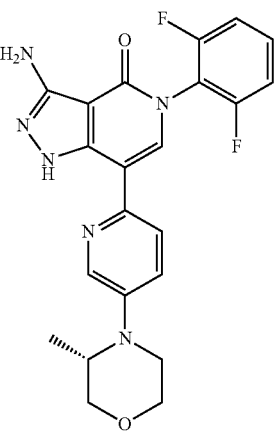 [SMILES: C[C@H]1COCCN1c1ccc(-c2cn(-c3c(F)cccc3F)c(=O)c3c(N)n[nH]c23)nc1] | 439 |
| 137 | 3-amino-5-(2,6-difluorophenyl)-7-(5-((3R)-3-methylmorpholin-4-yl)pyridin-2-yl)-1,5-dihydro-4H-pyrazolo[4,3-c]pyridin-4-one | 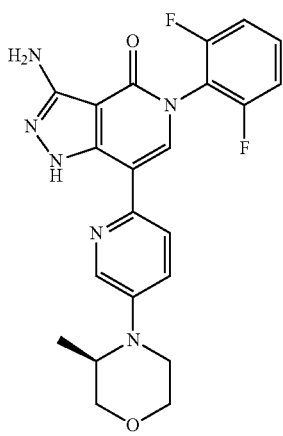 [SMILES: C[C@@H]1COCCN1c1ccc(-c2cn(-c3c(F)cccc3F)c(=O)c3c(N)n[nH]c23)nc1] | 439 |
| 138 | N-(2-((6-(3-amino-5-(2,6-difluorophenyl)-4-oxo-4,5-dihydro-1H-pyrazolo[4,3-c]pyridin-7-yl)pyridin-3-yl)oxy)ethyl)acetamide | 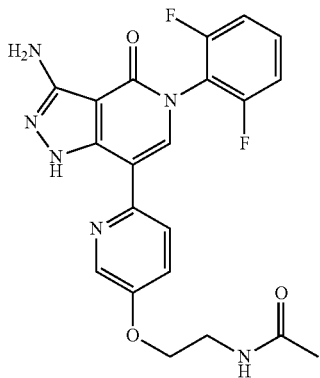 [SMILES: CC(=O)NCCOc1ccc(-c2cn(-c3c(F)cccc3F)c(=O)c3c(N)n[nH]c23)nc1] | 441.2 |

TABLE 7-1-continued
| Example number | IUPAC name | Structure | MS |
|---|---|---|---|
| 139 | 3-amino-5-(2,6-difluorophenyl)-7-(5-(2-hydroxy-2-methylpropoxy)pyridin-2-yl)-1,5-dihydro-4H-pyrazolo[4,3-c]pyridin-4-one | 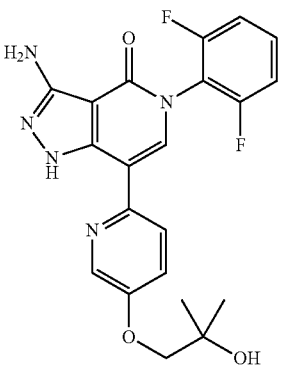 [SMILES: CC(C)(O)COc1ccc(-c2cn(-c3c(F)cccc3F)c(=O)c3c(N)n[nH]c23)nc1] | 428.2 |
| 140 | 3-amino-5-(2,6-difluorophenyl)-7-(5-(4-hydroxytetrahydro-2H-pyran-4-yl)pyridin-2-yl)-1,5-dihydro-4H-pyrazolo[4,3-c]pyridin-4-one | 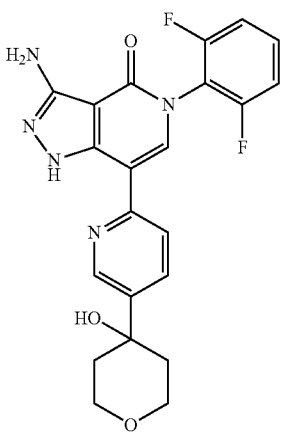 [SMILES: Nc1n[nH]c2c(-c3ccc(C4(O)CCOCC4)cn3)cn(-c3c(F)cccc3F)c(=O)c12] | 440.2 |
| 141 | 3-amino-5-(2,6-difluorophenyl)-7-(4-(2-(morpholin-4-yl)-2-oxoethyl)pyridin-2-yl)-1,5-dihydro-4H-pyrazolo[4,3-c]pyridin-4-one | 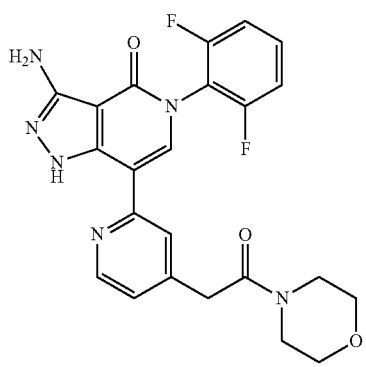 [SMILES: Nc1n[nH]c2c(-c3cc(CC(=O)N4CCOCC4)ccn3)cn(-c3c(F)cccc3F)c(=O)c12] | 467.2 |

TABLE 7-2

| Example number | IUPAC name | Structure | MS |
|---|---|---|---|
| 142 | 3-amino-5-(2,6-difluorophenyl)-7-(4-(2-(4-hydroxypiperidin-1-yl)-2-oxoethyl)pyridin-2-yl)-1,5-dihydro-4H-pyrazolo[4,3-c]pyridin-4-one | 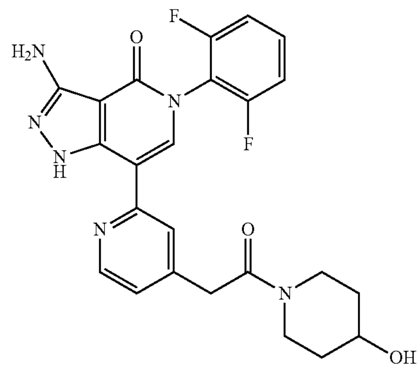 [SMILES: Nc1n[nH]c2c(-c3cc(CC(=O)N4CCC(O)CC4)ccn3)cn(-c3c(F)cccc3F)c(=O)c12] | 481.1 |
| 143 | 2-(2-(3-amino-5-(2,6-difluorophenyl)-4-oxo-4,5-dihydro-1H-pyrazolo[4,3-c]pyridin-7-yl)pyridin-4-yl)-N-(oxetan-3-yl)acetamide | 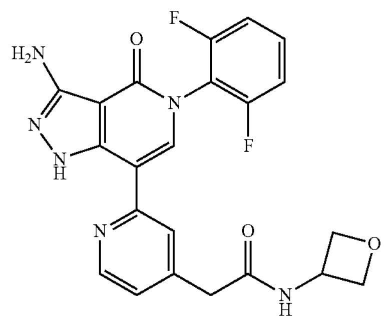 [SMILES: Nc1n[nH]c2c(-c3cc(CC(=O)NC4COC4)ccn3)cn(-c3c(F)cccc3F)c(=O)c12] | 453.2 |
| 144 | 2-(2-(3-amino-5-(2,6-difluorophenyl)-4-oxo-4,5-dihydro-1H-pyrazolo[4,3-c]pyridin-7-yl)pyridin-4-yl)-N,N-dimethylacetamide | 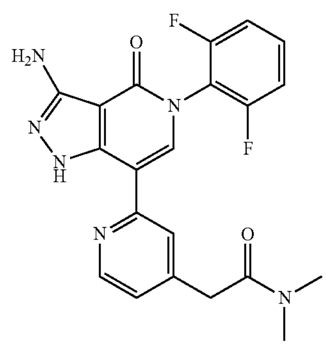 [SMILES: CN(C)C(=O)Cc1ccnc(-c2cn(-c3c(F)cccc3F)c(=O)c3c(N)n[nH]c23)c1] | 425.2 |
| 145 | 3-amino-5-(2,6-difluorophenyl)-7-(4-(2-(2-oxopyrrolidin-1-yl)ethoxy)pyridin-2-yl)-1,5-dihydro-4H-pyrazolo[4,3-c]pyridin-4-one | 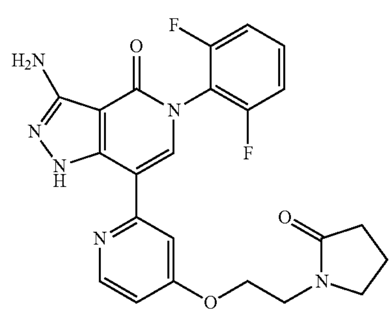 [SMILES: Nc1n[nH]c2c(-c3cc(OCCN4CCCC4=O)ccn3)cn(-c3c(F)cccc3F)c(=O)c12] | 467.4 |

TABLE 7-2-continued

| Example number | IUPAC name | Structure | MS |
|---|---|---|---|
| 146 | 3-amino-5-(2,6-difluorophenyl)-7-(4-(2-hydroxy-2-methylpropoxy)pyridin-2-yl)-1,5-dihydro-4H-pyrazolo[4,3-c]pyridin-4-one | 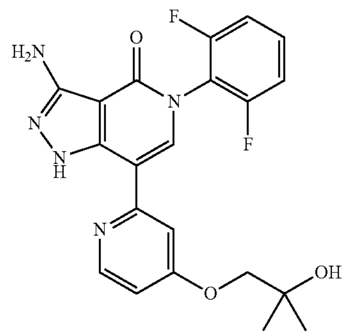 [SMILES: CC(C)(O)COc1ccnc(-c2cn(-c3c(F)cccc3F)c(=O)c3c(N)n[nH]c23)c1] | 428.3 |
| 147 | 3-amino-5-(2,6-difluorophenyl)-7-(4-(4-hydroxytetrahydro-2H-pyran-4-yl)pyridin-2-yl)-1,5-dihydro-4H-pyrazolo[4,3-c]pyridin-4-one | 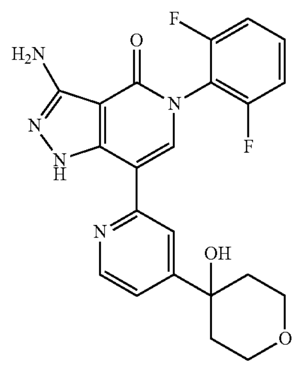 [SMILES: Nc1n[nH]c2c(-c3cc(C4(O)CCOCC4)ccn3)cn(-c3c(F)cccc3F)c(=O)c12] | 440.3 |
| 148 | N-(6-(3-amino-5-(2,6-difluorophenyl)-4-oxo-4,5-dihydro-1H-pyrazolo[4,3-c]pyridin-7-yl)pyridin-2-yl)formamide | 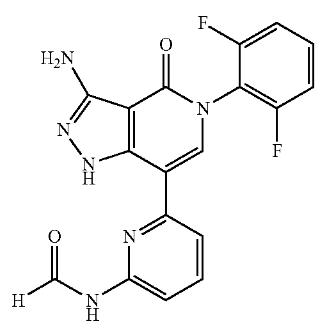 [SMILES: Nc1n[nH]c2c(-c3cccc(NC=O)n3)cn(-c3c(F)cccc3F)c(=O)c12] | 383.2 |
| 149 | N-((6-(3-amino-5-(2,6-difluorophenyl)-4-oxo-4,5-dihydro-1H-pyrazolo[4,3-c]pyridin-7-yl)pyridin-2-yl)methyl)formamide | 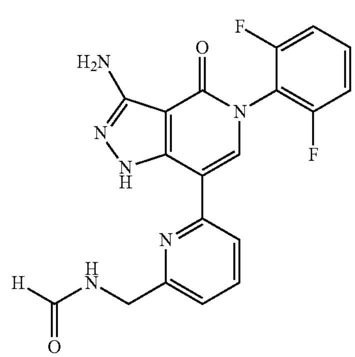 [SMILES: Nc1n[nH]c2c(-c3cccc(CNC=O)n3)cn(-c3c(F)cccc3F)c(=O)c12] | 397.1 |

TABLE 7-2-continued

| Example number | IUPAC name | Structure | MS |
|---|---|---|---|
| 150 | 3-amino-5-(2,6-difluorophenyl)-7-(6-(2-(2-oxopyrrolidin-1-yl)ethoxy)pyrimidin-4-yl)-1,5-dihydro-4H-pyrazolo[4,3-c]pyridin-4-one | 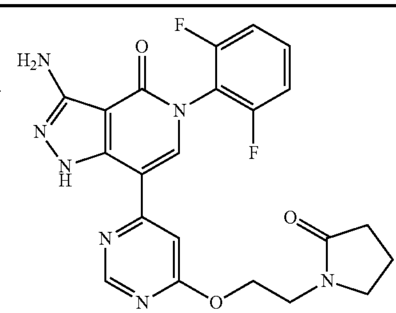 | 468.1 |

TABLE 7-3

| Example number | IUPAC name | Structure | MS |
|---|---|---|---|
| 151 | 3-amino-5-(2,6-difluorophenyl)-7-(5-((4-methoxybenzyl)oxy)pyrazin-2-yl)-1,5-dihydro-4H-pyrazolo[4,3-c]pyridin-4-one | 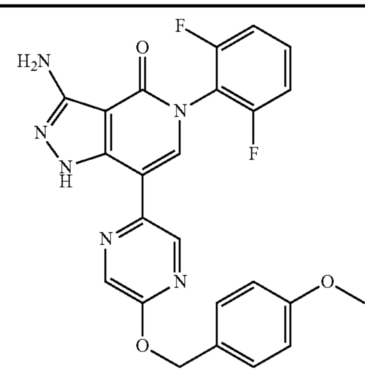 | 477.1 |

Example 152

3-amino-5-(2,6-difluorophenyl)-7-(6-oxo-1,6-dihydropyrimidin-4-yl)-1,5-dihydro-4H-pyrazolo[4,3-c]pyridin-4-one 2 tosylate

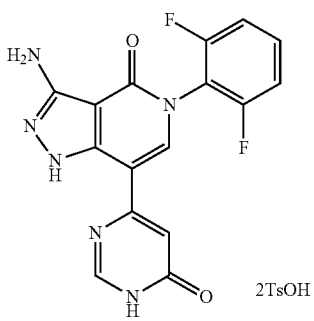 [SMILES: Nc1n[nH]c2c(-c3cc(=O)[nH]cn3)cn(-c3c(F)cccc3F)c(=O)c12]

A mixture of 3-amino-7-bromo-5-(2,6-difluorophenyl)-1,5-dihydro-4H-pyrazolo[4,3-c]pyridin-4-one obtained in Step G of Example 15 (200 mg), 4,4,4',4',5,5,5',5'-octamethyl-2,2'-bi-1,3,2-dioxaborolane (223 mg), (1,1'-bis(diphenylphosphino)ferrocene)dichloropalladium(II) (21 mg), potassium acetate (115 mg) and N,N-dimethylformamide (3.0 mL) was stirred at 110° C. for 4 hr under argon atmosphere. The reaction mixture was cooled to room temperature, 4-chloro-6-((4-methoxybenzyl)oxy)pyrimidine obtained in Reference Example 27 (296 mg), aqueous sodium carbonate solution (2 M, 0.59 mL) and tetrakis(triphenylphosphine)palladium(0) (68 mg) were added thereto, and the reaction mixture was stirred at 110° C. for 2 hr under argon atmosphere. The reaction mixture was cooled to room temperature, ethyl acetate and water were added thereto, and the insoluble substance was removed by filtration through Celite. The filtrate was extracted with ethyl acetate, and the extract was washed successively with water and saturated brine, and dried over anhydrous magnesium sulfate, and the solvent was evaporated under reduced pressure. The residue was purified by silica gel chromatography (dial silica gel, ethyl acetate/hexane). The obtained brown oil was purified by silica gel chromatography (basic silica gel, ethyl acetate/hexane) to give a white solid (105 mg). To the obtained white solid (100 mg) were added methanol (2 mL), tetrahydrofuran (3 mL) and p-toluenesulfonic acid monohydrate (34 mg), and the reaction mixture was stirred at room temperature for 1.5 hr. To the reaction mixture were added triethylamine (29.3 μL) and silica gel, and the solvent was evaporated under reduced pressure. The residue was purified by silica gel chromatography (ethyl acetate/methanol). The obtained residue was crystallized from ethyl acetate to give the title compound (76 mg).

MS(ESI+): [M+H]$^+$357.1.

Example 153

3-amino-5-(2,6-difluorophenyl)-7-(3-oxo-3,4-dihydropyrazin-2-yl)-1,5-dihydro-4H-pyrazolo[4,3-c]pyridin-4-one

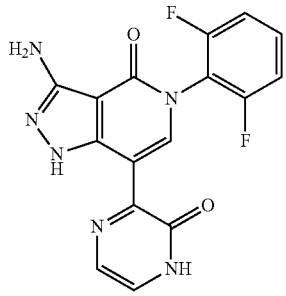 [SMILES: Nc1n[nH]c2c(-c3ncc[nH]c3=O)cn(-c3c(F)cccc3F)c(=O)c12]

The title compound was obtained from 3-amino-7-bromo-5-(2,6-difluorophenyl)-1,5-dihydro-4H-pyrazolo[4,3-c]pyridin-4-one obtained in Step G of Example 15 and 2-chloro-3-((4-methoxybenzyl)oxy)pyrazine obtained in Reference Example 24 in the same manner as in Example 152.

MS(ESI+): [M+H]⁺357.1.

Example 154

3-amino-5-(2,6-difluorophenyl)-7-(5-oxo-4,5-dihydropyrazin-2-yl)-1,5-dihydro-4H-pyrazolo[4,3-c]pyridin-4-one

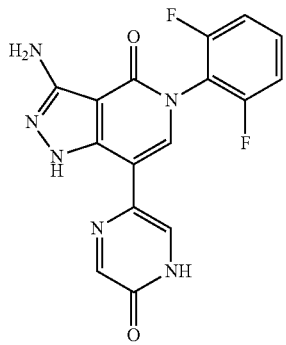 [SMILES: Nc1n[nH]c2c(-c3c[nH]c(=O)cn3)cn(-c3c(F)cccc3F)c(=O)c12]

To 3-amino-5-(2,6-difluorophenyl)-7-(5-((4-methoxybenzyl)oxy)pyrazin-2-yl)-1,5-dihydro-4H-pyrazolo[4,3-c]pyridin-4-one obtained in Example 151 (133 mg) were added methanol (2 mL), tetrahydrofuran (3 mL) and p-toluenesulfonic acid monohydrate (53 mg), and the reaction mixture was stirred at room temperature for 1 hr. p-Toluenesulfonic acid monohydrate (53 mg) was added thereto, and the reaction mixture was stirred at room temperature for 5 hr. To the reaction mixture were added triethylamine (97 μL) and silica gel, and the solvent was evaporated under reduced pressure. The residue was purified by silica gel chromatography (ethyl acetate/methanol). The obtained residue was crystallized from ethyl acetate/diethyl ether to give the title compound (92 mg).

MS(ESI+): [M+H]⁺357.1.

Example 155

3-amino-5-(2,6-difluorophenyl)-7-(6-oxo-1-(tetrahydro-2H-pyran-4-yl)-1,6-dihydropyrimidin-4-yl)-1,5-dihydro-4H-pyrazolo[4,3-c]pyridin-4-one

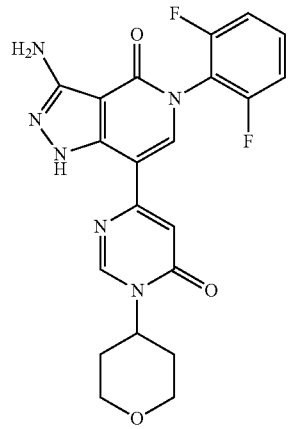 [SMILES: Nc1n[nH]c2c(-c3cc(=O)n(C4CCOCC4)cn3)cn(-c3c(F)cccc3F)c(=O)c12]

The title compound was obtained from 3-amino-7-bromo-5-(2,6-difluorophenyl)-1,5-dihydro-4H-pyrazolo[4,3-c]pyridin-4-one obtained in Step G of Example 15 and 6-chloro-3-(tetrahydro-2H-pyran-4-yl)pyrimidin-4(3H)-one obtained in Reference Example 26 in the same manner as in Example 23.

MS (ESI+): [M+H]⁺441.2.

Example 156

2-(3-amino-7-(5-(4,4-difluoropiperidin-1-yl)pyrazin-2-yl)-4-oxo-1,4-dihydro-5H-pyrazolo[4,3-c]pyridin-5-yl)-3-fluorobenzonitrile

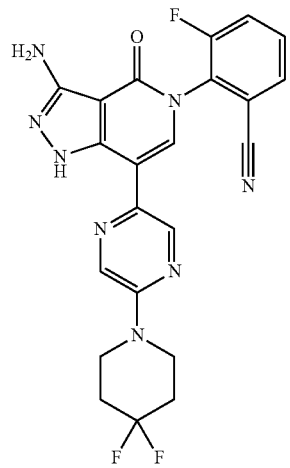 [SMILES: N#Cc1cccc(F)c1-n1cc(-c2cnc(N3CCC(F)(F)CC3)cn2)c2[nH]nc(N)c2c1=O]

The title compound was obtained from 2-(3-amino-7-bromo-4-oxo-1,4-dihydro-5H-pyrazolo[4,3-c]pyridin-5-yl)-

3-fluorobenzonitrile obtained in Step G of Example 104 and 2-bromo-5-(4,4-difluoropiperidin-1-yl)pyrazine obtained in Reference Example 28 in the same manner as in Example 23.

MS (ESI+): [M+H]⁺467.3.

Example 157

2-(3-amino-7-(5-((4-methylpiperazin-1-yl)methyl)pyrazin-2-yl)-4-oxo-1,4-dihydro-5H-pyrazolo[4,3-c]pyridin-5-yl)-3-fluorobenzonitrile

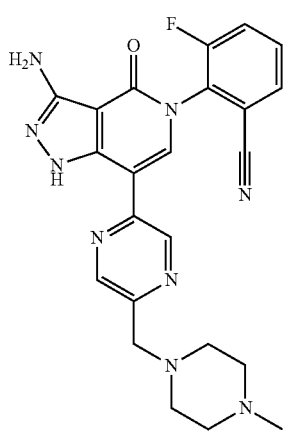 [SMILES: CN1CCN(Cc2cnc(-c3cn(-c4c(F)cccc4C#N)c(=O)c4c(N)n[nH]c34)cn2)CC1]

The title compound was obtained from 2-(3-amino-7-bromo-4-oxo-1,4-dihydro-5H-pyrazolo[4,3-c]pyridin-5-yl)-3-fluorobenzonitrile obtained in Step G of Example 104 and 2-chloro-5-((4-methylpiperazin-1-yl)methyl)pyrazine obtained in Reference Example 29 in the same manner as in Example 23.

MS (ESI+): [M+H]⁺460.3.

Example 158

3-amino-5-(2-fluoro-6-methylphenyl)-7-(5-(2-hydroxy-2-methylpropoxy)pyridin-2-yl)-1,5-dihydro-4H-pyrazolo[4,3-c]pyridin-4-one

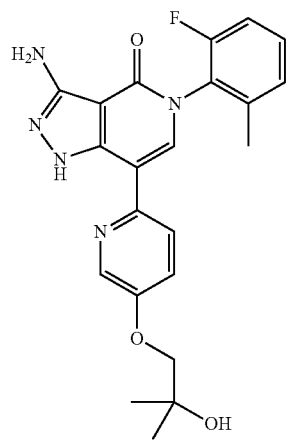 [SMILES: Cc1cccc(F)c1-n1cc(-c2ccc(OCC(C)(C)O)cn2)c2[nH]nc(N)c2c1=O]

The title compound was obtained from 1-((6-bromopyridin-3-yl)oxy)-2-methylpropan-2-ol obtained in Reference Example 9 and 2-fluoro-6-methylaniline in the same manner as in Example 13 and Example 23 or a method analogous thereto.

MS (ESI+): [M+H]⁺424.1.

Examples 159 to 162

In Examples 159 to 162, the title compound was obtained from the amine corresponding to the compounds of Examples 159 to 162, in the same manner as in Example 13 and Example 23 or a method analogous thereto. MS in the tables means actual measured value.

TABLE 8

| Example number | IUPAC name | Structure | MS |
|---|---|---|---|
| 159 | 3-amino-5-(2,2-dimethylcyclopentyl)-7-(1-methyl-1H-pyrazol-3-yl)-1,5-dihydro-4H-pyrazolo[4,3-c]pyridin-4-one | 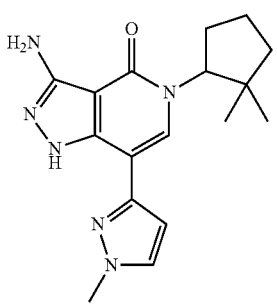 [SMILES: Cn1ccc(-c2cn(C3CCCC3(C)C)c(=O)c3c(N)n[nH]c23)n1] | 327.4 |

TABLE 8-continued

| Example number | IUPAC name | Structure | MS |
|---|---|---|---|
| 160 | 3-amino-5-(2,2-dimethylcyclopentyl)-7-(5-(morpholin-4-yl)pyridin-2-yl)-1,5-dihydro-4H-pyrazolo[4,3-c]pyridin-4-one | 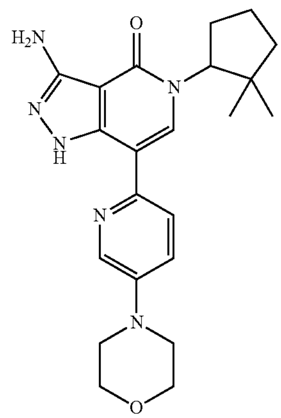 [SMILES: CC1(C)CCCC1n1cc(-c2ccc(N3CCOCC3)cn2)c2[nH]nc(N)c2c1=O] | 409.4 |
| 161 | 3-amino-5-(2,2-difluorocyclohexyl)-7-(1-methyl-1H-pyrazol-3-yl)-1,5-dihydro-4H-pyrazolo[4,3-c]pyridin-4-one | 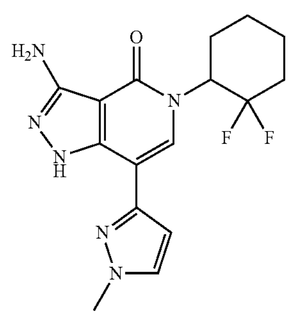 [SMILES: Cn1ccc(-c2cn(C3CCCCC3(F)F)c(=O)c3c(N)n[nH]c23)n1] | 349.3 |
| 162 | 3-amino-5-(2,2-difluorocyclohexyl)-7-(5-(morpholin-4-yl)pyridin-2-yl)-1,5-dihydro-4H-pyrazolo[4,3-c]pyridin-4-one | 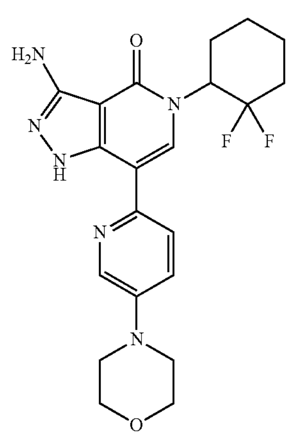 [SMILES: Nc1n[nH]c2c(-c3ccc(N4CCOCC4)cn3)cn(C3CCCCC3(F)F)c(=O)c12] | 431.4 |

Example 163

3-amino-5-(1-cyclopropylethyl)-7-(1-methyl-1H-pyrazol-3-yl)-1,5-dihydro-4H-pyrazolo[4,3-c]pyridin-4-one

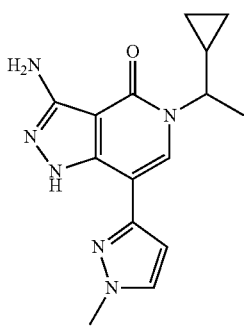 [SMILES: CC(C1CC1)n1cc(-c2ccn(C)n2)c2[nH]nc(N)c2c1=O]

A) 1-(1-cyclopropylethyl)-4-methoxy-2-oxo-1,2-dihydropyridine-3-carbonitrile

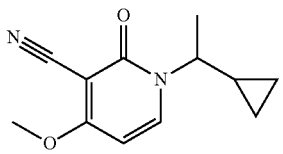 [SMILES: COc1ccn(C(C)C2CC2)c(=O)c1C#N]

To a mixture of 4-methoxy-2-oxo-1,2-dihydropyridine-3-carbonitrile (20.0 g), triphenylphosphine (52.4 g), 1-cyclopropylethanol (19.34 mL) and tetrahydrofuran (500 mL) was added bis(2-methoxyethyl) azodicarboxylate (46.8 g) at 0° C. The reaction mixture was stirred at room temperature for 15 hr. The reaction mixture was poured into water, and the mixture was extracted with ethyl acetate. The obtained organic layer was washed with water and saturated brine, and dried over anhydrous magnesium sulfate, and the solvent was evaporated under reduced pressure. The residue was dissolved in diethyl ether, and triphenylphosphine oxide (5 mg) was added thereto. The insoluble substance was removed by filtration. The filtrate was washed with water, and dried over anhydrous magnesium sulfate, and the solvent was evaporated under reduced pressure. The residue was purified by silica gel column chromatography (basic silica gel, hexane/ethyl acetate) to give a crude product. The crude product was purified by silica gel column chromatography (hexane/ethyl acetate) to give the title compound (2.45 g).

MS(ESI+): [M+H]$^+$218.9.

B) 5-bromo-1-(1-cyclopropylethyl)-4-methoxy-2-oxo-1,2-dihydropyridine-3-carbonitrile

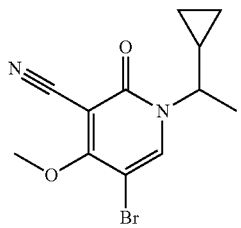 [SMILES: COc1c(Br)cn(C(C)C2CC2)c(=O)c1C#N]

A mixture of 1-(1-cyclopropylethyl)-4-methoxy-2-oxo-1,2-dihydropyridine-3-carbonitrile obtained in Step A of Example 163 (2.45 g), N-bromosuccinimide (3.00 g) and N,N-dimethylformamide (50 mL) was stirred at 60° C. for 16 hr. The reaction mixture was cooled to room temperature, and the solvent was evaporated under reduced pressure. The residue was purified by silica gel column chromatography (hexane/ethyl acetate) to give the title compound (2.73 g).

MS(ESI+): [M+H]$^+$296.8.

C) 1-(1-cyclopropylethyl)-4-methoxy-5-(1-methyl-1H-pyrazol-3-yl)-2-oxo-1,2-dihydropyridine-3-carbonitrile

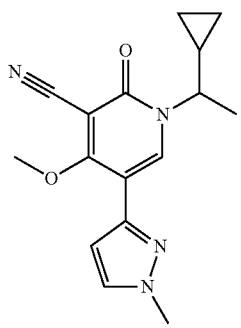 [SMILES: COc1c(-c2ccn(C)n2)cn(C(C)C2CC2)c(=O)c1C#N]

A mixture of 5-bromo-1-(1-cyclopropylethyl)-4-methoxy-2-oxo-1,2-dihydropyridine-3-carbonitrile obtained in Step B of Example 163 (66 mg), 1-methyl-3-(4,4,5,5-tetramethyl-1,3,2-dioxaborolan-2-yl)-1H-pyrazole (69 mg), tetrakis(triphenylphosphine)palladium(0) (26 mg), aqueous sodium carbonate solution (2 M, 0.666 mL) and 1,2-dimethoxyethane (3.0 mL) was heated with microwave irradiation at 100° C. for 1 hr under argon atmosphere. The reaction mixture was cooled to room temperature, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate), and then silica gel column chromatography (basic silica gel, hexane/ethyl acetate) to give the title compound (26 mg).

MS(ESI+): [M+H]$^+$299.3.

D) 3-amino-5-(1-cyclopropylethyl)-7-(1-methyl-1H-pyrazol-3-yl)-1,5-dihydro-4H-pyrazolo[4,3-c]pyridin-4-one A mixture of 1-(1-cyclopropylethyl)-4-methoxy-5-(1-methyl-1H-pyrazol-3-yl)-2-oxo-1,2-dihydropyridine-3-carbonitrile obtained in Step C of Example 163 (22 mg), hydrazine monohydrate (18 mg) and ethanol (2 mL) was stirred at 90° C. for 1 hr. The reaction mixture was cooled to room temperature, and the solvent was evaporated under reduced pressure. The residue was purified by silica gel column chromatography (basic silica gel, hexane/ethyl acetate). The residue was crystallized from ethyl acetate/hexane to give the title compound (13 mg).

MS(ESI+): [M+H]$^+$299.3.

$^1$H NMR (400 MHz, CDCl$_3$) δ 0.32-0.41 (1H, m), 0.46-0.55 (2H, m), 0.68-0.77 (1H, m), 1.09-1.18 (1H, m), 1.45 (3H, d, J=6.8 Hz), 3.96 (3H, s), 4.42-4.51 (1H, m), 4.78 (2H, brs), 6.45 (1H, d, J=2.4 Hz), 7.40 (1H, d, J=2.2 Hz), 7.58 (1H, s).

Example 164

3-amino-7-bromo-5-(1-cyclopropylethyl)-1,5-dihydro-4H-pyrazolo[4,3-c]pyridin-4-one

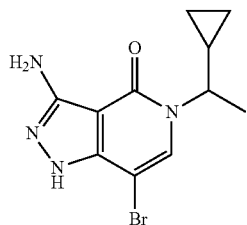 [SMILES: CC(C1CC1)n1cc(Br)c2[nH]nc(N)c2c1=O]

A mixture of 5-bromo-1-(1-cyclopropylethyl)-4-methoxy-2-oxo-1,2-dihydropyridine-3-carbonitrile obtained in Step B of Example 163 (1.2 g), hydrazine monohydrate (1.01 g) and ethanol (20 mL) was stirred at 90° C. for 2 hr. The reaction mixture was cooled to room temperature, and the solvent was evaporated under reduced pressure. The residue was purified by silica gel column chromatography (basic silica gel, hexane/ethyl acetate). The residue was dissolved in ethyl acetate, and the solution was washed with saturated brine, and dried over anhydrous magnesium sulfate, and the solvent was evaporated under reduced pressure to give the title compound (1.20 g).

MS(ESI+): [M+H]$^+$296.8.

Example 165

3-amino-7-bromo-5-((1S)-1-cyclopropylethyl)-1,5-dihydro-4H-pyrazolo[4,3-c]pyridin-4-one

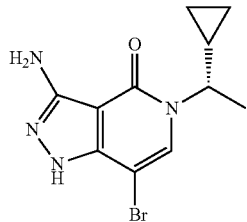 [SMILES: C[C@@H](C1CC1)n1cc(Br)c2[nH]nc(N)c2c1=O]

Racemic 3-amino-7-bromo-5-(1-cyclopropylethyl)-1,5-dihydro-4H-pyrazolo[4,3-c]pyridin-4-one obtained in Example 164 (1.1 g) was resolved by HPLC (column: CHIRALPAD AD, 50 mmID×500 mmL, manufactured by Daicel Chemical Industries, mobile phase: hexane/ethanol=800/200(v/v)) to give the title compound (533 mg) having a shorter retention time.

MS (ESI+): [M+H]$^+$297.1.

>99.9% ee (HPLC (column: CHIRALPAK AD, 4.6 mmID×250 mmL, manufactured by Daicel Chemical Industries, mobile phase: hexane/ethanol=800/200(v/v), flow rate: 1.0 mL/min, retention time: 8.86 min))

Example 166

3-amino-7-bromo-5-((1R)-1-cyclopropylethyl)-1,5-dihydro-4H-pyrazolo[4,3-c]pyridin-4-one

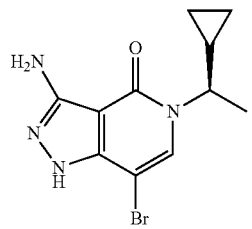 [SMILES: C[C@H](C1CC1)n1cc(Br)c2[nH]nc(N)c2c1=O]

Racemic 3-amino-7-bromo-5-(1-cyclopropylethyl)-1,5-dihydro-4H-pyrazolo[4,3-c]pyridin-4-one obtained in Example 164 (1.12 g) was resolved by HPLC (column: CHIRALPAD AD, 50 mmID×500 mmL, manufactured by Daicel Chemical Industries, mobile phase: hexane/ethanol=800/200(v/v)) to give the title compound (539 mg) having a longer retention time.

MS (ESI+): [M+H]$^+$297.1.

>99.9% ee (HPLC (column: CHIRALPAK AD, 4.6 mmID×250 mmL, manufactured by Daicel Chemical Industries, mobile phase: hexane/ethanol=800/200(v/v), flow rate: 1.0 mL/min, retention time: 10.95 min))

Example 167

3-amino-5-sec-butyl-7-(1-methyl-1H-pyrazol-3-yl)-1,5-dihydro-4H-pyrazolo[4,3-c]pyridin-4-one

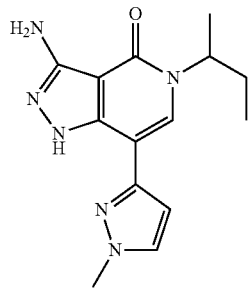 [SMILES: CCC(C)n1cc(-c2ccn(C)n2)c2[nH]nc(N)c2c1=O]

A) 1-(sec-butyl)-4-methoxy-2-oxo-1,2-dihydropyridine-3-carbonitrile

To a mixture of 4-methoxy-2-oxo-1,2-dihydropyridine-3-carbonitrile (500 mg), cesium carbonate (2.17 g), potassium iodide (553 mg) N,N-dimethylformamide (10 mL) and 1,2-dimethoxyethane (10 mL) was added 2-bromobutane (776 mg) at room temperature, and the mixture was stirred overnight at 60° C. The reaction mixture was diluted with saturated aqueous sodium hydrogen carbonate solution, and the mixture was extracted threetimes with ethyl acetate. The extracts were combined, washed with saturated brine, and dried over anhydrous magnesium sulfate, and the solvent was evaporated under reduced pressure. The residue was purified by silica gel column chromatography (ethyl acetate/hexane) to give the title compound (330 mg).

MS (ESI+): [M+H]$^+$206.8.

B) 5-bromo-1-(sec-butyl)-4-methoxy-2-oxo-1,2-dihydropyridine-3-carbonitrile

A mixture of 1-(sec-butyl)-4-methoxy-2-oxo-1,2-dihydropyridine-3-carbonitrile obtained in Step A (260 mg), N-bromosuccinimide (269 mg) and N,N-dimethylformamide (3 mL) was stirred at 60° C. for 2 hr 30 min. The reaction mixture was diluted with saturated aqueous sodium hydrogen carbonate solution, and the mixture was extracted threetimes with ethyl acetate. The extracts were combined, washed successively with water and saturated brine, and dried over anhydrous magnesium sulfate, and the solvent was evaporated under reduced pressure. The residue was purified by silica gel column chromatography (ethyl acetate/hexane) to give the title compound (260 mg).

$^1$H NMR (300 MHz, DMSO-d$_6$) δ0.75 (3H, t, J=7.4 Hz), 1.29 (3H, d, J=6.8 Hz), 1.60-1.80 (2H, m), 4.32 (3H, s), 4.65-4.82 (1H, m), 8.30 (1H, s).

C) 1-(sec-butyl)-4-methoxy-5-(1-methyl-1H-pyrazol-3-yl)-2-oxo-1,2-dihydropyridine-3-carbonitrile To a mixture of 5-bromo-1-(sec-butyl)-4-methoxy-2-oxo-1,2-dihydropyridine-3-carbonitrile obtained in Step B (130 mg), 1-methyl-3-(4,4,5,5-tetramethyl-1,3,2-dioxaborolan-2-yl)-1H-pyrazole (114 mg), 2M aqueous sodium carbonate solution (1.37 mL) and 1,2-dimethoxyethane (2.5 mL) was added tetrakis(triphenylphosphine)palladium(0) (52.7 mg), and the mixture was stirred with microwave irradiation at 100° C. for 1 hr. The reaction mixture was diluted with water, and the mixture was extracted twice with ethyl acetate. The extracts were combined, washed with saturated brine, and dried over anhydrous magnesium sulfate, and the solvent was evaporated under reduced pressure. The residue was purified by silica gel column chromatography (basic silica gel, ethyl acetate/hexane) to give the title compound (90 mg).

MS (ESI+): [M+H]$^+$287.0.

D) 3-amino-5-sec-butyl-7-(1-methyl-1H-pyrazol-3-yl)-1,5-dihydro-4H-pyrazolo[4,3-c]pyridin-4-one To a mixture of 1-(sec-butyl)-4-methoxy-5-(1-methyl-1H-pyrazol-3-yl)-2-oxo-1,2-dihydropyridine-3-carbonitrile obtained in Step C (140 mg) and ethanol (5 mL) was added hydrazine monohydrate (122 mg), and the mixture was stirred at 90° C. for 1 hr, cooled to room temperature, and concentrated under reduced pressure. The residue was purified by silica gel column chromatography (basic silica gel, ethyl acetate/hexane), and recrystallized from ethyl acetate/diisopropyl ether to give the title compound (82 mg).

MS (ESI+): [M+H]$^+$287.0.

Examples 168 and 169

In Examples 168 and 169, the title compound was obtained from the halide compound (which is compound XXIX) corresponding to the compounds of Examples 168 and 169, and 1-methyl-3-(4,4,5,5-tetramethyl-1,3,2-dioxaborolan-2-yl)-1H-pyrazole, in the same manner as in Example 167 or a method analogous thereto. MS in the tables means actual measured value.

TABLE 9

| Example number | IUPAC name | Structure | MS |
|---|---|---|---|
| 168 | 3-amino-7-(1-methyl-1H-pyrazol-3-yl)-5-(pentan-2-yl)-1,5-dihydro-4H-pyrazolo[4,3-c]pyridin-4-one | 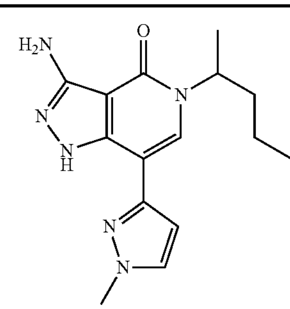 | 301.0 |
| 169 | 3-amino-5-(2-methylpentan-3-yl)-7-(1-methyl-1H-pyrazol-3-yl)-1,5-dihydro-4H-pyrazolo[4,3-c]pyridin-4-one | 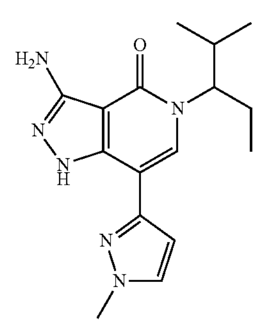 [SMILES: CCC(C(C)C)n1cc(-c2ccn(C)n2)c2[nH]nc(N)c2c1=O] | 315.0 |

Example 170

3-amino-5-(1,1-dioxidotetrahydro-2H-thiopyran-4-yl)-7-(1-methyl-1H-pyrazol-3-yl)-1,5-dihydro-4H-pyrazolo[4,3-c]pyridin-4-one

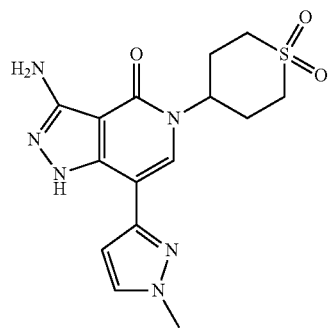 [SMILES: Cn1ccc(-c2cn(C3CCS(=O)(=O)CC3)c(=O)c3c(N)n[nH]c23)n1]

A) 4-methoxy-2-oxo-1-(tetrahydro-2H-thiopyran-4-yl)-1,2-dihydropyridine-3-carbonitrile To a mixture of 4-methoxy-2-oxo-1,2-dihydropyridine-3-carbonitrile (1.00 g), tetrahydro-2H-thiopyran-4-ol (1.18 g), triphenylphosphine (2.62 g) and tetrahydrofuran (30 mL) was added dropwise diisopropyl azodicarboxylate (2.02 g) at room temperature under nitrogen atmosphere, and the mixture was stirred overnight at room temperature. The reaction mixture was diluted with saturated aqueous sodium hydrogen carbonate solution, and the mixture was extracted twice with ethyl acetate. The extracts were combined, washed with saturated brine, and dried over anhydrous magnesium sulfate, and the solvent was evaporated under reduced pressure. The residue was purified by silica gel column chromatography (ethyl acetate/hexane) to give the title compound (320 mg).

MS (ESI+): [M+H]$^+$250.9.

B) 1-(1,1-dioxidotetrahydro-2H-thiopyran-4-yl)-4-methoxy-2-oxo-1,2-dihydropyridine-3-carbonitrile A mixture of 4-methoxy-2-oxo-1-(tetrahydro-2H-thiopyran-4-yl)-1,2-dihydropyridine-3-carbonitrile obtained in Step A (110 mg), m-chloroperbenzoic acid (271 mg) and N,N-dimethylformamide (5 mL) was stirred at room temperature for 2 hr. The reaction mixture was diluted with saturated aqueous sodium hydrogen carbonate solution, and the mixture was extracted twice with ethyl acetate. The extracts were combined, washed with saturated brine, and dried over anhydrous magnesium sulfate, and the solvent was evaporated under reduced pressure. The residue was purified by silica gel column chromatography (ethyl acetate/hexane) to give the title compound (60 mg).

MS (ESI+): [M+H]$^+$282.9.

C) 3-amino-5-(1,1-dioxidotetrahydro-2H-thiopyran-4-yl)-7-(1-methyl-1H-pyrazol-3-yl)-1,5-dihydro-4H-pyrazolo[4,3-c]pyridin-4-one The title compound was obtained in the same manner as in Steps B-D of Example 167.

MS (ESI+): [M+H]$^+$363.0.

Example 171

3-amino-5-(1,1-dioxidotetrahydro-2H-thiopyran-3-yl)-7-(1-methyl-1H-pyrazol-3-yl)-1,5-dihydro-4H-pyrazolo[4,3-c]pyridin-4-one

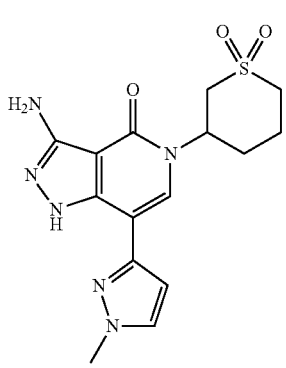 [SMILES: Cn1ccc(-c2cn(C3CCCS(=O)(=O)C3)c(=O)c3c(N)n[nH]c23)n1]

The title compound was obtained from 4-methoxy-2-oxo-1,2-dihydropyridine-3-carbonitrile and tetrahydro-2H-thiopyran-3-ol in the same manner as in Example 170.

MS (ESI+): [M+14]$^+$362.9.

Example 172

3-amino-5-(1-cyclobutylethyl)-7-(1-methyl-1H-pyrazol-3-yl)-1,5-dihydro-4H-pyrazolo[4,3-c]pyridin-4-one

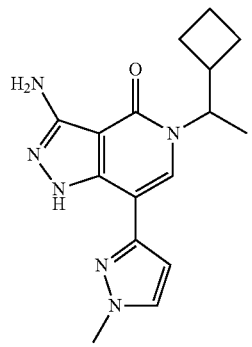 [SMILES: CC(C1CCC1)n1cc(-c2ccn(C)n2)c2[nH]nc(N)c2c1=O]

The title compound was obtained from 4-methoxy-2-oxo-1,2-dihydropyridine-3-carbonitrile and 1-cyclobutylethanol in the same manner as in Example 163.

MS (ESI+): [M+H]$^+$313.3.

Example 173

3-amino-5-isobutyl-7-(1-methyl-1H-pyrazol-3-yl)-1,5-dihydro-4H-pyrazolo[4,3-c]pyridin-4-one

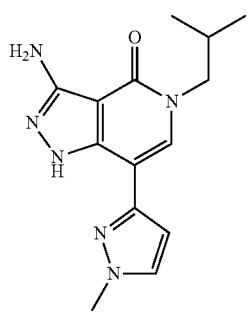 [SMILES: CC(C)Cn1cc(-c2ccn(C)n2)c2[nH]nc(N)c2c1=O]

A) 1-isobutyl-4-methoxy-2-oxo-1,2-dihydropyridine-3-carbonitrile

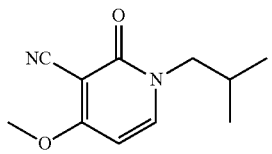

A mixture of 4-methoxy-2-oxo-1,2-dihydropyridine-3-carbonitrile (15.00 g), 1-bromo-2-methylpropane (21.4 g), cesium carbonate (65.2 g) and dimethyl sulfoxide (150 mL) was stirred at 50° C. for 24 hr. The reaction mixture was cooled to room temperature, and poured into water, and the mixture was extracted with ethyl acetate. The extract was washed successively with water and saturated brine, and dried over anhydrous sodium sulfate, and the solvent was evaporated under reduced pressure. The residue was washed with ether to give the title compound (13.0 g).

MS (ESI+): [M+H]$^+$207.1.

B) 5-bromo-4-hydroxy-1-isobutyl-2-oxo-1,2-dihydropyridine-3-carbonitrile

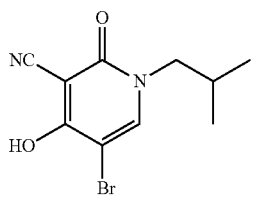

The title compound was obtained from 1-isobutyl-4-methoxy-2-oxo-1,2-dihydropyridine-3-carbonitrile obtained in Step A and N-bromosuccinimide in the same manner as in Step A of Example 2.

MS (ESI+): [M+H]$^+$271.1.

C) 5-bromo-4-chloro-1-isobutyl-2-oxo-1,2-dihydropyridine-3-carbonitrile

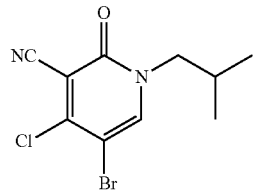

A mixture of 5-bromo-4-hydroxy-1-isobutyl-2-oxo-1,2-dihydropyridine-3-carbonitrile obtained in Step B (6.6 g) and phosphorus oxychloride (0.126 mL) was heated at 120° C. for 24 hr, and cooled to room temperature. The reaction mixture was poured into water, and the pH was adjusted to 10 with potassium carbonate. The reaction mixture was extracted with ethyl acetate. The extract was washed with washed with water and saturated brine, and dried over anhydrous sodium sulfate, and the solvent was evaporated under reduced pressure. The residue was purified by silica gel column chromatography (petroleum ether/ethyl acetate) to give the title compound (4.60 g).

MS (ESI+): [M+H]$^+$289.0.

D) 3-amino-7-bromo-5-isobutyl-1,5-dihydro-4H-pyrazolo[4,3-c]pyridin-4-one

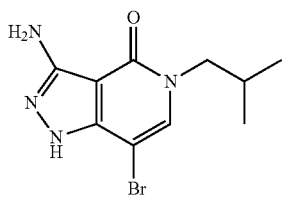

The title compound was obtained from 5-bromo-4-chloro-1-isobutyl-2-oxo-1,2-dihydropyridine-3-carbonitrile obtained in Step C and hydrazine monohydrate in the same manner as in Step E of Example 1.

MS (ESI+): [M+H]$^+$284.7.

E) 3-amino-5-isobutyl-7-(1-methyl-1H-pyrazol-3-yl)-1,5-dihydro-4H-pyrazolo[4,3-c]pyridin-4-one The title compound was obtained from 3-amino-7-bromo-5-isobutyl-1,5-dihydro-4H-pyrazolo[4,3-c]pyridin-4-one obtained in Step D and 1-methyl-3-(4,4,5,5-tetramethyl-1,3,2-dioxaborolan-2-yl)-1H-pyrazole in the same manner as in Step A of Example 4.

MS (ESI+): [M+H]$^+$287.2.

Example 174

N-(4-(3-amino-7-(1-methyl-1H-pyrazol-3-yl)-4-oxo-1,4-dihydro-5H-pyrazolo[4,3-c]pyridin-5-yl)-3,5-difluorophenyl)acetamide

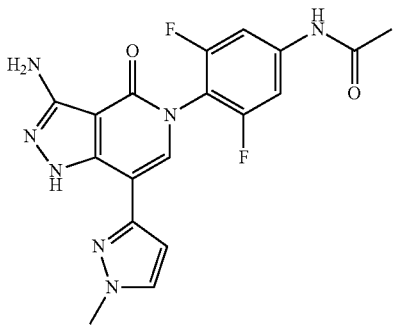 [SMILES: CC(=O)Nc1cc(F)c(-n2cc(-c3ccn(C)n3)c3[nH]nc(N)c3c2=O)c(F)c1]

A) 1-(2,6-difluoro-4-nitrophenyl)-4-methoxy-2-oxo-1,2-dihydropyridine-3-carbonitrile A mixture of 4-methoxy-2-oxo-1,2-dihydropyridine-3-carbonitrile (2.00 g), 1,2,3-trifluoro-5-nitrobenzene (3.54 g), potassium carbonate (3.73 g) and N,N-dimethylformamide (20 mL) was stirred at room temperature for 2 hr. The reaction mixture was slowly poured into saturated sodium hydrogen carbonate solution, and the mixture was extracted with ethyl acetate. The extract was washed with saturated brine, and dried over anhydrous magnesium sulfate, and the solvent was evaporated under reduced pressure. To the residue was added a mixed solvent (10 mL) of isopropyl ether/ethyl acetate=4/1, and the mixture was stirred for 15 min. The precipitate was collected by filtration to give the title compound (3.75 g).
MS (ESI+): [M+H]$^+$308.2.

B) 1-(4-amino-2,6-difluorophenyl)-4-methoxy-2-oxo-1,2-dihydropyridine-3-carbonitrile To a mixture of 1-(2,6-difluoro-4-nitrophenyl)-4-methoxy-2-oxo-1,2-dihydropyridine-3-carbonitrile obtained in Step A (3.00 g), ammonium chloride (5.22 g), ethanol (48 mL) and water (12 mL) was added iron powder (2.18 g) at room temperature, and the reaction mixture was heated at 90° C. for 1 hr. The reaction mixture was cooled to room temperature, and slowly poured into saturated sodium hydrogen carbonate solution, and the mixture was extracted with a mixed solvent of tetrahydrofuran/ethyl acetate=3/1. The extract was washed with saturated brine, and dried over anhydrous magnesium sulfate, and the solvent was evaporated under reduced pressure. To the residue was added isopropyl ether (10 mL), and the mixture was stirred for 15 min. The precipitate was collected by filtration to give the title compound (1.95 g).
MS (ESI+): [M+H]$^+$278.2.

C) N-(4-(3-cyano-4-methoxy-2-oxopyridin-1(2H)-yl)-3,5-difluorophenyl)acetamide To a mixture of 1-(4-amino-2,6-difluorophenyl)-4-methoxy-2-oxo-1,2-dihydropyridine-3-carbonitrile obtained in Step B (1.23 g), triethylamine (1.80 g) and tetrahydrofuran (80 mL) was slowly added acetyl chloride (0.70 g) at room temperature, and the reaction mixture was stirred for 3 hr. The reaction mixture was poured into a mixture of saturated sodium hydrogen carbonate solution/isopropyl ether=1/1, and the mixture was stirred for 15 min. The precipitate was collected by filtration, and washed successively with water and isopropyl ether to give the title compound (1.19 g).
MS (ESI+): [M+H]$^+$320.2.

D) N-(4-(3-amino-4-oxo-1H-pyrazolo[4,3-c]pyridin-5(4H)-yl)-3,5-difluorophenyl)acetamide A mixture of N-(4-(3-cyano-4-methoxy-2-oxopyridin-1(2H)-yl)-3,5-difluorophenyl)acetamide obtained in Step C (1.10 g), hydrazine monohydrate (0.52 g), ethanol (30 mL) and tetrahydrofuran (15 mL) was stirred at 60° C. for 2 hr. The solvent was evaporated under reduced pressure, and to the residue was added isopropyl ether, and the mixture was stirred for 15 min. The precipitate was collected by filtration to give the title compound (0.75 g).
$^1$H NMR (400 MHz, DMSO-$d_6$) δ 2.10 (3H, s), 4.76 (2H, brs), 6.56 (1H, d, J=7.2 Hz), 7.45 (2H, d, J=9.8 Hz), 7.62 (1H, brs), 10.48 (1H, s).

E) N-(4-(3-amino-7-bromo-4-oxo-1H-pyrazolo[4,3-c]pyridin-5(4H)-yl)-3,5-difluorophenyl)acetamide hydrobromide To a mixture of N-(4-(3-amino-4-oxo-1H-pyrazolo[4,3-c]pyridin-5(4H)-yl)-3,5-difluorophenyl)acetamide obtained in Step D (0.67 g) and acetic acid (30 mL) was slowly added bromine (0.21 mL) at 80° C., and the reaction mixture was stirred at 80° C. for 2 hr. The solvent was evaporated under reduced pressure, and the residue was recrystallized from acetic acid to give the title compound (0.65 g).
MS (ESI+): [M+H]$^+$399.1.

F) N-(4-(3-amino-7-(1-methyl-1H-pyrazol-3-yl)-4-oxo-1,4-dihydro-5H-pyrazolo[4,3-c]pyridin-5-yl)-3,5-difluorophenyl)acetamide The title compound was obtained from N-(4-(3-amino-7-bromo-4-oxo-1H-pyrazolo[4,3-c]pyridin-5(4H)-yl)-3,5-difluorophenyl)acetamide hydrobromide obtained in Step E and 1-methyl-3-(4,4,5,5-tetramethyl-1,3,2-dioxaborolan-2-yl)-1H-pyrazole in the same manner as in Step H of Example 13.
MS (ESI+): [M+H]$^+$400.3.

Example 175

4-(3-amino-7-(1-methyl-1H-pyrazol-3-yl)-4-oxo-1,4-dihydro-5H-pyrazolo[4,3-c]pyridin-5-yl)-3,5-difluorobenzonitrile

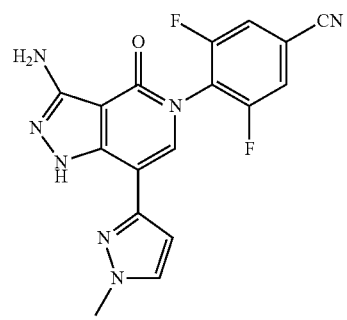

A) 1-(4-cyano-2,6-difluorophenyl)-4-methoxy-2-oxo-1,2-dihydropyridine-3-carbonitrile A mixture of 4-methoxy-2-oxo-1,2-dihydropyridine-3-carbonitrile (2.00 g), 3,4,5-trifluorobenzonitrile (2.93 g), potassium carbonate (3.68 g) and N,N-dimethylformamide (20 mL) was stirred at 50° C. for 5 hr. The reaction mixture was slowly poured into saturated sodium hydrogen carbonate solution, and the mixture was extracted with ethyl acetate. The extract was washed with saturated brine, and dried over anhydrous magnesium sulfate, and the solvent was evaporated under reduced pressure. To the residue was added a mixed solvent (10 mL) of isopropyl ether/ethyl acetate=4/1, and the mixture was stirred for 15 min. The precipitate was collected by filtration to give the title compound (1.65 g).
MS (ESI+): [M+H]$^+$288.2.

B) 4-(3-amino-4-oxo-1H-pyrazolo[4,3-c]pyridin-5(4H)-yl)-3,5-difluorobenzonitrile The title compound was obtained from 1-(4-cyano-2,6-difluorophenyl)-4-methoxy-2-oxo-1,2-dihydropyridine-3-carbonitrile obtained in Step A and hydrazine monohydrate in the same manner as in Step D of Example 174.
MS (ESI+): [M+H]$^+$288.2.

C) 4-(3-amino-7-bromo-4-oxo-1H-pyrazolo[4,3-c]pyridin-5(4H)-yl)-3,5-difluorobenzonitrile hydrobromide To a mixture of 4-(3-amino-4-oxo-1H-pyrazolo[4,3-c]pyridin-5(4H)-yl)-3,5-difluorobenzonitrile obtained in Step B (0.60 g) and acetic acid (40 mL) was slowly added bromine (0.21 mL) at 80° C., and the reaction mixture was stirred at 100° C. for 1 hr. The solvent was evaporated under reduced pressure, and the residue was recrystallized from acetic acid to give the title compound (0.81 g).
MS (ESI+): [M+H]$^+$368.1.

D) 4-(3-amino-7-(1-methyl-1H-pyrazol-3-yl)-4-oxo-1,4-dihydro-5H-pyrazolo[4,3-c]pyridin-5-yl)-3,5-difluorobenzonitrile The title compound was obtained from 4-(3-amino-7-bromo-4-oxo-1H-pyrazolo[4,3-c]pyridin-5(4H)-yl)-3,5-difluorobenzonitrile hydrobromide obtained in Step C and 1-methyl-3-(4,4,5,5-tetramethyl-1,3,2-dioxaborolan-2-yl)-1H-pyrazole in the same manner as in Step H of Example 13.
MS (ESI+): [M+H]$^+$368.2.

Example 176

3-amino-5-(3-chloropyridin-4-yl)-7-(1-methyl-1H-pyrazol-3-yl)-1,5-dihydro-4H-pyrazolo[4,3-c]pyridin-4-one

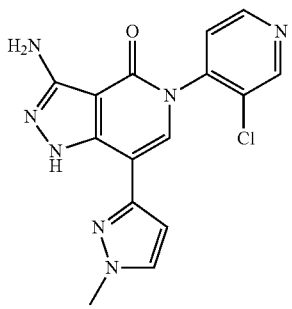 [SMILES: Cn1ccc(-c2cn(-c3ccncc3Cl)c(=O)c3c(N)n[nH]c23)n1]

A) 4-methoxy-3'-nitro-2-oxo-2H-[1,4'-bipyridine]-3-carbonitrile

A mixture of 4-methoxy-2-oxo-1,2-dihydropyridine-3-carbonitrile (3.00 g), 4-chloro-3-nitropyridine (6.34 g), cesium carbonate (13.02 g) and N,N-dimethylformamide (30 mL) was stirred at room temperature for 16 hr. The reaction mixture was slowly poured into saturated sodium hydrogen carbonate solution, and the mixture was extracted with ethyl acetate. The extract was washed with saturated brine, and dried over anhydrous magnesium sulfate, and the solvent was evaporated under reduced pressure. To the residue was added isopropyl ether (20 mL), and the mixture was stirred for 15 min. The precipitate was collected by filtration to give the title compound (5.00 g).
MS (ESI+): [M+H]$^+$273.2.

B) 3'-amino-4-methoxy-2-oxo-2H-[1,4'-bipyridine]-3-carbonitrile

To a mixture of 4-methoxy-3'-nitro-2-oxo-2H-[1,4'-bipyridine]-3-carbonitrile obtained in Step A (3.00 g), ammonium chloride (5.90 g), ethanol (60 mL) and water (15 mL) was added iron powder (2.46 g) at room temperature. The reaction mixture was heated at 90° C. for 2 hr. The reaction mixture was cooled to room temperature, and poured into saturated sodium hydrogen carbonate solution, and the mixture was extracted with a mixed solvent of tetrahydrofuran/ethyl acetate=2/1. The extract was washed with saturated brine, and dried over anhydrous magnesium sulfate, and the solvent was evaporated under reduced pressure. To the residue was added a mixed solvent (20 mL) of methanol/isopropyl ether=1/1, and the mixture was stirred for 15 min. The precipitate was collected by filtration to give the title compound (1.10 g).
MS (ESI+): [M+H]$^+$243.2.

C) 3'-chloro-4-methoxy-2-oxo-2H-[1,4'-bipyridine]-3-carbonitrile

To a mixture of 3'-amino-4-methoxy-2-oxo-2H-[1,4'-bipyridine]-3-carbonitrile obtained in Step B (1.00 g) and 1N hydrochloric acid (20 mL) was slowly added an aqueous solution (3 mL) of sodium nitrite (0.31 g) at 0° C., and the mixture was stirred for 2 hr. This reaction mixture was added to a mixture of copper(I) chloride (0.30 g) and 1N hydrochloric acid (5 mL) at 0° C., and the mixture was stirred at room temperature for 16 hr. The reaction mixture was slowly poured into saturated sodium hydrogen carbonate solution, and the mixture was extracted with a mixed solvent of tetrahydrofuran/ethyl acetate=1/1. The extract was washed with saturated brine, and dried over anhydrous magnesium sulfate, and the solvent was evaporated under reduced pressure. The residue was purified by silica gel column chromatography (ethyl acetate/hexane) to give the title compound (0.40 g).
MS (ESI+): [M+H]$^+$262.1.

D) 3-amino-5-(3-chloropyridin-4-yl)-1H-pyrazolo[4,3-c]pyridin-4(5H)-one

A mixture of 3'-chloro-4-methoxy-2-oxo-2H-[1,4'-bipyridine]-3-carbonitrile obtained in Step C (0.35 g), hydrazine monohydrate (0.17 g), ethanol (10 mL) and N,N-dimethylformamide (10 mL) was stirred at 60° C. for 2 hr. The solvent was evaporated under reduced pressure, to the residue was added isopropyl ether, and the mixture was stirred for 15 min. The precipitate was collected by filtration to give the title compound (0.30 g).
MS (ESI+): [M+H]$^+$262.2.

E) 3-amino-7-bromo-5-(3-chloropyridin-4-yl)-1H-pyrazolo[4,3-c]pyridin-4(5H)-one hydrobromide To a mixture of 3-amino-5-(3-chloropyridin-4-yl)-1H-pyrazolo[4,3-c]pyridin-4(5H)-one obtained in Step D (0.25 g) and acetic acid (30 mL) was slowly added bromine (0.10 mL) at 60° C., and the reaction mixture was stirred at 60° C. for 3 hr. The solvent was evaporated under reduced pressure, and the residue was recrystallized from acetic acid to give the title compound (0.27 g).
MS (ESI+): [M+H]$^+$342.1.

F) 3-amino-5-(3-chloropyridin-4-yl)-7-(1-methyl-1H-pyrazol-3-yl)-1,5-dihydro-4H-pyrazolo[4,3-c]pyridin-4-one The title compound was obtained from 3-amino-7-bromo-5-(3-chloropyridin-4-yl)-1H-pyrazolo[4,3-c]pyridin-4(5H)-one hydrobromide obtained in Step E and 1-methyl-3-(4,4,5,5-tetramethyl-1,3,2-dioxaborolan-2-yl)-1H-pyrazole in the same manner as in Step H of Example 13.
MS (ESI+): [M+H]$^+$342.2.

Example 177

2-(3-amino-7-(1-methyl-1H-pyrazol-3-yl)-4-oxo-1,4-dihydro-5H-pyrazolo[4,3-c]pyridin-5-yl)nicotinonitrile

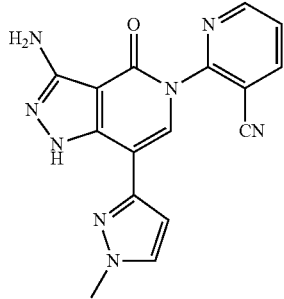 [SMILES: Cn1ccc(-c2cn(-c3ncccc3C#N)c(=O)c3c(N)n[nH]c23)n1]

A) 5-iodo-4-methoxy-2-oxo-1,2-dihydropyridine-3-carbonitrile

To a mixture of 4-methoxy-2-oxo-1,2-dihydropyridine-3-carbonitrile (3.00 g) and N,N-dimethylformamide (70 mL) was added N-iodosuccinimide (5.84 g) at room temperature, and the mixture was stirred at 70° C. for 16 hr. The reaction mixture was cooled to room temperature, and the solvent was evaporated under reduced pressure. To the residue was added methanol, and the precipitate was collected by filtration to give the title compound (4.60 g).
MS (ESI+): [M+H]$^+$277.1.

B) 5-iodo-4-methoxy-2-((4-methoxybenzyl)oxy)nicotinonitrile

To a mixture of 5-iodo-4-methoxy-2-oxo-1,2-dihydropyridine-3-carbonitrile obtained in Step A (3.00 g), silver(I) oxide (2.77 g) and toluene (80 mL) was added 4-methoxybenzyl chloride (2.21 g) at room temperature, and the mixture was stirred 110° C. for 5 hr. To the reaction mixture was added 4-methoxybenzyl chloride (2.21 g), and the mixture was stirred at 110° C. for 16 hr. The reaction mixture was cooled to room temperature, the insoluble substance was removed by filtration, and the filtrate was concentrated under reduced pressure. To the residue was added diethyl ether, and the precipitate was collected by filtration to give the title compound (3.32 g).
$^1$H NMR (400 MHz, DMSO-d$_6$) δ 3.76 (3H, s), 4.24 (3H, s), 5.38 (2H, s), 6.90-7.01 (2H, m), 7.40 (2H, d, J=8.3 Hz), 8.61 (1H, s).

C) 4-methoxy-2-((4-methoxybenzyl)oxy)-5-(1-methyl-1H-pyrazol-3-yl)nicotinonitrile The title compound was obtained from 5-iodo-4-methoxy-2-((4-methoxybenzyl)oxy)nicotinonitrile obtained in Step B and 1-methyl-3-(4,4,5,5-tetramethyl-1,3,2-dioxaborolan-2-yl)-1H-pyrazole in the same manner as in Step H of Example 13.
MS (ESI+): [M+H]$^+$351.3.

D) 2-hydroxy-4-methoxy-5-(1-methyl-1H-pyrazol-3-yl)nicotinonitrile trifluoroacetate A mixture of 4-methoxy-2-((4-methoxybenzyl)oxy)-5-(1-methyl-1H-pyrazol-3-yl)nicotinonitrile obtained in Step C (0.81 g) and trifluoroacetic acid (2.6 g) was stirred at room temperature for 15 min, and the solvent was evaporated under reduced pressure. To the residue was added a mixed solvent (5 mL) of isopropyl ether/ethyl acetate=1/1, and the mixture was stirred for 15 min. The precipitate was collected by filtration to give the title compound (0.57 g).
MS (ESI+): [M+H]$^+$231.2.

E) 4-methoxy-5-(1-methyl-1H-pyrazol-3-yl)-2-oxo-2H-[1,2'-bipyridine]-3,3'-dicarbonitrile A mixture of 2-hydroxy-4-methoxy-5-(1-methyl-1H-pyrazol-3-yl)nicotinonitrile trifluoroacetate obtained in Step D (0.20 g), 2-fluoronicotinonitrile (0.710 g), cesium carbonate (0.45 g) and N,N-dimethylformamide (30 mL) was stirred at room temperature for 16 hr. The reaction mixture was slowly poured into saturated sodium hydrogen carbonate solution, and the mixture was extracted with ethyl acetate. The extract was washed with saturated brine, and dried over anhydrous magnesium sulfate, and the solvent was evaporated under reduced pressure. To the residue was added a mixed solvent (2 mL) of isopropyl ether/ethyl acetate=1/2, and the mixture was stirred for 15 min. The precipitate was collected by filtration to give the title compound (0.12 g).
$^1$H NMR (400 MHz, DMSO-d$_6$) δ 3.85 (3H, s), 4.42 (3H, s), 6.53 (1H, d, J=2.3 Hz), 7.77 (1H, d, J=2.3 Hz), 7.82 (1H, dd, J=5.1, 7.7 Hz), 8.37 (1H, s), 8.56-8.64 (1H, m), 8.91 (1H, dd, J=1.9, 4.9 Hz).

F) 2-(3-amino-7-(1-methyl-1H-pyrazol-3-yl)-4-oxo-1,4-dihydro-5H-pyrazolo[4,3-c]pyridin-5-yl)nicotinonitrile A mixture of 4-methoxy-5-(1-methyl-1H-pyrazol-3-yl)-2-oxo-2H-[1,2'-bipyridine]-3,3'-dicarbonitrile obtained in Step E (0.12 g), hydrazine monohydrate (0.087 g), ethanol (10 mL) and tetrahydrofuran (5 mL) was stirred at 60° C. for 2 hr. The solvent was evaporated under reduced pressure, to the residue was added a mixed solvent (5 mL) of ethanol/ethyl acetate=1/1, and the mixture was stirred for 15 min. The precipitate was collected by filtration to give the title compound (0.069 g).
MS (ESI+): [M+H]$^+$333.2.

Example 178

2-(3-amino-5-((2S)-3-methylbutan-2-yl)-4-oxo-4,5-dihydro-1H-pyrazolo[4,3-c]pyridin-7-yl)-N-(2-methoxyethyl)-N-methyl-1,3-thiazole-5-carboxamide

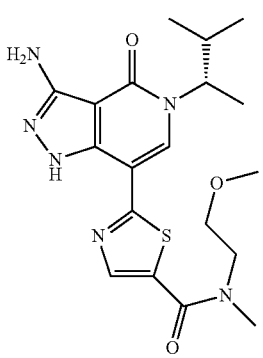 [SMILES: COCCN(C)C(=O)c1cnc(-c2cn([C@@H](C)C(C)C)c(=O)c3c(N)n[nH]c23)s1]

The title compound was obtained from 3-amino-7-bromo-5-((2S)-3-methylbutan-2-yl)-1,5-dihydro-4H-pyrazolo[4,3-c]pyridin-4-one obtained in Example 112 and 2-bromo-N-(2-methoxyethyl)-N-methyl-1,3-thiazole-5-carboxamide obtained in Reference Example 30 in the same manner as in Example 23.

MS (ESI+): [M+H]⁺419.3.

Example 179

3-amino-7-bromo-5-((2S)-3-methylbutan-2-yl)-1,5-dihydro-4H-pyrazolo[4,3-c]pyridin-4-one

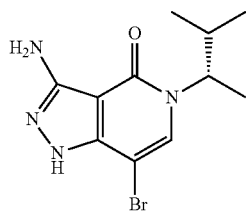 [SMILES: CC(C)[C@H](C)n1cc(Br)c2[nH]nc(N)c2c1=O]

A) N-((2S)-3-methylbutan-2-yl)-3-oxobutanamide

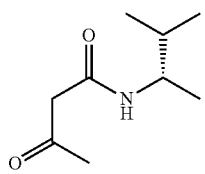

To a solution of (2S)-3-methylbutan-2-amine (30 g, >99% ee, Aldrich) in methanol (180 mL) was added dropwise diketene (29 mL) under ice bath, and the mixture was stirred at room temperature for 20 hr. The mixture was neutralized with acetic acid (120 mL) under ice bath, water was added thereto, and the mixture was extracted with ethyl acetate. The solvent was evaporated under reduced pressure, and the residue was purified by silica gel column chromatography (hexane/ethyl acetate) to give the title compound (56.6 g).

MS(ESI+): [M+H]⁺171.8.

B) 2-((dimethylamino)methylene)-N-((2S)-3-methylbutan-2-yl)-3-oxobutanamide

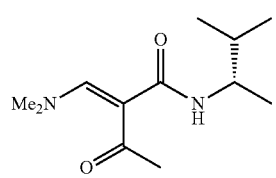 [SMILES: CC(=O)/C(=C\N(C)C)C(=O)N[C@@H](C)C(C)C]

To a solution of N-((2S)-3-methylbutan-2-yl)-3-oxobutanamide obtained in Step A (56.6 g) in N,N-dimethylformamide (220 mL) was added dropwise 1,1-dimethoxy-N,N-dimethylmethanamine (88 mL) over 15 min under ice bath, and the mixture was stirred at room temperature for 20 hr. The solvent was evaporated under reduced pressure to give the title compound (62.7 g).

¹H NMR (400 MHz, CDCl₃) δ0.84-0.99 (6H, m), 1.11 (3H, dd, J=6.6, 2.0 Hz), 1.68-1.79 (1H, m), 2.22 (3H, d, J=2.0 Hz), 3.11 (6H, brs), 3.85-4.07 (1H, m), 7.51 (1H, brs), 7.62 (1H, brs).

C) 4-chloro-1-((2S)-3-methylbutan-2-yl)-2-oxo-1,2-dihydropyridine-3-carbaldehyde

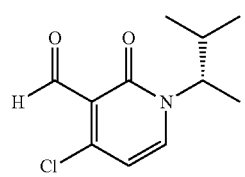

To a solution of 2-((dimethylamino)methylene)-N-((2S)-3-methylbutan-2-yl)-3-oxobutanamide obtained in Step B (31 g) in N,N-dimethylformamide (250 mL) was added (chloromethylene)dimethylammonium chloride (75 g) under ice bath, and the mixture was stirred at 100° C. for 40 min. The reaction mixture was slowly added dropwise to ice water, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (17.8 g).

MS(ESI+): [M+H]⁺228.2.

D) 4-chloro-3-((hydroxyimino)methyl)-1-((2S)-3-methylbutan-2-yl)pyridin-2(1H)-one

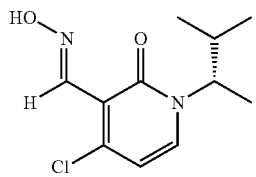 [SMILES: CC(C)[C@H](C)n1ccc(Cl)c(/C=N/O)c1=O]

To a solution of 4-chloro-1-((2S)-3-methylbutan-2-yl)-2-oxo-1,2-dihydropyridine-3-carbaldehyde obtained in Step C (31.8 g) in 2-propanol (300 mL) were added hydroxylamine hydrochloride (14.6 g) and conc. hydrochloric acid (0.43 mL), and the mixture was stirred at 100° C. for 1 hr. The reaction mixture was cooled to room temperature, and the solvent was evaporated under reduced pressure. The residue was crystallized from (2-propanol/diisopropyl ether), and the resulting solid was collected by filtration, and washed with 2-propanol/diisopropyl ether to give the title compound (23.2 g).

MS(ESI+): [M+H]⁺243.2.

E) 4-chloro-1-((2S)-3-methylbutan-2-yl)-2-oxo-1,2-dihydropyridine-3-carbonitrile

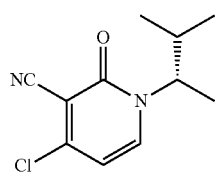

To a solution of 4-chloro-3-((hydroxyimino)methyl)-1-((2S)-3-methylbutan-2-yl)pyridin-2(1H)-one obtained in Step D (23.2 g) in acetonitrile (300 mL) was added dropwise thionyl chloride (13.9 mL), and the mixture was stirred at room temperature for 1 hr. The solvent was evaporated under reduced pressure, and to the residue were added diisopropyl ether/ethyl acetate/hexane. The insoluble substance was removed by filtration, and the filtrate was concentrated under reduced pressure. To the residue was added ethyl acetate, and the mixture was washed successively with saturated aqueous sodium hydrogen carbonate solution and saturated brine, and dried over anhydrous magnesium sulfate, and the solvent was evaporated under reduced pressure. The residue was purified by silica gel column chromatography (hexane/ethyl acetate) to give the title compound (14.6 g).

MS(ESI+): [M+H]⁺224.8.

F) 5-bromo-4-chloro-1-((2S)-3-methylbutan-2-yl)-2-oxo-1,2-dihydropyridine-3-carbonitrile

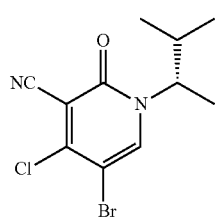 [SMILES: CC(C)[C@H](C)n1cc(Br)c(Cl)c(C#N)c1=O]

To a solution of 4-chloro-1-((2S)-3-methylbutan-2-yl)-2-oxo-1,2-dihydropyridine-3-carbonitrile obtained in Step E (14.6 g) in N,N-dimethylformamide (120 mL) was added N-bromosuccinimide (17.4 g), and the mixture was stirred at 50° C. for 20 hr. To the reaction mixture was added water, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (19.2 g).

MS(ESI+): [M+H]⁺303.2.

G) 3-amino-7-bromo-5-((2S)-3-methylbutan-2-yl)-1,5-dihydro-4H-pyrazolo[4,3-c]pyridin-4-one

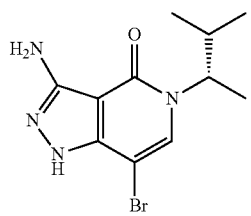 [SMILES: CC(C)[C@H](C)n1cc(Br)c2[nH]nc(N)c2c1=O]

To a solution of 5-bromo-4-chloro-1-((2S)-3-methylbutan-2-yl)-2-oxo-1,2-dihydropyridine-3-carbonitrile obtained in Step F (19.2 g) in ethanol (200 mL) was added hydrazine monohydrate (9.5 g), and the mixture was stirred at 90° C. for 1 hr. The reaction mixture was allowed to be cooled to room temperature, and the solvent was evaporated under reduced pressure. The residue was dissolved in a mixed solvent of ethyl acetate-tetrahydrofuran-water. The organic layer was separated, washed successively with saturated aqueous sodium hydrogen carbonate solution and saturated brine, and dried over anhydrous magnesium sulfate, and the solvent was evaporated under reduced pressure. The residue was purified by silica gel column chromatography (basic silica gel, ethyl acetate/hexane, and then ethyl acetate/methanol), and recrystallized from (ethyl acetate/diisopropyl ether) to give the title compound (15.5 g).

¹H NMR (400 MHz, CDCl₃) δ0.81 (3H, d, J=6.6 Hz), 1.05 (3H, d, J=6.6 Hz), 1.34 (3H, d, J=6.8 Hz), 1.78-1.92 (1H, m), 4.64-5.00 (3H, m), 7.12 (1H, s), 9.27 (1H, brs).

MS(ESI+): [M+H]⁺299.2.

99.4% ee (HPLC (column: CHIRALPAK AD, 4.6 mmID× 250 mmL, manufactured by Daicel Chemical Industries, mobile phase: hexane/ethanol=600/400(v/v), flow rate: 0.5 mL/min, retention time: 10.00 min))

Example 180

3-amino-7-(imidazo[1,2-a]pyridin-2-yl)-5-((2S)-3-methylbutan-2-yl)-1,5-dihydro-4H-pyrazolo[4,3-c]pyridin-4-one

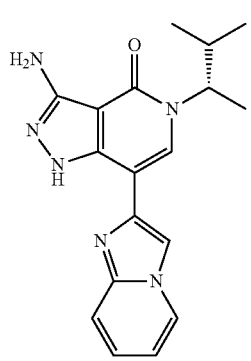 [SMILES: CC(C)[C@H](C)n1cc(-c2cn3ccccc3n2)c2[nH]nc(N)c2c1=O]

The title compound was obtained from 3-amino-7-bromo-5-((2S)-3-methylbutan-2-yl)-1,5-dihydro-4H-pyrazolo[4,3-c]pyridin-4-one obtained in Example 112 and 2-bromoimidazo[1,2-a]pyridine in the same manner as in Example 23.

MS (ESI+): [M+H]⁺337.0.

Example 181

3-amino-5-((2S)-3-methylbutan-2-yl)-7-(1-methyl-1H-pyrazol-3-yl)-1,5-dihydro-4H-pyrazolo[4,3-c]pyridin-4-one

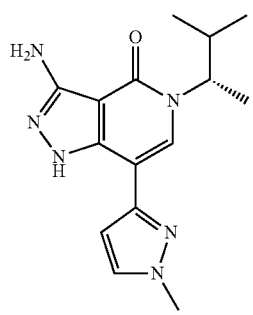 [SMILES: CC(C)[C@H](C)n1cc(-c2ccn(C)n2)c2[nH]nc(N)c2c1=O]

The title compound was obtained from 3-amino-7-bromo-5-((2S)-3-methylbutan-2-yl)-1,5-dihydro-4H-pyrazolo[4,3-c]pyridin-4-one obtained in Example 112, 2-bromoimidazo[1,2-a]pyridine and 1-methyl-3-(4,4,5,5-tetramethyl-1,3,2-dioxaborolan-2-yl)-1H-pyrazole in the same manner as in Step H of Example 13.

MS (ESI+): [M+H]$^+$301.3.

Experimental Example

Tyk2 Enzyme Inhibition Test

Tyk2 enzyme inhibitory activity of test compounds was measured by LANCE method (PerkinElmer). First, a test compound diluted with assay buffer (50 mM HEPES (pH=7.5), 10 mM MgCl$_2$, 1 mM EGTA, 2 mM DTT, 0.01% Tween20, 0.01% BSA) was added to 384-well plate at 2 µL each. Then, a Tyk2 (Invitrogen) solution and a fluorescence-labeled peptide substrate (ULight-JAK1, PerkinElmer) solution diluted with assay buffer at 375 ng/mL and 300 nM, respectively were added at 2 µL each. Then, enzyme reaction was started by adding 2 µL each of ATP solution prepared with assay buffer at 30 µM. After the reaction at room temperature for 1 hr, Detection Buffer (PerkinElmer) prepared to be 20 mM EDTA, 4 nM europium-labeled anti-phosphotyrosine antibody (PerkinElmer) was added at 6 µL each. After standing at room temperature for 1 hr, fluorescence intensity (excitation wavelength 340 nm, fluorescence wavelength 665 nm, delay time 100 microsecond) was measured by a plate reader, Envision (PerkinElmer). The inhibitory activity of each compound was calculated as relative value where fluorescence intensity of a well without enzyme is considered as 100% inhibition.

TABLE 10

| Ex. No. | Tyk2 enzyme inhibitory activity (%, 1 uM) |
|---|---|
| 1 | 40 |
| 13 | 98 |
| 14 | 98 |
| 15 | 100 |
| 16 | 82 |
| 24 | 98 |
| 28 | 100 |
| 38 | 95 |
| 43 | 92 |

Formulation Example 1

Production of Capsule

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

The compound of the present invention has a superior Tyk2 inhibitory action, which is useful as an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like.

This application is based on patent application No. 2012-034440 filed in Japan, the contents of which are encompassed in full herein.

The invention claimed is:

1. A compound represented by the formula (I):

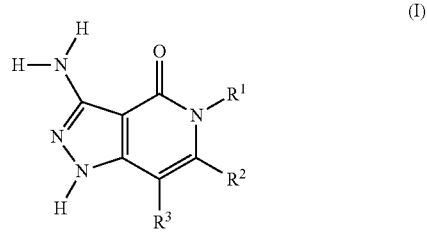

wherein
R$^1$ is an optionally substituted C$_{1-6}$ alkyl group or an optionally substituted cyclic group;
R$^2$ is a hydrogen atom or a cyano group; and
R$^3$ is a halogen atom, a 5-membered aromatic ring group optionally having one substituent, or an optionally substituted 6- to 12-membered aromatic ring group, or a salt thereof.

2. The compound or salt of claim 1, wherein R$^2$ is a hydrogen atom.

3. The compound or salt of claim 1, wherein R$^1$ is
(1) a C$_{1-6}$ alkyl group optionally substituted by 1 to 3 substituents selected from (a) a halogen atom, and (b) a C$_{3-8}$ cycloalkyl, (2) a $C_{3-10}$ cycloalkyl group optionally substituted by 1 to 3 substituents selected from (a) a halogen atom, and (b) a $C_{1-6}$ alkyl group,
(3) a $C_{6-14}$ aryl group optionally substituted by 1 to 3 substituents selected from (a) a halogen atom, (b) a $C_{1-6}$ alkyl group optionally substituted by 1 to 3 halogen atoms, (c) a cyano group, (d) an amino group optionally mono- or di-substituted by $C_{1-6}$ alkyl-carbonyl group(s), and (e) a $C_{1-6}$ alkoxy group,
(4) a 3- to 8-membered monocyclic non-aromatic heterocyclic group, or
(5) a 5- or 6-membered monocyclic aromatic heterocyclic group optionally substituted by 1 to 3 substituents selected from
(a) a halogen atom, and (b) a cyano group;
$R^2$ is a hydrogen atom or a cyano group; and
$R^3$ is
(1) a halogen atom,
(2) a $C_{6-12}$ aryl group optionally substituted by 1 to 3 halogen atoms,
(3) a 5-membered monocyclic aromatic heterocyclic group optionally substituted by one substituent selected from the following Substituent Group C,
(4) a 6-membered monocyclic aromatic heterocyclic group optionally substituted by 1 to 3 substituents selected from following Substituent Group C, or (5) a 8- to 12-membered fused aromatic heterocyclic group optionally substituted by 1 to 3 substituents selected from following Substituent Group C

[Substituent Group C:
(a) a $C_{1-6}$ alkyl group optionally substituted by 1 to 3 substituents selected from (i) a hydroxy group, (ii) a $C_{1-6}$ alkoxy group, (iii) a $C_{1-6}$ alkylsulfonyl group, (iv) an amino group optionally mono- or di-substituted by substituent(s) selected from a $C_{1-6}$ alkyl-carbonyl group, a formyl group and a $C_{1-6}$ alkyl group, (v) a cyano group, (vi) a 3- to 8-membered monocyclic non-aromatic heterocyclic group optionally substituted by 1 to 3 $C_{1-6}$ alkyl groups, (vii) a 3- to 8-membered monocyclic non-aromatic heterocyclylcarbonyl group optionally substituted by 1 to 3 hydroxy groups, and (viii) a carbamoyl group optionally mono- or di-substituted by substituent(s) selected from a 3- to 8-membered monocyclic non-aromatic heterocyclic group and a $C_{1-6}$ alkyl group,
(b) a cyano group,
(c) an amino group optionally mono- or di-substituted by substituent(s) selected from (i) a formyl group, (ii) a $C_{1-6}$ alkyl group optionally substituted by 1 to 3 amino groups optionally mono- or di-substituted by $C_{1-6}$ alkyl group(s), and (iii) a $C_{1-6}$ alkyl-carbonyl group,
(d) a carbamoyl group optionally mono- or di-substituted by substituent(s) selected from (i) a $C_{1-6}$ alkyl group optionally substituted by 1 to 3 substituents selected from a hydroxy group and a $C_{1-6}$ alkoxy group, and (ii) a 3- to 8-membered monocyclic non-aromatic heterocyclic group,
(e) a $C_{1-6}$ alkoxy-carbonyl group,
(f) a $C_{1-6}$ alkoxy group optionally substituted by 1 to 3 substituents selected from (i) a $C_{1-6}$ alkoxy group, (ii) an amino group optionally mono- or di-substituted by substituent(s) selected from a $C_{1-6}$ alkyl group and a $C_{1-6}$ alkyl-carbonyl group, (iii) a carbamoyl group optionally mono- or di-substituted by $C_{1-6}$ alkyl group(s), (iv) a 3- to 8-membered monocyclic non-aromatic heterocyclic group optionally substituted by oxo group(s), (v) a hydroxy group, and (vi) a $C_{6-14}$ aryl group optionally substituted by 1 to 3 $C_{1-6}$ alkoxy groups,
(g) a 3- to 8-membered monocyclic non-aromatic heterocyclic group optionally substituted by 1 to 3 substituents selected from (i) a $C_{1-6}$ alkyl group optionally substituted by 1 to 3 hydroxy groups, (ii) a $C_{1-6}$ alkoxy group, (iii) a $C_{1-6}$ alkyl-carbonyl group, (iv) an oxo group, (v) a hydroxy group, and (vi) a halogen atom,
(h) a 3- to 8-membered monocyclic non-aromatic heterocyclylcarbonyl group,
(i) a 3- to 8-membered monocyclic non-aromatic heterocyclyloxy group,
(j) a $C_{3-8}$ cycloalkyloxy group, and
(k) a hydroxy group].

4. 3-Amino-5-(2,6-difluorophenyl)-7(1-methyl-1H-pyrazol-3-yl)-1,5-dihydro-4H-pyrazolo[4,3-c]pyridin-4-one or a salt thereof.

5. 2-(3-Amino-7-(1-methyl-1H-pyrazol-3-yl)-4-oxo-1,4-dihydro-5H-pyrazolo[4,3-c]pyridin-5-yl)-3-fluorobenzonitrile or a salt thereof.

6. 3-Amino-5-(1-cyclopropylethyl)-7-(1-methyl-1H-pyrazol-3-yl)-1,5-dihydro-4H-pyrazolo[4,3-c]pyridin-4-one or a salt thereof.

7. A pharmaceutical composition comprising the compound or salt of claim 1 and a pharmaceutically acceptable carrier.

8. The pharmaceutical composition of claim 7, which is a tyrosine kinase 2 inhibitor.

* * * * *

UNITED STATES PATENT AND TRADEMARK OFFICE
CERTIFICATE OF CORRECTION

PATENT NO.         : 9,085,578 B2
APPLICATION NO.    : 14/379343
DATED              : July 21, 2015
INVENTOR(S)        : Hiroyuki Nagamiya It is certified that error appears in the above-identified patent and that said Letters Patent is hereby corrected as shown below:

Claims

In column 224, replace Claims 4 and 5 with the following corrected claims.

4. 3-Amino-5-(2,6-difluorophenyl)-7-(1-methyl-1H-pyrazol-3-yl)-1,5-dihydro-4H-pyrazolo[4,3-c]pyridin-4-one or a salt thereof.

5. 2-(3-Amino-7-(1-methyl-1H-pyrazol-3-yl)-4-oxo-1,4-dihydro-5H-pyrazolo[4,3-c]pyridin-5-yl)-3-fluorobenzonitrile or a salt thereof.

Signed and Sealed this
Twenty-second Day of March, 2016

Michelle K. Lee
*Director of the United States Patent and Trademark Office*